(12) United States Patent
Baker et al.

(10) Patent No.: US 8,895,534 B2
(45) Date of Patent: Nov. 25, 2014

(54) BORON CONTAINING SMALL MOLECULES

(75) Inventors: Stephen J. Baker, Mountain View, CA (US); Vincent S. Hernandez, Watsonville, CA (US); Rashmi Sharma, Edmonton (CA); James A. Nieman, Sherwood Park (CA); Tsutomu Akama, Sunnyvale, CA (US); Yong-Kang Zhang, San Jose, CA (US); Jacob J. Plattner, Orinda, CA (US); Michael Richard Kevin Alley, Santa Clara, CA (US); Rajeshwar Singh, Edmonton (CA); Fernando Rock, Los Altos, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 326 days.

(21) Appl. No.: 12/848,051

(22) Filed: Jul. 30, 2010

(65) Prior Publication Data

US 2010/0292504 A1 Nov. 18, 2010

Related U.S. Application Data

(63) Continuation of application No. 12/142,692, filed on Jun. 19, 2008.

(60) Provisional application No. 60/945,294, filed on Jun. 20, 2007, provisional application No. 61/041,178, filed on Mar. 31, 2008.

(30) Foreign Application Priority Data

Jun. 19, 2008 (WO) ................ PCT/US2008/067550

(51) Int. Cl.
*C07F 5/02* (2006.01)

(52) U.S. Cl.
CPC ...................................... *C07F 5/025* (2013.01)
USPC ................................................. 514/64; 564/8

(58) Field of Classification Search
None
See application file for complete search history.

(56) References Cited

U.S. PATENT DOCUMENTS

| 2,260,336 | A | 10/1941 | Prescott et al. |
| 3,873,279 | A | 3/1975 | Singer |
| 5,688,928 | A | 11/1997 | Stolowitz |
| 5,831,045 | A | 11/1998 | Stolowitz et al. |
| 5,880,188 | A | 3/1999 | Austin et al. |
| 5,962,498 | A | 10/1999 | Driedger et al. |
| 6,083,903 | A | 7/2000 | Adams et al. |
| 6,306,628 | B1 | 10/2001 | Rothschild et al. |
| 6,369,098 | B1 | 4/2002 | Pershadsingh et al. |
| 6,855,848 | B2 | 2/2005 | Scherer et al. |
| 7,169,603 | B2 | 1/2007 | Hedley et al. |
| 7,217,701 | B2 | 5/2007 | Mikoshiba et al. |
| 7,582,621 | B2 | 9/2009 | Baker et al. |
| 7,767,657 | B2 * | 8/2010 | Baker et al. ........... 514/64 |
| 2003/0032673 | A1 | 2/2003 | Nagy |
| 2004/0259842 | A1 | 12/2004 | Mikoshiba et al. |
| 2005/0239170 | A1 | 10/2005 | Hedley et al. |
| 2006/0009386 | A1 | 1/2006 | Stossel et al. |
| 2006/0234981 | A1 | 10/2006 | Baker et al. |
| 2007/0155699 | A1 | 7/2007 | Baker et al. |
| 2007/0286822 | A1 | 12/2007 | Sanders et al. |
| 2007/0293457 | A1 | 12/2007 | Baker et al. |
| 2010/0256092 | A1 * | 10/2010 | Xia et al. ........... 514/64 |

FOREIGN PATENT DOCUMENTS

| WO | WO 95/33754 | A1 | 12/1995 | |
| WO | WO 03/059916 | A2 | 7/2003 | |
| WO | 2005/013892 | | 2/2005 | |
| WO | WO 2005013892 | A3 | 2/2005 | |
| WO | 2006/089067 | | 8/2006 | |
| WO | WO 2007/078340 | A2 | 7/2007 | |
| WO | WO 2007/095638 | A2 | 8/2007 | |
| WO | 2007/146965 | | 12/2007 | |
| WO | WO 2007146965 | A2 | 12/2007 | |
| WO | WO 2008/019811 | A1 | 2/2008 | |
| WO | WO 2009/140309 | | * 11/2009 | ............... A62D 3/36 |

OTHER PUBLICATIONS

Tschampel et al., J. Org. Chem. 1964, 29(8), pp. 2168-2172.*
Austin, et al., CAS, 1996, vol. 124, pp. 234.
Baker, S., et al., "Discovery of a New Boron-Containing Antifungal Agent, 5-Fluoro-1,3-dihydro-1-hydroxy-2,1-benzoxaborole (AN2690) for Potential Treatment of Onychomycosis", *Journal of Medicinal Chemistry*, Jul. 27, 2006, vol. 49, No. 15; pp. 4447-4450.
Baker, S. J., et al., "Progress on New Therapeutics for Fungal Nail Infections," *Annual Reports in Medicinal Chemistry*, 2005, vol. 40; pp. 323-335.
Bessis, N., "Gene Therapy for Rheumatoid Arthritis," *J. Gene Med*, 2002, vol. 4, pp. 581-591.
Ferrer. "Targeting Aminocytl-tRNA Synthetases for the Treatment of Fungal Infections", *Drug News Perspective*, Jul.-Aug. 2006, vol. 19, No. 6; pp. 347-348.
Murdan, S., et al., "Drug Delivery to the Nail Following Topical Application," *International Journal of Pharmaceutics*, 2002, vol. 236; pp. 1-26.
Zhou, Huchen, et al., "Hemodextrin: a Self-assembled Cyclodextrin-Porphyrin Construct That Binds Dioxygen," *Biophysical Chemistry*, 2003, vol. 105; pp. 639-648.
Zhou, Huchen, et al., "Structure-activity Studies on a Library of Potent Calix[4]arene-based PDGF Antagonists that Inhibit PDGF-stimulated PDGFR Tyrosine Phosphorylation," *Org. Biomol. Chem.*, 2006, vol. 4; pp. 2376-2386.
Zhou, Huchen, et al., "Pattern Recognition of Proteins Based on an Array of Functionalized Porphyrins," *J. Am. Chem. Soc.*, 2006, vol. 128 pp. 2421-2425.

(Continued)

*Primary Examiner* — Alicia L Otton
(74) *Attorney, Agent, or Firm* — Morgan, Lewis & Bockius LLP

(57) ABSTRACT

Novel monosubstituted and disubstututited oxaboroles and pharmaceutical compositions containing such oxaboroles are provided, which are useful for treating bacterial infections, as well as combinations of these oxaboroles with at least one additional therapeutically effective agent.

29 Claims, 33 Drawing Sheets

(56) References Cited

OTHER PUBLICATIONS

Hauck, et al., Preparation and Anticonvulsant Activity of Some Aryldialkylsuccinimides, Research Labs of Parke Davis Co (1967).
Austin, et al., CAS, vol. 124, p. 234 (1996).
Vippagunta, S. R., Crystalline Solids, Advanced Drug Delivery Reviews, vol. 48, pp. 3-26 (2001).
Bessis, N., Gene Therapy for Rheumatoid Arthritis, J. Gene Med. vol. 4, pp. 581-591 (2002).
Lampe, et al., Synthesis and Protein Kinase Inhibitory Activity of Balanol Analogues with Modified Benzophenone Subunits, J. Med. Chem., vol. 45, No. 12, pp. 2624-2643 (2002).
Murdan, Drug delivery to the nail following topical application, Int'l J. Pharmaceutics, vol. 236, pp. 1-26 (2002)S.
Zhou, et al., Hemodextrin: a self-assembled cyclodextrin-porphyrin construct that binds dioxygen, Biophysical Chemistry, vol. 105, pp. 639-648 (2003).
Morissette, et al., High-throughput crystalization: polymorphs, salts, co-crystals and solvates of pharmaceutical solids, Advanced Drug Delivery Reviews, vol. 56, pp. 275-300 (2004).
Baker, et al., Progress on New Therapeutics for Fungal Nail Infections, Annual Reports in Medicinal Chemistry, vol. 40, pp. 323-335 (2005).
Baker, et al., Discovery of a New Boron-Containing Antifungal Agent, 5-Fluoro-1,3-dihydro-1-hydroxy-2,1-benzoxaborole (AN2690) for the Potential Treatment of Onychomycosis, J. Med. Chem., vol. 49, No. 15, pp. 4447-4450 (2006).
Ferrer, Targeting Aminoacyl-tRNA Synthetases for the Treatment of Fungal Infections, Drug News Perspective, vol. 19, No. 6, pp. 347-348 (2006).
Zhou, et al. Structure-activity studies on a library of potent calix[4]arene-based PDGF antagonists that inhibit PDGF-stimulated PDGFR tyrosine phosphorylation, Org. Biomol. Chem. vol. 4, pp. 2376-2386 (2006).
Zhou, et al., Pattern Recognition of Proteins Based on an Array of Functionalized Porphyrins, J. Am. Chem. Soc., vol. 128, pp. 2421-2425 (2006).
Dale, et al. "Substituted Styrenes. VII. The Syntheses and Some Reactions of the Vinylbenzeneboronic Acids", vol. 27, Department of Chemistry, University of Missouri, Columbia, Missouri, Feb. 12, 1962.
Lennarz, et al., "Arylboronic Acids. IV. Ractions of Boronophthalide [1]", Journal of the American Chemical Society, 1960, 82, 2172-5.

* cited by examiner

FIG 1A
| Reg # | Structure | 32< = *<br>32 - 8.01 = **<br>8.00 - 2.00 = ***<br>2> = **** | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|---|
| A1 | 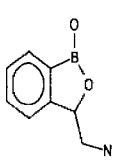 | | ** |  | ** | * | * | * | * |  | ** | * | *** |
| A46 | 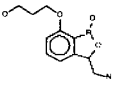 | | ** | * | ** |  | ** | * |  | | | * | **** |

FIG 1B
| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A2 | 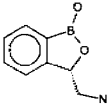 | ** | * | **** | * | * | * | ** |  |  | * | *** |
| A52 | 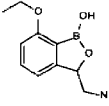 | ** | * | *** | * | ** | * |  |  |  |  | *** |
| A15 | 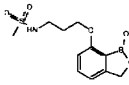 |  |  | *** | * |  |  | * | * |  |  | *** |

FIG 1C

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A49 | 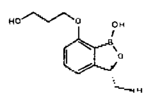 | ** | * | * | * | ** |  | * | ** |  | * | *** |
| A11 | 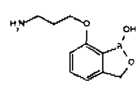 | * | * | * |  | * | * | * | | |  | *** |
| A16 | 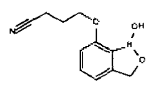 |  |  | *** | * |  |  | * | | |  | * |

FIG 1D
| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A12 | 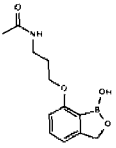 |  |  | *** | * | ** | * | * | | |  | * |
| A13 | 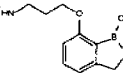 | * | * | *** | * | * | * |  | | |  | **** |
| A39 | 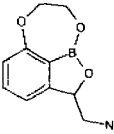 | ** | * | *** | * | ** | * | * |  | ** | * | **** |

FIG 1E

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A38 | 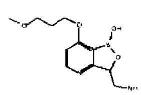 | * | * | *** | * | * | * |  | * | *** | * | *** |
| A3 | 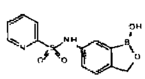 | * | * | *** | * | * |  | * | | | * | *** |
| A16 | 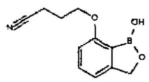 | | | | | * | | | | | | * |

FIG 1F
| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A22 | 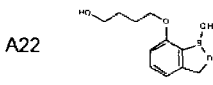 | ** | * | *** | * | ** | * | * | | |  | * |
| A61 | 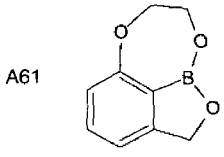 |  |  | *** | * |  |  | * | | |  | * |
| A52 | 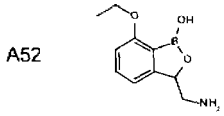 | * | * | *** | * | * | * |  | | |  | *** |

FIG 1G
| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A53 | 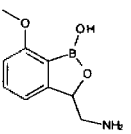 | ** | * | *** | * | * | * | *** |  |  | * | **** |
| A14 | 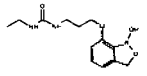 | * |  | * | * |  |  | ** |  |  | * | *** |
| A10 | 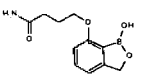 | * |  | * | * |  |  | * | * | ** | * | *** |

FIG 1H
| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A9 | 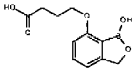 |  |  | *** | * | * | ** | * | * | ** | * | **** |
| A26 | 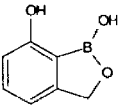 |  |  | ** | * | * | ** | * |  |  | * | ** |
| A17 | 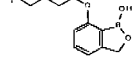 | * | * | ** | * | * | * |  |  |  |  | *** |

FIG 1I

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A18 | 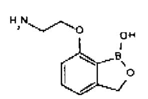 | * |  | ** | * |  |  | ** | | | * | ** |
| A42 | 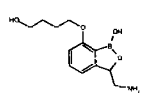 | * |  |  | * | * | * | ** | | | * | *** |
| A23 | 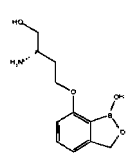 | * |  | ** | * | * | * | * | * | **** | * | *** |

FIG 1J

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A32 | 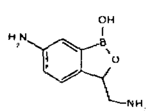 | * |  | ** | * | * | * | *** | | | * | ** |
| A41 | 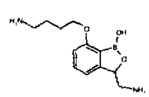 | ** | * | ** | * |  |  | ** | | | * | ** |
| A29 | 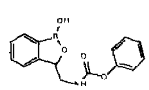 | * | * | ** | * | ** | * | * | | | * | ** |

FIG 1K
| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A27 | 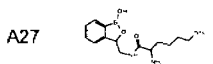 | * |  |  | * | ** | * | * | | | * | *** |
| A44 | 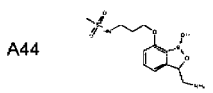 | ** | * | ** | * |  |  | * |  | * | * | *** |
| A4 | 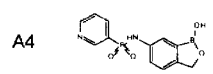 | * | * | * | * | *** | * | * | | |  | * |

FIG 1L

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A25 | 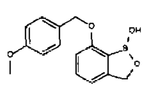 | * | * | * | * | * | ** | * | | | * | * |
| A54 | 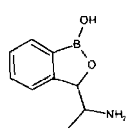 | * | * | * | * | * | * | * | | | * | * |
| A59 | 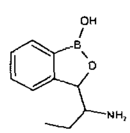 | * | * | * | * | * | * | * | | | * | * |

FIG 1M

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A58 | 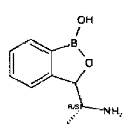 | * | * | * | * | * | * | * | | | * | * |
| A21 | 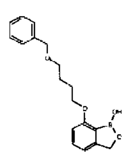 | * | * | * | * | * | * | * | | |  |  |
| A43 | 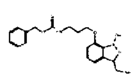 | * | * | * | * |  |  | * | | | * | *** |

FIG 1N

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A7 | 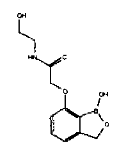 | * | * | * | * | * | * | * | * | | * | *** |
| A27a | 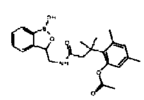 | * | * | * | * | * | * | * | * | | * | * |
| A35 | 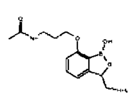 | ** | * | * | * | * | * | * | * | *** | * | *** |

FIG 10

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A33 | 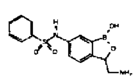 | * | * | * | * | ** | * | * | | | * | ** |
| A34 | 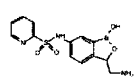 | | * | * | |  | |  | | | * | ** |
| A30 | 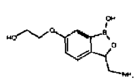 | ** | * | * | * | *** | * | ** | | | * | ** |

FIG 1P

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A31 | 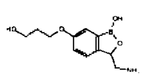 | ** | * | * | * | *** | * | * | | | * | * |
| A36 | 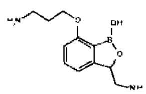 | ** | * | * | * | ** | * | * | | | * | ** |
| A55 | 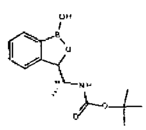 | * | * | * | * | * | * | * | | | * | * |

FIG 1Q
| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A56 | 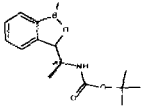 | * | * | * | * | * | * | * | | | * | * |
| A40 | 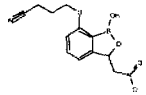 | * | * | * | * | ** | * | * | | |  |  |
| A57 | 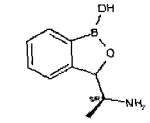 | * | * | * | * | * | * | * | | | * | * |

FIG 1R

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A19 | 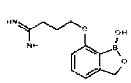 | * | * | * | * | ** | * | * | | | * | * |
| A51 | 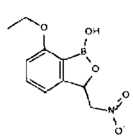 | * | * | * | * | ** | * | * | | | * | * |
| A6 | 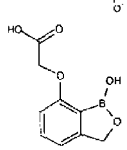 | * | * | * | * | * | * | * | | | * | *** |

FIG 1S

| Reg # | Structure | E. cloacae ATCC 13047 MIC | E. coli ECM 1194 MIC | E. coli ECM 1888 MIC | E. faecalis ATCC 29212 MIC | H. influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A24 | 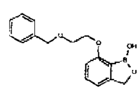 | | * | * | | * | | * | | | * | * |
| A28 | 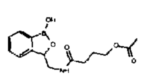 | * | * | * | * | * | * | * | | | * | * |
| A50 | 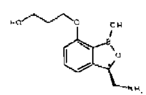 | * | * | * | * | * | * | * | * | * | * | ** |

FIG 1T

| Reg # | Structure | E. cloacae ATCC 13047 MIC | E. coli ECM 1194 MIC | E. coli ECM 1888 MIC | E. faecalis ATCC 29212 MIC | H. Influenzae ATCC 49766 MIC | K. pneumoniae ATCC 13883 MIC | P. aeruginosa ATCC 27853 MIC | P. aeruginosa PAO1 MIC | P. aeruginosa PAO1d3 MIC | S. aureus ATCC 29213 MIC | S. pneumoniae ATCC 6301 MIC |
|---|---|---|---|---|---|---|---|---|---|---|---|---|
| A45 | 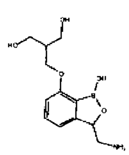 | * |  | * | * | * | * |  | * | * |  | * |

FIG 2A
| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| | 400< = #<br>400 - 100.1 = ##<br>100 - 5 = ###<br>5> = #### | | | |
| A49 | 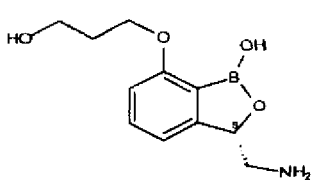 | #### | #### | |
| A41 | 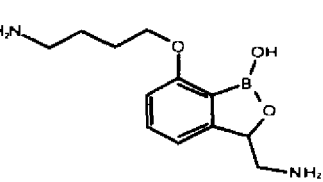 | #### | #### | #### |
| A46 | 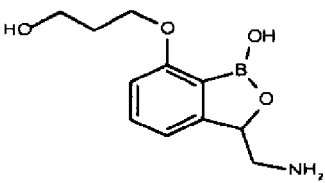 | #### | #### | #### |

FIG 2B

| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A44 | 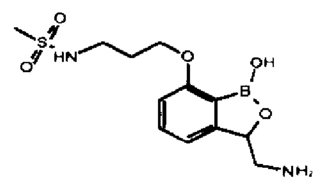 | #### | #### | #### |
| A36 | 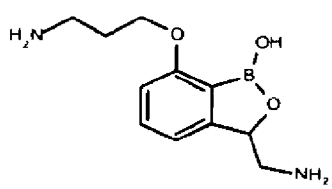 | #### | #### | #### |
| A42 | 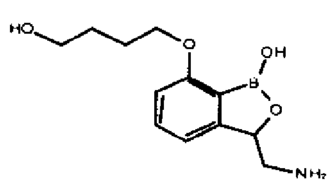 | #### | #### | ### |
| A11 | 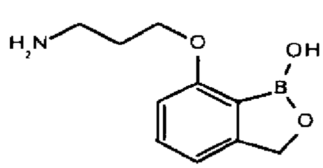 | #### | #### | ### |

FIG 2C

| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A52 | (structure) | #### | #### | #### |
| A17 | (structure) | #### | #### | ### |
| A19 | (structure) | #### | #### | ### |
| A45 | (structure) | #### | #### | #### |

FIG 2D

| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A23 | 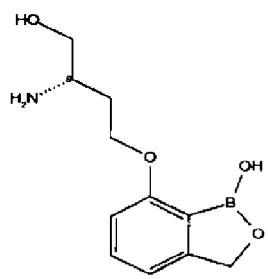 | #### | #### | #### |
| A39 | 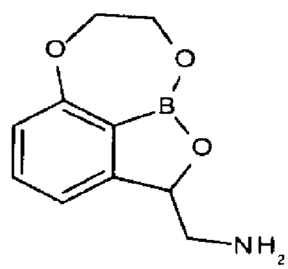 | #### | #### | #### |
| A13 | 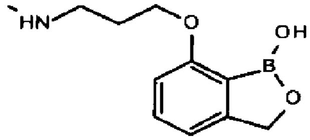 | #### | #### | ### |
| A2 | 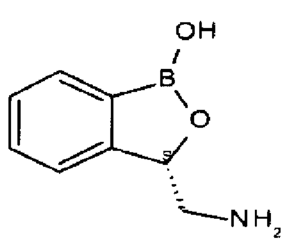 | #### | #### | #### |

FIG 2E

| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A12 | 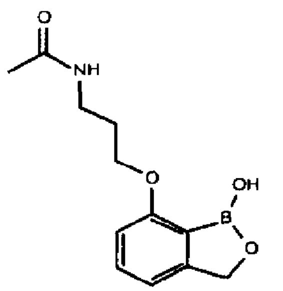 | #### | #### | ### |
| A43 | 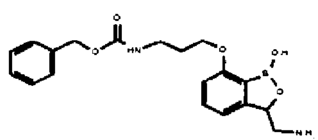 | #### | #### | #### |
| A38 | 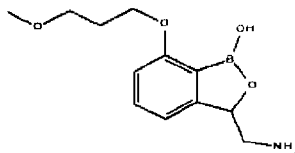 | #### | ### | ### |
| A14 | 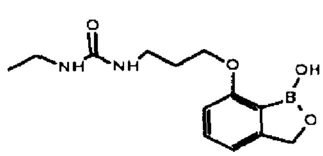 | #### | #### | |

FIG 2F

| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A15 | (structure) | #### | #### | ### |
| A53 | (structure) | #### | #### | #### |
| A1 | (structure) | #### | ### | #### |
| A33 | (structure) | #### | ### | ### |

FIG 2G

| Compound ID | Structure | Escherichia_coli_K12_LeuRS_wt IC50 | Pseudomonas_aeruginosa_PAO1 _LeuRS_wt IC50 | Staphylococcus_aureus_NCTC83 25_LeuRS_wt IC50 |
|---|---|---|---|---|
| A31 | 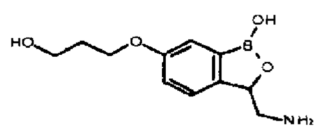 | #### | #### | #### |
| A3 | 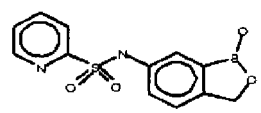 | #### | #### | ### |
| A32 | 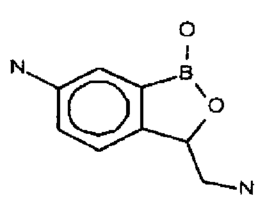 | #### | #### | #### |
| A30 | 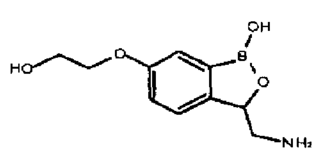 | #### | ### | #### |

FIG 2H
| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A34 | 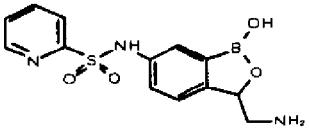 | #### | ### | ### |
| A22 | 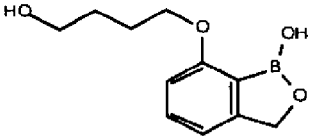 | #### | #### | # |
| A58 | 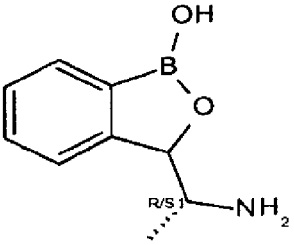 | ### | ### | # |
| A4 | 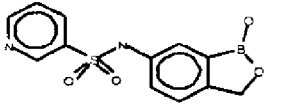 | ### | ### | ### |

FIG 2I
| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A54 | 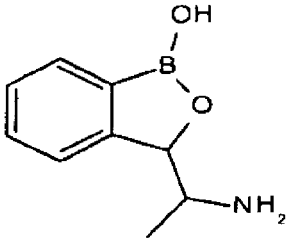 | ### | ### | # |
| A26 | 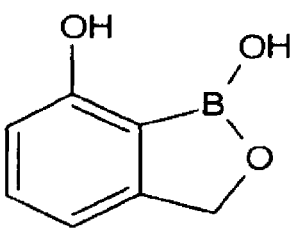 | ### | # | ### |
| A18 | 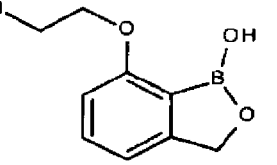 | ### | #### | # |
| A16 | 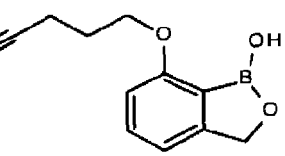 | ### | #### | # |

FIG 2J

| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A7 | 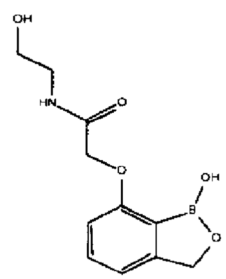 | ### | ### | # |
| A25 | 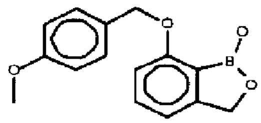 | ### | ### | # |
| A40 | 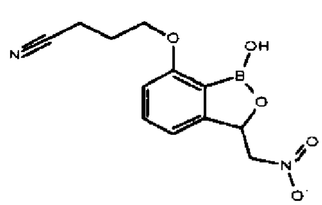 | ### | ## | # |
| A51 | 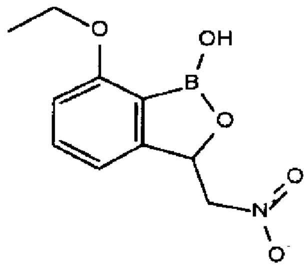 | ### | ## | # |

FIG 2K

| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A6 | 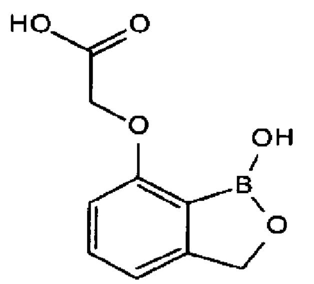 | ## | ### | |
| A56 | 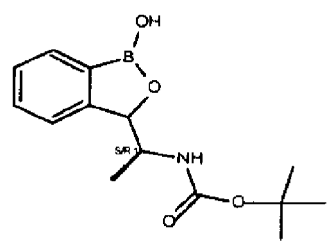 | ## | ## | # |
| A55 | 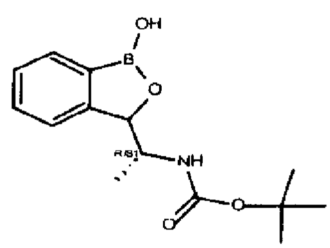 | ## | # | # |
| A59 | 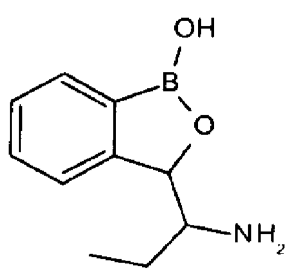 | # | # | # |

FIG 2L

| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A57 | 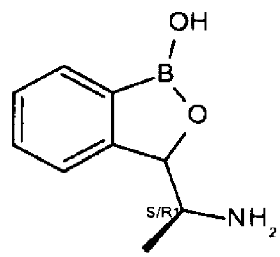 | # | ### | # |
| A21 | 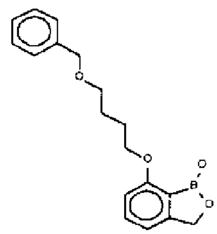 | # | # | # |
| A24 | 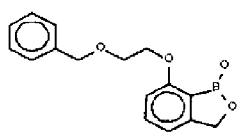 | # | # | # |
| A29 | 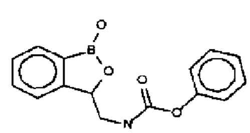 | # | # | # |

FIG 2M

| Compound ID | Structure | Escherichia_coli_K12_LeuRS_wt IC50 | Pseudomonas_aeruginosa_PAO1_LeuRS_wt IC50 | Staphylococcus_aureus_NCTC8325_LeuRS_wt IC50 |
|---|---|---|---|---|
| A27 | 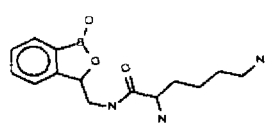 | # | # | # |

SEQUENCE LISTING

```
<160> NUMBER OF SEQ ID NOS: 24

<210> SEQ ID NO 1
<211> LENGTH: 85
<212> TYPE: DNA
<213> ORGANISM: Saccharomyces cerevisiae

<400> SEQUENCE: 1
gggagtttgg ccgagtggtt taaggcgtca gatttaggct ctgatatctt cggatgcaag      60
ggttcgaatc ccttagctct cacca                                            85

<210> SEQ ID NO 2
<211> LENGTH: 77
<212> TYPE: DNA
<213> ORGANISM: Saccharomyces cerevisiae

<400> SEQUENCE: 2
gaaactataa ttcaattggt tagaatagta ttttgataag gtacaaatat aggttcaatc      60
cctgttagtt tcatcca                                                     77

<210> SEQ ID NO 3
<211> LENGTH: 258
<212> TYPE: PRT
<213> ORGANISM: Artificial sequence
<220> FEATURE:
<223> OTHER INFORMATION: Polypeptide fragment corresponding to the
      editing domain of a tRNA synthetase molecule

<400> SEQUENCE: 3

Thr Pro Gln Glu Tyr Ile Gly Val Lys Ile Glu Ala Leu Glu Phe Ala
1               5                   10                  15

Asp Asp Ala Ala Lys Ile Ile Asp Ser Ser Ser Asp Leu Asp Lys Ser
            20                  25                  30

Lys Lys Phe Tyr Phe Val Ala Ala Thr Leu Arg Pro Glu Thr Met Tyr
        35                  40                  45

Gly Gln Thr Cys Cys Phe Val Ser Pro Thr Ile Glu Tyr Gly Ile Phe
```

```
            50                  55                  60
Asp Ala Gly Asp Ser Tyr Phe Ile Thr Thr Glu Arg Ala Phe Lys Asn
 65                  70                  75                  80

Met Ser Tyr Gln Lys Leu Thr Pro Lys Arg Gly Phe Tyr Lys Pro Ile
                 85                  90                  95

Val Thr Val Pro Gly Lys Ala Phe Ile Gly Thr Lys Ile His Ala Pro
             100                 105                 110

Gln Ser Val Tyr Pro Glu Leu Arg Ile Leu Pro Met Glu Thr Val Ile
             115                 120                 125

Ala Thr Lys Gly Thr Gly Val Val Thr Cys Val Pro Ser Asn Ser Pro
130                 135                 140

Asp Asp Tyr Ile Thr Thr Lys Asp Leu Leu His Lys Pro Glu Tyr Tyr
145                 150                 155                 160

Gly Ile Lys Pro Glu Trp Ile Asp His Glu Ile Val Pro Ile Met His
                165                 170                 175

Thr Glu Lys Tyr Gly Asp Leu Thr Ala Lys Ala Ile Val Glu Glu Lys
            180                 185                 190

Lys Ile Gln Ser Pro Lys Asp Lys Asn Leu Leu Ala Glu Ala Lys Lys
            195                 200                 205

Ile Ala Tyr Lys Glu Asp Tyr Tyr Thr Gly Thr Met Ile Tyr Gly Pro
        210                 215                 220

Tyr Lys Gly Glu Lys Val Glu Gln Ala Lys Asn Lys Val Lys Ala Asp
225                 230                 235                 240

Met Ile Ala Ala Gly Glu Ala Phe Val Tyr Asn Glu Pro Glu Ser Gln
                245                 250                 255

Asp Pro

<210> SEQ ID NO 4
<211> LENGTH: 280
<212> TYPE: PRT
<213> ORGANISM: Artificial sequence
<220> FEATURE:
<223> OTHER INFORMATION: Polypeptide fragment corresponding to the
      editing domain of a tRNA synthetase molecule

<400> SEQUENCE: 4

Met Thr Pro Gln Glu Tyr Ile Gly Val Lys Ile Glu Ala Leu Glu Phe
 1               5                  10                  15

Ala Asp Asp Ala Ala Lys Ile Ile Asp Ser Ser Ser Asp Leu Asp Lys
                 20                  25                  30

Ser Lys Lys Phe Tyr Phe Val Ala Ala Thr Leu Arg Pro Glu Thr Met
             35                  40                  45

Tyr Gly Gln Thr Cys Cys Phe Val Ser Pro Thr Ile Glu Tyr Gly Ile
         50                  55                  60

Phe Asp Ala Gly Asp Ser Tyr Phe Ile Thr Thr Glu Arg Ala Phe Lys
 65                  70                  75                  80

Asn Met Ser Tyr Gln Lys Leu Thr Pro Lys Arg Gly Phe Tyr Lys Pro
                 85                  90                  95

Ile Val Thr Val Pro Gly Lys Ala Phe Ile Gly Thr Lys Ile His Ala
            100                 105                 110

Pro Gln Ser Val Tyr Pro Glu Leu Arg Ile Leu Pro Met Glu Thr Val
            115                 120                 125

Ile Ala Thr Lys Gly Thr Gly Val Val Thr Cys Val Pro Ser Asn Ser
130                 135                 140

Pro Asp Asp Tyr Ile Thr Thr Lys Asp Leu Leu His Lys Pro Glu Tyr
```

```
                145                 150                 155                 160
Tyr Gly Ile Lys Pro Glu Trp Ile Asp His Glu Ile Val Pro Ile Met
                165                 170                 175

His Thr Glu Lys Tyr Gly Asp Leu Thr Ala Lys Ala Ile Val Glu Glu
                180                 185                 190

Lys Lys Ile Gln Ser Pro Lys Asp Lys Asn Leu Leu Ala Glu Ala Lys
                195                 200                 205

Lys Ile Ala Tyr Lys Glu Asp Tyr Tyr Thr Gly Thr Met Ile Tyr Gly
                210                 215                 220

Pro Tyr Lys Gly Glu Lys Val Glu Gln Ala Lys Asn Lys Val Lys Ala
225                 230                 235                 240

Asp Met Ile Ala Ala Gly Glu Ala Phe Val Tyr Asn Glu Pro Glu Ser
                245                 250                 255

Gln Asp Pro Gln Asp Pro Asn Ser Ser Ser Val Asp Lys Leu Ala Ala
                260                 265                 270

Ala Leu Glu His His His His His
                275                 280

<210> SEQ ID NO 5
<211> LENGTH: 303
<212> TYPE: PRT
<213> ORGANISM: Artificial sequence
<220> FEATURE:
<223> OTHER INFORMATION: Polypeptide fragment corresponding to the
      editing domain of a tRNA synthetase molecule

<400> SEQUENCE: 5

Thr Cys Thr Pro Glu Tyr Tyr Arg Trp Glu Gln Lys Phe Phe Thr Glu
1               5                   10                  15

Leu Tyr Lys Lys Gly Leu Val Tyr Lys Lys Thr Ser Ala Val Asn Trp
                20                  25                  30

Cys Pro Asn Asp Gln Thr Val Leu Ala Asn Glu Gln Val Ile Asp Gly
                35                  40                  45

Cys Cys Trp Arg Cys Asp Thr Lys Val Glu Arg Lys Glu Ile Pro Gln
        50                  55                  60

Trp Phe Ile Lys Ile Thr Ala Tyr Ala Asp Glu Leu Leu Asn Asp Leu
65                  70                  75                  80

Asp Lys Leu Asp His Trp Pro Asp Thr Val Lys Thr Met Gln Arg Asn
                85                  90                  95

Trp Ile Gly Arg Ser Glu Gly Val Glu Ile Thr Phe Asn Val Asn Asp
                100                 105                 110

Tyr Asp Asn Thr Leu Thr Val Tyr Thr Thr Arg Pro Asp Thr Phe Met
                115                 120                 125

Gly Cys Thr Tyr Leu Ala Val Ala Ala Gly His Pro Leu Ala Gln Lys
                130                 135                 140

Ala Ala Glu Asn Asn Pro Glu Leu Ala Ala Phe Ile Asp Glu Cys Arg
145                 150                 155                 160

Asn Thr Lys Val Ala Glu Ala Glu Met Ala Thr Met Glu Lys Lys Gly
                165                 170                 175

Val Asp Thr Gly Phe Lys Ala Val His Pro Leu Thr Gly Glu Glu Ile
                180                 185                 190

Pro Val Trp Ala Ala Asn Phe Val Leu Met Glu Tyr Gly Thr Gly Ala
                195                 200                 205

Val Met Ala Val Pro Gly His Asp Gln Arg Asp Tyr Glu Phe Ala Ser
        210                 215                 220
```

```
Lys Tyr Gly Leu Asn Ile Lys Pro Val Ile Leu Ala Ala Asp Gly Ser
225                 230                 235                 240

Glu Pro Asp Leu Ser Gln Gln Ala Leu Thr Glu Lys Gly Val Leu Phe
                245                 250                 255

Asn Ser Gly Glu Phe Asn Gly Leu Asp His Glu Ala Ala Phe Asn Ala
            260                 265                 270

Ile Ala Asp Lys Leu Thr Ala Met Gly Val Gly Glu Arg Lys Val Asn
        275                 280                 285

Tyr Arg Leu Arg Asp Trp Gly Val Ser Arg Gln Arg Tyr Trp Gly
290                 295                 300

<210> SEQ ID NO 6
<211> LENGTH: 308
<212> TYPE: PRT
<213> ORGANISM: Artificial sequence
<220> FEATURE:
<223> OTHER INFORMATION: Polypeptide fragment corresponding to the
      editing domain of a tRNA synthetase molecule

<400> SEQUENCE: 6

Thr Cys Lys Pro Asp Tyr Tyr Arg Trp Glu Gln Trp Leu Phe Thr Arg
1               5                   10                  15

Leu Phe Glu Lys Gly Val Ile Tyr Arg Lys Asn Gly Thr Val Asn Trp
                20                  25                  30

Asp Pro Ala Asp Gln Thr Val Leu Ala Asn Glu Gln Val Ile Asp Gly
            35                  40                  45

Arg Gly Trp Arg Ser Gly Ala Leu Ile Glu Lys Arg Glu Ile Pro Met
        50                  55                  60

Tyr Tyr Phe Arg Ile Thr Asp Tyr Ala Asp Glu Leu Leu Glu Ser Leu
65                  70                  75                  80

Asp Glu Leu Pro Gly Trp Pro Glu Gln Val Lys Thr Met Gln Arg Asn
                85                  90                  95

Trp Ile Gly Lys Ser Arg Gly Met Glu Val Gln Phe Pro Tyr Asp Gln
            100                 105                 110

Ala Ser Ile Gly His Glu Gly Thr Leu Lys Val Phe Thr Thr Arg Pro
        115                 120                 125

Asp Thr Leu Met Gly Ala Thr Tyr Val Ala Val Ala Ala Glu His Pro
130                 135                 140

Leu Ala Thr Gln Ala Ala Gln Gly Asn Ala Ala Leu Gln Ala Phe Ile
145                 150                 155                 160

Asp Glu Cys Lys Ser Gly Ser Val Ala Glu Ala Asp Met Ala Thr Gln
                165                 170                 175

Glu Lys Lys Gly Met Ala Thr Ser Leu Phe Val Glu His Pro Leu Thr
            180                 185                 190

Gly Glu Lys Leu Pro Val Trp Val Ala Asn Tyr Val Leu Met His Tyr
        195                 200                 205

Gly Asp Gly Ala Val Met Ala Val Pro Ala His Asp Glu Arg Asp Phe
210                 215                 220

Glu Phe Ala His Lys Tyr Asn Leu Pro Val Lys Ala Val Val Arg Thr
225                 230                 235                 240

Ser Ala Gly Asp Val Gly Ser Glu Trp Leu Ala Ala Tyr Gly Glu
                245                 250                 255

His Gly Gln Leu Ile Asn Ser Gly Glu Phe Asp Gly Leu Asp Phe Gln
            260                 265                 270

Gly Ala Phe Asp Ala Ile Glu Ala Ala Leu Ile Arg Lys Asp Leu Gly
        275                 280                 285
```

Lys Ser Arg Thr Gln Phe Arg Leu Arg Asp Trp Gly Ile Ser Arg Gln
            290                 295                 300

Arg Tyr Trp Gly
305

<210> SEQ ID NO 7
<211> LENGTH: 298
<212> TYPE: PRT
<213> ORGANISM: Artificial sequence
<220> FEATURE:
<223> OTHER INFORMATION: Polypeptide fragment corresponding to the
      editing domain of a tRNA synthetase molecule

<400> SEQUENCE: 7

Thr Thr Asp Pro Glu Tyr Tyr Lys Trp Thr Gln Trp Ile Phe Ile Gln
1               5                   10                  15

Leu Tyr Asn Lys Gly Leu Ala Tyr Val Asp Glu Val Ala Val Asn Trp
            20                  25                  30

Cys Pro Ala Leu Gly Thr Val Leu Ser Asn Glu Val Ile Asp Gly
        35                  40                  45

Val Ser Glu Arg Gly Gly His Pro Val Tyr Arg Lys Pro Met Lys Gln
50                  55                  60

Trp Val Leu Lys Ile Thr Glu Tyr Ala Asp Gln Leu Leu Ala Asp Leu
65                  70                  75                  80

Asp Asp Leu Asp Trp Pro Glu Ser Leu Lys Asp Met Gln Arg Asn Trp
                85                  90                  95

Ile Gly Arg Ser Glu Gly Ala Lys Val Ser Phe Asp Val Asp Asn Thr
            100                 105                 110

Glu Gly Lys Val Glu Val Phe Thr Thr Arg Pro Asp Thr Ile Tyr Gly
        115                 120                 125

Ala Ser Phe Leu Val Leu Ser Pro Glu His Ala Leu Val Asn Ser Ile
130                 135                 140

Thr Thr Asp Glu Tyr Lys Glu Lys Val Lys Ala Tyr Gln Thr Glu Ala
145                 150                 155                 160

Ser Lys Lys Ser Asp Leu Glu Arg Thr Asp Leu Ala Lys Asp Lys Ser
                165                 170                 175

Gly Val Phe Thr Gly Ala Tyr Ala Ile Asn Pro Leu Ser Gly Glu Lys
            180                 185                 190

Val Gln Ile Trp Ile Ala Asp Tyr Val Leu Ser Thr Tyr Gly Thr Gly
        195                 200                 205

Ala Ile Met Ala Val Pro Ala His Asp Arg Asp Tyr Glu Phe Ala
210                 215                 220

Lys Lys Phe Asp Leu Leu Ile Ile Glu Val Ile Glu Gly Gly Asn Val
225                 230                 235                 240

Glu Glu Ala Ala Tyr Thr Gly Glu Gly Lys His Ile Asn Ser Gly Glu
                245                 250                 255

Leu Asp Gly Leu Glu Asn Glu Ala Ala Ile Thr Lys Ala Ile Gln Leu
            260                 265                 270

Leu Glu Gln Lys Gly Ala Gly Glu Lys Lys Val Tyr Lys Leu Arg Asp
        275                 280                 285

Trp Leu Phe Ser Arg Gln Arg Tyr Trp Gly
        290                 295

<210> SEQ ID NO 8
<211> LENGTH: 192
<212> TYPE: PRT

-continued

<213> ORGANISM: Escherichia coli

<400> SEQUENCE: 8

Gly Arg Ser Glu Gly Val Glu Ile Thr Phe Asn Val Asn Asp Tyr Asp
1               5                   10                  15

Asn Thr Leu Thr Val Tyr Thr Thr Arg Pro Asp Thr Phe Met Gly Cys
            20                  25                  30

Thr Tyr Leu Ala Val Ala Ala Gly His Pro Leu Ala Gln Lys Ala Ala
        35                  40                  45

Glu Asn Asn Pro Glu Leu Ala Ala Phe Ile Asp Glu Cys Arg Asn Thr
    50                  55                  60

Lys Val Ala Glu Ala Glu Met Ala Thr Met Glu Lys Lys Gly Val Asp
65                  70                  75                  80

Thr Gly Phe Lys Ala Val His Pro Leu Thr Gly Glu Glu Ile Pro Val
                85                  90                  95

Trp Ala Ala Asn Phe Val Leu Met Glu Tyr Gly Thr Gly Ala Val Met
            100                 105                 110

Ala Val Pro Gly His Asp Gln Arg Asp Tyr Glu Phe Ala Ser Lys Tyr
        115                 120                 125

Gly Leu Asn Ile Lys Pro Val Ile Leu Ala Ala Asp Gly Ser Glu Pro
    130                 135                 140

Asp Leu Ser Gln Gln Ala Leu Thr Glu Lys Gly Val Leu Phe Asn Ser
145                 150                 155                 160

Gly Glu Phe Asn Gly Leu Asp His Glu Ala Ala Phe Asn Ala Ile Ala
                165                 170                 175

Asp Lys Leu Thr Ala Met Gly Val Gly Glu Arg Lys Val Asn Tyr Arg
            180                 185                 190

<210> SEQ ID NO 9
<211> LENGTH: 197
<212> TYPE: PRT
<213> ORGANISM: Pseudomonas aeruginosa

<400> SEQUENCE: 9

Gly Lys Ser Arg Gly Met Glu Val Gln Phe Pro Tyr Asp Gln Ala Ser
1               5                   10                  15

Ile Gly His Glu Gly Thr Leu Lys Val Phe Thr Thr Arg Pro Asp Thr
            20                  25                  30

Leu Met Gly Ala Thr Tyr Val Ala Val Ala Ala Glu His Pro Leu Ala
        35                  40                  45

Thr Gln Ala Ala Gln Gly Asn Ala Ala Leu Gln Ala Phe Ile Asp Glu
    50                  55                  60

Cys Lys Ser Gly Ser Val Ala Glu Ala Asp Met Ala Thr Gln Glu Lys
65                  70                  75                  80

Lys Gly Met Ala Thr Ser Leu Phe Val Glu His Pro Leu Thr Gly Glu
                85                  90                  95

Lys Leu Pro Val Trp Val Ala Asn Tyr Val Leu Met His Tyr Gly Asp
            100                 105                 110

Gly Ala Val Met Ala Val Pro Ala His Asp Glu Arg Asp Phe Glu Phe
        115                 120                 125

Ala His Lys Tyr Asn Leu Pro Val Lys Ala Val Arg Thr Ser Ala
    130                 135                 140

Gly Asp Asp Val Gly Ser Glu Trp Leu Ala Ala Tyr Gly Glu His Gly
145                 150                 155                 160

Gln Leu Ile Asn Ser Gly Glu Phe Asp Gly Leu Asp Phe Gln Gly Ala

```
                    165                 170                 175

Phe Asp Ala Ile Glu Ala Ala Leu Ile Arg Lys Asp Leu Gly Lys Ser
                180                 185                 190

Arg Thr Gln Phe Arg
        195

<210> SEQ ID NO 10
<211> LENGTH: 188
<212> TYPE: PRT
<213> ORGANISM: Staphylococcus aureus

<400> SEQUENCE: 10

Gly Arg Ser Glu Gly Ala Lys Val Ser Phe Asp Val Asp Asn Thr Glu
1               5                   10                  15

Gly Lys Val Glu Val Phe Thr Thr Arg Pro Asp Thr Ile Tyr Gly Ala
            20                  25                  30

Ser Phe Leu Val Leu Ser Pro Glu His Ala Leu Val Asn Ser Ile Thr
        35                  40                  45

Thr Asp Glu Tyr Lys Glu Lys Val Lys Ala Tyr Gln Thr Glu Ala Ser
    50                  55                  60

Lys Lys Ser Asp Leu Glu Arg Thr Asp Leu Ala Lys Lys Ser Gly
65                  70                  75                  80

Val Phe Thr Gly Ala Tyr Ala Ile Asn Pro Leu Ser Gly Glu Lys Val
                85                  90                  95

Gln Ile Trp Ile Ala Asp Tyr Val Leu Ser Thr Tyr Gly Thr Gly Ala
            100                 105                 110

Ile Met Ala Val Pro Ala His Asp Asp Arg Asp Tyr Glu Phe Ala Lys
        115                 120                 125

Lys Phe Asp Leu Leu Ile Ile Glu Val Ile Glu Gly Gly Asn Val Glu
    130                 135                 140

Glu Ala Ala Tyr Thr Gly Glu Gly Lys His Ile Asn Ser Gly Glu Leu
145                 150                 155                 160

Asp Gly Leu Glu Asn Glu Ala Ala Ile Thr Lys Ala Ile Gln Leu Leu
                165                 170                 175

Glu Gln Lys Gly Ala Gly Glu Lys Lys Val Tyr Lys
            180                 185

<210> SEQ ID NO 11
<211> LENGTH: 860
<212> TYPE: PRT
<213> ORGANISM: Escherichia coli

<400> SEQUENCE: 11

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Met Leu Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
```

-continued

```
            100                 105                 110
Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
        130                 135             140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
        210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
        290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
        370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
        435                 440                 445

Gln Leu Pro Val Ile Leu Pro Glu Asp Val Val Met Asp Gly Ile Thr
        450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Tyr Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Tyr Ile
        515                 520                 525
```

Gly Gly Ile Glu His Ala Ile Met His Leu Tyr Phe Arg Phe Phe
        530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
        595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
    755                 760                 765

Cys Phe Thr Leu Trp Gln Glu Leu Lys Gly Glu Gly Asp Ile Asp Asn
770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
    835                 840                 845

Tyr Val Pro Gly Lys Leu Leu Asn Leu Val Val Gly
850                 855                 860

<210> SEQ ID NO 12
<211> LENGTH: 868
<212> TYPE: PRT
<213> ORGANISM: Pseudomonas aeruginosa

<400> SEQUENCE: 12

Met His Glu Gln Tyr Thr Pro Arg Asp Val Glu Ala Ala Ala Gln Asn
1               5                   10                  15

Ala Trp Asp Glu Gln Gln Ser Phe Ala Val Thr Glu Gln Pro Gly Lys
            20                  25                  30

Glu Thr Tyr Tyr Cys Leu Ser Met Phe Pro Tyr Pro Ser Gly Lys Leu

```
                35                  40                  45
His Met Gly His Val Arg Asn Tyr Thr Ile Gly Asp Val Ile Ala Arg
             50                  55                  60

Tyr Gln Arg Met Leu Gly Lys Asn Val Leu Gln Pro Met Gly Trp Asp
 65                  70                  75                  80

Ala Phe Gly Met Pro Ala Glu Asn Ala Ala Met Lys Asn Asn Val Ala
                 85                  90                  95

Pro Ala Lys Trp Thr Tyr Glu Asn Ile Asp Tyr Met Lys Thr Gln Leu
                100                 105                 110

Lys Ser Leu Gly Leu Ala Ile Asp Trp Ser Arg Glu Val Thr Thr Cys
                115                 120                 125

Lys Pro Asp Tyr Tyr Arg Trp Glu Gln Trp Leu Phe Thr Arg Leu Phe
            130                 135                 140

Glu Lys Gly Val Ile Tyr Arg Lys Asn Gly Thr Val Asn Trp Asp Pro
145                 150                 155                 160

Ala Asp Gln Thr Val Leu Ala Asn Glu Gln Val Ile Asp Gly Arg Gly
                165                 170                 175

Trp Arg Ser Gly Ala Leu Ile Glu Lys Arg Glu Ile Pro Met Tyr Tyr
                180                 185                 190

Phe Arg Ile Thr Asp Tyr Ala Asp Glu Leu Leu Glu Ser Leu Asp Glu
            195                 200                 205

Leu Pro Gly Trp Pro Glu Gln Val Lys Thr Met Gln Arg Asn Trp Ile
210                 215                 220

Gly Lys Ser Arg Gly Met Glu Val Gln Phe Pro Tyr Asp Gln Ala Ser
225                 230                 235                 240

Ile Gly His Glu Gly Thr Leu Lys Val Phe Thr Thr Arg Pro Asp Thr
                245                 250                 255

Leu Met Gly Ala Thr Tyr Val Ala Val Ala Ala Glu His Pro Leu Ala
                260                 265                 270

Thr Gln Ala Ala Gln Gly Asn Ala Ala Leu Gln Ala Phe Ile Asp Glu
            275                 280                 285

Cys Lys Ser Gly Ser Val Ala Glu Ala Asp Met Ala Thr Gln Glu Lys
290                 295                 300

Lys Gly Met Ala Thr Ser Leu Phe Val Glu His Pro Leu Thr Gly Glu
305                 310                 315                 320

Lys Leu Pro Val Trp Val Ala Asn Tyr Val Leu Met His Tyr Gly Asp
                325                 330                 335

Gly Ala Val Met Ala Val Pro Ala His Asp Glu Arg Asp Phe Glu Phe
                340                 345                 350

Ala His Lys Tyr Asn Leu Pro Val Lys Ala Val Val Arg Thr Ser Ala
            355                 360                 365

Gly Asp Asp Val Gly Ser Glu Trp Leu Ala Ala Tyr Gly Glu His Gly
            370                 375                 380

Gln Leu Ile Asn Ser Gly Glu Phe Asp Gly Leu Asp Phe Gln Gly Ala
385                 390                 395                 400

Phe Asp Ala Ile Glu Ala Ala Leu Ile Arg Lys Asp Leu Gly Lys Ser
                405                 410                 415

Arg Thr Gln Phe Arg Leu Arg Asp Trp Gly Ile Ser Arg Gln Arg Tyr
                420                 425                 430

Trp Gly Cys Pro Ile Pro Ile Ile His Cys Pro Ser Cys Gly Asp Val
            435                 440                 445

Pro Val Pro Glu Asp Gln Leu Pro Val Thr Leu Pro Glu Asn Val Val
            450                 455                 460
```

```
Pro Asp Gly Ala Gly Ser Pro Leu Ala Arg Met Pro Glu Phe Tyr Glu
465                 470                 475                 480

Cys Thr Cys Pro Lys Cys Gly Thr Ala Ala Lys Arg Glu Thr Asp Thr
            485                 490                 495

Met Asp Thr Phe Val Glu Ser Ser Trp Tyr Phe Ala Arg Tyr Ala Ser
        500                 505                 510

Pro Asn Tyr Asp Lys Gly Leu Val Asp Pro Lys Ala Ala Asn His Trp
    515                 520                 525

Leu Pro Val Asp Gln Tyr Ile Gly Ile Glu His Ala Ile Leu His
530                 535                 540

Leu Leu Tyr Ala Arg Phe His Lys Leu Met Arg Asp Glu Gly Leu
545                 550                 555                 560

Val Thr Ser Asn Glu Pro Phe Lys Asn Leu Leu Thr Gln Gly Met Val
            565                 570                 575

Val Ala Glu Thr Tyr Tyr Arg Val Ala Ser Asn Gly Gly Lys Asp Trp
        580                 585                 590

Phe Asn Pro Ala Asp Val Glu Ile Glu Arg Asp Ala Lys Ala Lys Ile
    595                 600                 605

Ile Gly Ala Arg Leu Lys Thr Asp Gly Leu Pro Val Glu Ile Gly Gly
610                 615                 620

Thr Glu Lys Met Ser Lys Ser Lys Asn Asn Gly Val Asp Pro Gln Ser
625                 630                 635                 640

Met Ile Glu Gln Tyr Gly Ala Asp Thr Cys Arg Leu Phe Met Met Phe
            645                 650                 655

Ala Ser Pro Pro Asp Met Ser Leu Glu Trp Ser Asp Ser Gly Val Glu
            660                 665                 670

Gly Ala Ser Arg Phe Leu Arg Arg Val Trp Arg Leu Ala Gln Ala His
        675                 680                 685

Val Ala Gln Gly Leu Pro Gly Gln Leu Asp Ile Ala Ala Leu Ser Asp
    690                 695                 700

Glu Gln Lys Val Ile Arg Arg Ala Ile His Ala Ala Ile Lys Gln Ala
705                 710                 715                 720

Ser Thr Asp Val Gly Gln Phe His Lys Phe Asn Thr Ala Ile Ala Gln
            725                 730                 735

Val Met Thr Val Met Asn Val Leu Glu Lys Ala Pro Gln Val Thr Ala
        740                 745                 750

Gln Asp Arg Ala Leu Leu Gln Glu Gly Leu Glu Ala Val Thr Leu Leu
    755                 760                 765

Leu Ala Pro Ile Thr Pro His Ile Ser His Glu Leu Trp Lys Gln Leu
770                 775                 780

Gly His Glu Gln Ala Val Ile Asp Ala Thr Trp Pro Ser Val Asp Glu
785                 790                 795                 800

Ser Ala Leu Val Gln Asp Thr Val Thr Leu Val Val Gln Val Asn Gly
            805                 810                 815

Lys Leu Arg Gly Gln Val Glu Met Pro Ala Ala Ala Ser Arg Glu Glu
        820                 825                 830

Ile Glu Ala Ala Ala Arg Asn Asn Glu Asn Val Leu Arg Phe Thr Asp
    835                 840                 845

Gly Leu Thr Ile Arg Lys Val Ile Val Pro Gly Lys Leu Val Asn
850                 855                 860

Ile Val Ala Asn
865
```

```
<210> SEQ ID NO 13
<211> LENGTH: 804
<212> TYPE: PRT
<213> ORGANISM: Staphylococcus aureus

<400> SEQUENCE: 13

Met Asn Tyr Asn His Asn Gln Ile Glu Lys Lys Trp Gln Asp Tyr Trp
1               5                   10                  15

Asp Glu Asn Lys Thr Phe Lys Thr Asn Asp Asn Leu Gly Gln Lys Lys
            20                  25                  30

Phe Tyr Ala Leu Asp Met Phe Pro Tyr Pro Ser Gly Ala Gly Leu His
        35                  40                  45

Val Gly His Pro Glu Gly Tyr Thr Ala Thr Asp Ile Ile Ser Arg Tyr
    50                  55                  60

Lys Arg Met Gln Gly Tyr Asn Val Leu His Pro Met Gly Trp Asp Ala
65                  70                  75                  80

Phe Gly Leu Pro Ala Glu Gln Tyr Ala Leu Asp Thr Gly Asn Asp Pro
                85                  90                  95

Arg Glu Phe Thr Lys Lys Asn Ile Gln Thr Phe Lys Arg Gln Ile Lys
            100                 105                 110

Glu Leu Gly Phe Ser Tyr Asp Trp Asp Arg Glu Val Asn Thr Thr Asp
        115                 120                 125

Pro Glu Tyr Tyr Lys Trp Thr Gln Trp Ile Phe Ile Gln Leu Tyr Asn
    130                 135                 140

Lys Gly Leu Ala Tyr Val Asp Glu Val Ala Val Asn Trp Cys Pro Ala
145                 150                 155                 160

Leu Gly Thr Val Leu Ser Asn Glu Glu Val Ile Asp Gly Val Ser Glu
                165                 170                 175

Arg Gly Gly His Pro Val Tyr Arg Lys Pro Met Lys Gln Trp Val Leu
            180                 185                 190

Lys Ile Thr Glu Tyr Ala Asp Gln Leu Leu Ala Asp Leu Asp Asp Leu
        195                 200                 205

Asp Trp Pro Glu Ser Leu Lys Asp Met Gln Arg Asn Trp Ile Gly Arg
    210                 215                 220

Ser Glu Gly Ala Lys Val Ser Phe Asp Val Asp Asn Thr Glu Gly Lys
225                 230                 235                 240

Val Glu Val Phe Thr Thr Arg Pro Asp Thr Ile Tyr Gly Ala Ser Phe
                245                 250                 255

Leu Val Leu Ser Pro Glu His Ala Leu Val Asn Ser Ile Thr Thr Asp
            260                 265                 270

Glu Tyr Lys Glu Lys Val Lys Ala Tyr Gln Thr Glu Ala Ser Lys Lys
        275                 280                 285

Ser Asp Leu Glu Arg Thr Asp Leu Ala Lys Asp Lys Ser Gly Val Phe
    290                 295                 300

Thr Gly Ala Tyr Ala Ile Asn Pro Leu Ser Gly Glu Lys Val Gln Ile
305                 310                 315                 320

Trp Ile Ala Asp Tyr Val Leu Ser Thr Tyr Gly Thr Gly Ala Ile Met
                325                 330                 335

Ala Val Pro Ala His Asp Asp Arg Asp Tyr Glu Phe Ala Lys Lys Phe
            340                 345                 350

Asp Leu Leu Ile Ile Glu Val Ile Glu Gly Gly Asn Val Glu Glu Ala
        355                 360                 365

Ala Tyr Thr Gly Glu Gly Lys His Ile Asn Ser Gly Glu Leu Asp Gly
    370                 375                 380
```

```
Leu Glu Asn Glu Ala Ala Ile Thr Lys Ala Ile Gln Leu Leu Glu Gln
385                 390                 395                 400

Lys Gly Ala Gly Glu Lys Lys Val Asn Tyr Lys Leu Arg Asp Trp Leu
            405                 410                 415

Phe Ser Arg Gln Arg Tyr Trp Gly Glu Pro Ile Pro Val Ile His Trp
        420                 425                 430

Glu Asp Gly Thr Met Thr Thr Val Pro Glu Glu Leu Pro Leu Leu
            435                 440                 445

Leu Pro Glu Thr Asp Glu Ile Lys Pro Ser Gly Thr Gly Glu Ser Pro
450                 455                 460

Leu Ala Asn Ile Asp Ser Phe Val Asn Val Asp Glu Lys Thr Gly
465                 470                 475                 480

Met Lys Gly Arg Arg Glu Thr Asn Thr Met Pro Gln Trp Ala Gly Ser
                485                 490                 495

Cys Trp Tyr Tyr Leu Arg Tyr Ile Asp Pro Lys Asn Glu Asn Met Leu
            500                 505                 510

Ala Asp Pro Glu Lys Leu Lys His Trp Leu Pro Val Asp Leu Tyr Ile
            515                 520                 525

Gly Gly Val Glu His Ala Val Leu His Leu Leu Tyr Ala Arg Phe Trp
530                 535                 540

His Lys Val Leu Tyr Asp Leu Gly Ile Val Pro Thr Lys Glu Pro Phe
545                 550                 555                 560

Gln Lys Leu Phe Asn Gln Gly Met Ile Leu Gly Gly Asn Glu Lys
            565                 570                 575

Met Ser Lys Ser Lys Gly Asn Val Ile Asn Pro Asp Asp Ile Val Gln
            580                 585                 590

Ser His Gly Ala Asp Thr Leu Arg Leu Tyr Glu Met Phe Met Gly Pro
            595                 600                 605

Leu Asp Ala Ala Ile Ala Trp Ser Glu Lys Gly Leu Asp Gly Ser Arg
610                 615                 620

Arg Phe Leu Asp Arg Val Trp Arg Leu Ile Val Asn Glu Asp Gly Thr
625                 630                 635                 640

Leu Ser Ser Lys Ile Val Thr Thr Asn Lys Ser Leu Asp Lys Val
            645                 650                 655

Tyr Asn Gln Thr Val Lys Lys Val Thr Asp Asp Phe Glu Thr Leu Gly
            660                 665                 670

Phe Asn Thr Ala Ile Ser Gln Leu Met Val Phe Ile Asn Glu Cys Tyr
            675                 680                 685

Lys Val Asp Glu Val Tyr Lys Pro Tyr Ile Glu Gly Phe Val Lys Met
            690                 695                 700

Leu Ala Pro Ile Ala Pro His Ile Gly Glu Glu Leu Trp Ser Lys Leu
705                 710                 715                 720

Gly His Glu Glu Ser Ile Thr Tyr Gln Pro Trp Pro Thr Tyr Asp Glu
                725                 730                 735

Ala Leu Leu Val Asp Asp Glu Val Glu Ile Val Val Gln Val Asn Gly
            740                 745                 750

Lys Leu Arg Ala Lys Ile Lys Ile Ala Lys Asp Thr Ser Lys Glu Glu
            755                 760                 765

Met Gln Glu Ile Ala Leu Ser Asn Asp Asn Val Lys Ala Ser Ile Glu
            770                 775                 780

Gly Lys Asp Ile Met Lys Val Ile Ala Val Pro Gln Lys Leu Val Asn
785                 790                 795                 800
```

Ile Val Ala Lys

<210> SEQ ID NO 14
<211> LENGTH: 87
<212> TYPE: DNA
<213> ORGANISM: Escherichia coli

<400> SEQUENCE: 14
gcgaaggtgg cggaattggt agacgcgcta gcttcaggtg ttagtgtcct tacggacgtg    60
ggggttcaag tcccccccct cgcacca                                        87

<210> SEQ ID NO 15
<211> LENGTH: 85
<212> TYPE: DNA
<213> ORGANISM: Escherichia coli

<400> SEQUENCE: 15
gcgggagtgg cgaaattggt agacgcacca gatttaggtt ctggcgccgc aaggtgtgcg    60
agttcaagtc tcgcctcccg cacca                                          85

<210> SEQ ID NO 16
<211> LENGTH: 85
<212> TYPE: DNA
<213> ORGANISM: Escherichia coli

<400> SEQUENCE: 16
gccgaagtgg cgaaatcggt agacgcagtt gattcaaaat caaccgtaga aatacgtgcc    60
ggttcgagtc cggccttcgg cacca                                          85

<210> SEQ ID NO 17
<211> LENGTH: 87
<212> TYPE: DNA
<213> ORGANISM: Escherichia coli

<400> SEQUENCE: 17
gccgaggtgg tggaattggt agacacgcta ccttgaggtg gtagtgccca atagggctta    60
cgggttcaag tcccgtcctc ggtacca                                        87

<210> SEQ ID NO 18
<211> LENGTH: 87
<212> TYPE: DNA
<213> ORGANISM: Escherichia coli

<400> SEQUENCE: 18
gcccggatgg tggaatcggt agacacaagg gatttaaaat ccctcggcgt tcgcgctgtg    60
cgggttcaag tcccgctccg ggtacca                                        87

<210> SEQ ID NO 19
<211> LENGTH: 87
<212> TYPE: DNA
<213> ORGANISM: Escherichia coli
<220> FEATURE:
<221> NAME/KEY: modified_base
<222> LOCATION: (8)..(8)
<223> OTHER INFORMATION: s4u
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (35)..(35)
<223> OTHER INFORMATION: unidentified derivative of adenosine
<220> FEATURE:
<221> NAME/KEY: modified_base
<222> LOCATION: (38)..(38)
<223> OTHER INFORMATION: ms2i6a

<400> SEQUENCE: 19
gcccggaugg uggaadcggd agacacaagg gayuaaaaay cccucggcgu ucgcgcugug      60
cgggtycaag ucccgcuccg gguacca      87

<210> SEQ ID NO 20
<211> LENGTH: 87
<212> TYPE: DNA
<213> ORGANISM: Escherichia coli
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (38)..(38)
<223> OTHER INFORMATION: unidentified guanosine derivative

<400> SEQUENCE: 20
gcgaaggugg cggaaddggd agacgcgcua gcuucaggyg yuaguguccu uacggacgug      60
ggggtycaag uccccccccu cgcacca      87

<210> SEQ ID NO 21
<211> LENGTH: 87
<212> TYPE: DNA
<213> ORGANISM: Escherichia coli
<220> FEATURE:
<221> NAME/KEY: modified_base
<222> LOCATION: (18)..(18)
<223> OTHER INFORMATION: gm
<220> FEATURE:
<221> NAME/KEY: modified_base
<222> LOCATION: (38)..(38)
<223> OTHER INFORMATION: unidentified guanosine derivative

<400> SEQUENCE: 21
gccgaggugg uggaaddggd agacacgcua ccuugaggyg guagugccca auagggcuua      60
cgggtycaag ucccguccuc gguacca      87

<210> SEQ ID NO 22
<211> LENGTH: 85
<212> TYPE: DNA
<213> ORGANISM: Pseudomonas aeruginosa

<400> SEQUENCE: 22
gcggacgtgg tggaattggt agacacactg gatttaggtt ccagcgccgc aaggcgtgag      60
agttcgagtc tctccgtccg cacca      85

<210> SEQ ID NO 23
<211> LENGTH: 89
<212> TYPE: DNA
<213> ORGANISM: Staphylococcus aureus

<400> SEQUENCE: 23
gccggggtgg cggaactggc agacgcacag gacttaaaat cctgcggtga gagatcaccg      60
taccggttcg attccggtcc tcggcacca      89

<210> SEQ ID NO 24
<211> LENGTH: 89
<212> TYPE: DNA

```
<213> ORGANISM: Staphylococcus aureus

<400> SEQUENCE: 24
gccggggtgg cggaactggc agacgcacag gacttaaaat cctgcggtga gtgatcaccg      60
taccggttcg attccggtcc tcggcacca                                        89
```

BORON CONTAINING SMALL MOLECULES

CROSS-REFERENCE TO RELATED APPLICATIONS

This application is a continuation of U.S. patent application Ser. No. 12/142,692; filed on Jun. 19, 2008 which claims the benefit of U.S. Provisional Pat. App. No. 60/945,294, filed Jun. 20, 2007, and U.S. Provisional Pat. App. No. 61/041,178, filed Mar. 31, 2008, each of which is incorporated by reference in its entirety for all purposes.

BACKGROUND OF THE INVENTION

The global rise of bacteria and other microorganisms resistant to antibiotics and antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antibiotics, useful in combating microorganisms, especially those with multidrug-resistance.

Boron-containing molecules, such as oxaboroles, useful as antimicrobials have been described previously, such as in U.S. Pat. Pubs. US20060234981 and US20070155699. Generally speaking, an oxaborole has the following structure and substituent numbering system:

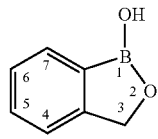

It has been discovered that certain classes of oxaboroles which are monosubstituted at the 3-, 6-, or 7-position, or disubstituted at the 3-/6- or 3-/7-positions are surprisingly effective antibacterials. This, and other uses of these oxaboroles are described herein.

SUMMARY OF THE INVENTION

This invention provides, among other things, novel compounds useful for treating bacterial infections, pharmaceutical compositions containing such compounds, as well as combinations of these compounds with at least one additional therapeutically effective agent.

BRIEF DESCRIPTION OF THE DRAWINGS

FIG. 1 displays MIC data for representative compounds of the invention.

FIG. 2 displays IC50 data for representative compounds of the invention.

DETAILED DESCRIPTION OF THE INVENTION

I. Definitions and Abbreviations

The abbreviations used herein generally have their conventional meaning within the chemical and biological arts.

The following abbreviations have been used: aq.-aqueous; HATU-O-(7-azabenzotriazol-1-yl)-N,N,N',N'-tetramethyluronium exafluorophosphate; EDCI-N-(3-dimethylaminopropyl)-N'-ethylcarbodiimide hydrochloride; m-CPBA-3-chloroperoxybenzoic acid; equiv-equivalent; DIAD-diisopropyl azodicarboxylate; DMF-N,N-dimethylformamide; DMSO-dimethylsulfoxide; AcOH-acetic acid; NaCNBH$_3$-sodium cyanoborohydride; Rt-room temperature; THF-tetrahydrofuran; Boc$_2$O-di-tert-butyl dicarbonate; MeOH-methanol; EtOH-ethanol; TFA-trifluoroacetic acid; DIPEA-N,N-diisopropylethylamine; PrOH-1-propanol; i-PrOH-2-propanol; mp-melting point; NMM-N-methylmorpholine; B$_2$pin$_2$-bis(pinacolato)diboron; O/N-overnight; BzOOH-benzoyl peroxide; THP-tetrahydropyranyl; Ac-acetyl; PTSA-para-toluene sulfonic acid; Pyr.-Pyridine; Cbz-benzyloxycarbonyl; MPM-p-methoxybenzyl; DHP-dihydropyran; CSA-camphor sulfonic acid; CTAB-cetyltrimethylammonium bromide; sat.-saturated; Cy-cyclohexyl.

"Compound of the invention," as used herein refers to the compounds discussed herein, salts (e.g. pharmaceutically acceptable salts), prodrugs, solvates and hydrates of these compounds.

MIC, or minimum inhibitory concentration, is the point where the compound stops more than 50% of cell growth, preferably 60% of cell growth, preferably 70% of cell growth, preferably 80% of cell growth, preferably 90% of cell growth, relative to an untreated control.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "poly" as used herein means at least 2. For example, a polyvalent metal ion is a metal ion having a valency of at least 2.

"Moiety" refers to a radical of a molecule that is attached to the remainder of the molecule.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, dioxaborolane, dioxaborinane and dioxaborepane. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes those radicals in which an aryl group is attached through the next moiety to the rest of the molecule. Thus, the term "arylalkyl" is meant to include those radicals in which an aryl group is attached to an alkyl group (e.g., benzyl, 1-(3-nitrophenyl)ethyl and the like). A substituent such as benzyl or 1-(3-nitrophenyl)ethyl can also be represented by 'substituted alkyl' wherein the ethyl radical is substituted with a 3-nitrophenyl moiety. The term "aryloxy" is meant to include those radicals in which an aryl group is attached to an oxygen atom. The term "aryloxyalkyl" is meant to include those radicals in which an aryl group is attached to an oxygen atom which is then attached to an alkyl group (e.g., phenoxymethyl, 3-(1-naphthyloxy)propyl, and the like).

For brevity, the term "heteroaryl" when used in combination with other terms (e.g., heteroaryloxy, heteroarylthioxy, heteroarylalkyl) includes those radicals in which a heteroaryl group is attached through the next moiety to the rest of the molecule. Thus, the term "heteroarylalkyl" is meant to include those radicals in which a heteroaryl group is attached to an alkyl group (e.g., pyridylmethyl and the like). The term "heteroaryloxy" is meant to include those radicals in which a heteroaryl group is attached to an oxygen atom. The term "heteroaryloxyalkyl" is meant to include those radicals in which an aryl group is attached to an oxygen atom which is then attached to an alkyl group. (e.g., 2-pyridyloxymethyl and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —N$_3$, —CH(Ph)$_2$, fluoro($C_1$-$C_4$)alkoxy, and fluoro($C_1$-$C_4$)alkyl, in a number ranging from zero to (2m'+1), where m' is the total number of carbon atoms in such radical. R', R", R'", R"" and R""" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""-C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The term "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

The term "derived from" includes its plain language meaning and also refers to a molecule that is 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, or 60% homologous to a referenced molecule. The molecules referred to in this definition include chains of RNA or DNA, oligonucleotides, polypeptides, or proteins of any length and composition.

The term "noncognate" is meant to encompass both the singular and plural forms of the word, i.e. the phrase "non-cognate amino acid" comprises one or more amino acids.

By "effective" amount of a drug, formulation, or permeant is meant a sufficient amount of a active agent to provide the desired local or systemic effect. A "Topically effective," "Cosmetically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

"Cosmetically effective" refers to a material that, when applied to the skin, nail, hair, claw or hoof, produces a desired cosmetic result locally at the place of application of an active ingredient in the material.

The term "pharmaceutically acceptable salts" is meant to include salts of the compounds of the invention which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds or complexes described herein readily undergo chemical changes under physiological conditions to provide the compounds of the present invention. Additionally, prodrugs can be converted to the compounds of the present invention by chemical or biochemical methods in an ex vivo environment.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

"Pharmaceutically acceptable topical carrier" and equivalent terms refer to pharmaceutically acceptable carriers, as described herein above, suitable for topical application. An inactive liquid or cream vehicle capable of suspending or dissolving the active agent(s), and having the properties of being nontoxic and non-inflammatory when applied to the skin, nail, hair, claw or hoof is an example of a pharmaceutically-acceptable topical carrier. This term is specifically intended to encompass carrier materials approved for use in topical cosmetics as well.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The terms "enhancement," "penetration enhancement" or "permeation enhancement" relate to an increase in the permeability of the skin, nail, hair, claw or hoof to a drug, so as to increase the rate at which the drug permeates through the skin, nail, hair, claw or hoof. The enhanced permeation effected through the use of such enhancers can be observed, for example, by measuring the rate of diffusion of the drug through animal skin, nail, hair, claw or hoof using a diffusion cell apparatus. A diffusion cell is described by Merritt et al. Diffusion Apparatus for Skin Penetration, J of Controlled Release, 1 (1984) pp. 161-162. The term "permeation enhancer" or "penetration enhancer" intends an agent or a mixture of agents, which, alone or in combination, act to increase the permeability of the skin, nail, hair or hoof to a drug.

The term "excipients" is conventionally known to mean carriers, diluents and/or vehicles used in formulating drug compositions effective for the desired use.

The term "topical administration" refers to the application of a pharmaceutical agent to the external surface of the skin, nail, hair, claw or hoof, such that the agent crosses the external surface of the skin, nail, hair, claw or hoof and enters the underlying tissues. Topical administration includes application of the composition to intact skin, nail, hair, claw or hoof, or to a broken, raw or open wound of skin, nail, hair, claw or hoof. Topical administration of a pharmaceutical agent can result in a limited distribution of the agent to the skin and surrounding tissues or, when the agent is removed from the treatment area by the bloodstream, can result in systemic distribution of the agent.

The term "transdermal delivery" refers to the diffusion of an agent across the barrier of the skin, nail, hair, claw or hoof resulting from topical administration or other application of a composition. The stratum corneum acts as a barrier and few pharmaceutical agents are able to penetrate intact skin. In contrast, the epidermis and dermis are permeable to many solutes and absorption of drugs therefore occurs more readily through skin, nail, hair, claw or hoof that is abraded or otherwise stripped of the stratum corneum to expose the epidermis. Transdermal delivery includes injection or other delivery through any portion of the skin, nail, hair, claw or hoof or mucous membrane and absorption or permeation through the remaining portion. Absorption through intact skin, nail, hair, claw or hoof can be enhanced by placing the active agent in an appropriate pharmaceutically acceptable vehicle before application to the skin, nail, hair, claw or hoof. Passive topical administration may consist of applying the active agent directly to the treatment site in combination with emollients or penetration enhancers. As used herein, transdermal delivery is intended to include delivery by permeation through or past the integument, i.e. skin, nail, hair, claw or hoof.

The term "microbial infection" or "infection by a microorganism" refers to any infection of a host tissue by an infectious agent including, but not limited to, viruses, bacteria, mycobacteria, fungus and parasites (see, e.g., Harrison's Principles of Internal Medicine, pp. 93-98 (Wilson et al., eds., 12th ed. 1991); Williams et al., J. of Medicinal Chem. 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of enzyme. In an exemplary embodiment, the enzyme is an editing domain of a tRNA synthetase.

A "human nail unit", as defined herein, can be the nail plate, the nail bed, proximal nail fold, lateral nail fold and combinations thereof.

Boron is able to form dative bonds with oxygen or nitrogen under some circumstances in this invention. Dative bonds are usually weaker than covalent bonds. In situations where a boron is covalently bonded to at least one oxygen or nitrogen, and is at the same time datively bonded to an oxygen or nitrogen, respectively, the dative bond and covalent bond between the boron and the two identical heteroatoms can interconvert or be in the form of a resonance hybrid. There is potential uncertainty surrounding the exact nature and extent of electron sharing in these situations. The structures supplied are not intended to include any and all possible bonding scenarios between boron and the atom to which it is bound. Non limiting examples of these bonds are as follows:

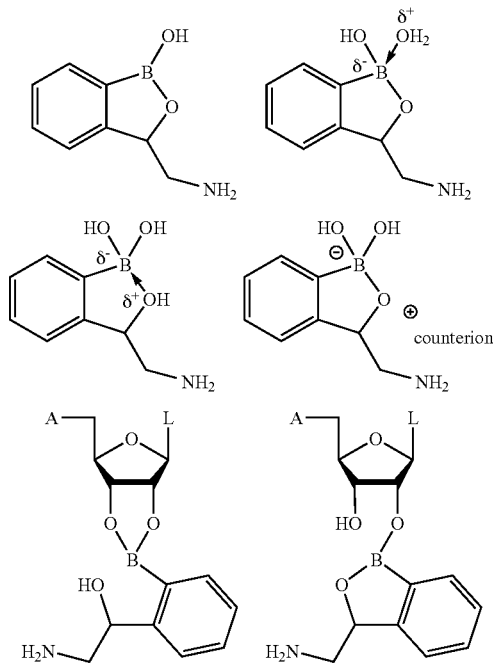

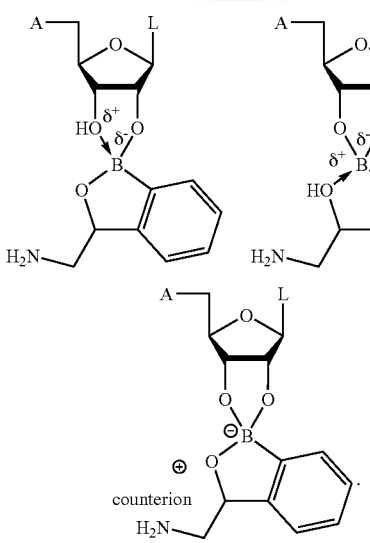

The compounds comprising a boron bonded to a carbon and three heteroatoms (such as three oxygens described in this section) can optionally contain a fully negatively charged boron or partially negatively charged boron, due to the nature of the dative bond between the boron and one of the oxygens. Due to the negative charge, a positively charged counterion may associate with this compound, thus forming a salt. Examples of positively charged counterions include $H^+$, $H_3O^+$, calcium, sodium, ammonium, potassium. The salts of these compounds are implicitly contained in descriptions of these compounds.

The present invention also encompasses compounds that are poly- or multi-valent species, including, for example, species such as dimers, trimers, tetramers and higher homologs of the compounds of use in the invention or reactive analogues thereof. For example, dimers of (A1) can form under the following conditions:

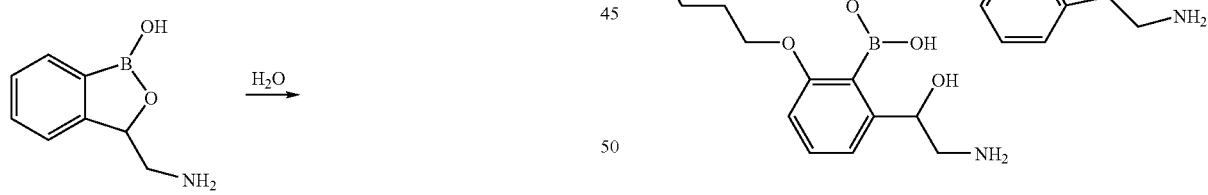

In another example, dimers of (A46) can form under the following conditions:

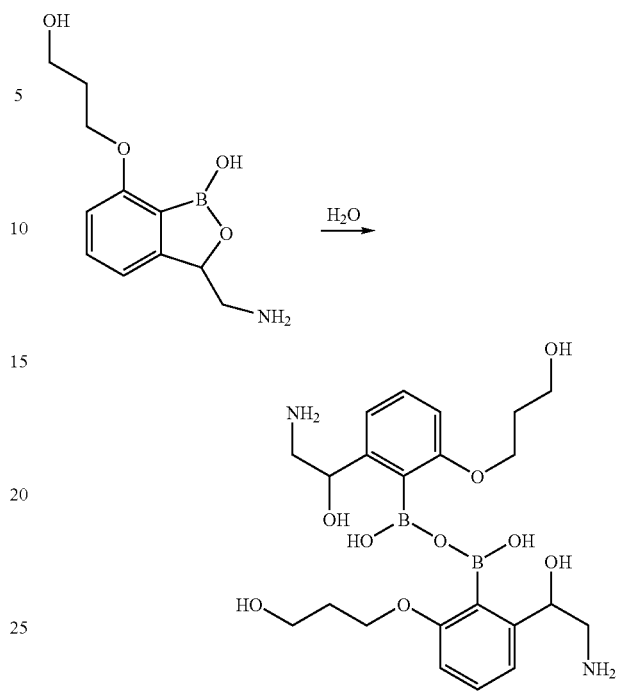

The present invention also encompasses compounds that are anhydrides of the cyclic boronic esters are synthesized by subjecting these compounds to dehydrating conditions. Examples of these anhydrides are provided below:

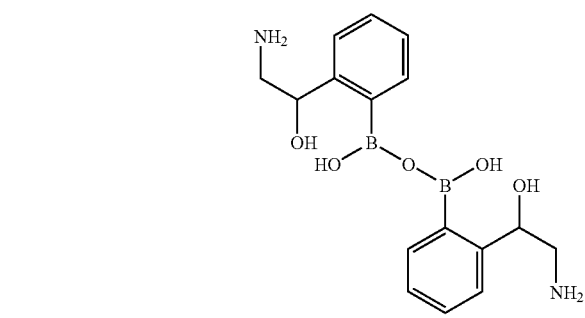

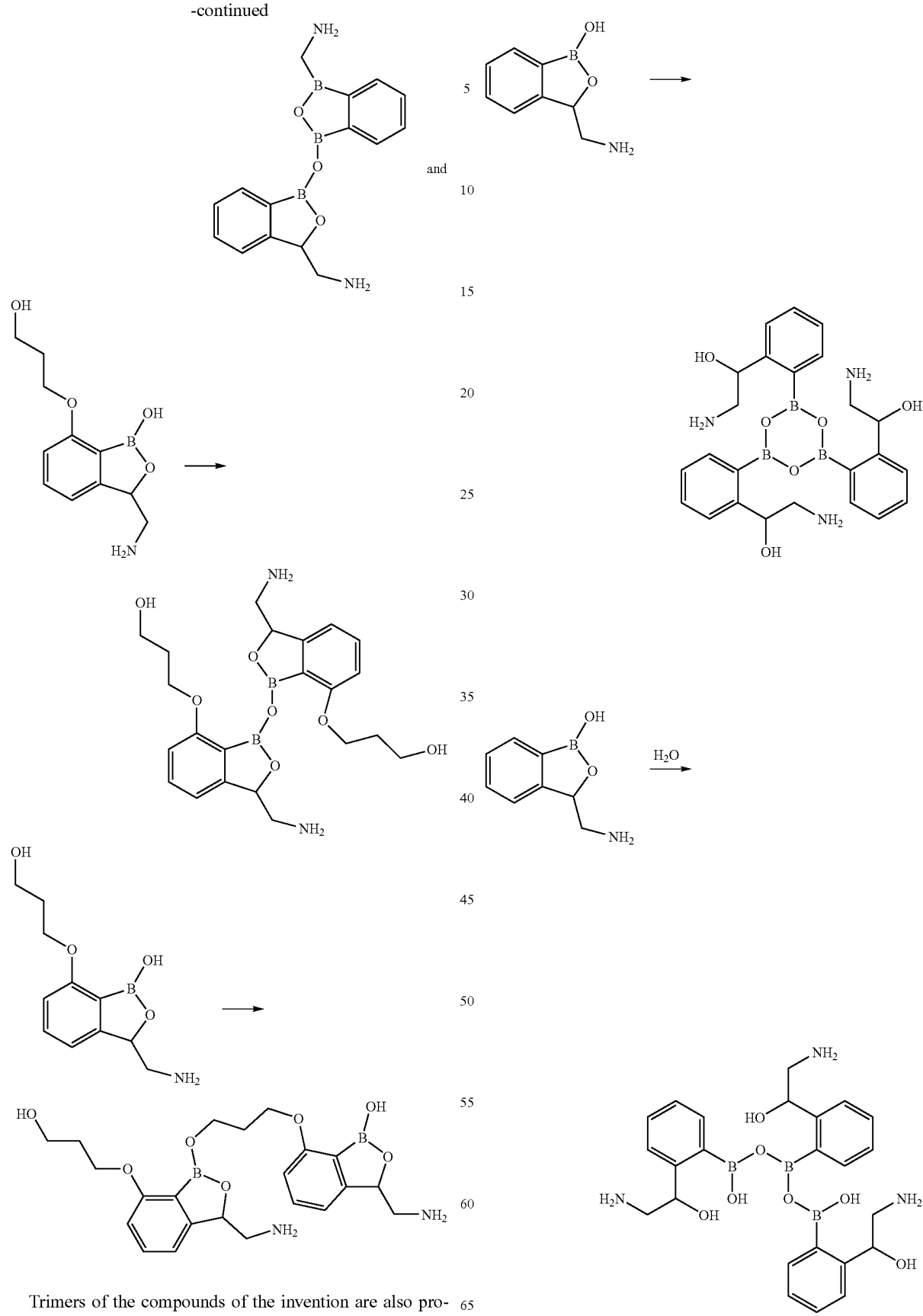
Trimers of the compounds of the invention are also produced. For example, trimers of acyclic boronic esters can be formed as follows:

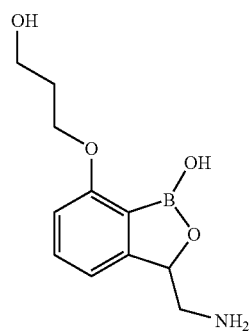
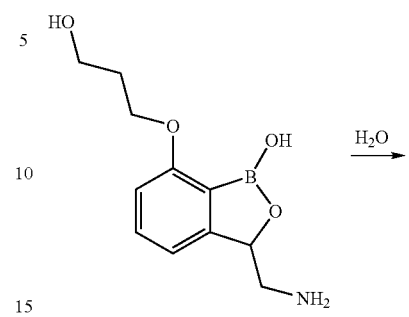
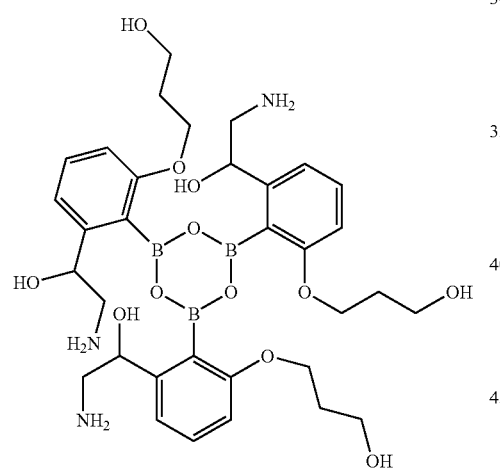
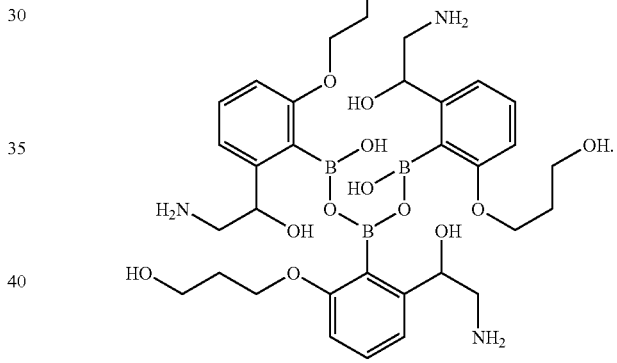
Polymers of the compounds of the invention are also produced through the removal of certain protecting groups in strong acid. For example, trimers of acyclic boronic esters can be formed as follows:
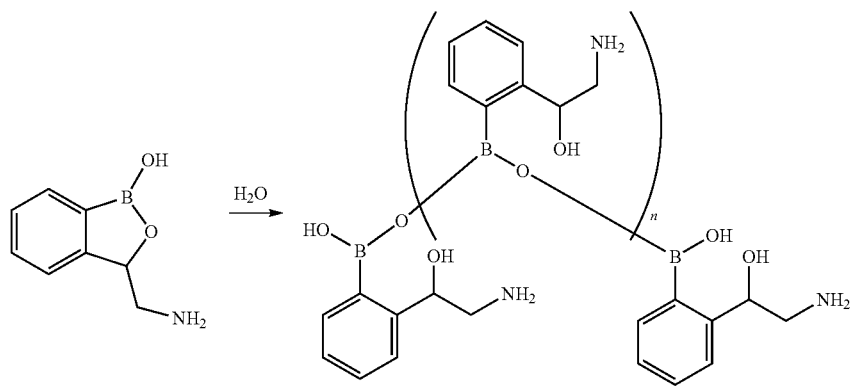

-continued

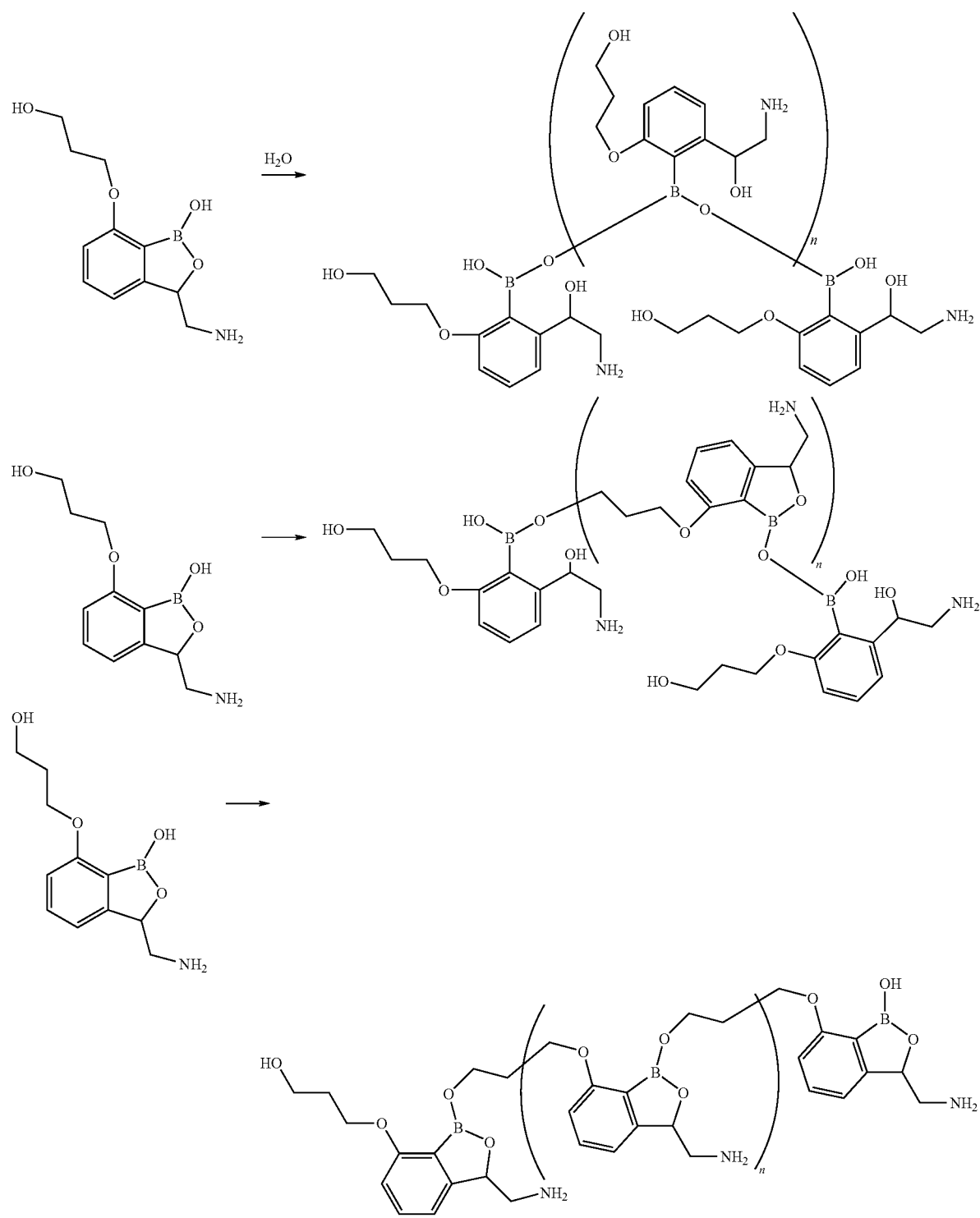

Also of use in the present invention are compounds that are poly- or multi-valent species, including, for example, species such as dimers, trimers, tetramers and higher homologs of the compounds of use in the invention or reactive analogues thereof. The poly- and multi-valent species can be assembled from a single species or more than one species of the invention. For example, a dimeric construct can be "homo- dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of use in the invention). Moreover, the framework can be derivatized with a single species of the invention or more than one species of the invention.

Moreover, the present invention includes the use of compounds within the motif set forth in the formulae contained herein, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to replace a hydroxyl group with a diol, or an amine with a quaternary amine, hydroxy amine or similar more water-soluble moiety. In a preferred embodiment, additional water solubility is imparted by substitution at a site not essential for the activity towards the editing domain of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly(ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

II. Introduction

The present invention provides novel boron compounds.

III. The Compounds

III.a) Cyclic Boronic Esters

In an exemplary embodiment, the compound of the invention has a structure which is a member selected from:

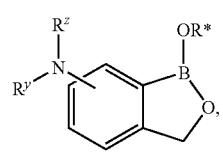
(Iaa)

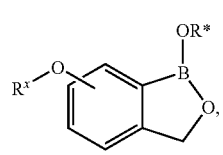
(Iab)

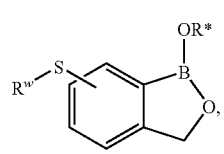
(Iac)

with the proviso that the compound is not

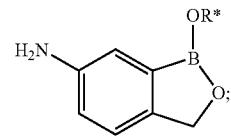

$R^z$, $R^y$, $R^x$ and $R^w$ are members independently selected from a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. R* is a member selected from H and a negative charge.

In an exemplary embodiment, the compound has a structure according to

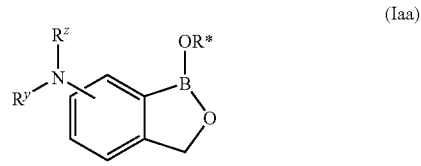
(Iaa)

wherein R* is as described herein, $R^z$ is H and $R^y$ is a member selected from substituted or unsubstituted aminoalkyl, substituted or unsubstituted hydroxyalkyl, substituted or unsubstituted carboxyalkyl. In another exemplary embodiment, the compound has a structure which is

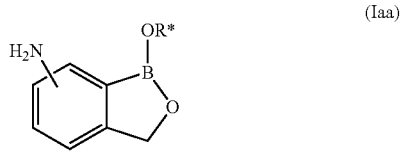
(Iaa)

wherein R* is as described herein. In another exemplary embodiment, the compound has a structure which is a member selected from:

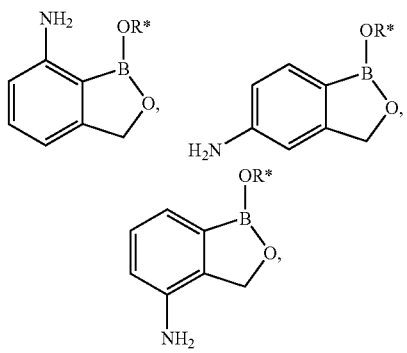

wherein R* is as described herein.

In another exemplary embodiment, the compound has a structure:

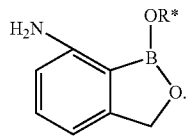

In another exemplary embodiment, R* is H.

In another aspect, the invention provides a compound having a structure according to the formula:

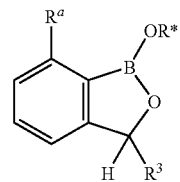

wherein R* is a member selected from H and a negative charge. $R^3$ is a member selected from H, cyano, substituted or unsubstituted nitroalkyl and substituted or unsubstituted aminoalkyl. $R^a$ is a member selected from H and —$YR^5$ wherein Y is a member selected from O and S. $R^5$ is a member independently selected from H, substituted or unsubstituted alkyl and substituted or unsubstituted heteroalkyl; with the proviso that $R^a$ and $R^3$ cannot both be H; with the proviso that $R^a$ and R*, together with the atoms to which they are attached, are optionally combined to form a 6- to 10-membered substituted or unsubstituted heterocycloalkyl ring, or a salt, prodrug, hydrate or solvate thereof, or a combination thereof. In an exemplary embodiment, the invention provides a compound of the invention, or a salt, prodrug, hydrate or solvate thereof.

In an exemplary embodiment, there is a proviso that when $R^3$ is H, $R^a$ does not have a structure which is a member selected from: unsubstituted benzyloxy, —$OCH_2COOH$, methoxy, ethoxy. In an exemplary embodiment, there is a proviso that when $R^3$ is H, $R^a$ is not substituted benzyloxy. In an exemplary embodiment, there is a proviso that when $R^3$ is H, $R^a$ is not unsubstituted alkyloxy. In an exemplary embodiment, there is a proviso that when $R^3$ is H, $R^a$ is not substituted unsubstituted alkylthio. In an exemplary embodiment, there is a proviso that when $R^3$ is H, $R^a$ does not comprise a carboxylic acid moiety.

In an exemplary embodiment, there is a proviso that when $R^a$ is H, $R^3$ is not cyano.

In an exemplary embodiment, the compound has a structure according to the following formula:

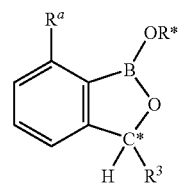

wherein $R^a$, R* and $R^3$ are as described herein, and C* is a carbon atom, and with the proviso that when $R^3$ is not H, C* is a stereocenter which has a configuration which is a member selected from (R) and (S).

In an exemplary embodiment, Y is O. In an exemplary embodiment, Y is S.

In another aspect, the invention provides a compound having a structure according to the formula which is a member selected from:

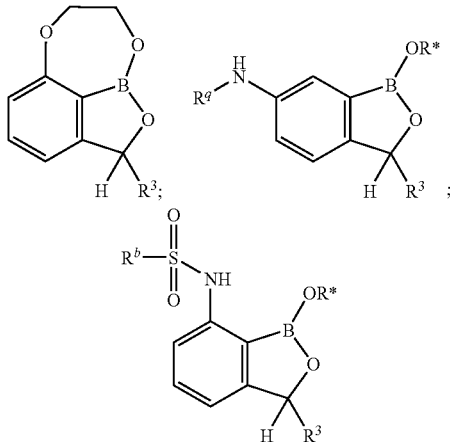

wherein R* is a member selected from H and a negative charge. $R^q$ is a member selected from H and —$SO_2$—$R^b$. $R^b$ is a member selected from unsubstituted phenyl and unsubstituted pyridinyl. $R^3$ is a member selected from H, cyano, substituted or unsubstituted nitroalkyl and substituted or unsubstituted aminoalkyl.

In an exemplary embodiment, the compound has a structure according to the following formula:

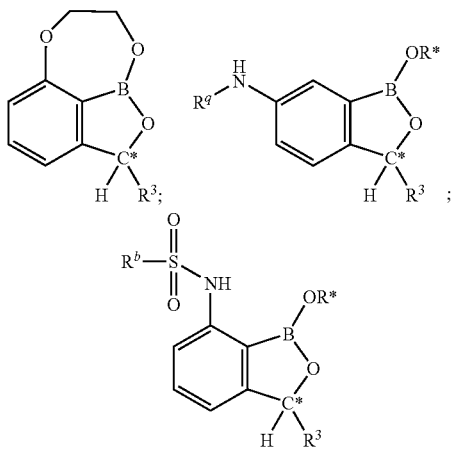

wherein $R^a$, R* and $R^3$ are as described herein, and C* is a carbon atom, and with the proviso that when $R^3$ is not H, C* is a stereocenter which has a configuration which is a member selected from (R) and (S). In an exemplary embodiment, $R^3$ is a member selected from H, —$CH_2NH_2$ and —$CH_2NO_2$. In another exemplary embodiment, the invention has the following structure:

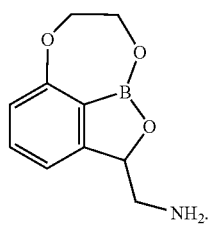 [SMILES: NCC1OB2OCCOc3cccc1c32]

In an exemplary embodiment, $R^3$ is $—(CR^{20}R^{21})_n NR^{22}R^{23}$ in which the index n is an integer selected from 1 to 10; each $R^{20}$ and each $R^{21}$ is a member independently selected from H, $R^{26}$, $OR^{26}$, $NR^{26}R^{27}$, $SR^{26}$, $—S(O)R^{26}$, $—S(O)_2R^{26}$, $—S(O)_2NR^{26}R^{27}$, $—C(O)R^{27}$, $—C(O)OR^{27}$, $—C(O)NR^{26}R^{27}$; $R^{22}$ and $R^{23}$ are members independently selected from H, $—S(O)R^{28}$, $—S(O)_2R^{28}$, $—S(O)_2NR^{28}R^{29}$, $—C(O)R^{28}$, $—C(O)OR^{28}$, $—C(O)NR^{28}R^{29}$, nitro, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl wherein each $R^{26}$, each $R^{27}$, each $R^{28}$ and each $R^{29}$ is a member independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, n is an integer selected from 1 to 5. In an exemplary embodiment, n is 1. In an exemplary embodiment, $R^{20}$ is substituted or unsubstituted alkyl. In an exemplary embodiment, $R^{20}$ is unsubstituted alkyl. In an exemplary embodiment, $R^{20}$ is $C_1$-$C_4$ unsubstituted alkyl. In an exemplary embodiment, $R^{20}$ is methyl. In an exemplary embodiment, $R^{21}$ is H. In an exemplary embodiment, $R^{23}$ is H. In an exemplary embodiment, $R^3$ is a member selected from cyano and $—CH_2NO_2$. In an exemplary embodiment, $R^{22}$ is a member selected from $—C(O)R^{28}$ and $—C(O)OR^{28}$. In an exemplary embodiment, $R^{28}$ is a member selected from substituted or unsubstituted alkyl, substituted or unsubstituted heteroalkyl and substituted or unsubstituted aryl. In an exemplary embodiment, $R^{28}$ is a member selected from $—(CR^{30}R^{31})_mR^{32}$, wherein $R^{32}$ is a member selected from substituted or unsubstituted aryl, $—NR^{33}R^{34}$ and $OR^{33}$, wherein the index m is an integer selected from 0 to 10; each $R^{33}$ and each $R^{34}$ is a member independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{28}$ is a member selected from

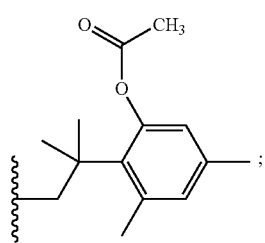

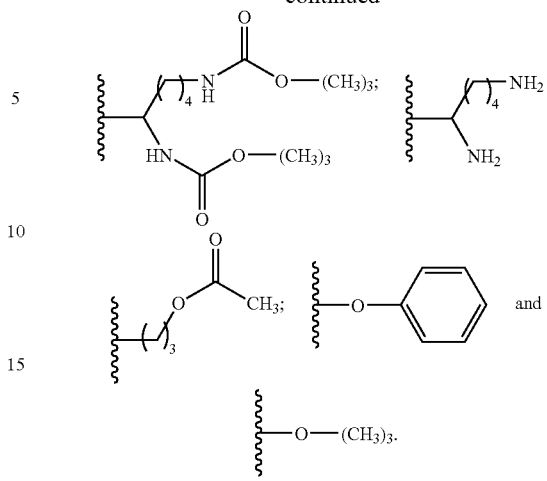

In an exemplary embodiment, $R^5$ is

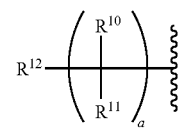

wherein the index a is a member selected from 1 to 10. Each $R^{10}$ and each $R^{11}$ is a member selected from H, substituted or unsubstituted alkyl, OH and $NH_2$. $R^{12}$ is a member selected from H, $R^7$, halogen, cyano, amidino, $OR^7$, $NR^7R^8$, $SR^7$, $—N(R^7)S(O)_2R^8$, $—C(O)R^7$, $—C(O)OR^7$, $—C(O)NR^7R^8$. Each $R^7$ and each $R^8$ is a member independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the index a is an integer selected from 1 to 8. In an exemplary embodiment, the index a is an integer selected from 2 to 4. In an exemplary embodiment, each $R^{10}$ and each $R^{11}$ is a member selected from H, substituted or unsubstituted alkyl, OH and $NH_2$. In an exemplary embodiment, each $R^{10}$ and each $R^{11}$ is a member selected from H, hydroxyalkyl and $NH_2$. In an exemplary embodiment, at least one $R^{10}$ or $R^{11}$ is a member selected from hydroxyalkyl and $NH_2$. In an exemplary embodiment, each $R^{10}$ and each $R^{11}$ is H. In an exemplary embodiment, $R^{12}$ is a member selected from H, cyano, amidino, $—N(R^7)S(O)_2R^8$, $OR^7$, $NR^7R^8$, $—C(O)OR^7$, $—C(O)NR^7R^8$, each $R^7$ and each $R^8$ is a member independently selected from H substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, each $R^7$ and each $R^8$ is a member independently selected from H, $—C(O)R^9$, $—C(O)NHR^9$, substituted or unsubstituted $C_1$-$C_4$ alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^9$ is substituted or unsubstituted $C_1$-$C_4$ alkyl. In an exemplary embodiment, at least one member selected from $R^7$ and $R^8$ is a member independently selected from $—C(O)R^9$ and $—C(O)NHR^9$, wherein $R^9$ is substituted or unsubstituted $C_1$-$C_4$ alkyl. In an exemplary embodiment, $R^{12}$ is a member selected from OH, $NH_2$, methyl, ethyl, —NHS(O)$_2$CH$_3$, cyano, —NHC(O)CH$_3$, —NHC(O)NHCH$_2$CH$_3$, —C(O)NH$_2$, —C(O)OH, 4-(methoxy)phenyl, benzyl, —NHC(O)OCH$_2$Ph, —C(O)NHCH$_2$CH$_2$OH and —C(NH$_2$)(NH). In an exemplary embodiment, when $R^{12}$ comprises $OR^7$, the $R^7$ comprises a hydroxy-protecting group; and when $R^{12}$ comprises $NR^7R^8$, at least one of the $R^7$ or $R^8$ comprises an amino-protecting group.

In another exemplary embodiment, the compound has a structure which is a member selected from:

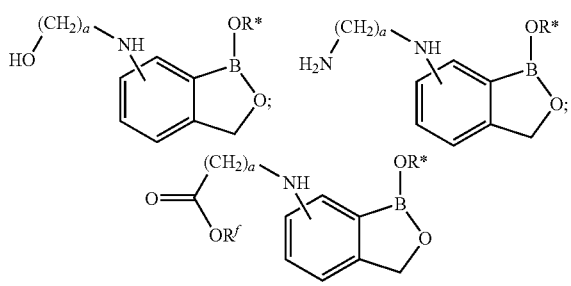

wherein the index a is an integer selected from 1 to 20 and $R^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, the index a is a member selected from 1 to 10. In another exemplary embodiment, a is a member selected from 1 to 5. In another exemplary embodiment, R* is H, $R^f$ is H and a is an integer selected from 2, 3 and 4.

In another exemplary embodiment, the compound has a structure which is a member selected from:

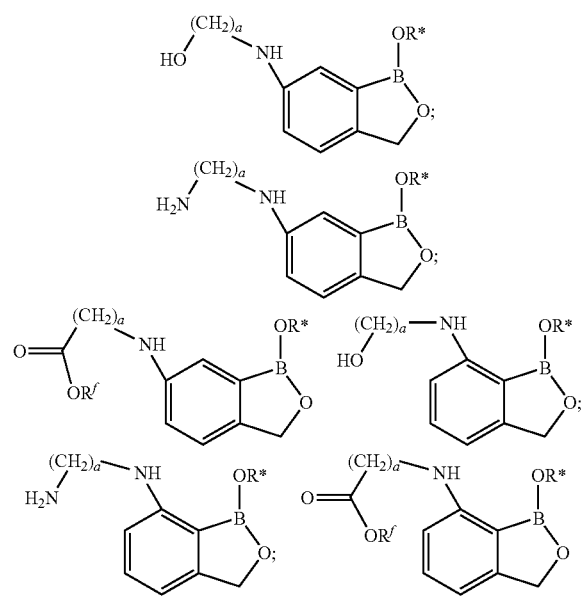

wherein a is an integer selected from 1 to 20 and $R^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5. In another exemplary embodiment, R* is H, $R^f$ is H and a is an integer selected from 2, 3 and 4.

In an exemplary embodiment, the compound has a structure according to

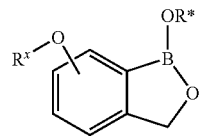

wherein R* is as described herein and $R^x$ is a member selected from substituted or unsubstituted aminoalkyl, substituted or unsubstituted hydroxyalkyl, substituted or unsubstituted carboxyalkyl. In an exemplary embodiment, $R^x$ is a member selected from substituted or unsubstituted alkyl and substituted or unsubstituted heteroalkyl. In an exemplary embodiment, $R^x$ is substituted or unsubstituted hydroxyalkyl. In an exemplary embodiment, the compound is:

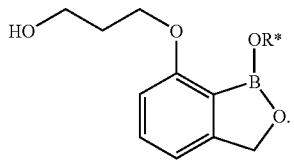

In another exemplary embodiment, the compound has a structure which is a member selected from:

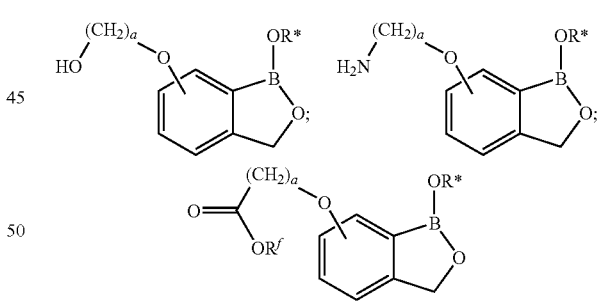

wherein a is an integer selected from 1 to 20 and $R^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5. In another exemplary embodiment, R* is H, $R^f$ is H and a is an integer selected from 2, 3 and 4.

In another exemplary embodiment, the compound has a structure which is a member selected from:

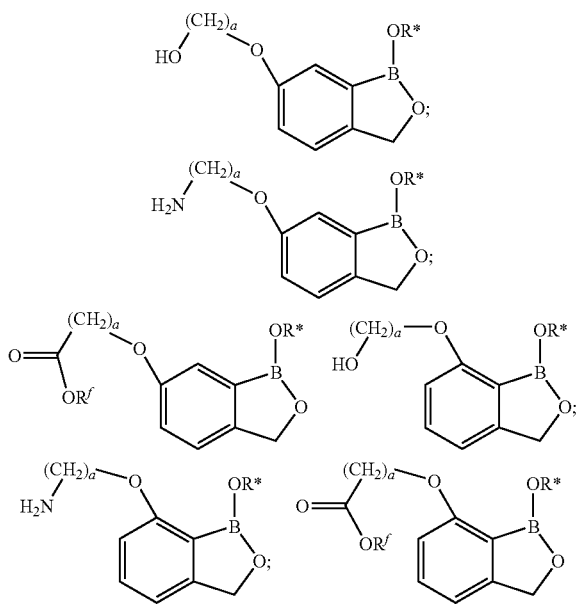

wherein a is an integer selected from 1 to 20 and $R^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5. In another exemplary embodiment, R* is H, $R^f$ is H and a is an integer selected from 2, 3 and 4.

In an exemplary embodiment, the compound has a structure according to

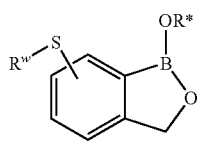

(Iac)

wherein R* is as described herein and $R^w$ is a member selected from substituted or unsubstituted aminoalkyl, substituted or unsubstituted hydroxyalkyl, substituted or unsubstituted carboxyalkyl. In an exemplary embodiment, $R^w$ is a member selected from substituted or unsubstituted alkyl and substituted or unsubstituted heteroalkyl. In an exemplary embodiment, $R^w$ is substituted or unsubstituted hydroxyalkyl.

In another exemplary embodiment, the compound has a structure which is a member selected from:

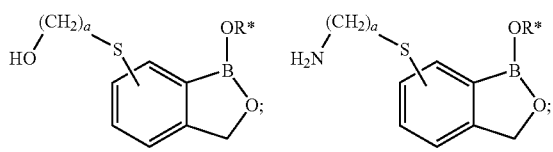

-continued

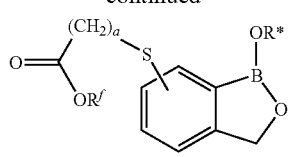

wherein a is an integer selected from 1 to 20 and $R^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5. In another exemplary embodiment, R* is H, $R^f$ is H and a is an integer selected from 2, 3 and 4.

In another exemplary embodiment, the compound has a structure which is a member selected from:

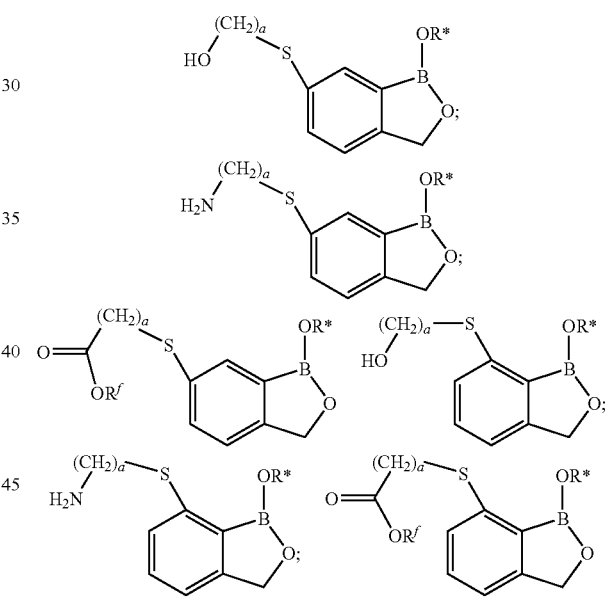

wherein a is an integer selected from 1 to 20 and $R^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5. In another exemplary embodiment, R* is H, $R^f$ is H and a is an integer selected from 2, 3 and 4.

In another exemplary embodiment, the compound has a structure which is a member selected from:

(IIa)

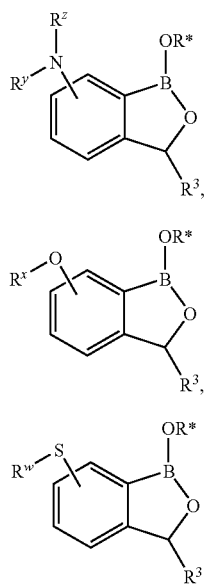

(IIb)

(IIc)

wherein $R^z$, $R^y$, $R^x$ and $R^w$ are members independently selected from substituted or unsubstituted alkyl and substituted or unsubstituted heteroalkyl. $R^*$ and $R^3$ are as described herein. In an exemplary embodiment, the compound has a structure which is a member selected from:

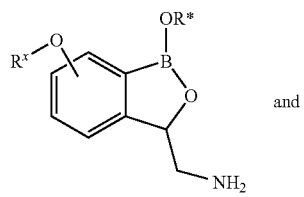 and 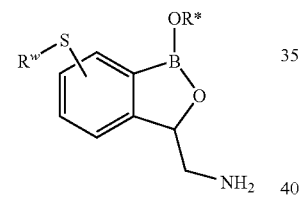

wherein $R^*$ is as defined herein, and $R^x$ and $R^w$ are members independently selected from a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another exemplary embodiment, $R^x$ and $R^w$ are members independently selected from substituted or unsubstituted alkyl and substituted or unsubstituted heteroalkyl. In another exemplary embodiment, $R^x$ and $R^w$ are members independently selected from substituted or unsubstituted hydroxyalkyl. In another exemplary embodiment, the compound is:

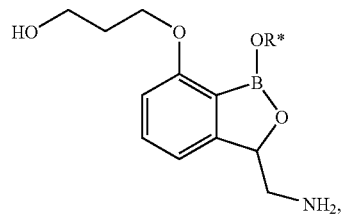

wherein $R^*$ is as defined herein.

In an exemplary embodiment, the compound of the invention has a structure which is a member selected from:

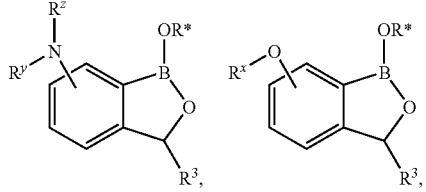



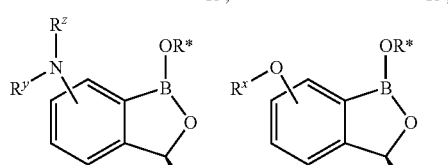

and

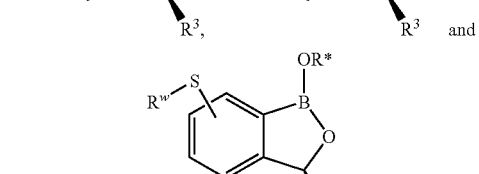

wherein $R^*$ is as defined herein, $R^3$ is substituted or unsubstituted aminoalkyl; $R^z$, $R^y$, $R^x$ and $R^w$ are members independently selected from a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another exemplary embodiment, the compound of the invention has a structure which is a member selected from

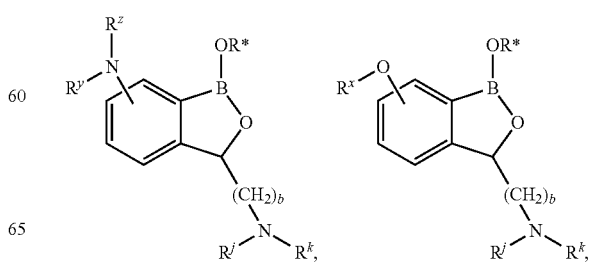

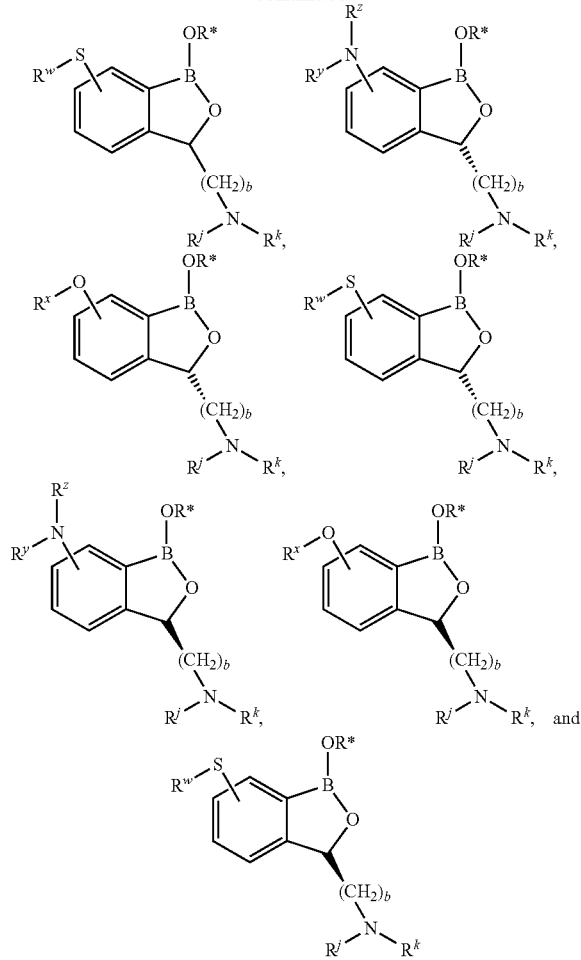

wherein R* is as defined herein, b is an integer selected from 1 to 20 and $R^z$, $R^y$, $R^x$, $R^w$, $R^j$ and $R^k$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, b is a member selected from 1 to 10. In another exemplary embodiment, b is a member selected from 1 to 5. In another exemplary embodiment, b is 1, $R^j$ and $R^k$ is H. In another exemplary embodiment, at least one member selected from $R^j$ and $R^k$ is an amino protecting group.

In an exemplary embodiment, the compound has the following structure:

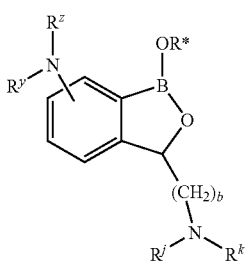

wherein R*, b, $R^j$ and $R^k$ are as described herein, $R^z$ and $R^y$ are each members independently selected from substituted or unsubstituted aminoalkyl, substituted or unsubstituted hydroxyalkyl, substituted or unsubstituted carboxyalkyl. In another exemplary embodiment, b is 1, $R^j$ and $R^k$ is H. In another exemplary embodiment, at least one member selected from $R^j$ and $R^k$ is an amino protecting group. In an exemplary embodiment, the compound has a structure which is a member selected from

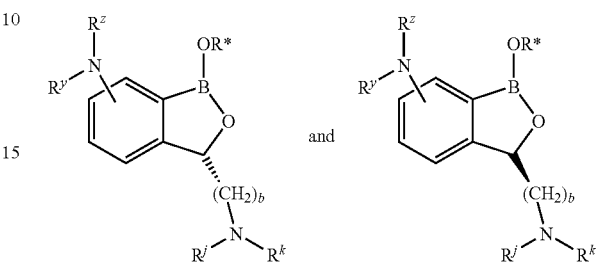

wherein R* is as described herein, $R^y$ is H and $R^z$ is a member selected from substituted or unsubstituted aminoalkyl, substituted or unsubstituted hydroxyalkyl, substituted or unsubstituted carboxyalkyl. In another exemplary embodiment, b is 1, $R^j$ and $R^k$ is H. In an exemplary embodiment, the compound has the following structure:

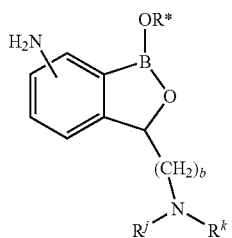

wherein R*, b, $R^j$ and $R^k$ are as defined herein. In an exemplary embodiment, the compound has a structure which is a member selected from:

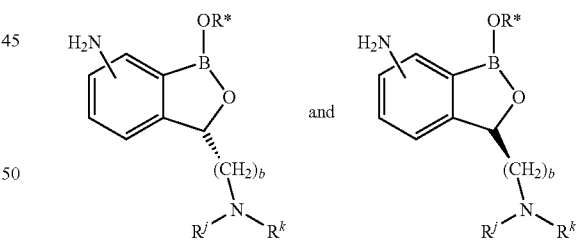

wherein R*, b, $R^j$ and $R^k$ are as defined herein. In another exemplary embodiment, the compound has a structure which is a member selected from:

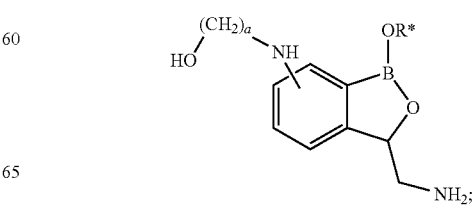

-continued

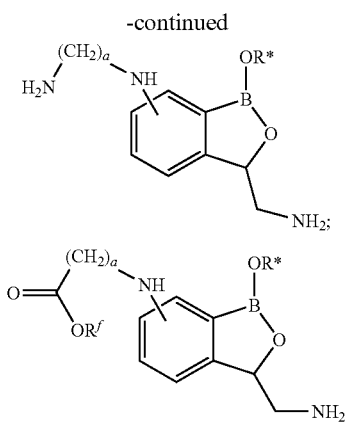

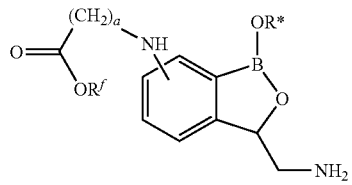

wherein R* is as defined herein. In another exemplary embodiment, the compound has a structure which is a member selected from:

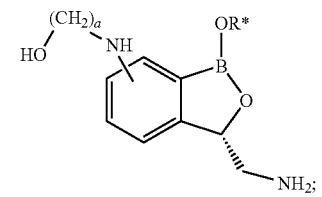

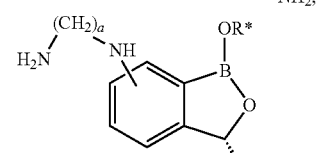

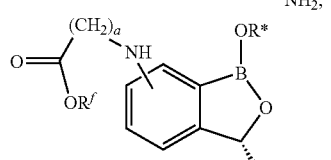

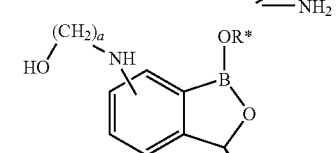

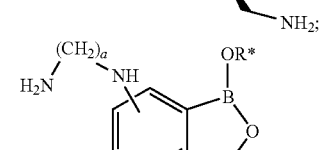

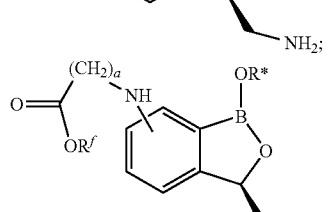

wherein R* is as defined herein, a is an integer selected from 1 to 20 and R$^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, the index a is a member selected from 1 to 10. In another exemplary embodiment, the index a is a member selected from 1 to 5. In another exemplary embodiment, the compound is a member selected from

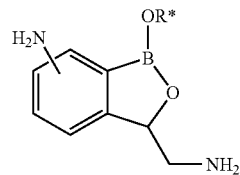

wherein R* is as defined herein. In another exemplary embodiment, the compound is a member selected from

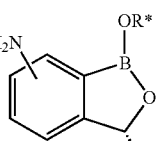 and 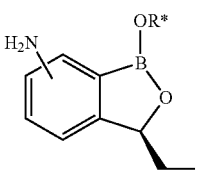

wherein R* is as defined herein.

In another exemplary embodiment, the compound has a structure which is a member selected from:

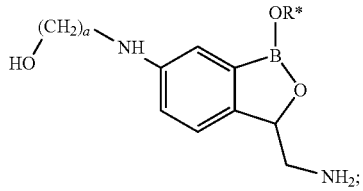

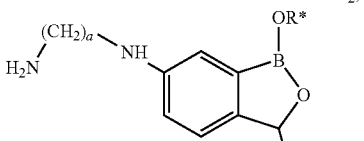

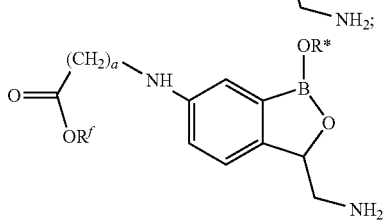

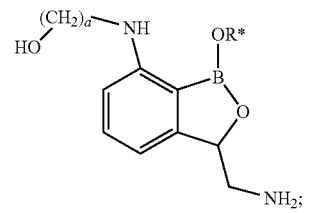

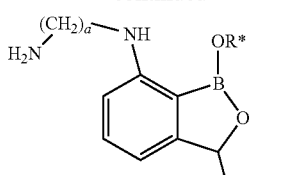

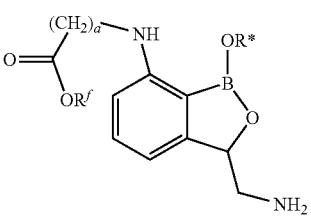

wherein R* is as defined herein. In another exemplary embodiment, the compound has a structure which is a member selected from:

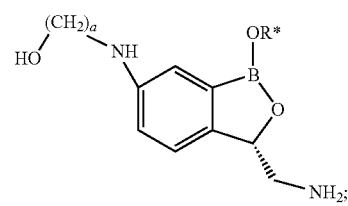

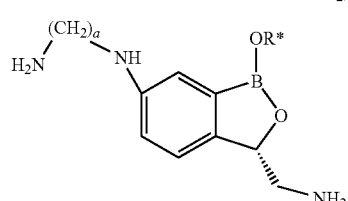

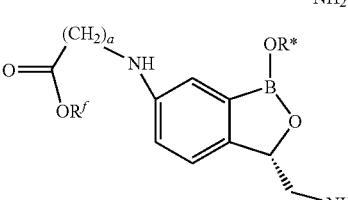

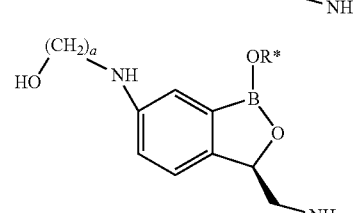

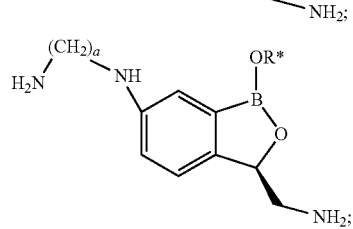

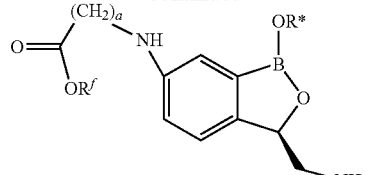

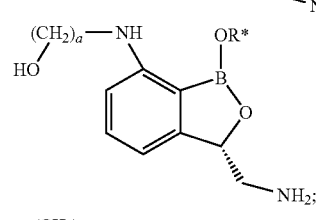

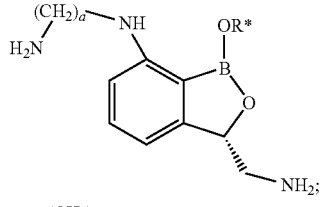

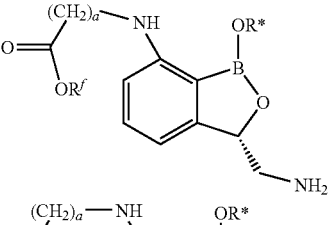

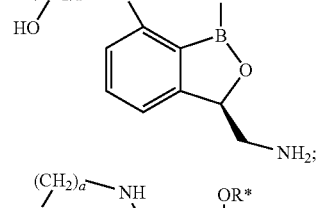

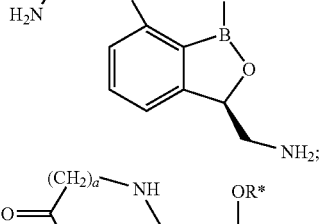

wherein R* is as described herein, a is an integer selected from 1 to 20 and $R^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5.

In another exemplary embodiment, R* is H, $R^f$ is H and a is an integer selected from 2, 3 and 4.

In another exemplary embodiment, the compound has a structure which is a member selected from:

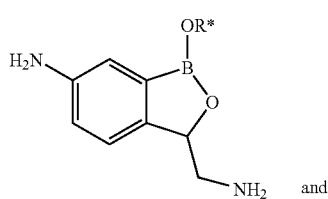

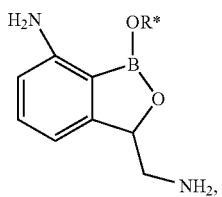

wherein R* is as defined herein. In another exemplary embodiment, the compound has a structure which is a member selected from:

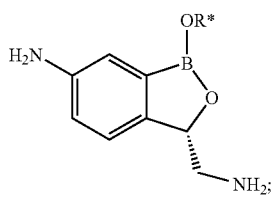

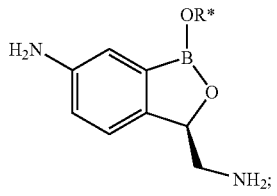

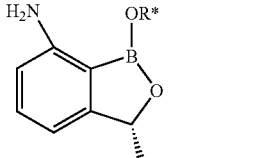

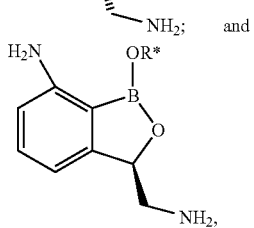

wherein R* is as defined herein. In another exemplary embodiment, the compound has a structure which is a member selected from:

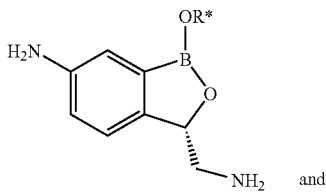

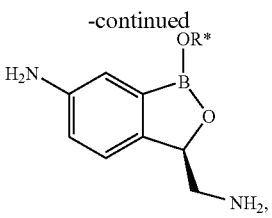

wherein R* is as defined herein.

In an exemplary embodiment, the compound has a structure which is a member selected from

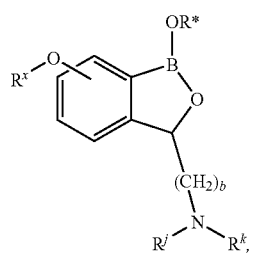

wherein R*, b, $R^x$, $R^j$ and $R^k$ are as defined herein. In another exemplary embodiment, at least one member selected from $R^j$ and $R^k$ is an amino protecting group. In an exemplary embodiment, the compound has a structure which is a member selected from

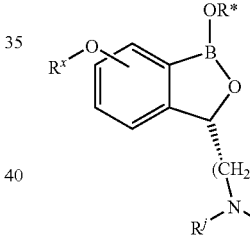 and 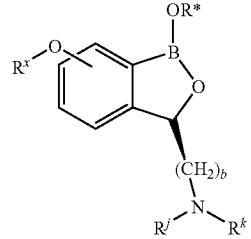

wherein R*, b, $R^x$, $R^j$ and $R^k$ are as defined herein and $R^x$ is a member selected from substituted or unsubstituted aminoalkyl, substituted or unsubstituted hydroxyalkyl, substituted or unsubstituted carboxyalkyl. In another exemplary embodiment, the compound has a structure which is a member selected from:

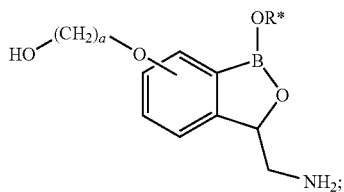

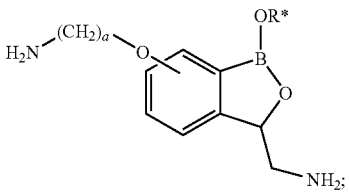

-continued

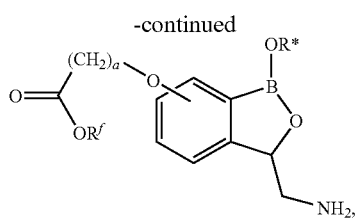

R*, R$^f$ and a are as defined herein. In another exemplary embodiment, the compound has a structure which is a member selected from:

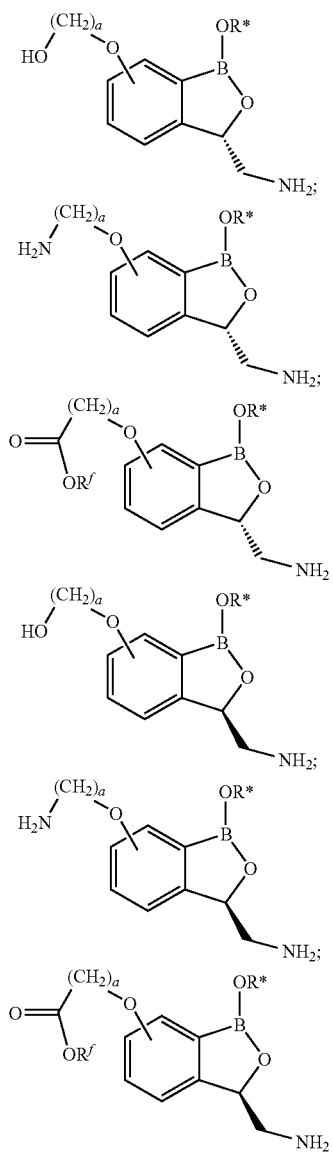

wherein R* is as described herein, a is an integer selected from 1 to 20 and R$^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5. In another exemplary embodiment, R* is H, R$^f$ is H and a is an integer selected from 2, 3 and 4.

In another exemplary embodiment, the compound has a structure which is a member selected from:

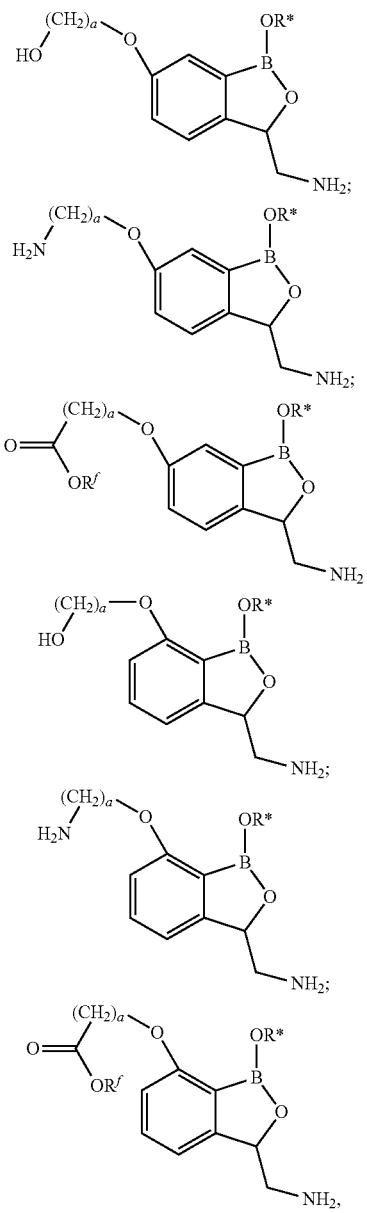

wherein R* and R$^a$ are as described herein. In another exemplary embodiment, the compound has a structure which is a member selected from:

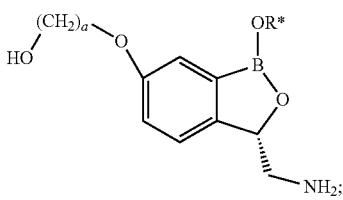

-continued

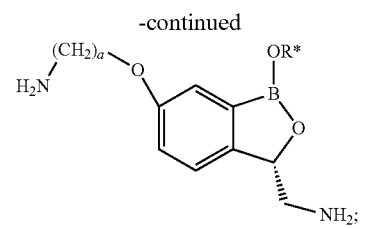

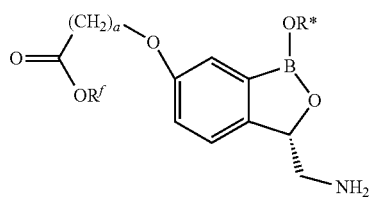

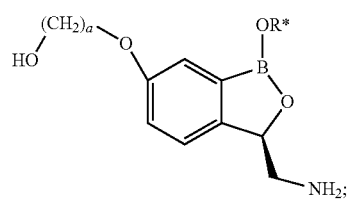

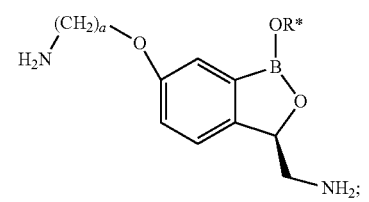

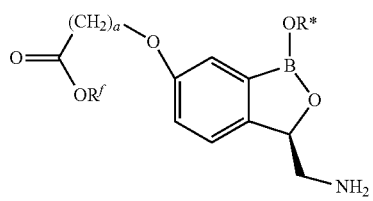

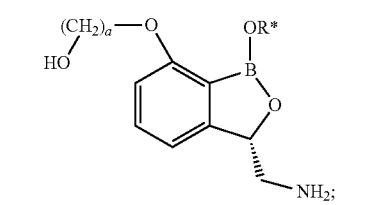

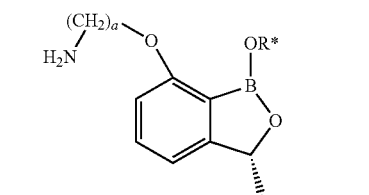

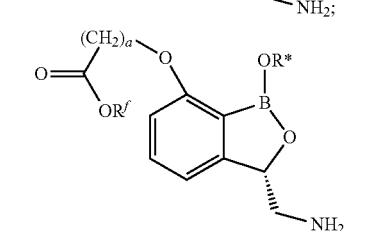

-continued

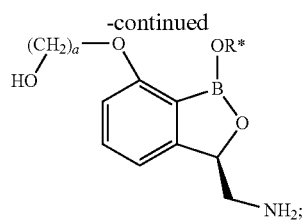

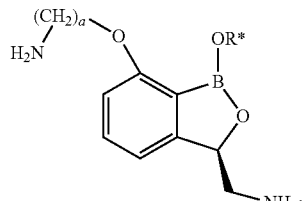

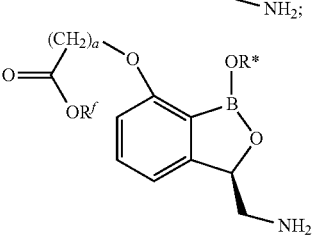

wherein R* is as described herein, and a is an integer selected from 1 to 20 and $R^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5. In another exemplary embodiment, $R^1$ is H, $R^f$ is H and a is an integer selected from 2, 3 and 4.

In another exemplary embodiment, the compound has the following structure:

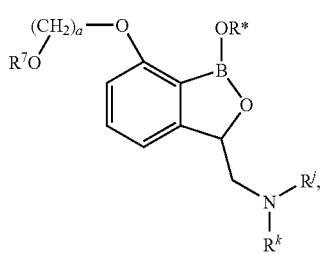

wherein a and R* are as defined herein, $R^7$ is a member selected from H and a hydroxyl protecting group and $R^j$ and $R^k$ are members independently selected from H and an amino protecting group. In an exemplary embodiment, at least one member selected from $R^j$ and $R^k$ is an amino protecting group. In an exemplary embodiment, a is a member selected from 2, 3, and 4. In another exemplary embodiment, the compound has the following structure:

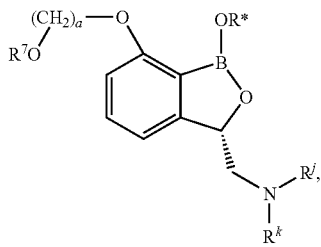

wherein a and R* are as defined herein, $R^7$ is a member selected from H and a hydroxyl protecting group and $R^j$ and $R^k$ are members independently selected from H and an amino protecting group. In an exemplary embodiment, at least one member selected from $R^j$ and $R^k$ is an amino protecting group. In an exemplary embodiment, the index a is a member selected from 2, 3, and 4.

In an exemplary embodiment, the compound is

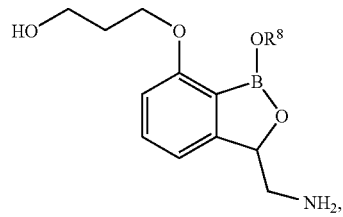

wherein R* is as described herein. In another exemplary embodiment, R* is H. In an exemplary embodiment, the compound is

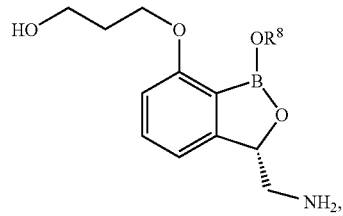

wherein R* is as described herein. In another exemplary embodiment, R* is H.

In an exemplary embodiment, the compound has the following structure:

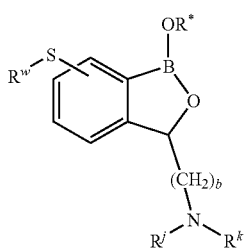

wherein R*, b, $R^w$, $R^j$ and $R^k$ are as defined herein. In another exemplary embodiment, at least one member selected from $R^j$ and $R^k$ is an amino protecting group. In an exemplary embodiment, the compound has a structure which is a member selected from:

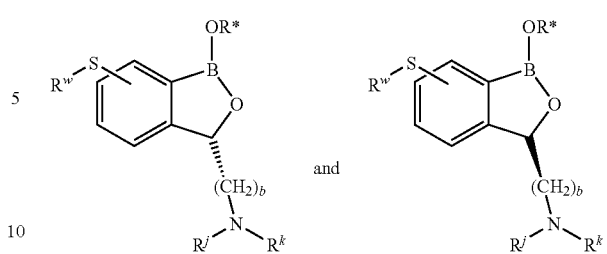

wherein R*, b, $R^j$ and $R^k$ are as described herein and $R^w$ is a member selected from substituted or unsubstituted aminoalkyl, substituted or unsubstituted hydroxyalkyl, substituted or unsubstituted carboxyalkyl. In another exemplary embodiment, the compound has a structure which is a member selected from:

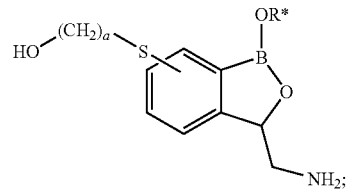

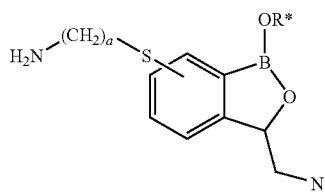

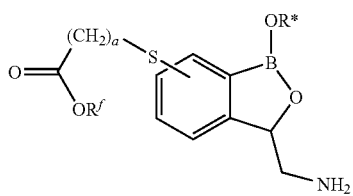

wherein R*, $R^f$ and a are as described herein. In another exemplary embodiment, the compound has a structure which is a member selected from:

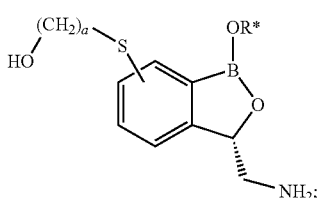

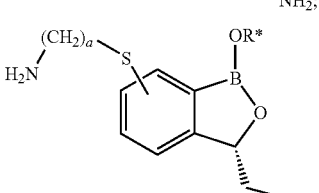

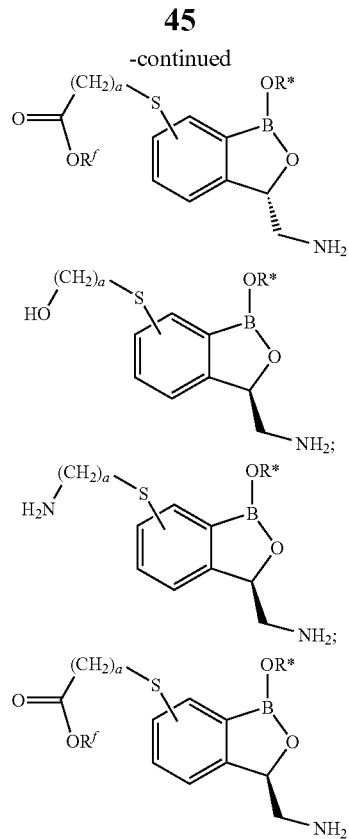

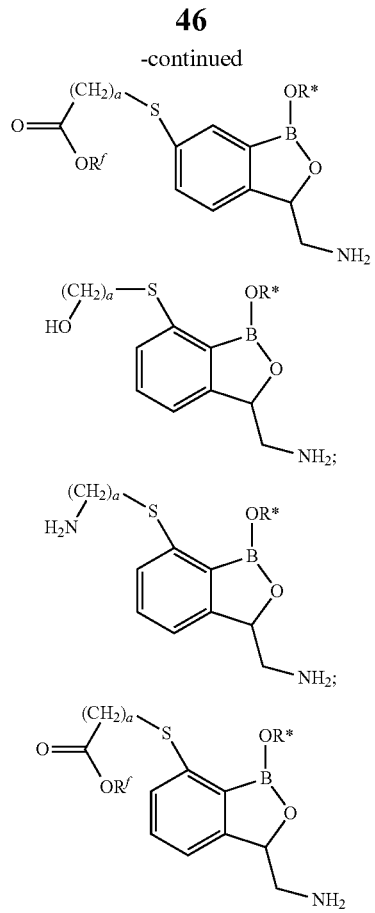

wherein R* is as described herein, a is an integer selected from 1 to 20 and R$^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5.

In another exemplary embodiment, R* is H, R$^f$ is H and a is an integer selected from 2, 3 and 4.

In another exemplary embodiment, the compound has a structure which is a member selected from:

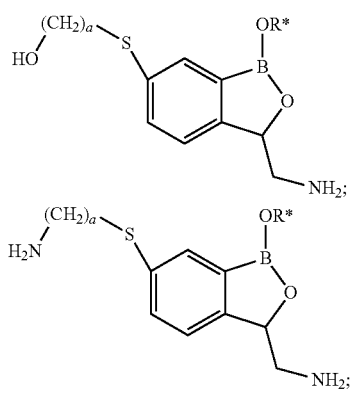

wherein R*, R$^f$ and a are as described herein. In another exemplary embodiment, the compound has a structure which is a member selected from:

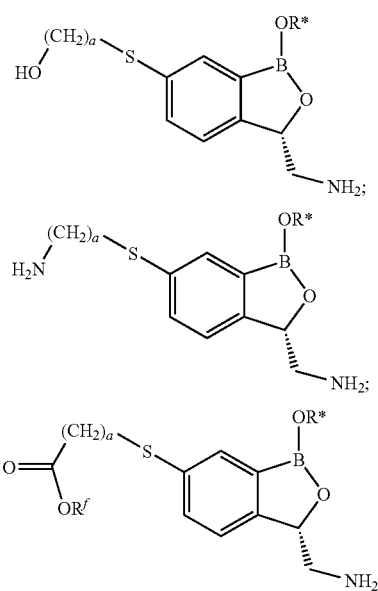

-continued

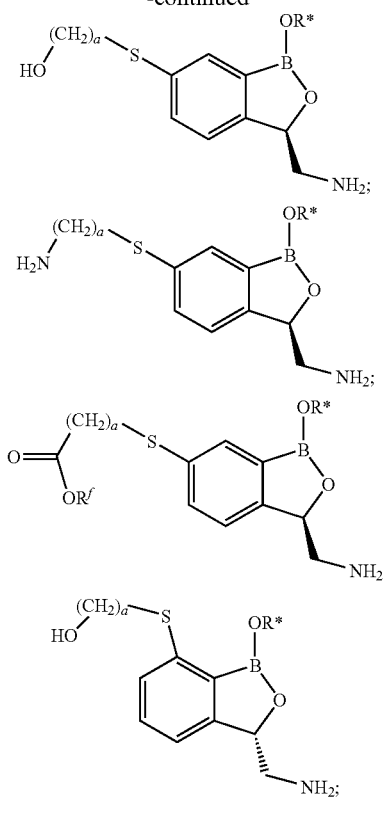

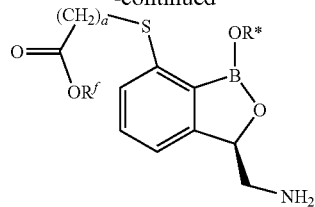

wherein R* is as described herein, a is an integer selected from 1 to 20 and $R^f$ is a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another exemplary embodiment, a is a member selected from 1 to 10. In another exemplary embodiment, a is a member selected from 1 to 5. In another exemplary embodiment, R* is H, $R^f$ is H and a is an integer selected from 2, 3 and 4.

In another exemplary embodiment, the compound has the following structure:

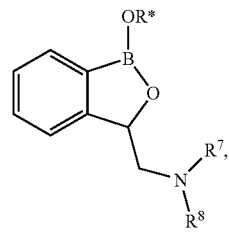

wherein R* is as defined herein, and $R^j$ and $R^k$ are members independently selected from H and an amino protecting group. In an exemplary embodiment, at least one member selected from $R^j$ and $R^k$ is an amino protecting group.

In another exemplary embodiment, the compound has the following structure:

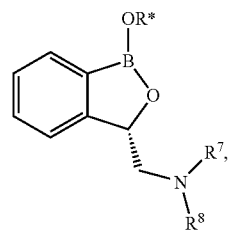

wherein R* is as defined herein, and $R^j$ and $R^k$ are members independently selected from H and an amino protecting group. In an exemplary embodiment, at least one member selected from $R^j$ and $R^k$ is an amino protecting group.

In another exemplary embodiment, the compound has the following structure:

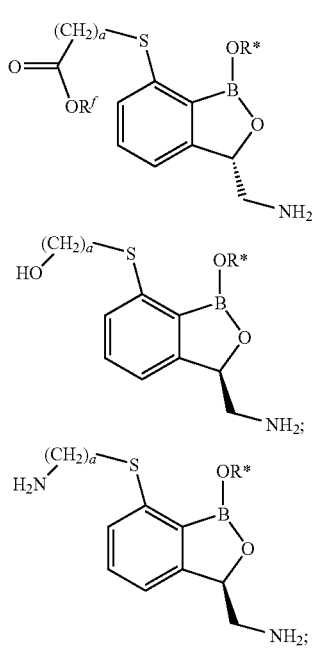

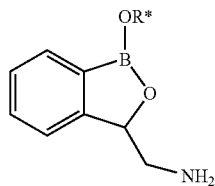

wherein R* is as described herein. In another exemplary embodiment, the compound has the following structure:

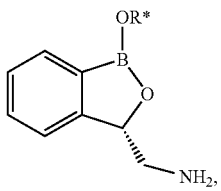

wherein R* is as described herein. In another exemplary embodiment, R* is H. In another exemplary embodiment, the compound has the following structure:

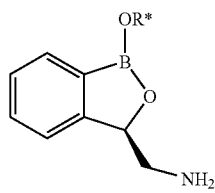

wherein R* is as described herein. In another exemplary embodiment, R* is H.

In an exemplary embodiment, the compound has a structure which is a member selected from:

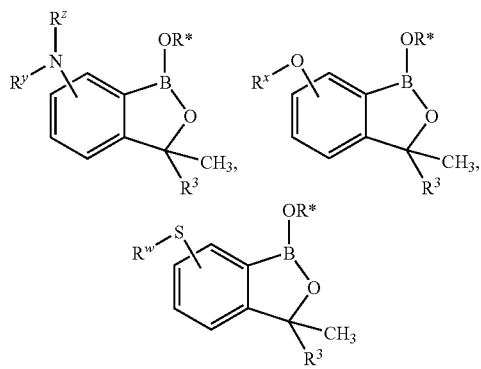

wherein R* is as described herein, $R^3$ is substituted or unsubstituted aminoalkyl; $R^z$, $R^y$, $R^x$ and $R^w$ are members independently selected from a member selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound has a structure which is a member selected from:

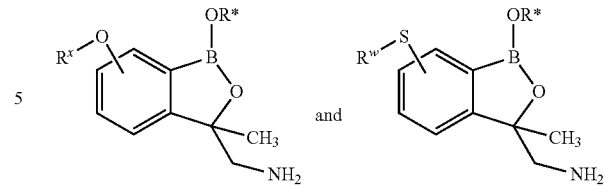

wherein R* is as described herein, $R^x$ and $R^w$ are members independently selected from a member selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^x$ and $R^w$ are members independently selected from substituted or unsubstituted alkyl and substituted or unsubstituted heteroalkyl. In an exemplary embodiment, $R^x$ and $R^w$ are members independently selected from substituted or unsubstituted hydroxyalkyl. In an exemplary embodiment, the compound has a structure which is a member selected from:

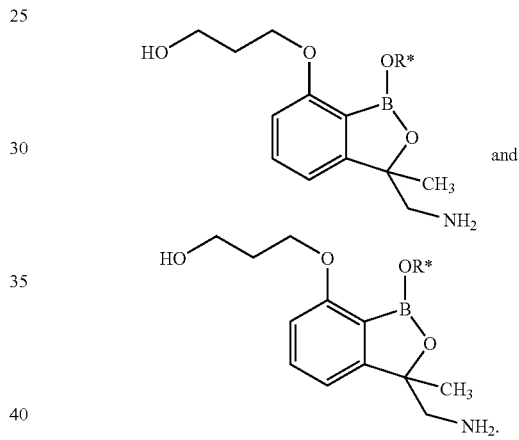

In an exemplary embodiment, $R^3$ is a member selected from H, —$CH_2NH_2$ and —$CH_2NO_2$; and $R^{12}$ is a member selected from OH, $NH_2$, methyl, ethyl, —$NHS(O)_2CH_3$, cyano, —$NHC(O)CH_3$, —$NHC(O)NHCH_2CH_3$, —$C(O)NH_2$, —$C(O)OH$, 4-(trifluoromethyl)phenyl, 4-(methoxy)phenyl, benzyl, —$NHC(O)OCH_2Ph$, —$C(O)NHCH_2CH_2OH$ and —$C(NH_2)(NH)$. In an exemplary embodiment, $R^3$ is a member selected from H, —$CH_2NH_2$ and —$CH_2NO_2$; and $R^a$ is a member selected from H, —$O(CH_2)_3NH_2$, —$O(CH_2)_3OH$, —$OCH_2CH_3$, —$O(CH_2)_3NHS(O)_2CH_3$, —$O(CH_2)_3CN$, —$O(CH_2)_3NHC(O)CH_3$, —$O(CH_2)_3NHCH_3$, —$O(CH_2)_3OCH_3$, —$O(CH_2)_4OH$, —$OCH_3$, —$O(CH_2)_3NHC(O)NHCH_2CH_3$, —$O(CH_2)_3C(O)NH_2$, —$O(CH_2)_3C(O)OH$, —$C(O)NHCH_2Ph(4-CF_3)$, —$O(CH_2)_4NH_2$, —$O(CH_2)_2NH_2$, —$OCH_2CH_2CH(NH_2)CH_2OH$, —$OCH_2Ph(4-methoxy)$, —$O(CH_2)_4OCH_2Ph$, —$O(CH_2)_3NHC(O)OCH_2Ph$, —$OCH_2C(O)NH(CH_2)_2OH$, —$O(CH_2)_3NHC(O)CH_3$, —$O(CH_2)_3C(NH_2)(NH)$, —$C(O)OCH_3$, —$OCH_2C(O)OH$ and —$OCH_2CH(CH_2OH)(CH_2)OH$.

In an exemplary embodiment, when $R^3$ is H, $R^a$ is a member selected from —$O(CH_2)_3NH_2$, —$O(CH_2)_3NHS(O)_2CH_3$, —$O(CH_2)_3CN$, —$O(CH_2)_3NHC(O)CH_3$, —$O(CH_2)_3NHCH_3$, —$O(CH_2)_4OH$, —$O(CH_2)_3NHC(O)NHCH_2CH_3$, —$O(CH_2)_3C(O)NH_2$, —$O(CH_2)_3C(O)OH$, —$O(CH_2)_4NH_2$, —O(CH$_2$)$_2$NH$_2$, —OCH$_2$CH$_2$CH(NH$_2$)CH$_2$OH, —OCH$_2$Ph(4-methoxy), —O(CH$_2$)$_4$OCH$_2$Ph, —OCH$_2$C(O)NH(CH$_2$)$_2$OH and —OCH$_2$CH(CH$_2$OH)(CH$_2$)OH. In an exemplary embodiment, when R$^3$ is —CH$_2$NH$_2$, R$^a$ is a member selected from H, —O(CH$_2$)$_3$OH, —OCH$_2$CH$_3$, —O(CH$_2$)$_3$OCH$_3$, —OCH$_3$, —O(CH$_2$)$_4$NH$_2$, —O(CH$_2$)$_3$NHS(O)$_2$CH$_3$, —O(CH$_2$)$_3$NHC(O)OCH$_2$Ph, —O(CH$_2$)$_3$NHC(O)CH$_3$, —O(CH$_2$)$_3$NH$_2$. In an exemplary embodiment, when R$^3$ is —CH$_2$NO$_2$, R$^a$ is a member selected from —O(CH$_2$)$_3$CN and —OCH$_2$CH$_3$. In an exemplary embodiment, when R$^3$ is H, R$^a$ is a member selected from —O(CH$_2$)$_3$NH$_2$, —O(CH$_2$)$_3$NHS(O)$_2$CH$_3$, —O(CH$_2$)$_3$CN, —O(CH$_2$)$_3$NHC(O)CH$_3$, —O(CH$_2$)$_3$NHCH$_3$, —O(CH$_2$)$_4$OH, —O(CH$_2$)$_3$NHC(O)NHCH$_2$CH$_3$, —O(CH$_2$)$_3$C(O)NH$_2$, —O(CH$_2$)$_3$C(O)OH, —O(CH$_2$)$_4$NH$_2$, —O(CH$_2$)$_2$NH$_2$, —OCH$_2$CH$_2$CH(NH$_2$)CH$_2$OH. In an exemplary embodiment, when R$^3$ is —CH$_2$NH$_2$, R$^a$ is a member selected from H, —O(CH$_2$)$_3$OH, —OCH$_2$CH$_3$, —O(CH$_2$)$_3$OCH$_3$, —OCH$_3$. In an exemplary embodiment, when R$^3$ is H, R$^a$ is a member selected from —O(CH$_2$)$_3$NH$_2$, —O(CH$_2$)$_3$CN, —O(CH$_2$)$_3$NHC(O)CH$_3$, —O(CH$_2$)$_3$NHCH$_3$. In an exemplary embodiment, when R$^3$ is —CH$_2$NH$_2$, R$^a$ is a member selected from H, —O(CH$_2$)$_3$OH and —OCH$_2$CH$_3$.

In another exemplary embodiment, the compound is

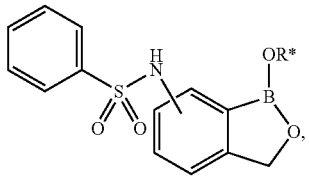

wherein R* is as described herein. In another exemplary embodiment, the compound is a member selected from

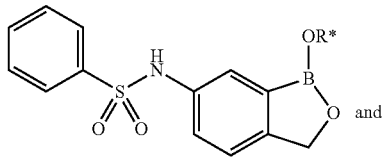

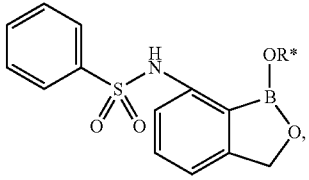

wherein R* is as described herein.

In another exemplary embodiment, the compound is

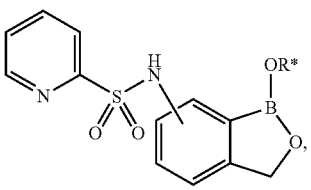

wherein R* is as described herein. In another exemplary embodiment, the compound is a member selected from

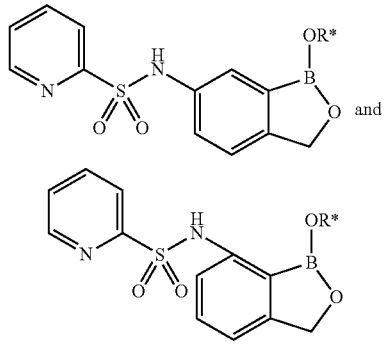

wherein R* is as described herein.

In another exemplary embodiment, the compound is a member selected from

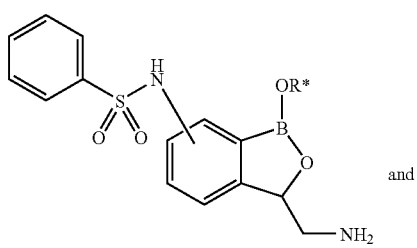

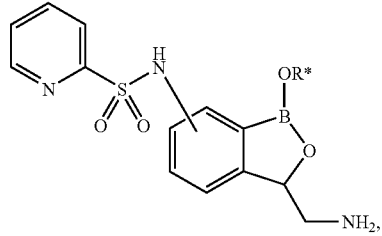

wherein R* is as described herein. In another exemplary embodiment, the compound is a member selected from

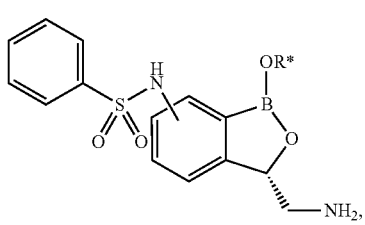

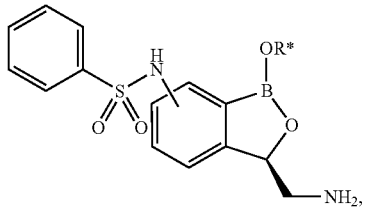

-continued
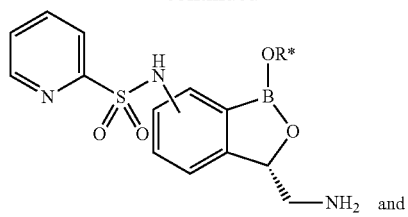
and
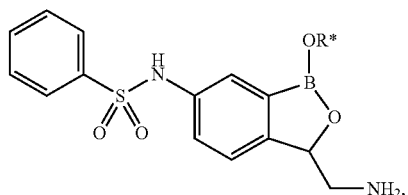
wherein R* is as described herein. In another exemplary embodiment, the compound is a member selected from
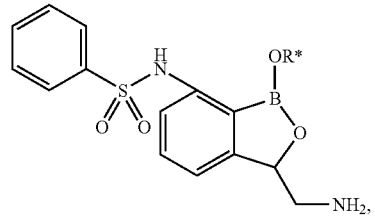
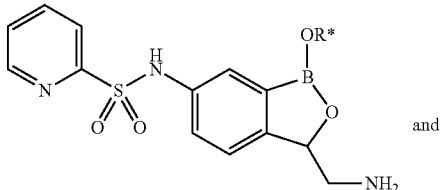
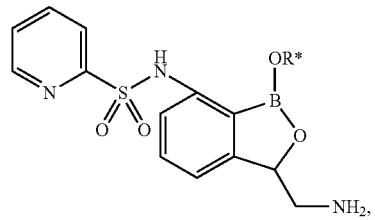
and
In another exemplary embodiment, the compound is a member selected from
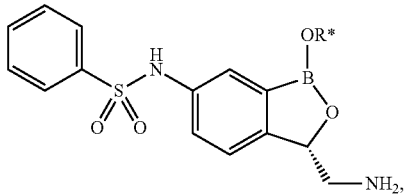
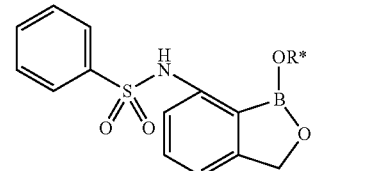
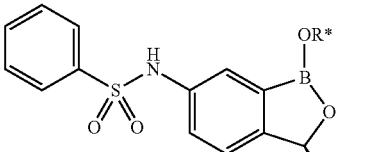
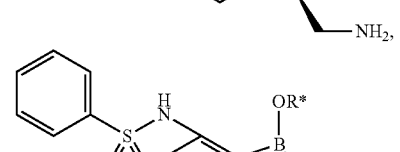
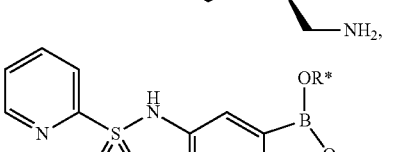
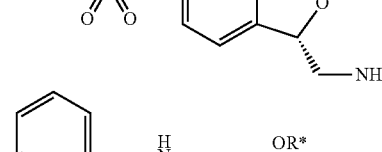
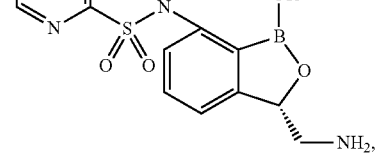
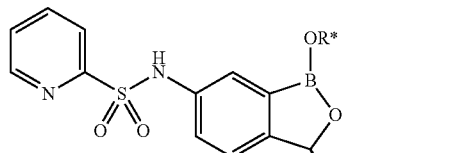
and
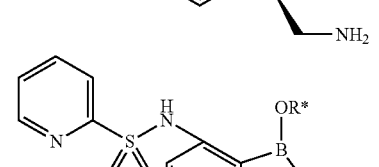
wherein R* is as described herein.

In an exemplary embodiment, R* is H. In an exemplary embodiment, the C* stereocenter is in a configuration which is a member selected from (R) and (S). In an exemplary embodiment, the C* stereocenter is in a (S) configuration. In an exemplary embodiment, the C* stereocenter is in a (S) configuration and $R^3$ is —$CH_2NH_2$. In an exemplary embodiment, the C* stereocenter is in a (S) configuration, $R^3$ is —$CH_2NH_2$ and $R^a$ is a member selected from H and —$O(CH_2)_3OH$.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein. In an exemplary embodiment, the invention provides a compound as described in FIG. 1 or FIG. 2.

In an exemplary embodiment, alkyl is a member selected from linear alkyl and branched alkyl. In another exemplary embodiment, heteroalkyl is a member selected from linear heteroalkyl and branched heteroalkyl.

III.b) Compositions Involving Stereoisomers

As used herein, the term "chiral", "enantiomerically enriched" or "diastereomerically enriched" refers to a composition having an enantiomeric excess (ee) or a diastereomeric excess (de) of greater than about 50%, preferably greater than about 70% and more preferably greater than about 90%. In general, higher than about 90% enantiomeric or diastereomeric excess is particularly preferred, e.g., those compositions with greater than about 95%, greater than about 97% and greater than about 99% ee or de.

The terms "enantiomeric excess" and "diastereomeric excess" are used interchangeably herein. Compounds with a single stereocenter are referred to as being present in "enantiomeric excess", those with at least two stereocenters are referred to as being present in "diastereomeric excess".

The term "enantiomeric excess" is well known in the art and is defined as:

$$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being enantiomerically pure. A composition which in the past might have been called 98% optically pure is now more precisely characterized by 96% ee. A 90% ee reflects the presence of 95% of one enantiomer and 5% of the other(s) in the material in question.

Hence, in one embodiment, the invention provides a composition including a first stereoisomer and at least one additional stereoisomer of a compound of the invention. The first stereoisomer can be present in a diastereomeric or enantiomeric excess of at least about 80%, or at least about 90%, or at least about 92% or at least about 95%. In another exemplary embodiment, the first stereoisomer is present in a diastereomeric or enantiomeric excess of at least about 96%, at least about 97%, at least about 98%, at least about 99% or at least about 99.5%. In another embodiment, the compound of the invention is enantiomerically or diastereomerically pure (diastereomeric or enantiomeric excess is about 100%). Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

As used herein, and unless otherwise indicated, a composition that is "substantially free" of a compound means that the composition contains less than about 20% by weight, or less than about 15% by weight, or less than about 10% by weight, or less than about 5% by weight, or less than about 3% by weight, or less than about 2% by weight, or less than about 1% by weight of the compound.

As used herein, the term "substantially free of the (or its) enantiomer" means that a composition containing a compound of the invention is made up of a significantly greater proportion of one enantiomer than of its optical antipode. In one embodiment of the invention, the term "substantially free of the enantiomer" means that the compound is made up of at least about 90% by weight of the (S) enantiomer and about 10% by weight or less of the (R) stereoisomer. In a more preferred embodiment of the invention, the term "substantially free of the enantiomer" means that the compound is made up of at least about 95% by weight of the (S) enantiomer and about 5% by weight or less of the (R) stereoisomer. In an even more preferred embodiment, the term "substantially free of the enantiomer" means that the compound is made up of at least about 98% by weight of the (S) enantiomer and about 2% or less of the (R) stereoisomer. In an even more preferred embodiment, the term "substantially free of the enantiomer" means that the compound is made up of at least about 99% by weight of the (S) enantiomer and about 1% or less of the (R) stereoisomer.

In an exemplary embodiment, the invention provides a composition comprising a) a first stereoisomer of a compound described herein, wherein $R^3$ is not H; b) at least one additional stereoisomer of the first stereoisomer, wherein the first stereoisomer is present in an enantiomeric excess of at least 80% relative to said at least one additional stereoisomer. In an exemplary embodiment, the enantiomeric excess is at least 92%. In an exemplary embodiment, the C* stereocenter of the first stereoisomer is in a (S) configuration. In an exemplary embodiment, the C* stereocenter of the first stereoisomer is in a (S) configuration, and $R^3$ is —$CH_2NH_2$.

In an exemplary embodiment, the invention provides a composition comprising a compound of the invention, wherein $R^3$ is not H and the C* stereocenter is in a (S) configuration, and said composition is substantially free of the enantiomer of the compound. In an exemplary embodiment, the composition comprises A2, A49 or combinations thereof, wherein the composition is substantially free of the enantiomer of A2 or A49. In an exemplary embodiment, the invention provides a composition comprising a compound described herein, wherein $R^3$ is not H and the C* stereocenter is in a (R) configuration.

III.c) Combinations Comprising Additional Therapeutic Agents

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described in section III.c).

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. In an exemplary embodiment, the additional therapeutic agent is an antibiotic. Examples of classes of antibiotics which may be utilized in the application include an aminoglycoside, an ansamycin, a carbacephem, a carbapenem, a first-generation cephalosporin, a second-generation cephalosporin, a third-generation cephalosporin, a fourth-generation cephalosporin, a fifth-generation cephalosporin, a glycopeptide, a macrolide, a quinolone, a sulfonamide, and a tetracycline. In an exemplary embodiment, the additional therapeutic agent is a member selected from amikacin, gentamicin, kanamycin, neomycin, netilmicin, streptomycin, tobramycin, paromomycin. In an exemplary embodiment, the additional therapeutic agent is a member selected from geldanamycin and herbimycin. In an exemplary embodiment, the additional therapeutic agent is loracarbef. In an exemplary embodiment, the additional therapeutic agent is a member selected from ertapenem, doripenem, imipenem, cilastatin and meropenem. In an exemplary embodiment, the additional therapeutic agent is a member selected from cefadroxil, cefazolin, cefalotin and cefalexin. In an exemplary embodiment, the additional therapeutic agent is a member selected from cefaclor, cefamandole, cefoxitin, cefprozil and cefuroxime. In an exemplary embodiment, the additional therapeutic agent is a member selected from cefixime, cefdinir, cefditoren, cefoperazone, cefotaxime, cefpodoxime, ceftazidime, ceftibuten, ceftizoxime and ceftriaxone. In an exemplary embodiment, the additional therapeutic agent is cefepime. In an exemplary embodiment, the additional therapeutic agent is ceftobiprole. In an exemplary embodiment, the additional therapeutic agent is a member selected from teicoplanin and vancomycin. In an exemplary embodiment, the additional therapeutic agent is a member selected from azithromycin, clarithromycin, dirithromycin, erythromycin, roxithromycin, troleandomycin, telithromycin and spectinomycin. In an exemplary embodiment, the additional therapeutic agent is aztreonam. In an exemplary embodiment, the additional therapeutic agent is a member selected from amoxicillin, ampicillin, azlocillin, carbenicillin, cloxacillin, dicloxacillin, flucloxacillin, mezlocillin, meticillin, nafcillin, oxacillin, penicillin, piperacillin and ticarcillin. In an exemplary embodiment, the additional therapeutic agent is a member selected from bacitracin, colistin and polymyxin B. In an exemplary embodiment, the additional therapeutic agent is a member selected from ciprofloxacin, enoxacin, gatifloxacin, levofloxacin, lomefloxacin, moxifloxacin, norfloxacin, ofloxacin and trovafloxacin. In an exemplary embodiment, the additional therapeutic agent is a member selected from mafenide, prontosil, sulfacetamide, sulfamethizole, sulfanilimide, sulfasalazine, sulfisoxazole, trimethoprim and sulfamethoxazole. In an exemplary embodiment, the additional therapeutic agent is a member selected from demeclocycline, doxycycline, minocycline, oxytetracycline and tetracycline. In an exemplary embodiment, the additional therapeutic agent is a member selected from arsphenamine, chloramphenicol, lincomycin, ethambutol, fosfomycin, fusidic acid, furazolidone, isoniazid, linezolid, metronidazole, mupirocin, nitrofurantoin, platensimycin, pyrazinamide, quinupristin, rifampin and tinidazole.

The compounds of the invention, or pharmaceutical formulations thereof may also be used in combination with other therapeutic agents, for example immune therapies [e.g. interferon, such as interferon alfa-2a (ROFERON®-A; Hoffmann-La Roche), interferon alpha-2b (INTRON®-A; Schering-Plough), interferon alfacon-1 (INFERGEN®; Intermune), peginterferon alpha-2b (PEGINTRON™; Schering-Plough) or peginterferon alpha-2a (PEGASYS®; Hoffmann-La Roche)], therapeutic vaccines, antifibrotic agents, anti-inflammatory agents [such as corticosteroids or NSAIDs], bronchodilators [such as beta-2 adrenergic agonists and xanthines (e.g. theophylline)], mucolytic agents, anti-muscarinics, anti-leukotrienes, inhibitors of cell adhesion [e.g. ICAM antagonists], anti-oxidants [e.g. N-acetylcysteine], cytokine agonists, cytokine antagonists, lung surfactants and/or antimicrobial. The compositions according to the invention may also be used in combination with gene replacement therapy.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the patient ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient.

III.d) Additional Compounds of the Invention

Additional compounds of the invention include those formed between the 2',3' diol of the ribose ring of a nucleic acid, nucleoside or nucleotide, and a compound described herein or according to a formula described herein. In an exemplary embodiment, the compound is a cyclic or acyclic boronic ester such as those described herein. These compounds can be used in an animal to kill or inhibit the growth of a microorganism described herein, as well as to treat the diseases described herein. These compounds can be formed in vitro as well as in vivo. Methods of making these compounds are provided in the Examples section.

In another aspect, the invention provides a compound having a structure according to the following formula:

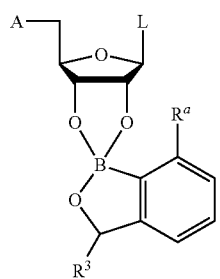

(XII)

wherein $R^a$ and $R^3$ are as described herein. L is a member selected from $OR^7$, substituted or unsubstituted purine, substituted or unsubstituted pyrimidine, substituted or unsubstituted pyridine and substituted or unsubstituted imidazole. $R^7$ is a member selected from H, substituted or unsubstituted alkyl, substituted or unsubstituted heteroalkyl, substituted or unsubstituted cycloalkyl, substituted or unsubstituted aryl and substituted or unsubstituted heteroaryl. A is a member selected from OH, substituted or unsubstituted monophosphate, substituted or unsubstituted diphosphate, substituted or unsubstituted triphosphate,

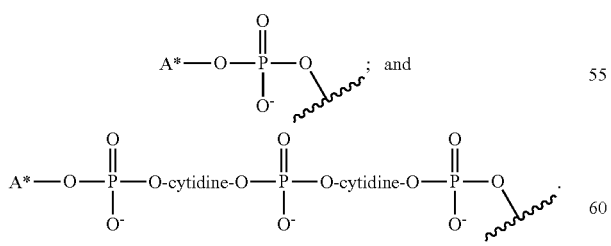

A* is a nucleic acid sequence which comprises between 1 and 100 nucleotides.

In an exemplary embodiment, the compound has a structure according to the formula:

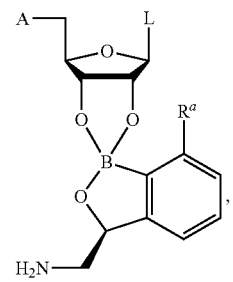

wherein $R^a$, L and A are as described herein.

In an exemplary embodiment, the compound has a structure which is a member selected from:

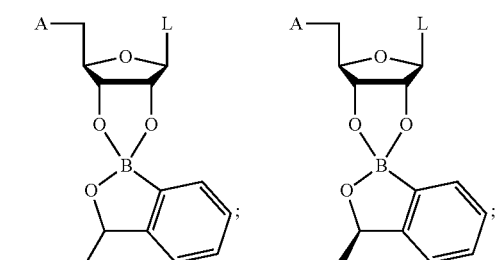

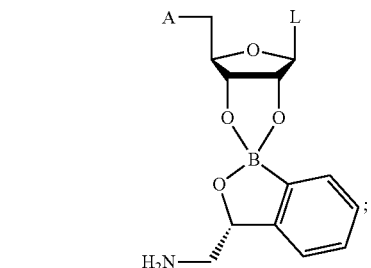

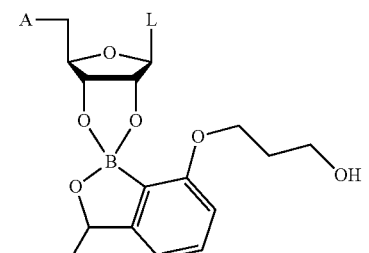

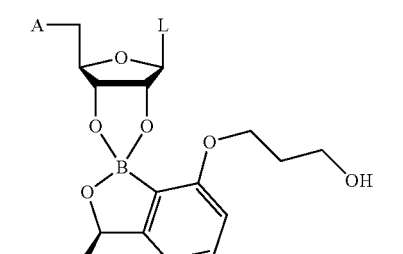

and

-continued

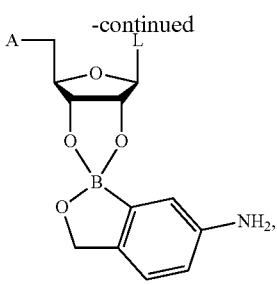

wherein L and A are as described herein. In an exemplary embodiment, the compound has a structure which is a member selected from

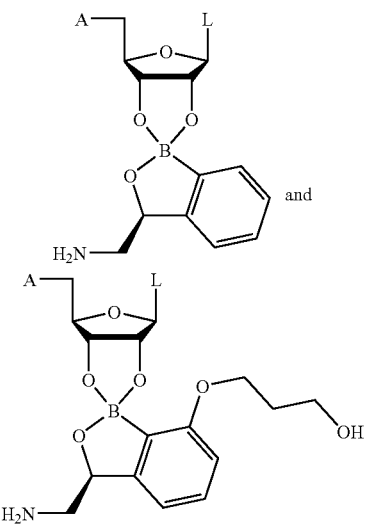

wherein L and A are as described herein.

III.e) Formulations with Keratin

When a compound of the invention is applied to a nail component of a human, the compound absorbs or penetrates into the nail. The human nail is primarily composed of keratin (i.e. hair keratin or α-keratin) as well as trace amounts of lipid components. Therefore, in the process of treating a disease of the nail or killing or inhibiting the growth of a microorganism, a formulation comprising a human nail unit and a compound of the invention is formed.

In another aspect, the invention provides a formulation comprising: (a) a compound of the invention; and (b) a keratin containing component of an animal. In an exemplary embodiment, the compound of the invention is a compound described herein, or a pharmaceutically acceptable salt thereof. In an exemplary embodiment, the compound of the invention a compound described in a formula provided herein. In an exemplary embodiment, the compound of the invention is a compound described herein. In an exemplary embodiment, the keratin containing component of an animal is a member selected from an animal nail unit, skin and hair. In an exemplary embodiment, the compound of part (a) contacts the component of part (b). In an exemplary embodiment, the animal is a human. In an exemplary embodiment, the keratin containing component is a nail plate of the human nail unit. In an exemplary embodiment, the keratin containing component is a nail bed of the human nail unit. In an exemplary embodiment, the keratin containing component is a proximal nail fold of the human nail unit. In an exemplary embodiment, the keratin containing component is a lateral nail fold of the human nail unit. In another exemplary embodiment, the human nail unit comprises a member selected from keratin and lipid. In another exemplary embodiment, keratin is a member selected from skin keratin and nail/hair keratin. In another exemplary embodiment, lipid is a member selected from cholesterol sulfate, cerebroside, ceramide, free sterol, free fatty acids, triglycerides, sterol esters, wax esters, and squalene.

In an exemplary embodiment, the compound is present in the formulation at a concentration which is a member selected from about 0.001%, about 0.01%, about 0.05%, about 0.1%, about 0.5%, about 1%, about 1.5%, about 2%, about 2.5%, about 3%. In another exemplary embodiment, the keratin is present in said formulation at a concentration which is a member selected from about 99.99%, about 99.95%, about 99.90%, about 99.5%, about 99.0%, about 98.5%, about 98.0%, about 97.5% and about 97%. In another exemplary embodiment, the compound of the invention is a compound described herein, or a pharmaceutically acceptable salt thereof. In another exemplary embodiment, the compound is described herein. In another exemplary embodiment, a compound which is a member selected from

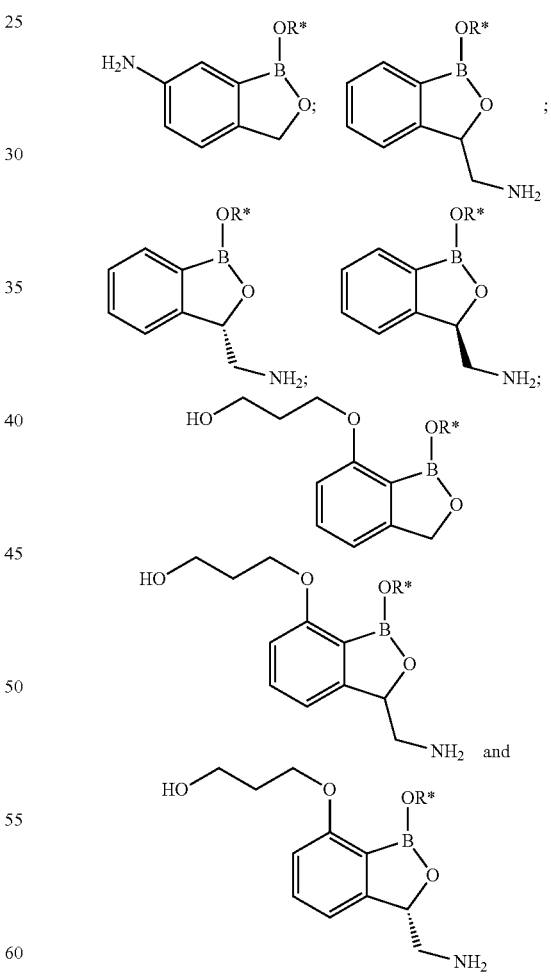

is present is said formulation at a concentration which is a member selected from about 0.001%, about 0.01%, about 0.05%, about 0.1%, about 0.5%, about 1%, and about 1.5%.

In another aspect, the invention provides a method of forming this formulation, wherein said method comprises applying said compound to a formulation comprising keratin, thereby forming said formulation. In an exemplary embodiment, the formulation comprising keratin is a human nail unit. In an exemplary embodiment, the formulation comprising keratin is a member selected from a nail plate, nail bed, proximal nail fold, and lateral nail fold. Methods of making these formulations are described in the Examples section.

It is to be understood that the present invention covers all combinations of aspects and/or embodiments, as well as suitable, convenient and preferred groups described herein.

III.f) Preparation of Boron-Containing Editing Domain Inhibitors

Compounds of use in the present invention can be prepared using commercially available starting materials, known intermediates, or by using the synthetic methods published in references described and incorporated by reference herein, such as U.S. Pat. Pubs. US20060234981, US20070155699 and US20070293457.

The following general procedures were used as indicated in generating the examples and can be applied, using the knowledge of one of skill in the art, to other appropriate compounds to obtain additional analogues.

General Procedure 1: Sulfonylation of Amino 3H-benzo[c][1,2]oxaborol-1-ols

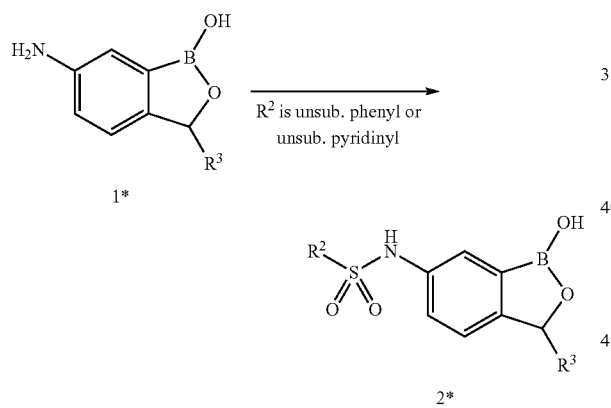

Through subjecting it to sulfonylation conditions, compound 1* can be converted to compound 2*.

In some applications of this general procedure, unsubstituted phenyl or unsubstituted pyridinyl sulfonyl chloride (1-1.2 equiv) and a base (such as NMM, $K_2CO_3$, or pyridine 3-4 equiv) were added sequentially to a solution of the amine in MeCN (20 mL/g) at rt. After completion (typical duration O/N) the volatiles were removed in vacuo. $H_2O$ was added to the residue and the mixture adjusted to ~pH 6 with dilute HCl. The aqueous layer was then extracted with an organic solvent (such as EtOAc), and the combined organic fractions dried with a desiccant, such as $Na_2SO_4$ or $MgSO_4$, filtered, and concentrated in vacuo. The product was typically purified by either recrystallization from $H_2O$, trituration with $CH_2Cl_2$ or EtOAc, or flash chromatography.

General Procedure 2: Deprotection of Benzyl Protected Alcohols or Thiols

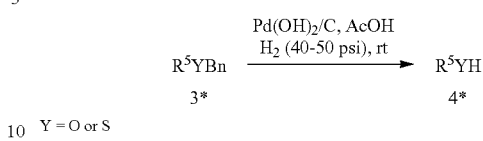

Y = O or S

Through subjecting it to deprotection conditions, compound 3* can be converted to compound 4*.

A mixture of the benzylated alcohol or thiol (1 equiv) and 20% $Pd(OH)_2$ on carbon (50% weight-wet, 1:2 w/w substrate to catalyst) in glacial AcOH (10 mL/g) was shaken under an atmosphere of $H_2$ (40-50 psi) in a Parr shaker. Once the reaction was complete (TLC), the mixture was filtered through Celite. The filtrate was concentrated in vacuo and the remaining AcOH was removed by co-evaporation with toluene (3×) to give the alcohol. Further purification was carried out by flash chromatography or preparative HPLC as required.

General Procedure 3: Phenol or Thiophenol Alkylation using Mitsunobu Conditions

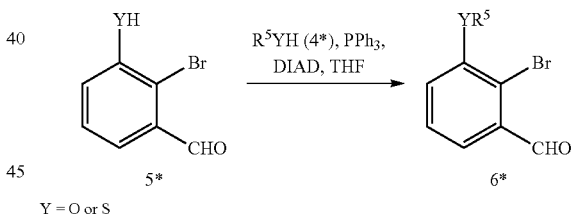

Y = O or S

Through subjecting it to Mitsunobu conditions, compound 5* can be converted to compound 6*.

DIAD (1 equiv) was added to a solution of the phenol or thiophenol (1 equiv) and $PPh_3$ (1 equiv) in anhydrous THF (200 mL/7 g phenol). The mixture was stirred at rt until the reaction was complete (as determined by TLC). The mixture was then concentrated in vacuo. $Et_2O$ was added to the residue and the mixture was then concentrated in vacuo. $Et_2O$ was added again and the precipitate that formed was removed by filtration. The filtrate was extracted with 2 N NaOH and $H_2O$. The organic layer was dried ($Na_2SO_4$) and concentrated in vacuo. The residue was further purified by flash chromatography.

General Procedure 4: Phenol or Thiophenol Alkylation with Alkyl Bromides and Alkyl Mesylates

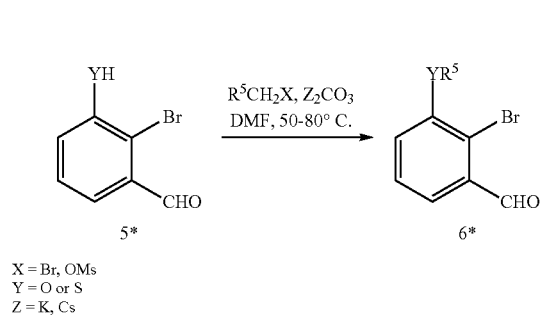

X = Br, OMs
Y = O or S
Z = K, Cs

A solution of the alkyl halide or mesylate (1-1.5 equiv), 2-bromo-3-hydroxy-benzaldehyde or 2-bromo-3-mercapto-benzaldehyde (1 equiv), and a base, such as $K_2CO_3$ (1-1.2 equiv) or $Cs_2CO_3$ (1.5-2 equiv), in an aprotic solvent such as DMF was stirred at 50-80° C. (bath temp) until the reaction was complete (typically O/N). The reaction mixture cooled to rt, diluted with $H_2O$, and extracted with a solvent such as EtOAc. The organic fractions were washed with $H_2O$ then brine, dried with a desiccant, such as $MgSO_4$, and concentrated in vacuo. Further purification was performed by flash chromatography if required.

General Procedure 5: Borylation of Aryl Halides and Triflates

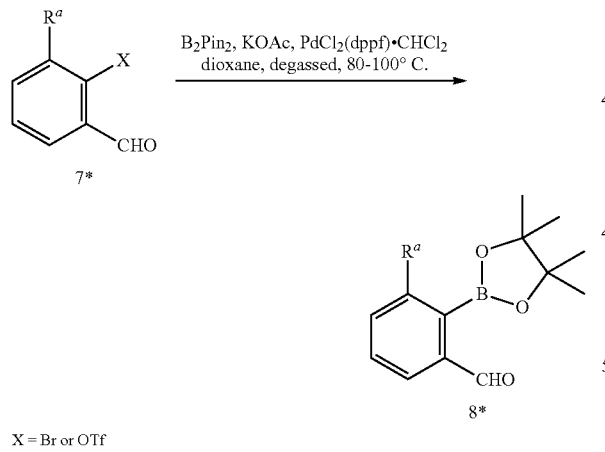

X = Br or OTf

Through subjecting it to borylation conditions, compound 7* can be converted to compound 8*.

A solution of aryl bromide or triflate in anhydrous 1,4-dioxane (20 mL/1 g) was added $B_2pin_2$ (2 equiv) and KOAc (3 equiv) at rt, then degassed with $N_2$ for 10 to 40 min. $PdCl_2$(dppf).$CH_2Cl_2$ (4-8 mol %) was added and the resulting solution was stirred at 80-100° C. until the reaction was complete (2 to 16 h). The solution was cooled to rt and diluted with EtOAc. The organic layer was then washed with $H_2O$ then brine, dried ($Na_2SO_4$), filtered, and concentrated in vacuo. The product was typically purified by flash chromatography.

General Procedure 6: Borylation of Phenols or Thiophenols via their Aryl Triflates

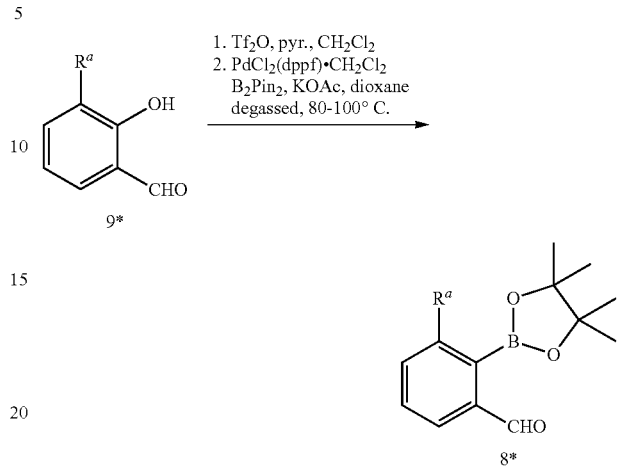

Through subjecting it to borylation conditions, compound 9* can be converted to compound 8*.

Trifluoromethanesulfonic anhydride (1.2 equiv) was added dropwise to a solution of pyridine (1.2 equiv) and the phenol in $CH_2Cl_2$ (40 mL/8.6 g) at 0° C. (bath temp). The reaction mixture was then allowed to warm to rt and was stirred until complete consumption of starting material (as determined by TLC). $Et_2O$ and 2 N HCl were then added. The organic layer was separated and washed with sat. $NaHCO_3$ then brine. The organic layer was dried ($Na_2SO_4$) and filtered through a short silica gel plug, washing with $Et_2O$. The filtrate was concentrated in vacuo to give the desired triflate that was used directly in general procedure 5.

General procedure 7: Ring Closure of Substituted 2-(4,4,5,5-Tetramethyl-[1,3,2]dioxaborolan-2-yl)-benzaldehydes

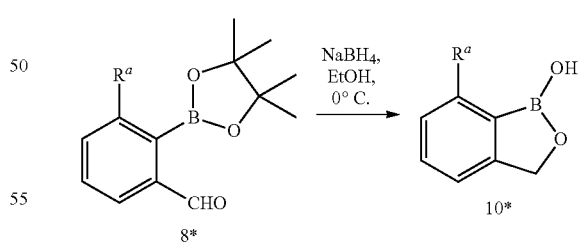

Through subjecting it to ring closure conditions, compound 8* can be converted to compound 10*.

$NaBH_4$ (1.5 equiv) was added portionwise to an ice-cold solution of the aldehyde in alcohol (typically absolute EtOH or anhydrous MeOH (c=0.1 M). The reaction was allowed to warm to rt and monitored by TLC. The mixture was then acidified to ~pH 3 using a 1 N $NaHSO_4$ or 2 M HCl and stirred O/N. The precipitate was collected by filtration, washed repeatedly with H₂O and dried in vacuo. Further purification was carried out by flash chromatography when required.

General procedure 8: Henry Reaction of Substituted 2-(4,4,5,5-Tetramethyl-[1,3,2]dioxaborolan-2-yl)-benzaldehydes

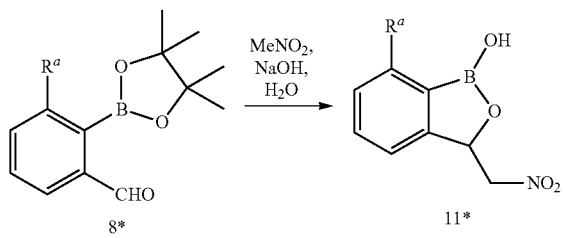

Through subjecting it to Henry reaction conditions, compound 8* can be converted to compound 11*.

NaOH aq. (1.0 equiv) was added to the aldehyde (either in H₂O or THF) at rt and the reaction mixture was stirred at rt for 5 min. MeNO₂ (3 equiv) was added dropwise and the mixture was stirred at rt for 16 h. The reaction mixture was acidified with 2 N HCl and extracted with EtOAc. The organic fraction was washed with H₂O then brine, dried (MgSO₄), and concentrated in vacuo. Purification was typically accomplished by either flash chromatography or precipitation from the acidified reaction mixture.

General Procedure 9: Henry Reaction using Phase Transfer Catalyst of Substituted 2-(4,4,5,5-Tetramethyl-[1,3,2]dioxaborolan-2-yl)-benzaldehydes

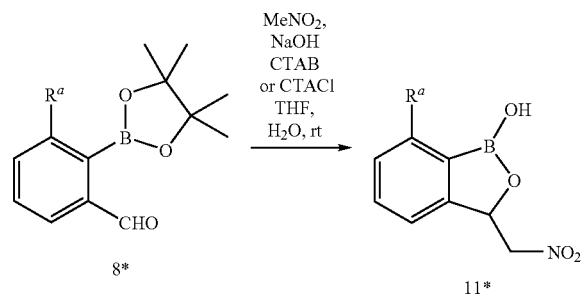

CTAB or CTACl (5 mol %) was added to a mixture of MeNO₂ and aldehyde, in aq. NaOH, and THF (1 mL/300 mg aldehyde) at rt. The reaction was monitored by TLC. Upon completion (typically 1-1.5 h), the mixture was adjusted to pH 2-3 using 2 N HCl or 1 M NaHSO₄ and the mixture was then stirred for 30 min. The solid was filtered and dried to afford the desired nitro compound which was used directly in next step. If there was no precipitation, the organic material was extracted from the reaction mixture with EtOAc. The organic fraction was then dried (MgSO₄) and concentrated in vacuo. The residue was purified by flash chromatography.

General Procedure 10: Reduction of Alkyl Nitro and/or Alkyl Nitrile compounds to N-Boc Protected Amines

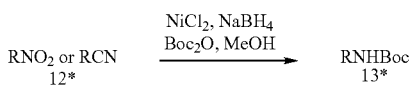

Through subjecting it to reducing conditions, compound 12* can be converted to compound 13*.

Boc₂O (2 equiv) and NiCl₂·6H₂O (1 equiv) were added to a stirred solution of the alkyl nitro or alkyl nitrile in anhydrous MeOH (3 mL/mmol) at rt. Stirring was continued until most of the NiCl₂ had dissolved in MeOH (typically ~10 min). The reaction mixture was then cooled to 0° C. (bath temp) and NaBH₄ (6 equiv) was added portionwise over 10 min. The reaction was exothermic, effervescent, and resulted in the formation of a finely divided black precipitate. The reaction mixture was allowed to warm to rt and left to stir O/N. The mixture was then concentrated in vacuo and the residue was diluted with EtOAc. The resulting suspension was filtered through Celite and the filtrate was concentrated in vacuo. The residue was then further purified by flash chromatography if required.

General Procedure 11: Deprotection of Boc-protected Amines

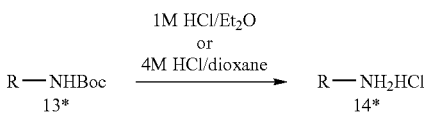

Through subjecting it to deprotection conditions, compound 13* can be converted to compound 14*.

A mixture of the N-Boc protected amine and either 1 M HCl in Et₂O or 4 M HCl in dioxane (2 mL/mmol) was stirred at rt. After the complete consumption of starting material (monitored by TLC, typically 3-16 h), the mixture was concentrated in vacuo and the crude residue was triturated with Et₂O and filtered. If necessary, the final product was purified by preparative HPLC.

General Procedure 12: Reduction of Alkyl Nitro and/or Alkyl Nitrile using Raney Nickel

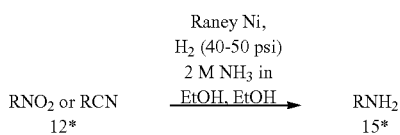

Through subjecting it to reducing conditions, compound 12* can be converted to compound 15*.

A mixture of the 3-nitromethyl-3H-benzo[c][1,2]oxaborol-1-ol, Raney Ni (2 equiv w/w), 2.0 M NH₃ in EtOH (5 mL/1 g), and absolute EtOH (20 mL/1 g) was shaken under an atmosphere of H₂ (40-50 psi) for 3 h at rt. The resultant mixture was filtered through a pad of Celite and washed with EtOH. The filtrate was concentrated in vacuo to give the free amine.

General Procedure 13: Reduction of Substituted-3-nitromethyl-3H-benzo[c][1,2]oxaborol-1-ols using Pearlman's Catalyst

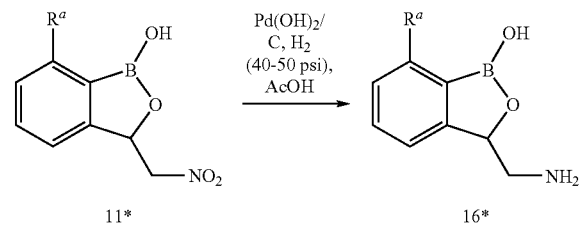

Through subjecting it to reducing conditions, compound 11* can be converted to compound 16*.

A mixture of the 3-nitromethyl-3H-benzo[c][1,2]oxaborol-1-ol (1 equiv) and 20% Pd(OH)$_2$ on carbon (50% weight-wet, 1:2 w/w substrate to catalyst) in glacial AcOH (10 mL/g) was shaken under an atmosphere of H$_2$ (45-50 psi) in a Parr shaker. Once the reaction was complete (TLC), the mixture was filtered through Celite. The filtrate was concentrated in vacuo to give a gummy material. The remaining AcOH was removed by co-evaporation with toluene (3×) to give the amine, typically as a fluffy solid. Purification was accomplished by preparative HPLC.

General Procedure 14: Synthesis of Substituted (S)-3-(aminomethyl)-3-methylbenzo[c][1,2]oxaborol-1(3H)-ol hydrochloride (A??)

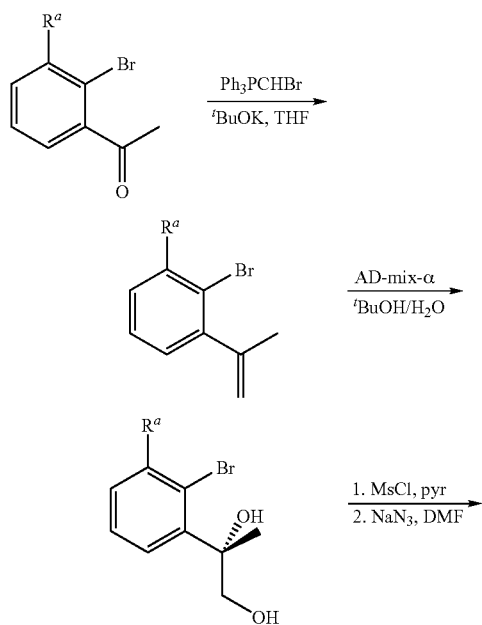

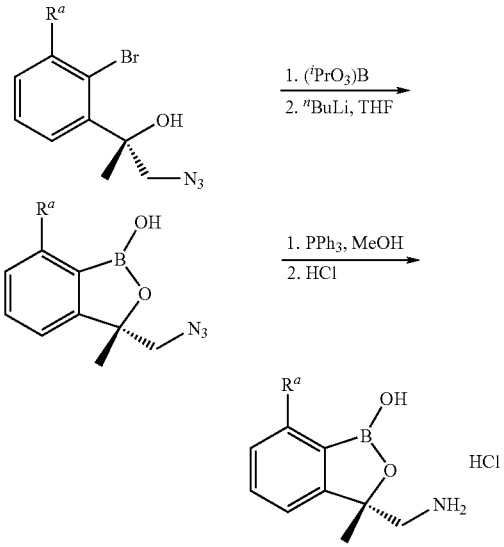

To a suspension of methyltriphenyl phosphonium bromide (1.2 eq) in THF at room temperature is added KOtBu (1.2 eq) in portions. After being stirred for 5 min, the reaction mixture is treated with appropriately substituted 2'bromoacetophenone (1 eq). The reaction mixture is stirred for 3 hrs at room temperature then quenched with saturated ammonium chloride. The quenched mixture is then extracted 3× with Et$_2$O and the combined organic layers are washed with brine, dried over MgSO$_4$ and evaporated under vacuum. The layers are then purified by silica gel chromatography to give substituted 1-bromo-2-(prop-1-en-2-yl)benzene.

The mixture is then is dissolved in a biphasic mixture of water and tBuOH and cooled to 0° C. Substituted 1-bromo-2-(prop-1-en-2-yl)benzene is added and the heterogeneous mixture is stirred at 0° C. for 18 hrs, quenched with sodium sulfate, warmed to room temperature and stirred for an additional hour. The quenched mixture is then extracted 5× with DCM and the combined organic layers are dried over MgSO$_4$ and evaporated under vacuum. Purified by silica gel chromatography to give substituted (S)-2-(2-bromophenyl)propane-1,2-diol.

Substituted (S)-2-(2-bromophenyl)propane-1,2-diol is dissolved in pyridine (1 eq) and cooled to 0° C. before the addition of methanesulphonyl chloride (1 eq). The reaction mixture is allowed to warm to room temperature and stirred for 2 hrs. The pyridine is removed under vacuum and the residue portioned between DCM and aqueous NaHCO$_3$. The organic layer is dried over MgSO$_4$ and evaporated under vacuum to give the crude mesylate. This material is combined with NaN$_3$ (4.5 eq), dissolved in DMF and heated to 80° C. for 18 hrs. Water is added and extracted 3× with Et$_2$O. The combined organic layers are washed with brine, dried over MgSO$_4$ and evaporated under vacuum. Next the mixture is purified by silica gel chromatography to give substituted (S)-1-azido-2-(2-bromophenyl)propan-2-ol.

Substituted (S)-1-azido-2-(2-bromophenyl)propan-2-ol (1 eq) and triisopropyl borate (1.2 eq) are dissolved in 20 eq of toluene. The reaction mixture is refluxed with a Dean/Stark apparatus to remove the toluene and the residue is dissolved in 17 eq of dry THF. This solution is cooled to −78° C. and BuLi (25M in Hexanes, 1.15 eq) is added dropwise and stirred for 30 min. The reaction mixture is warmed to room temperature and allowed to stir for 3 hrs before being quenched with 6M HCl and concentrated under vacuum. This is extracted 3× with DCM. The combined organic layers are dried over MgSO$_4$ and evaporated under vacuum. Next the mixture is purified by silica gel chromatography to give substituted (S)-3-(azidomethyl)-3-methylbenzo[c][1,2]oxaborol-1(3H)-ol.

Substituted (S)-3-(azidomethyl)-3-methylbenzo[c][1,2]oxaborol-1(3H)-ol (1 eq) and triphenyl phosphine (2 eq) are dissolved in acetonitrile. After 5 min concentrated hydrochloric acid (2 eq) is added and the reaction mixture stirred for 24 hrs at room temperature before being concentrated under vacuum. The residue is taken up in DCM and washed 3× with 2M HCl. The combined aqueous layers are evaporated to dryness under vacuum. The resulting solid is washed with EtOH and filtered to remove byproducts, concentrated and crystallized from acetonitrile to give substituted (S)-3-(aminomethyl)-3-methylbenzo[c][1,2]oxaborol-1(3H)-ol hydrochloride as a white solid.

General Procedure for Chiral HPLC Separation of Enantiomers

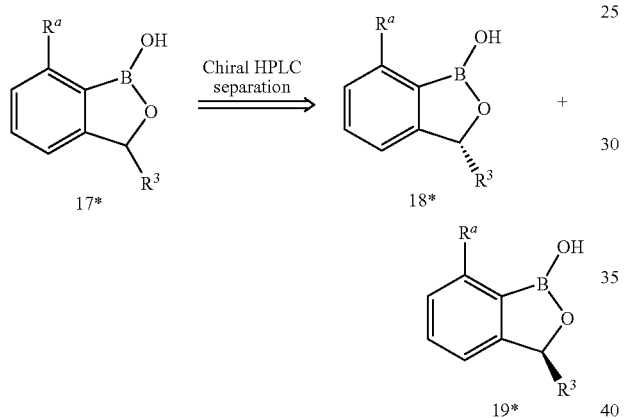

Through subjecting it to chiral HPLC separation conditions, compound 17* can be separated into enantiomers 18* and 19*.

The separation of the two enantiomers was achieved by dissolving the material in a suitable solvent and applying to an appropriate chiral column and eluent system. The collected separated enantiomer samples were then concentrated and used in the next step without further purification. Using this technique, it is possible to achieve a range of enantiomeric excesses of the separated enantiomers.

General Procedure for Chiral Synthesis of 3-aminomethylbenzoxaboroles

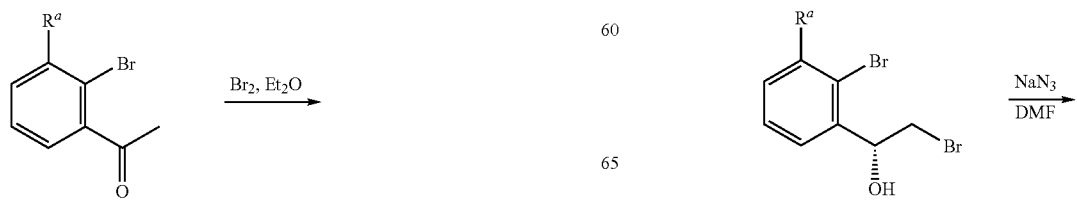

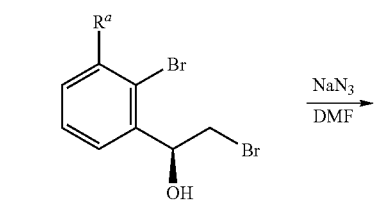

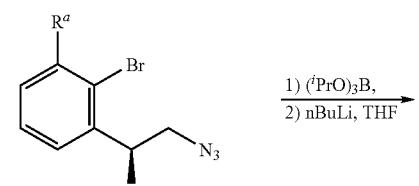

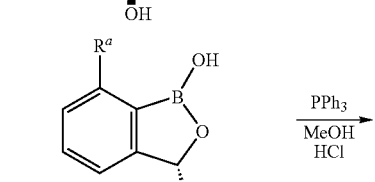

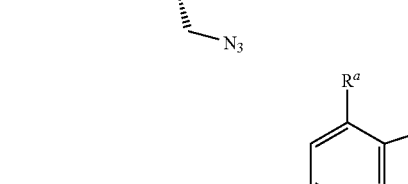

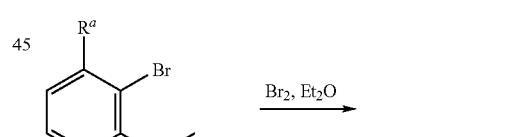

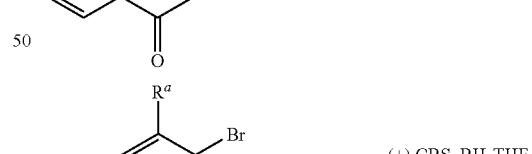

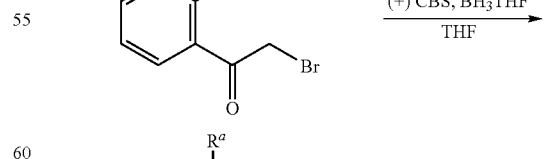

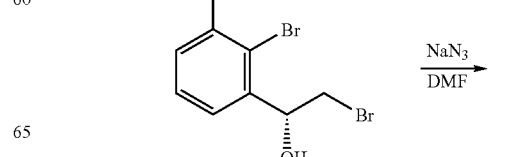

-continued

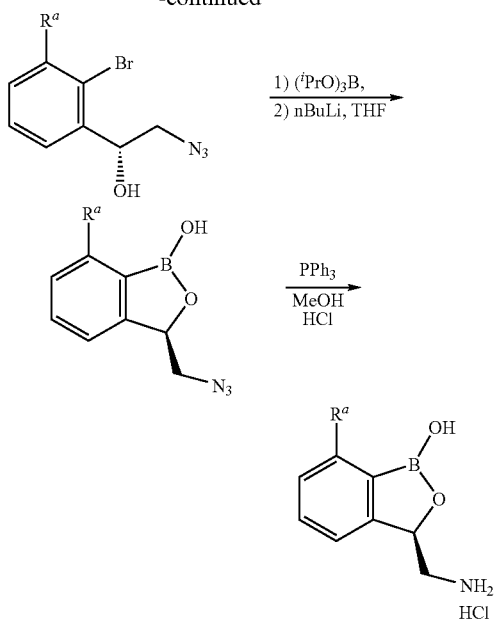

The direct stereospecific synthesis of 3-aminomethylbenzoxaboroles can be achieved starting from the 5- or 6-substituted 2-bromoacetophenone. Bromine (1.0 eq) is added slowly to appropriately substituted 2'-bromoacetophenone (1.0 eq) in diethyl ether at room temperature and stirred for 2 hours. Water is added and the reaction mixture stirred until the color fades. The phases are separated and the aqueous layer extracted with diethyl ether. The combined organic phases are washed with brine, dried over $MgSO_4$, filtered and concentrated under reduced pressure to give substituted 2-bromo-1-(2-bromophenyl)ethanone. (R)-(+)-2-Methyl-CBS-oxazaborolidine [For R-isomer] or (S)-(−)-2-Methyl-CBS-oxazaborolidine [For S-isomer] (0.11 eq) is added to a stirred solution of substituted 2-bromo-1-(2-bromophenyl)ethanone (1.0 eq) in THF. The reaction mixture is cooled to −10° C. where $BH_3$-THF (1.0 M in THF, 1.20 eq) is added over 4 hours. The reaction mixture is stirred for a further 45 minutes at −10° C. before the addition of methanol (130 mL). The reaction mixture is concentrated under reduced pressure. The resultant residue is subjected to flash column chromatography to provide the substituted chiral 2-bromo-1-(2-bromophenyl)ethanol. To a solution of this alcohol (1.00 eq) in DMF is added sodium azide at room temperature. The reaction mixture is then heated to 8° C. for 24 hours. Water (150 mL) is added and this solution is extracted with diethyl ether. The combined organic phases are washed with brine (50 mL), dried over $MgSO_4$, filtered and concentrated under reduced pressure. The residue is subjected to flash column chromatography to yield the substituted 2-azido-1-(2-bromophenyl) ethanol. To a solution of this material (1.00 eq) in toluene is added triisopropyl borate (1.50 eq). The reaction flask is equipped with a Dean and Stark condenser attached and the reaction mixture is refluxed to remove approximately ¾ of the volume of solvent. The dark reaction mixture is cooled to room temperature where THF is added and then cooled to −78° C. n-Butyl lithium (2.5 M in hexanes, 1.15 eq) is added dropwise to the reaction mixture at −78° C. and then stirred for 30 minutes at this temperature. The reaction mixture is then allowed to warm to room temperature where it is stirred for 3 hours before being quenched with 6 M HCl (30 mL). The reaction mixture is concentrated under reduced pressure and the resulting residue is subjected to flash column chromatography to give the substituted 3-(azidomethyl)benzo[c][1,2] oxaborol-1(3H)-ol.

To a solution of this compound (1.0 eq) in methanol is added triphenylphosphine (1.0 eq) and this is stirred for 3 hours at room temperature. Concentrated HCl is added and the reaction mixture stirred for a further 2 hours before being concentrated to dryness under reduced pressure. Dichloromethane is added and extracted with 2 M HCl. The combined aqueous layers are washed with dichloromethane before being contracted under reduced pressure. The residue is then recrystalised from hot water/acetonitrile (3 mL water/ 50-80 mL acetonitrile per gram of compound) to give the substituted chiral (R or S) 3-(aminomethyl)benzo[c][1,2]oxaborol-1(3H)-ol as the hydrochloride salt.

Compounds described herein can be converted into hydrates and solvates by methods similar to those described herein.

IV. Assays for Inhibitors of tRNA Synthetase Editing Domains

Art-recognized techniques of genetics and molecular biology are of use to identify compounds that bind to and/or inhibit the editing domain of a tRNA synthetase. Moreover, these techniques are of use to distinguish whether a compound binds to and/or inhibits the synthetic domain, the editing domain, or both the editing and synthetic domains.

In an exemplary assay, activity of a representative compound against the editing domain was confirmed. To identify the target of the novel boron-containing antibacterial compound (A1), mutants in E. coli showing resistance to compound (A1) were isolated. Characterization of mutants showed that they have an 32-256 fold increase in resistance to (A1) over wildtype. The mutants were furthermore shown to be sensitive to various antibacterial agents with known modes of action, suggesting that the cellular target of (A1) is distinct from the target of the other antibacterial agents. The leus gene from the mutants was cloned onto a plasmid and their resistance was confirmed by MIC. The editing domain from these mutants were sequenced and the mutations were all located in the editing domain of this enzyme.

Assays to determine whether, and how effectively, a particular compound binds to and/or inhibits the editing domain of a selected tRNA synthetase are also set forth herein, and additional assays are readily available to those of skill in the art. Briefly, in an exemplary assay, an improperly charged tRNA and a tRNA synthetase that is capable of editing the improperly charged tRNA are combined. The resulting mixture is contacted with the putative inhibitor and the degree of editing inhibition is observed.

Another assay uses genetics to show that a drug works via the editing domain. In this assay, the compound is first tested against a strain of cells over-expressing copies of the tRNA synthetase gene. The compound's effect on the over-expressing strain is compared with a control strain to determine whether the compound is active against the synthetase. If the minimum inhibitory concentration (MIC) is 2-fold higher in the strain with extra copies of the synthetase gene than the MIC of the inhibitor against a wild type cell, a further genetic screen is conducted to determine whether the increased resistance is due to mutations in the editing domain. In this second screen, the control strain is challenged against a high concentration of the inhibitor. The colonies surviving the challenge are isolated and DNA from these cells is isolated. The editing domain is amplified using a proof-reading PCR enzyme and the appropriate primers. The PCR product can be purified using standard procedures. The sequence amplified mutant DNA is compared to wild-type. If the mutant DNA bears mutations in the editing domain, such results would suggest that the compound binds to the editing domain and affects the editing function of the molecule through this domain.

The assays set forth above are useful in essentially any microbial system, e.g., bacterial, fungal, parasitic, viral and the like.

Generally, the compounds to be tested are present in the assays in ranges from about 1 µM to about 100 mM, preferably from about 1 µM to about 1 µM. Other compounds range from about 1 nM to about 100 nM, preferably from about 1 nM to about 1 µM.

The effects of the test compounds upon the function of the enzymes can also be measured by any suitable physiological change. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

High throughput screening (HTS) is also of use in identifying promising candidates of the invention.

Utilizing the assays set forth herein and others readily available in the art, those of skill in the art will be able to readily and routinely determine other compounds and classes of compounds that operate to bind to and/or inhibit the editing domain of tRNA synthetases.

In another aspect, the invention provides a method for identifying a compound which binds to an editing domain of a tRNA synthetase comprising: a) contacting said editing domain with a test compound under conditions suitable for binding; and b) detecting binding of said test compound to said editing domain. In an exemplary embodiment, detecting binding of said compound comprises use of at least one detectable element, isotope, or chemical label attached to said compound. In an exemplary embodiment, the element, isotope or chemical label is detected by a fluorescent, luminescent, radioactive, or absorbance readout. In an exemplary embodiment, the contacting of said test compound with said editing domain also includes further contacting said test compound and said editing domain with a member selected from AMP and a molecule with a terminal adenosine. In an exemplary embodiment, said tRNA synthetase is derived from a member selected from alanyl tRNA synthetase, isoleucyl tRNA synthetase, leucyl tRNA synthetase, methionyl tRNA synthetase, lysyl tRNA synthetase, phenylalanyl tRNA synthetase, prolyl tRNA synthetase, threonyl tRNA synthetase and valyl tRNA synthetase. In an exemplary embodiment, the tRNA synthetase is derived from leucyl tRNA synthetase. In an exemplary embodiment, the tRNA synthetase is derived from a mutated tRNA synthetase, wherein said mutated tRNA synthetase comprises amino acid mutations in an editing domain. In another exemplary embodiment, wherein said editing domain of a tRNA synthetase comprises the amino acid sequence of a peptide sequence described herein.

In another aspect, the invention provides a method for identifying a compound which binds to an editing domain of a tRNA synthetase, said assay comprising: a) contacting said editing domain of a tRNA synthetase with said compound under conditions suitable for binding of said compound with said editing domain of a tRNA synthetase; b) comparing a biological activity of said editing domain of a tRNA synthetase contacting said compound to said biological activity when not contacting said compound; and c) identifying said compound as binding to said editing domain of a tRNA synthetase if said biological activity of said editing domain of a tRNA synthetase is reduced when contacting said compound.

In an exemplary embodiment, the biological activity is hydrolysis of noncognate amino acid. In another exemplary embodiment, the hydrolysis of said noncognate amino acid is detected through the use of one or more labels. In another exemplary embodiment, the labels include a radiolabel, a fluorescent marker, an antibody, or a combination thereof. In another exemplary embodiment, said labels can be detected using spectroscopy. In another exemplary embodiment, the editing domain of a tRNA synthetase is derived from a member selected from alanyl tRNA synthetase, isoleucyl tRNA synthetase, leucyl tRNA synthetase, methionyl tRNA synthetase, lysyl tRNA synthetase, phenylalanyl tRNA synthetase, prolyl tRNA synthetase, threonyl tRNA synthetase and valyl tRNA synthetase. In another exemplary embodiment, said editing domain of a tRNA synthetase is derived from leucyl tRNA synthetase.

In another aspect, the invention provides a method of generating tRNA molecules with noncognate amino acid comprising: a) creating or isolating a mutated tRNA synthetase with altered amino acid editing domains; and b) contacting a tRNA molecule with said mutated tRNA synthetase and a noncognate amino acid. In another exemplary embodiment, the mutated tRNA synthetase contains one or more amino acid mutations in an editing domain. In another exemplary embodiment, the mutated tRNA synthetase is unable to bind with a compound of the invention. In another exemplary embodiment, the mutated tRNA synthetase is unable to bind with a compound described herein, or a pharmaceutically acceptable salt thereof. In another exemplary embodiment, the mutated tRNA synthetase is unable to bind with a compound according to a formula described herein, or a pharmaceutically acceptable salt thereof. In another exemplary embodiment, the compound of the invention is a member selected from

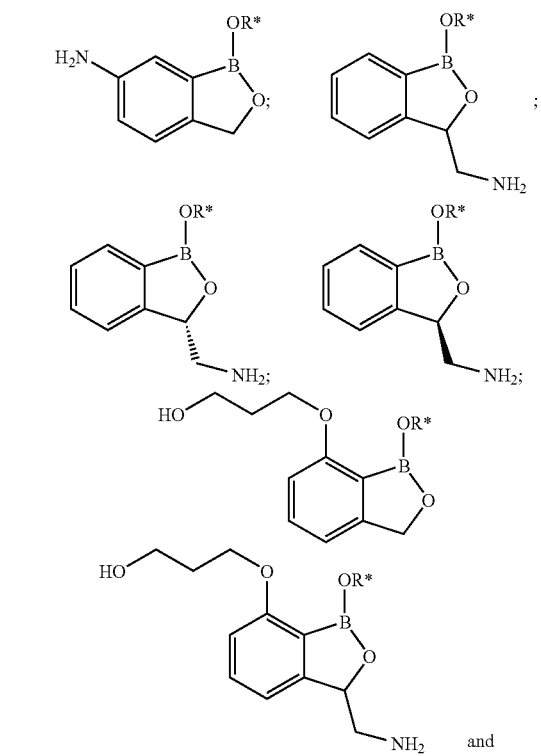

-continued

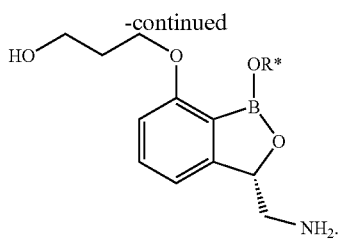

In an exemplary embodiment, the compound is a member selected from

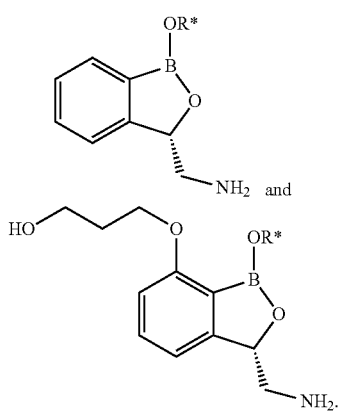

In another exemplary embodiment, R* is H.

In another aspect, the invention provides a composition that comprises one or more tRNA molecules attached to noncognate amino acids, wherein said tRNA molecules are synthesized using one or more mutated tRNA synthetases isolated from a microorganism or a cell line derived from a microorganism. In an exemplary embodiment, the microorganism is a bacteria. In an exemplary embodiment, wherein said mutated tRNA synthetases contain amino acid mutations in their editing domains.

V. Amino Acid and Nucleotide Sequences Used in Assays tRNA Sequences that Interact with the tRNA Synthetase-compound of the Invention-AMP Complex Transfer RNAs (tRNAs) translate mRNA into a protein on a ribosome. Each transfer RNA contains an anti-codon region that hybridizes with mRNA, and an amino acid which may be attached to the growing peptide. The structural gene of tRNA is about 72 to 90 nucleotides long and folds into a cloverleaf structure (Sharp S. J., Schaack J., Coolen L., Burke D. J. and Soll D., "Structure and transcription of eukaryotic tRNA genes", Crit. Rev. Biochem, 19:107 144 (1985); Geiduschek E. O., and Tocchini-Valentini, "Transcription by RNA polymerase III", Annu. Rev. Biochem. 57:873 914 (1988)).

In one embodiment, a compound described herein contacts AMP and a tRNA synthetase, and the tRNA synthetase in turn contacts a tRNA molecule. In another embodiment, a compound described herein contacts AMP from the tRNA molecules and a tRNA synthetase. The nucleotide sequence of the tRNA molecule can be determined by the identity of the tRNA synthetase involved. For example, for leucyl tRNA synthetase, the cognate tRNA molecule bound will be tRNA-leucine (SEQ ID NO: 1), but a noncognate tRNA, such as isoleucine, (SEQ ID NO: 2) may be bound under certain conditions. In another embodiment, the tRNA molecule is a leucyl t-RNA. In another embodiment, the tRNA molecule is represented by a SEQ ID described herein. In another embodiment, the tRNA molecule is represented by SEQ ID NO: 14, SEQ ID NO:15, SEQ ID NO:16, SEQ ID NO:17, SEQ ID NO:18, SEQ ID NO: 19, SEQ ID NO:20, SEQ ID NO:21, SEQ ID NO:22, SEQ ID NO:23 and SEQ ID NO:24. In this and other embodiments, the term "noncognate" is meant to encompass both the singular and plural forms of the word, i.e. the phrase "noncognate amino acid" comprises one or more amino acids. In the following sequences; s4U=s$^4$U; 4-thiouridine; Gm=methylguanine; Y=pyrimidine; ms2i6A=ms$^2$i$^6$A; 2-methylthio-N-6-isopentenyl adenosine and D=dihydrouridine.

SEQ ID NO: 1 corresponds to the nucleotide sequence of the tRNA-Leu gene from *Saccharomyces cerevisiae*: gggagtttgg ccgagtggtt taaggcgtca gatttaggct ctgatatctt cggat-gcaagggttcgaatc ccttagctct cacca SEQ ID NO: 2 corresponds to the nucleotide sequence of the tRNA-Ile gene from *Saccharomyces cerevisiae*: gaaac-tataa ttcaattggt tagaatagta ttttgataag gtacaaatat aggttcaatc cct-gttagtt tcatcca SEQ ID NO: 14 corresponds to the nucleotide sequence of a tRNA-Leu gene from *E. coli*:

gcgaaggtggcggaattggtagacgcgctagcttcaggtgttagtgtcct tacggacgtggggttcaagtcccccccctcgcacca SEQ ID NO: 15 corresponds to the nucleotide sequence of a tRNA-Leu gene from *E. coli*:

gcgggagtggcgaaattggtagacgcaccagatttaggttctggcgccgc aaggtgtgcgagttcaagtctcgcctcccgcacca SEQ ID NO: 16 corresponds to the nucleotide sequence of a tRNA-Leu gene from *E. coli*:

gccgaagtggcgaaatcggtagacgcagttgattcaaaatcaaccgtaga aatacgtgccggttcgagtccggccttcggcacca SEQ ID NO: 17 corresponds to the nucleotide sequence of a tRNA-Leu gene from *E. coli*:

gccgaggtggtggaattggtagacacgctaccttgaggtggtagtgccca atagggcttacgggttcaagtcccgtcctcggtacca SEQ ID NO: 18 corresponds to the nucleotide sequence of a tRNA-Leu gene from *E. coli*:

gcccggatggtggaatcggtagacacaagggatttaaaatccctcggcgt tcgcgctgtgcgggttcaagtcccgctccgggtacca SEQ ID NO: 19 corresponds to the nucleotide sequence of a tRNA-Leu gene from *E. coli*:

GCCCGGAs4UGGUGGAADCGmGDAGACACAAGGGAYUunkAAAms2i6AAY

CCCUCGGCGUUCGCGCUGUGCGGGTYCAAGUCCCGCUCCGGGUACCA

SEQ ID NO: 20 corresponds to the nucleotide sequence of a tRNA-Leu gene from *E. coli*:

```
GCGAAGGUGGCGGAADDGmGDAGACGCGCUAGCUUCAGunkGYGYUAGU

GUCCUUACGGACGUGGGGGTYCAAGUCCCCCCCCUCGCACCA
```

SEQ ID NO: 21 corresponds to the nucleotide sequence of a tRNA-Leu gene from *E. coli*:

```
GCCGAGGUGGUGGAADDGmGDAGACACGCUACCUUGAGunkGYGGUAGU

GCCCAAUAGGGCUUACGGGTYCAAGUCCCGUCCUCGGUACCA
```

SEQ ID NO: 22 corresponds to the nucleotide sequence of a tRNA-Leu gene from *Pseudomonas aeruginosa*

```
gcggacgtggtggaattggtagacacactggatttaggttccagcgccg caaggcgtgagagttcgagtctctccgtccgcacca
```

SEQ ID NO: 23 corresponds to the nucleotide sequence of a tRNA-Leu gene from *Staphylococcus aureus*

```
gccggggtggcggaactggcagacgcacaggacttaaaatcctgcggtg agagatcaccgtaccggttcgattccggtcctcggcacca
```

SEQ ID NO: 24 corresponds to the nucleotide sequence of a tRNA-Leu gene from *Staphylococcus aureus*

```
gccggggtggcggaactggcagacgcacaggacttaaaatcctgcggtg agtgatcaccgtaccggttcgattccggtcctcggcacca
```

Polypeptides Used in Binding and Inhibition Assays

In some binding and inhibition assays, it is more effective to use a portion of a tRNA synthetase molecule rather than the whole protein itself. In such assays, polypeptides derived from tRNA synthetases are used in the experiment.

In one preferred embodiment, polypeptide fragments corresponding to the editing domain of a tRNA synthetase molecule are used in assay and binding experiments. Such fragments are represented by SEQ ID NO:3, SEQ ID NO:4, SEQ ID NO:5, SEQ ID NO:6 and SEQ ID NO:7. In an exemplary embodiment, the fragments are represented by SEQ ID NO:5, SEQ ID NO:6 and SEQ ID NO:7.

SEQ ID NO 3:

```
TPQEYIGVKIEALEFADDAAKIIDSSSDLDKSKKFYFVAATLRPETMYG

QTCCFVSPTIEYGIFDAGDSYFITTERAFKNMSYQKLTPKRGFYKPIVT

VPGKAFIGTKIHAPQSVYPELRILPMETVIATKGTGVVTCVPSNSPDDY

ITTKDLLHKPEYYGIKPEWIDHEIVPIMHTEKYGDLTAKAIVEEKKIQS

PKDKNLLAEAKKIAYKEDYYTGTMIYGPYKGEKVEQAKNKVKADMIAAG

EAFVYNEPESQDP
```

SEQ ID NO 4:

```
MTPQEYIGVKIEALEFADDAAKIIDSSSDLDKSKKFYFVAATLRPETMY

GQTCCFVSPTIEYGIFDAGDSYFITTERAFKNMSYQKLTPKRGFYKPIV

TVPGKAFIGTKIHAPQSVYPELRILPMETVIATKGTGVVTCVPSNSPDD

YITTKDLLHKPEYYGIKPEWIDHEIVPIMHTEKYGDLTAKAIVEEKKIQ

SPKDKNLLAEAKKIAYKEDYYTGTMIYGPYKGEKVEQAKNKVKADMIAA

GEAFVYNEPESQDPQDPNSSSVDKLAAALEHHHHH
```

SEQ ID NO 5:

```
TCTPEYYRWEQKFFTELYKKGLVYKKTSAVNWCPNDQTVLANEQVIDGC

CWRCDTKVERKEIPQWFIKITAYADELLNDLDKLDHWPDTVKTMQRNWI

GRSEGVEITFNVNDYDNTLTVYTTRPDTFMGCTYLAVAAGHPLAQKAAE

NNPELAAFIDECRNTKVAEAEMATMEKKGVDTGFKAVHPLTGEEIPVWA

ANFVLMEYGTGAVMAVPGHDQRDYEFASKYGLNIKPVILAADGSEPDLS

QQALTEKGVLFNSGEFNGLDHEAAFNAIADKLTAMGVGERKVNYRLRDW

GVSRQRYWG
```

SEQ ID NO 6:

```
TCKPDYYRWEQWLFTRLFEKGVIYRKNGTVNWDPADQTVLANEQVIDGR

GWRSGALIEKREIPMYYFRITDYADELLESLDELPGWPEQVKTMQRNWI

GKSRGMEVQFPYDQASIGHEGTLKVFTTRPDTLMGATYVAVAAEHPLAT

QAAQGNAALQAFIDECKSGSVAEADMATQEKKGMATSLFVEHPLTGEKL

PVWVANYVLMHYGDGAVMAVPAHDERDFEFAHKYNLPVKAVVRTSAGDD

VGSEWLAAYGEHGQLINSGEFDGLDFQGAFDAIEAALIRKDLGKSRTQF

RLRDWGISRQRYWG
```

SEQ ID NO 7:

```
TTDPEYYKWTQWIFIQLYNKGLAYVDEVAVNWCPALGTVLSNEEVIDGV

SERGGHPVYRKPMKQWVLKITEYADQLLADLDDLDWPESLKDMQRNWIG

RSEGAKVSFDVDNTEGKVEVFTTRPDTIYGASFLVLSPEHALVNSITTD

EYKEKVKAYQTEASKKSDLERTDLAKDKSGVFTGAYAINPLSGEKVQIW

IADYVLSTYGTGAIMAVPAHDDRDYEFAKKFDLLIIEVIEGGNVEEAAY

TGEGKHINSGELDGLENEAAITKAIQLLEQKGAGEKKVYKLRDWLFSRQ

RYWG
```

SEQ ID NO 8 corresponds to a peptide sequence for a leu-tRNA synthetase editing domain for *Escherichia coli*

```
GRSEGVEITFNVNDYDNTLTVYTTRPDTFMGCTYLAVAAGHPLAQKAAE

NNPELAAFIDECRNTKVAEAEMATMEKKGVDTGFKAVHPLTGEEIPVWA

ANFVLMEYGTGAVMAVPGHDQRDYEFASKYGLNIKPVILAADGSEPDLS

QQALTEKGVLFNSGEFNGLDHEAAFNAIADKLTAMGVGERKVNYR
```

SEQ ID NO 9 corresponds to a peptide sequence for a leu-tRNA synthetase editing domain for *Pseudomonas*

```
GKSRGMEVQFPYDQASIGHEGTLKVFTTRPDTLMGATYVAVAAEHPLAT

QAAQGNAALQAFIDECKSGSVAEADMATQEKKGMATSLFVEHPLTGEKL

PVWVANYVLMHYGDGAVMAVPAHDERDFEFAHKYNLPVKAVVRTSAGDD

VGSEWLAAYGEHGQLINSGEFDGLDFQGAFDAIEAALIRKDLGKSRTQF

R
```

SEQ ID NO 10 corresponds to a peptide sequence for a leu-tRNA synthetase editing domain for *Staphylococcus aureus*

GRSEGAKVSFDVDNTEGKVEVFTTRPDTIYGASFLVLSPEHALVNSITT

DEYKEKVKAYQTEASKKSDLERTDLAKDKSGVFTGAYAINPLSGEKVQI

WIADYVLSTYGTGAIMAVPAHDDRDYEFAKKFDLLIIEVIEGGNVEEAA

YTGEGKHINSGELDGLENEAAITKAIQLLEQKGAGEKKVYK

In one preferred embodiment, polypeptides corresponding to a tRNA synthetase molecule are used in assay and binding experiments. Such polypeptides are represented by SEQ ID NO:11, SEQ ID NO:12 and SEQ ID NO:13.

SEQ ID NO 11 corresponds to a peptide sequence for a leu-tRNA synthetase for *Escherichia coli*

MQEQYRPEEIESKVQLHWDEKRTFEVTEDESKEKYYCLSMLPYPSGRLH

MGHVRNYTIGDVIARYQRMLGKNVLQPIGWDAFGLPAEGAAVKNNTAPA

PWTYDNIAYMKNQLKMLGFGYDWSRELATCTPEYYRWEQKFFTELYKKG

LVYKKTSAVNWCPNDQTVLANEQVIDGCCWRCDTKVERKEIPQWFIKIT

AYADELLNDLDKLDHWPDTVKTMQRNWIGRSEGVEITFNVNDYDNTLTV

YTTRPDTFMGCTYLAVAAGHPLAQKAAENNPELAAFIDECRNTKVAEAE

MATMEKKGVDTGFKAVHPLTGEEIPVWAANFVLMEYGTGAVMAVPGHDQ

RDYEFASKYGLNIKPVILAADGSEPDLSQQALTEKGVLFNSGEFNGLDH

EAAFNAIADKLTAMGVGERKVNYRLRDWGVSRQRYWGAPIPMVTLEDGT

VMPTPDDQLPVILPEDVVMDGITSPIKADPEWAKTTVNGMPALRETDTF

DTFMESSWYYARYTCPQYKEGMLDSEAANYWLPVDIYIGGIEHAIMHLL

YFRFFHKLMRDAGMVNSDEPAKQLLCQGMVLADAFYYVGENGERNWVSP

VDAIVERDEKGRIVKAKDAAGHELVYTGMSKMSKSKNNGIDPQVMVERY

GADTVRLFMMFASPADMTLEWQESGVEGANRFLKRVWKLVYEHTAKGDV

AALNVDALTENQKALRRDVHKTIAKVTDDIGRRQTFNTAIAAIMELMNK

LAKAPTDGEQDRALMQEALLAVVRMLNPFTPHICFTLWQELKGEGDIDN

APWPVADEKAMVEDSTLVVVQVNGKVRAKITVPVDATEEQVRERAGQEH

LVAKYLDGVTVRKVIYVPGKLLNLVVG

SEQ ID NO 12 corresponds to a peptide sequence for a leu-tRNA synthetase for *Pseudomonas*

MHEQYTPRDVEAAAQNAWDEQQSFAVTEQPGKETYYCLSMFPYPSGKLH

MGHVRNYTIGDVIARYQRMLGKNVLQPMGWDAFGMPAENAAMKNNVAPA

KWTYENIDYMKTQLKSLGLAIDWSREVTTCKPDYYRWEQWLFTRLFEKG

VIYRKNGTVNWDPADQTVLANEQVIDGRGWRSGALIEKREIPMYYFRIT

DYADELLESLDELPGWPEQVKTMQRNWIGKSRGMEVQFPYDQASIGHEG

TLKVFTTRPDTLMGATYVAVAAEHPLATQAAQGNAALQAFIDECKSGSV

AEADMATQEKKGMATSLFVEHPLTGEKLPVWVANYVLMHYGDGAVMAVP

AHDERDFEFAHKYNLPVKAVVRTSAGDDVGSEWLAAYGEHGQLINSGEF

DGLDFQGAFDAIEAALIRKDLGKSRTQFRLRDWGISRQRYWGCPIPIIH

CPSCGDVPVPEDQLPVTLPENVVPDGAGSPLARMPEFYECTCPKCGTAA

KRETDTMDTFVESSWYFARYASPNYDKGLVDPKAANHWLPVDQYIGGIE

HAILHLLYARFFHKLMRDEGLVTSNEPFKNLLTQGMVVAETYYRVASNG

GKDWFNPADVEIERDAKAKIIGARLKTDGLPVEIGGTEKMSKSKNNGVD

PQSMIEQYGADTCRLFMMFASPPDMSLEWSDSGVEGASRFLRRVWRLAQ

AHVAQGLPGQLDIAALSDEQKVIRRAIHAAIKQASTDVGQFHKFNTAIA

QVMTVMNVLEKAPQVTAQDRALLQEGLEAVTLLLAPITPHISHELWKQL

GHEQAVIDATWPSVDESALVQDTVTLVVQVNGKLRGQVEMPAAASREEI

EAAARNNENVLRFTDGLTIRKVIVVPGKLVNIVAN

SEQ ID NO 13 corresponds to a peptide sequence for a leu-tRNA synthetase for *Staphylococcus aureus*

MNYNHNQIEKKWQDYWDENKTFKTNDNLGQKKFYALDMFPYPSGAGLHV

GHPEGYTATDIISRYKRMQGYNVLHPMGWDAFGLPAEQYALDTGNDPRE

FTKKNIQTFKRQIKELGFSYDWDREVNTTDPEYYKWTQWIFIQLYNKGL

AYVDEVAVNWCPALGTVLSNEEVIDGVSERGGHPVYRKPMKQWVLKITE

YADQLLADLDDLDWPESLKDMQRNWIGRSEGAKVSFDVDNTEGKVEVFT

TRPDTIYGASFLVLSPEHALVNSITTDEYKEKVKAYQTEASKKSDLERT

DLAKDKSGVFTGAYAINPLSGEKVQIWIADYVLSTYGTGAIMAVPAHDD

RDYEFAKKFDLLIIEVIEGGNVEEAAYTGEGKHINSGELDGLENEAAIT

KAIQLLEQKGAGEKKVNYKLRDWLFSRQRYWGEPIPVIHWEDGTMTTVP

EEELPLLLPETDEIKPSGTGESPLANIDSFVNVVDEKTGMKGRRETNTM

PQWAGSCWYYLRYIDPKNENMLADPEKLKHWLPVDLYIGGVEHAVLHLL

YARFWHKVLYDLGIVPTKEPFQKLFNQGMILGEGNEKMSKSKGNVINPD

DIVQSHGADTLRLYEMFMGPLDAAIAWSEKGLDGSRRFLDRVWRLIVNE

DGTLSSKIVTTNNKSLDKVYNQTVKKVTDDFETLGFNTAISQLMVFINE

CYKVDEVYKPYIEGFVKMLAPIAPHIGEELWSKLGHEESITYQPWPTYD

EALLVDDEVEIVVQVNGKLRAKIKIAKDTSKEEMQEIALSNDNVKASIE

GKDIMKVIAVPQKLVNIVAK

VI. Methods for Inhibiting an Enzyme

The compounds of the invention can be utilized to inhibit an enzyme. In an exemplary embodiment, the compounds of the invention exhibit the ability of inhibiting the editing domain of tRNA synthetases, such as leucyl tRNA synthetase, of microorganisms, such as bacteria, and therefore have the potential to be used as editing domain inhibitors of microorganism tRNA synthetases.

According to another aspect of the invention, a method for binding to and/or inhibiting the editing domain of a tRNA synthetase is provided which comprises contacting a tRNA synthetase with a compound of the invention that inhibits the editing domain under conditions in which the tRNA synthetase interacts with its substrate to form an aminoacyl adenylate intermediate and, preferably, to form a charged tRNA. Such conditions are known to those skilled in the art. In an exemplary embodiment, the compound is described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the invention provides a compound described herein, or a salt thereof. The tRNA synthetase is contacted with an amount of compound of the invention sufficient to result in a detectable amount of tRNA synthetase inhibition. This method can be performed on a tRNA synthetase that is contained within an organism or which is outside an organism. In an exemplary embodiment, the method is performed on a tRNA synthetase that is contained within a microorganism or a microbial cell that is in, or on the surface of, an animal. In an exemplary embodiment, the animal is a human. The method results in a decrease in the amount of charged tRNA produced by the tRNA synthetase that has an inhibited editing domain. In an exemplary embodiment, the inhibition takes place in a cell, such as a microbial cell. In another exemplary embodiment, the microbial cell is a bacteria, fungus, yeast or parasite. In another exemplary embodiment, the tRNA synthetase is a mitochondrial tRNA synthetase or a cytoplasmic tRNA synthetase. In another exemplary embodiment, the tRNA synthetase is a member selected from alanyl tRNA synthetase, isoleucyl tRNA synthetase, leucyl tRNA synthetase, methionyl tRNA synthetase, lysyl tRNA synthetase, phenylalanyl tRNA synthetase, prolyl tRNA synthetase, threonyl tRNA synthetase and valyl tRNA synthetase. In another exemplary embodiment, the tRNA synthetase is leucyl tRNA synthetase.

In an exemplary embodiment, the invention provides a method of inhibiting conversion of a tRNA molecule into a charged tRNA molecule. The method involves contacting a tRNA synthetase with a compound of the invention effective to inhibit activity of an editing domain of said tRNA synthetase, under conditions sufficient to inhibit said activity, thereby inhibiting said conversion. In an exemplary embodiment, the compound of the invention is a compound described herein, or a pharmaceutically acceptable salt thereof. In an exemplary embodiment, the inhibition occurs within a cell, and the cell is a microbial cell. In another exemplary embodiment, the microbial cell is a member selected from a bacteria, fungus, yeast, and parasite. In an exemplary embodiment, the tRNA synthetase is a member selected from a mitochondrial tRNA synthetase and a cytoplasmic tRNA synthetase. In another exemplary embodiment, the tRNA synthetase is a member selected from alanyl tRNA synthetase, isoleucyl tRNA synthetase, leucyl tRNA synthetase, methionyl tRNA synthetase, lysyl tRNA synthetase, phenylalanyl tRNA synthetase, prolyl tRNA synthetase, threonyl tRNA synthetase and valyl tRNA synthetase. In another exemplary embodiment, the tRNA synthetase is leucyl tRNA synthetase. In another exemplary embodiment, the compound has a $K_{D, synthesis}$ of greater than 100 µM against a synthetic domain of said tRNA synthetase.

In certain embodiments, the mechanism of action of a compound of the invention is to inhibit the conversion of a tRNA molecule into a charged tRNA molecule by binding to and/or inhibiting at least the editing domain of the synthetase. The compounds of use in this method may also inhibit or otherwise interact with the synthetic domain (e.g., the active site of the synthetic domain). In a presently preferred embodiment, the editing domain is inhibited selectively in the presence of the synthetic domain. In a preferred embodiment, the synthetic domain is essentially uninhibited, while the editing domain is inhibited at least 50%, preferably at least 60%, more preferably at least 70%, still more preferably, at least 80% and even still more preferably at least 90% of the activity of the tRNA synthetase. In another preferred embodiment, the synthetic domain is inhibited by at most 50%, preferably at most 30%, preferably at most 20%, 10%, preferably at most 8%, more preferably at most 5%, still more preferably, at most 3% and even still more preferably at most 1%. Inhibition of the editing domain produces a decrease in the amount of the properly charged tRNA which results in retardation or cessation of cell growth and division.

In another exemplary embodiment, the ratio of a minimum concentration of said compound inhibiting said editing domain to a minimum concentration of said compound inhibiting said synthetic domain of said tRNA synthetase, represented as $K_{D, edit}/K_{D, synthesis}$, is less than one. In another exemplary embodiment, the $K_{D, edit} K_{D, synthesis}$ of the compound is a member selected from less than 0.5, less than 0.1 and less than 0.05.

VII. Methods of Inhibiting Microorganism Growth or Killing Microorganisms

The compounds of the present invention exhibit potency against microorganisms, such as bacteria, and therefore have the potential to kill and/or inhibit the growth of microorganisms.

In a further aspect, the invention provides a method of killing and/or inhibiting the growth of a microorganism, said method comprising: contacting said microorganism with an effective amount of a compound of the invention, thereby killing and/or inhibiting the growth of the microorganism. In an exemplary embodiment, the microorganism is a member selected from a bacteria, fungus, virus, yeast or parasite. In an exemplary embodiment, the compound is described herein, or a salt, prodrug, hydrate or solvate thereof, or a combination thereof. In an exemplary embodiment, the invention provides a compound described herein, or a salt, hydrate or solvate thereof. In an exemplary embodiment, the invention provides a compound described herein, or a prodrug thereof. In an exemplary embodiment, the invention provides a compound described herein, or a salt thereof. In another exemplary embodiment, the compound of the invention is a compound described herein, or a pharmaceutically acceptable salt thereof. In another exemplary embodiment, the compound is described by a formula listed herein, or a pharmaceutically acceptable salt thereof. In an exemplary embodiment, the compound is part of a pharmaceutical formulation described herein. In another exemplary embodiment, the contacting occurs under conditions which permit entry of the compound into the organism. In an exemplary embodiment, the compound inhibits the tRNA synthetase through the editing domain of the synthetase. Such conditions are known to one skilled in the art and specific conditions are set forth in the Examples appended hereto. This method involves contacting a microbial cell with a therapeutically-effective amount of an editing domain inhibitor to inhibit tRNA synthetase in vivo or in vitro. In another exemplary embodiment, the compound is a member selected from

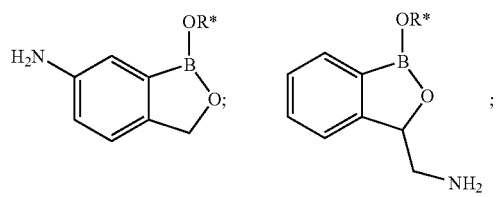

-continued

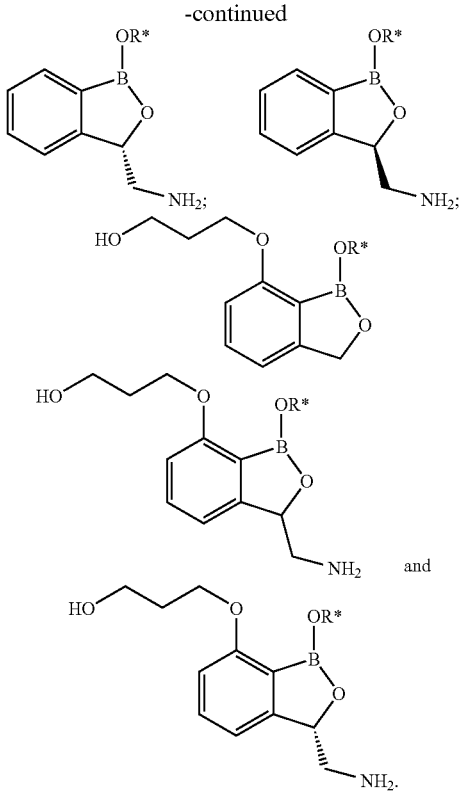

In an exemplary embodiment, the compound is a member selected from

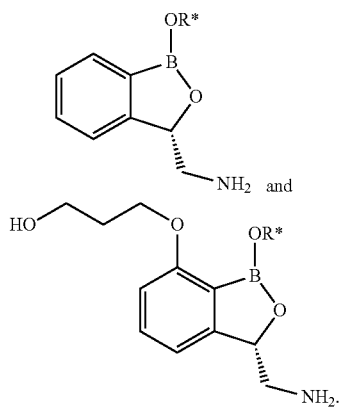

In another exemplary embodiment, R* is H.

In another aspect, the microorganism is inside, or on the surface of an animal. In an exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism is killed or its growth is inhibited through oral administration of the compound of the invention. In an exemplary embodiment, the microorganism is killed or its growth is inhibited through intravenous administration of the compound of the invention.

In an exemplary embodiment, the microorganism is a bacterium. In an exemplary embodiment, the bacterium is a gram-positive bacteria. In another exemplary embodiment, the gram-positive bacterium is a member selected from *Staphylococcus* species, *Streptococcus* species, *Bacillus* species, *Mycobacterium* species, *Corynebacterium* species (*Propionibacterium* species), *Clostridium* species, *Actinomyces* species, *Enterococcus* species and *Streptomyces* species. In another exemplary embodiment, the gram-positive bacterium is a member selected from *Propionibacterium acnes; Staphylococcus aureus; Staphylococcus epidermidis, Staphylococcus saprophyticus; Staphylococcus haemolyticus; Streptococcus pyogenes; Streptococcus agalactiae; Streptococcus pneumoniae; Enterococcus faecalis; Enterococcus faecium; Bacillus anthracis; Mycobacterium avium-intracellulare; Mycobacterium tuberculosis, Acinetobacter baumanii; Corynebacterium diphtheria; Clostridium perfringens; Clostridium botulinum; Clostridium tetani; Clostridium difficile*. In another exemplary embodiment, the gram-positive bacterium is a member selected from *Staphylococcus aureus, Staphylococcus epidermidis, Streptococcus pneumoniae, Streptococcus pyogenes, Enterococcus faecalis, Enterococcus faecium, Clostridium difficile* and *Propionibacter acnes*. In another exemplary embodiment, the bacterium is a gram-negative bacterium. In another exemplary embodiment, the gram-negative bacterium is a member selected from *Acinetobacter* species, *Neisseria* species, *Pseudomonas* species, *Brucella* species, *Agrobacterium* species, *Bordetella* species, *Escherichia* species, *Shigelia* species, *Yersinia* species, *Salmonella* species, *Klebsiella* species, *Enterobacter* species, *Haemophilus* species, *Pasteurella* species, *Streptobacillus* species, *spirochetal* species, *Campylobacter* species, *Vibrio* species, *Helicobacter* species, *Bacteroides* species, *Citrobacter* species, *Proteus* species, *Providencia* species, *Serratia* species, *Stenotrophomonas* species and *Burkholderia* species. In another exemplary embodiment, the gram-negative bacterium is a member selected from *Acinetobacter* species, *Pseudomonas* species, *Escherichia* species, *Klebsiella* species, *Enterobacter* species, *Bacteroides* species, *Citrobacter* species, *Proteus* species, *Providencia* species, *Serratia* species, *Stenotrophomonas* species and *Burkholderia* species. In another exemplary embodiment, the gram-negative bacterium is a member selected from *Neisseria gonorrhoeae; Neisseria meningitidis; Pseudomonas aeruginosa; Legionella pneumophila; Escherichia coli; Yersinia pestis; Haemophilus influenzae; Helicobacter pylori; Campylobacter fetus; Campylobacter jejuni; Vibrio cholerae; Vibrio parahemolyticus; Trepomena pallidum; Actinomyces israelii; Rickettsia prowazekii; Rickettsia rickettsii; Chlamydia trachomatis; Chlamydia psittaci; Brucella abortus; Agrobacterium tumefaciens; Francisella tularensis, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia* and *Burkholderia cepacia*. In another exemplary embodiment, the gram-negative bacterium is a member selected from *Pseudomonas aeruginosa; Escherichia coli; Haemophilus influenzae, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia* and *Burkholderia cepacia*.

In another exemplary embodiment, the bacterium is a *Pseudomonas* species. In another exemplary embodiment, the bacterium is *Pseudomonas aeruginosa*. In another exemplary embodiment, the bacterium is a member selected from Pseudomonas aeruginosa; Acinetobacter baumannii, Stenotrophomonas maltophilia and Burkholderia cepacia. In another exemplary embodiment, the bacterium is Acinetobacter species. In another exemplary embodiment, the bacterium is Acinetobacter anitratus. In another exemplary embodiment, the bacterium is a member selected from Enterobacter aerogenes, Enterobacter cloacae, Enterobacter sakazakii, E. coli, K. pneumoniae, P. mirabilis, Serratia marcescens, Citrobacter freundii and Providencia spp. In another exemplary embodiment, the bacterium is a member selected from Enterobacter aerogenes, Enterobacter cloacae, Enterobacter sakazakii, E. coli, K. pneumoniae, P. mirabilis, Serratia marcescens, Citrobacter freundii, Providencia spp., S. aureus, S. pneumonia, S. pyogenes, E. faecalis, and E. faecium. In another exemplary embodiment, the bacterium is a member selected from Viridans group Strep. In another exemplary embodiment, the bacterium is a member selected from Strep. mitis, Strep. mutans, Strep. oralis, Strep. sanguis, Strep. sobrinus and Strep. millari. In another exemplary embodiment, the bacterium is a member selected from S. pneumonia, H. influenzae, S. aureus, M. catarrhalis, M. pneumoniae, L. pneumoniae and C. pneumoniae. In another exemplary embodiment, the bacterium is S. aureus. In another exemplary embodiment, the bacterium is an anaerobe. In another exemplary embodiment, the bacterium is an Alcaligenes species. In another exemplary embodiment, the bacterium is a B. cepacia. In another exemplary embodiment, the bacterium is a member selected from Enterobacter cloacae, Escherichia coli; Klebsiella pneumoniae, Proteus mirabilis, Providencia stuartii, Serratia marcescens, and Citrobacter freundii. In another exemplary embodiment, the bacterium is resistant to methicillin. In another exemplary embodiment, the bacterium is methicillin-resistant staphylococcus aureus. In another exemplary embodiment, the bacterium is a member selected from Streptococcus pneumoniae; Haemophilus influenzae; Staphylococcus aureus; Mycobacterium catarrhalis; Mycobacterium pneumoniae; Legionella pneumophila and Chlamydia pneumoniae. In another exemplary embodiment, the bacterium is a member selected from Enterobacter cloacae, Escherichia coli; Klebsiella pneumoniae, Proteus mirabilis, Serratia marcescens, Citrobacter freundii, Providencia stuartii, Pseudomonas aeruginosa; Acinetobacter baumannii, Stenotrophomonas maltophilia, Burkholderia cepacia, Staphylococcus aureus; Streptococcus pneumoniae; Streptococcus pyogenes; Enterococcus faecalis; and Enterococcus faecium.

In an exemplary embodiment, the microorganism is a bacterium, which is a member selected from acid-fast bacteria, including Mycobacterium species; bacilli, including Bacillus species, Corynebacterium species (also Propionibacterium) and Clostridium species; filamentous bacteria, including Actinomyces species and Streptomyces species; bacilli, such as Pseudomonas species, Brucella species, Agrobacterium species, Bordetella species, Escherichia species, Shigella species, Yersinia species, Salmonella species, Klebsiella species, Enterobacter species, Haemophilus species, Pasteurella species, and Streptobacillus species; spirochetal species, Campylobacter species, Vibrio species; and intracellular bacteria including Rickettsiae species and Chlamydia species. In an exemplary embodiment, the microorganism is described in a Figure provided herein.

In an exemplary embodiment, the microorganism is a member selected from a fungus and a yeast. In another exemplary embodiment, the fungus or yeast is a member selected from Candida species, Trichophyton species, Microsporium species, Aspergillus species, Cryptococcus species, Blastomyces species, Cocciodiodes species, Histoplasma species, Paracoccidiodes species, Phycomycetes species, Malassezia species, Fusarium species, Epidermophyton species, Scytalidium species, Scopulariopsis species, Alternaria species, Penicillium species, Phialophora species, Rhizopus species, Scedosporium species and Zygomycetes class. In another exemplary embodiment, the fungus or yeast is a member selected from Aspergilus fumigatus (A. fumigatus), Blastomyces dermatitidis, Candida Albicans (C. albicans, both fluconazole sensitive and resistant strains), Candida glabrata (C. glabrata), Candida krusei (C. krusei), Cryptococcus neoformans (C. neoformans), Candida parapsilosis (C. parapsilosis), Candida tropicalis (C. tropicalis), Cocciodiodes immitis, Epidermophyton floccosum (E. floccosum), Fusarium solani (F. solani), Histoplasma capsulatum, Malassezia furfur (M. furfur), Malassezia pachydermatis (M. pachydermatis), Malassezia sympodialis (M. sympodialis), Microsporum audouinii (M. audouinii), Microsporum canis (M. canis), Microsporum gypseum (M. gypseum), Paracoccidiodes brasiliensis and Phycomycetes spp, Trichophyton mentagrophytes (T. mentagrophytes), Trichophyton rubrum (T. rubrum), Trichophyton tonsurans (T. tonsurans). In another exemplary embodiment, the fungus or yeast is a member selected from Trichophyton concentricum, T. violaceum, T. schoenleinii, T. verrucosum, T. soudanense, Microsporum gypseum, M. equinum, Candida guilliermondii, Malassezia globosa, M. obtuse, M. restricta, M. slooffiae, and Aspergillus flavus. In another exemplary embodiment, the fungus or yeast is a member selected from dermatophytes, Trichophyton, Microsporum, Epidermophyton and yeast-like fungi. In another exemplary embodiment, the fungus or yeast is Candida Albicans.

In an exemplary embodiment, the microorganism is a virus. In an exemplary embodiment, the virus is a member selected from hepatitis A-B, human rhinoviruses, Yellow fever virus, human respiratory coronaviruses, Severe acute respiratory syndrome (SARS), respiratory syncytial virus, influenza viruses, parainfluenza viruses 1-4, human immunodeficiency virus 1 (HIV-1), human immunodeficiency virus 2 (HIV-2), Herpes simplex virus 1 (HSV-1), Herpes simplex virus 2 (HSV-2), human cytomegalovirus (HCMV), Varicella zoster virus, Epstein-Barr (EBV), polioviruses, coxsackieviruses, echoviruses, rubella virus, neuroderma-tropic virus, variola virus, papoviruses, rabies virus, dengue virus, West Nile virus and SARS virus. In another exemplary embodiment, the virus is a member selected from picornaviridae, flaviviridae, coronaviridae, paramyxoviridae, orthomyxoviridae, retroviridae, herpesviridae and hepadnaviridae. In another exemplary embodiment, the virus is a member selected from a virus included in the following table:

TABLE A

| Virus Category | Pertinent Human Infections |
| --- | --- |
| RNA Viruses | |
| Picornaviridae | Polio |
|  | Human hepatitis A |
|  | Human rhinovirus |
| Togaviridae and Flaviviridae | Rubella - German measles |
|  | Yellow fever |
| Coronaviridae | Human respiratory coronavirus (HCV) |
|  | Severe acute respiratory syndrome (SAR) |
| Rhabdoviridae | Lyssavirus - Rabies |
| Paramyxoviridae | Paramyxovirus - Mumps |
|  | Morbillvirus - measles |
|  | Pneumovirus - respiratory syncytial virus |

TABLE A-continued

Viruses

| Virus Category | Pertinent Human Infections |
|---|---|
| Orthomyxoviridae | Influenza A-C |
| Bunyaviridae | Bunyavirus - Bunyamwera (BUN) |
| | Hantavirus - Hantaan (HTN) |
| | Nairevirus - Crimean-Congo hemorrhagic fever (CCHF) |
| | Phlebovirus - Sandfly fever (SFN) |
| | Uukuvirus - Uukuniemi (UUK) |
| | Rift Valley Fever (RVFN) |
| Arenaviridae | Junin - Argentine hemorrhagic fever |
| | Machupo - Bolivian hemorrhagic fever |
| | Lassa - Lassa fever |
| | LCM - aseptic lymphocyctic choriomeningitis |
| Reoviridae | Rotovirus |
| | Reovirus |
| | Orbivirus |
| Retroviridae | Human immunodeficiency virus 1 (HIV-1) |
| | Human immunodeficiency virus 2 (HIV-2) |
| | Simian immunodeficiency virus (SIV) |
| | DNA Viruses |
| Papovaviridae | Pediatric viruses that reside in kidney |
| Adenoviridae | Human respiratory distress and some deep-seated eye infections |
| Parvoviridae | Human gastro-intestinal distress (Norwalk Virus) |
| Herpesviridae | Herpes simplex virus 1 (HSV-1) |
| | Herpes simplex virus 2 (HSV-2) |
| | Human cytomegalovirus (HCMV) |
| | Varicella zoster virus (VZV) |
| | Epstein-Barr virus (EBV) |
| | Human herpes virus 6 (HHV6) |
| Poxviridae | Orthopoxvirus is sub-genus for smallpox |
| Hepadnaviridae | Hepatitis B virus (HBV) |
| | Hepatitis C virus (HCV) |

In another exemplary embodiment, the microorganism is a parasite. In an exemplary embodiment, the parasite is a member selected from *Plasmodium falciparum, P. vivax, P. ovale P. malariae, P. berghei, Leishmania donovani, L. infantum, L. chagasi, L. mexicana, L. amazonensis, L. venezuelensis, L. tropics, L. major, L. minor, L. aethiopica, L. Biana braziliensis, L.* (V.) *guyanensis, L.* (V.) *panamensis, L.* (V.) *peruviana, Trypanosoma brucei rhodesiense, T. brucei gambiense, T. cruzi, Giardia intestinalis, G. lambda, Toxoplasma gondii, Entamoeba histolytica, Trichomonas vaginalis, Pneumocystis carinii,* and *Cryptosporidium parvu.*

VIII. Methods of Treating and/or Preventing Disease

The compounds of the present invention exhibit potency against microorganisms, such as bacteria, and therefore have the potential to achieve therapeutic efficacy in the animals described herein.

In another aspect, the invention provides a method of treating and/or preventing a disease. The method includes administering to the animal a therapeutically effective amount of the compound of the invention, sufficient to treat and/or prevent the disease. In an exemplary embodiment, the compound of the invention can be used in human or veterinary medical therapy, particularly in the treatment or prophylaxis of bacterial-associated disease. In an exemplary embodiment, the compound is described herein, or a salt, prodrug, hydrate or solvate thereof, or a combination thereof. In an exemplary embodiment, the invention provides a compound described herein, or a prodrug thereof. In an exemplary embodiment, the invention provides a compound described herein, or a salt, hydrate or solvate thereof. In an exemplary embodiment, the invention provides a compound described herein, or a salt thereof. In another exemplary embodiment, the compound of the invention is a compound described herein, or a pharmaceutically acceptable salt thereof. In an exemplary embodiment, the compound is a compound described herein, or a pharmaceutically acceptable salt thereof. In an exemplary embodiment, the compound is according to a formula described herein, or a pharmaceutically acceptable salt thereof. In an exemplary embodiment, the compound is part of a pharmaceutical formulation described herein. In another exemplary embodiment, the animal is a member selected from human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is a member selected from a human, cattle, goat, pig, sheep, horse, cow, bull, dog, guinea pig, gerbil, rabbit, cat, chicken and turkey. In another exemplary embodiment, the disease is a member selected from a systemic disease, a cutaneous disease, and an ungual, periungual or subungual disease. In another exemplary embodiment, the disease is a systemic disease. In another exemplary embodiment, the compound is a member selected from

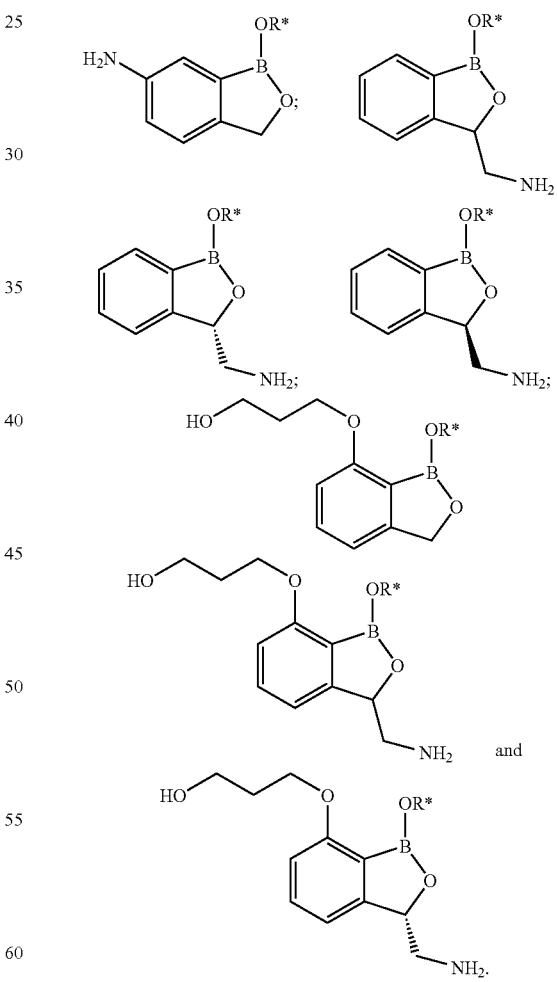

In an exemplary embodiment, the compound is a member selected from

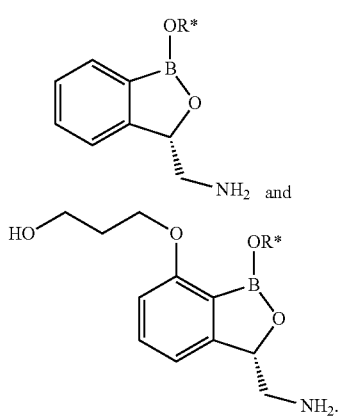

In another exemplary embodiment, R* is H.

In another exemplary embodiment, the treatment of a disorder or condition occurs through inhibition of an editing domain of an aminoacyl tRNA synthetase. In an exemplary embodiment, the disease is treated through oral administration of the compound of the invention. In an exemplary embodiment, the disease is treated through intravenous administration of the compound of the invention.

VIII. a) Methods of Treating Systemic Diseases

In another aspect, the invention provides a method of treating a systemic disease. The method involves contacting an animal with a compound of the invention.

In an exemplary embodiment, the disease is a member selected from candidiasis, aspergillosis, coccidioidomycosis, cryptococcosis, histoplasmosis, blastomycosis, paracoccidioidomycosis, zygomycosis, phaeohyphomycosis and rhinosporidiosis.

In an exemplary embodiment, the disease is associated with an infection by a microorganism described herein. In an exemplary embodiment, the disease is associated with an infection by a bacterium described herein.

In another exemplary embodiment, the disease is associated with infection by a Gram-positive bacteria. In an exemplary embodiment, the disease is associated with a *Staphylococcus* species. In another exemplary embodiment, the disease is a member selected from pneumonia, gastroenteritis, toxic shock syndrome, CAP, meningitis, septic arthritis, urinary tract infections, bacteremia, endocarditis, osteomylitis, skin and skin-structure infections. In an exemplary embodiment, the disease is associated with a *Streptococcus* species. In another exemplary embodiment, the disease is a member selected from strep throat, skin infections, necrotizing fasciitis, toxic shock syndrome, pneumonia, otitis media and sinusitis. In an exemplary embodiment, the disease is associated with an *Actinomyces* species. In another exemplary embodiment, the disease is actinomycosis. In an exemplary embodiment, the disease is associated with a *Norcardia* species. In another exemplary embodiment, the disease is pneumonia. In an exemplary embodiment, the disease is associated with a *Corynebacterium* species. In another exemplary embodiment, the disease is diptheria. In an exemplary embodiment, the disease is associated with a *Listeria* species. In another exemplary embodiment, the disease is meningitis. In an exemplary embodiment, the disease is associated with a *Bacillus* species. In another exemplary embodiment, the disease is a member selected from anthrax and food poisoning.

In an exemplary embodiment, the disease is associated with a *Clostridium* species. In another exemplary embodiment, the disease is a member selected from botulism, tetanus, gas gangrene and diarrhea. In an exemplary embodiment, the disease is associated with a *Mycobacterium* species. In another exemplary embodiment, the disease is a member selected from tuberculosis and leprosy.

In another exemplary embodiment, the disease is associated with infection by a Gram-negative bacteria. In an exemplary embodiment, the disease is associated with a *Neisseria* species. In another exemplary embodiment, the disease is a member selected from meningitis, gonorrhea, otitis extema and folliculitis. In an exemplary embodiment, the disease is associated with an *Escherichia* species. In another exemplary embodiment, the disease is a member selected from diarrhea, urinary tract infections, meningitis, sepsis and HAP. In an exemplary embodiment, the disease is associated with a *Shigella* species. In another exemplary embodiment, the disease is a member selected from diarrhea, bacteremia, endocarditis, meningitis and gastroenteritis. In an exemplary embodiment, the disease is associated with a *Salmonella* species. In another exemplary embodiment, the disease is a member selected from Typhoid fever, supsis, gastroenteritis, endocarditis, sinusitis and meningitis. In an exemplary embodiment, the disease is associated with a *Yersinia* species. In another exemplary embodiment, the disease is a member selected from Typhoid fever, bubonic plague, enteric fever and gastroenteritis. In an exemplary embodiment, the disease is associated with a *Klebsiella* species. In another exemplary embodiment, the disease is a member selected from sepsis and urinary tract infection. In an exemplary embodiment, the disease is associated with a *Proteus* species. In another exemplary embodiment, the disease is an urinary tract infection. In an exemplary embodiment, the disease is associated with an *Enterobacter* species. In another exemplary embodiment, the disease is a hospital-acquired infection. In an exemplary embodiment, the disease is associated with a *Serratia* species. In another exemplary embodiment, the disease is a member selected from a urinary tract infection, skin and skin-structure infection and pneumonia. In an exemplary embodiment, the disease is associated with a *Vibrio* species. In another exemplary embodiment, the disease is a member selected from cholera and gastroenteritis. In an exemplary embodiment, the disease is associated with a *Campylobacter* species. In another exemplary embodiment, the disease is gastroenteritis. In an exemplary embodiment, the disease is associated with a *Helicobacter* species. In another exemplary embodiment, the disease is chronic gastritis. In an exemplary embodiment, the disease is associated with a *Pseudomonas* species. In another exemplary embodiment, the disease is a member selected from pneumonia, osteomylitis, burn-wound infections, sepsis, UTIs, endocarditis, otitis, corneal infections. In an exemplary embodiment, the disease is associated with a *Bacteroides* species. In another exemplary embodiment, the disease is a member selected from periodontal disease and aspiration pneumonia. In an exemplary embodiment, the disease is associated with a *Haemophilus* species. In another exemplary embodiment, the disease is a member selected from meningitis, epiglottitis, septic arthritis, sepsis, chancroid and vaginitis. In an exemplary embodiment, the disease is associated with a *Bordetella* species. In another exemplary embodiment, the disease is Whooping cough. In an exemplary embodiment, the disease is associated with a *Legionella* species. In another exemplary embodiment, the disease is a member selected from pneumonia and pontiac fever. In an exemplary embodiment, the disease is associated with a *Francisella* species. In another exemplary embodiment, the disease is tularemia. In an exemplary embodiment, the disease is associated with a *Brucella* species. In another exemplary embodiment, the disease is brucellosis. In an exemplary embodiment, the disease is associated with a *Pasteurella* species. In another exemplary embodiment, the disease is a skin infection. In an exemplary embodiment, the disease is associated with a *Gardnerella* species. In another exemplary embodiment, the disease is vaginitis. In an exemplary embodiment, the disease is associated with a *Spirochetes* species. In another exemplary embodiment, the disease is syphilis and Lyme disease. In an exemplary embodiment, the disease is associated with a *Chlamydia* species. In another exemplary embodiment, the disease is chlamydia. In an exemplary embodiment, the disease is associated with a *Rickettsiae* species. In another exemplary embodiment, the disease is a member selected from Rocky Mountain spotted fever and typhus.

In an exemplary embodiment, the disease is associated with *Mycoplasma pneumoniae*. In another exemplary embodiment, the disease is a member selected from tracheobronchitis and walking pneumonia. In an exemplary embodiment, the disease is associated with *Ureaplasma urealyticum*. In another exemplary embodiment, the disease is urethritis. In another exemplary embodiment, the disease is pyelonenephritis. In another exemplary embodiment, the disease is an intra-abdominal infection. In another exemplary embodiment, the disease is febrile neutropenia. In another exemplary embodiment, the disease is a pelvic infection. In another exemplary embodiment, the disease is bacteraemia. In another exemplary embodiment, the disease is septicaemia.

In an exemplary embodiment, the compound administered has a structure which is a member selected from

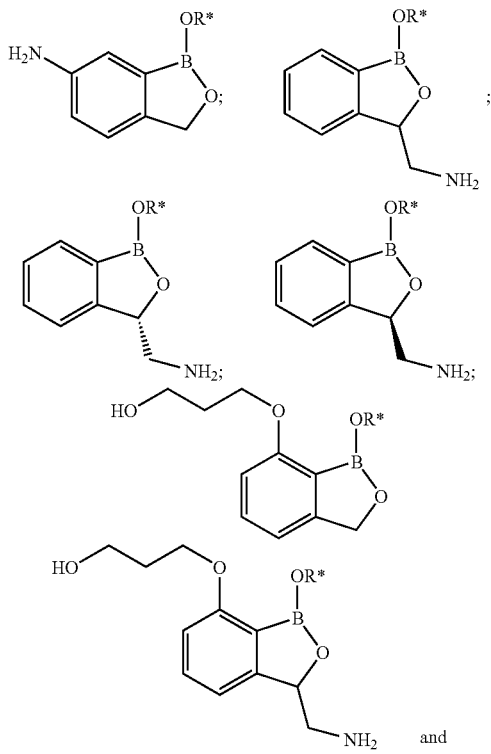

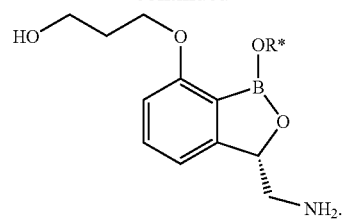

In an exemplary embodiment, the compound is a member selected from

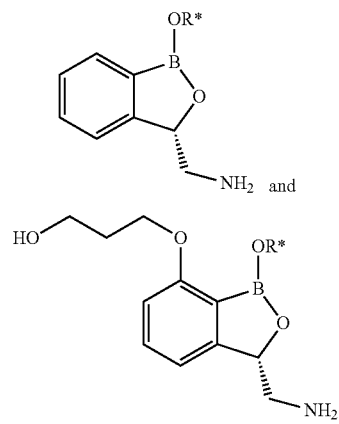

In another exemplary embodiment, R* is H.

VIII. b) Methods of Treating of Preventing Ungual and/or Periungual Diseases

In another aspect, the invention provides a method of treating or preventing an ungual and/or periungual disease. The method includes administering to the animal a therapeutically effective amount of a compound or pharmaceutical formulation of the invention, sufficient to treat or prevent said disease. In another exemplary embodiment, the method includes administering the compound or pharmaceutical formulation of the invention at a site which is a member selected from the skin, nail, hair, hoof, claw and the skin surrounding the nail, hair, hoof and claw. In another exemplary embodiment, the compound is a member selected from

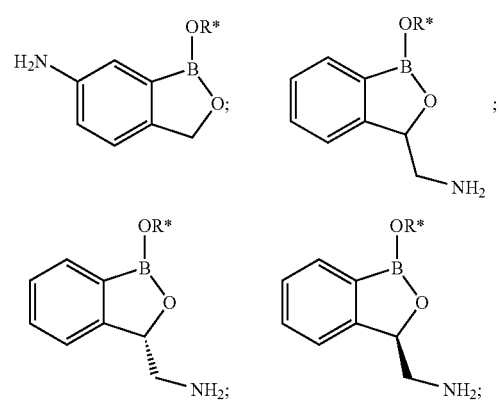

-continued

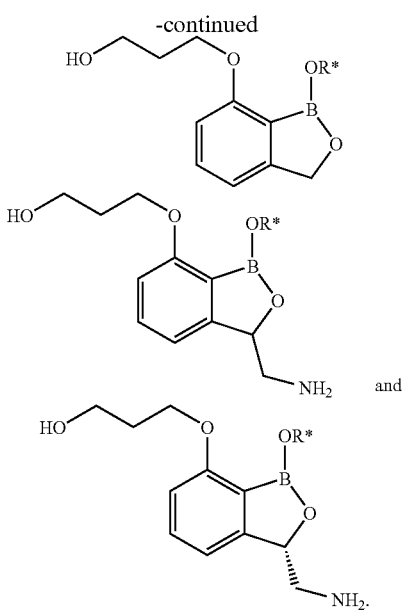

In an exemplary embodiment, the compound is a member selected from

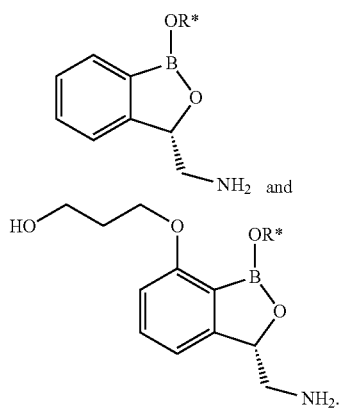

In another exemplary embodiment, R* is H.

VIII. b) 1) Onychomycosis

Onychomycosis is a disease of the nail caused by yeast, dermatophytes, or other molds, and represents approximately 50% of all nail disorders. Toenail infection accounts for approximately 80% of onychomycosis incidence, while fingernails are affected in about 20% of the cases. Dermatophytes are the most frequent cause of nail plate invasion, particularly in toenail onychomycosis. Onychomycosis caused by a dermatophyte is termed Tinea unguium. *Trichophyton* rubrum is by far the most frequently isolated dermatophyte, followed by *T. mentagrophytes*. Distal subungual onychomycosis is the most common presentation of tinea unguium, with the main site of entry through the hyponychium (the thickened epidermis underneath the free distal end of a nail) progressing in time to involve the nail bed and the nail plate. Discoloration, onycholysis, and accumulation of subungual debris and nail plate dystrophy characterize the disease. The disease adversely affects the quality of life of its victims, with subject complaints ranging from unsightly nails and discomfort with footwear, to more serious complications including secondary bacterial infections.

Many methods are known for the treatment of fungal infections, including the oral and topical use of antibiotics (e.g., nystatin and amphotericin B), imidazole anti-fungal agents such as miconazole, clotrimazole, fluconazole, econazole and sulconazole, and non-imidazole fungal agents such as the allylamine derivatives terbinafine and naftifine, and the benzylamine butenafine.

However, onychomycosis has proven to be resistant to most treatments. Nail fungal infections reside in an area difficult to access by conventional topical treatment and anti-fungal drugs cannot readily penetrate the nail plate to reach the infection sites under the nail. Therefore, onychomycosis has traditionally been treated by oral administration of anti-fungal drugs; however, clearly this is undesirable due to the potential for side effects of such drugs, in particular those caused by the more potent anti-fungal drugs such as itraconazole and ketoconazole. An alternative method of treatment of onychomycosis is by removal of the nail before treating with a topically active anti-fungal agent; such a method of treatment is equally undesirable. Systemic antimycotic agents require prolonged use and have the potential for significant side effects. Topical agents have usually been of little benefit, primarily because of poor penetration of the anti-fungal agents into and through the nail mass.

In an exemplary embodiment, the invention provides a method of treating or preventing onychomycosis. The method includes administering to an animal a therapeutically effective amount of a compound of the invention, sufficient to treat or prevent onychomycosis. In another exemplary embodiment, the method includes administering the compound of the invention at a site which is a member selected from the skin, nail, hair, hoof, claw and the skin surrounding the nail, hair, hoof and claw. In another exemplary embodiment, the animal is a human. In another exemplary embodiment, the compound of the invention is a compound described herein. In another exemplary embodiment, the compound is a member selected from

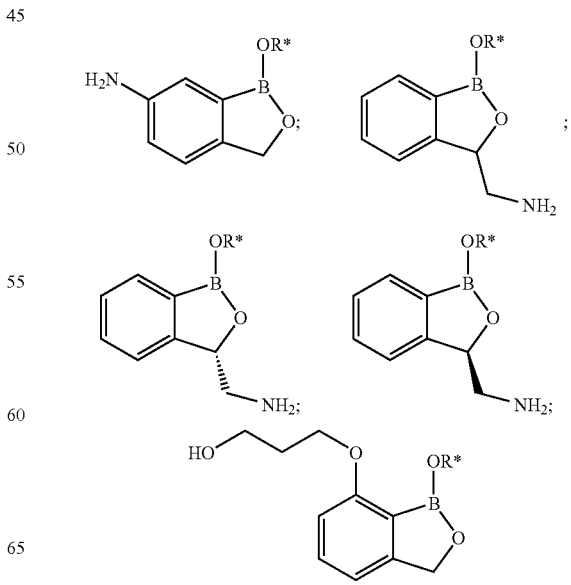

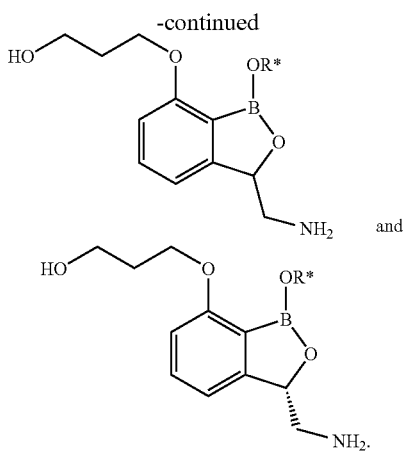

In an exemplary embodiment, the compound is a member selected from

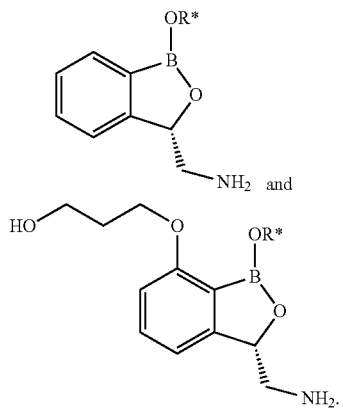

VIII. b) 2) Other Ungual and Periungual Diseases

In an exemplary embodiment, the invention provides a method of treating or preventing an ungual or periungual disease in an animal. This method comprising administering to the animal a therapeutically effective amount of a compound of the invention, thereby treating or preventing the ungual or periungual disease. In an exemplary embodiment, the ungual or periungual disease is a member selected from: chloronychia, paronychias, erysipeloid, onychorrhexis, gonorrhea, swimming-pool granuloma, larva migrans, leprosy, Orf nodule, milkers' nodules, herpetic whitlow, acute bacterial perionyxis, chronic perionyxis, sporotrichosis, syphilis, tuberculosis verrucosa cutis, tularemia, tungiasis, peri- and subungual warts, zona, nail dystrophy (trachyonychia), and dermatological diseases with an effect on the nails, such as psoriasis, pustular psoriasis, alopecia aerata, parakeratosis pustulosa, contact dermatosis, Reiter's syndrome, psoriasiform acral dermatitis, lichen planus, idiopathy atrophy in the nails, lichin nitidus, lichen striatus, inflammatory linear verrucous epidermal naevus (ILVEN), alopecia, pemphigus, bullous pemphigoid, acquired epidermolysis bullosa, Darier's disease, pityriasis rubra pilaris, palmoplantar keratoderma, contact eczema, polymorphic erythema, scabies, Bazex syndrome, systemic scleroderma, systemic lupus erythematosus, chronic lupus erythematosus and dermatomyositus.

The compounds and pharmaceutical formulations of the invention useful for ungual and periungual applications also find application in the cosmetics field, in particular for the treatment of irregularities of the nails, koilonychias, Beau's lines, longitudinal ridging, ingrown nails.

In an exemplary embodiment, the disease is of the skin, nail, hair, claw or hoof, hair, ear and eye and is a member selected from Sporotrichosis, Mycotic keratitis, Extension oculomycosis, Endogenous oculomycosis, Lobomycosis, Mycetoma, Piedra, Pityriasis versicolor, Tinea corporis, Tinea cruris, Tinea pedis, Tinea barbae, Tinea capitis, Tinea nigra, Otomycosis, Tinea favosa, Chromomycosis, and Tinea Imbricata. In an exemplary embodiment, the compound useful for treating these diseases is a compound of the invention. In another exemplary embodiment, the compound of the invention has a structure which is a member selected from

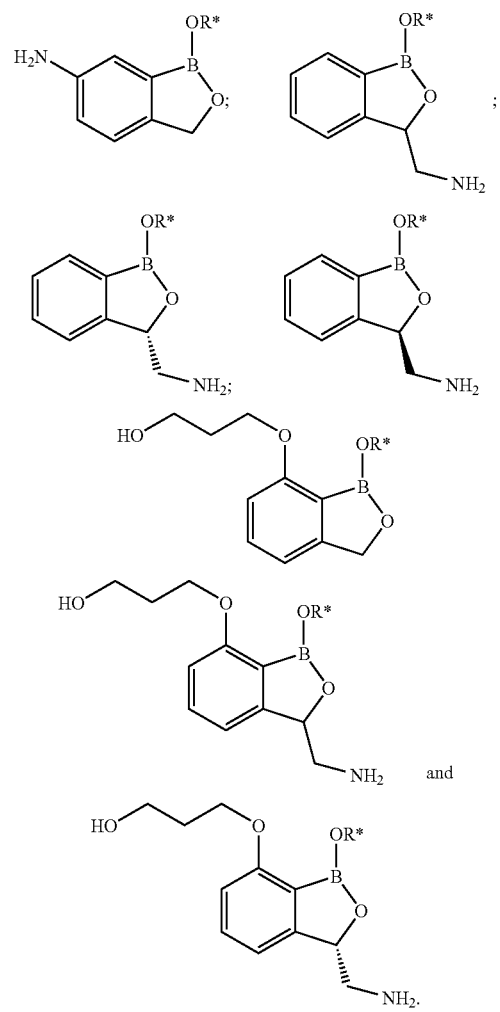

In another exemplary embodiment, R* is H.

VIII. c) Methods of Treating Diseases Involving Viruses

The compounds of the invention are useful for the treatment of diseases of animals (such as humans), involving viruses. In an exemplary embodiment, the disease is a member selected from hepatitis A-B-C, yellow fever, respiratory syncytial, influenza, AIDS, herpes simplex, chicken pox, varicella zoster, and Epstein-Barr disease. In another exemplary embodiment, the compound is a member selected from

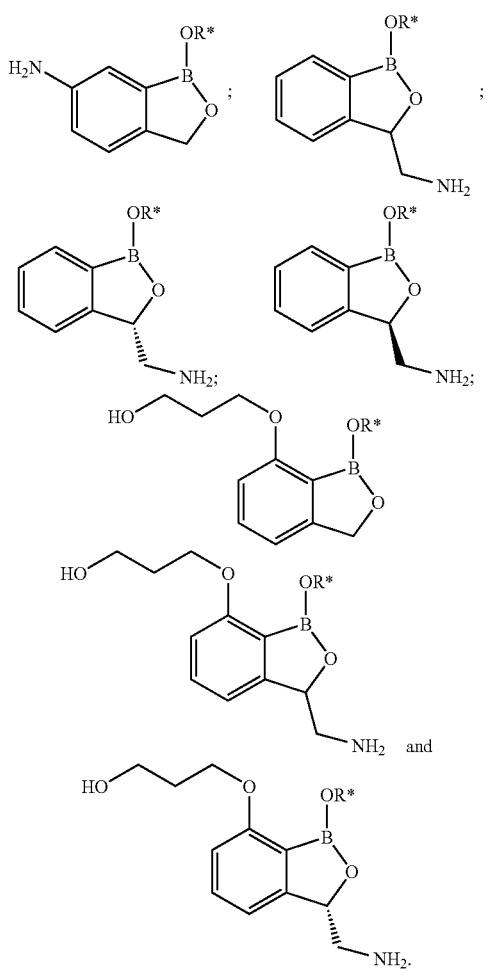

In an exemplary embodiment, the compound is a member selected from

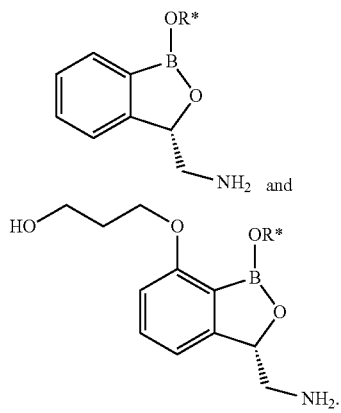

In another exemplary embodiment, R* is H.

VIII. d) Methods of Treating Diseases Involving Parasites

The compounds of the invention are useful for the treatment of diseases of animals (such as humans), involving parasites. In an exemplary embodiment, the disease is a member selected from malaria, Chagas' disease, Leishmaniasis, African sleeping sickness (African human trypanosomiasis), giardiasis, toxoplasmosis, amebiasis and cryptosporidiosis.

In any of the methods according to the present invention set forth above, it is preferred that the aminoacyl tRNA synthetase is an aminoacyl tRNA synthetase comprising an editing domain. The editing domain is encoded by a portion of the aminoacyl tRNA synthetase involved in proofreading. The editing domain is preferably encoded by a DNA portion having at least conserved residues compared after alignment with the editing site of the leucyl-tRNA synthetase, valyl-tRNA synthetase and isoleucyl-tRNA synthetase. More preferably the synthetase is selected from the group consisting of the valyl-tRNA synthetase, isoleucyl-tRNA synthetase, leucyl-tRNA synthetase, alanyl-tRNA synthetase, prolyl-tRNA synthetase, threonyl-tRNA synthetase, phenyl-tRNA synthetase and lysyl-tRNA synthetase which are known to have an editing site or domain (see for Ile RS Baldwin, A. N. and Berg, P. (1966) J. Biol. Chem. 241, 839-845 and Eldred, E. W. and Schimmel, P. R. (1972) J. Biol. Chem. 247, 2961-2964; for Val RS, Fersht, A. R. and Kaethner, M. M. (1976) Biochemistry. 15 (15), 3342-3346; for Leu RS, English, S. et al., (1986) Nucleic Acids Research. 14 (19), 7529-7539; for Ala RS, Tsui, W. C. and Fersht, A. R. (1981) Nucleic Acids Research. 9, 7529-7539; for Pro RS, Beuning, P. J. and Musier-Forsyth, K. (2000) PNAS. 97 (16), 8916-8920; for Thr RS, Sankaranarayanan, R. et al., (2000) Nat. Struct. Biol. 7, 461-465 and Musier-Foryth, K. and Beuning, P. J. (2000) Nat. Struct. Biol. 7, 435-436; for PheRS, Yarus, M. (1972) PNAS. 69, 1915-1919 and for LysRS, Jakubowski, H. (1997) Biochemistry. 36, 11077-11085. In another exemplary embodiment, the compound of the invention is a member selected from

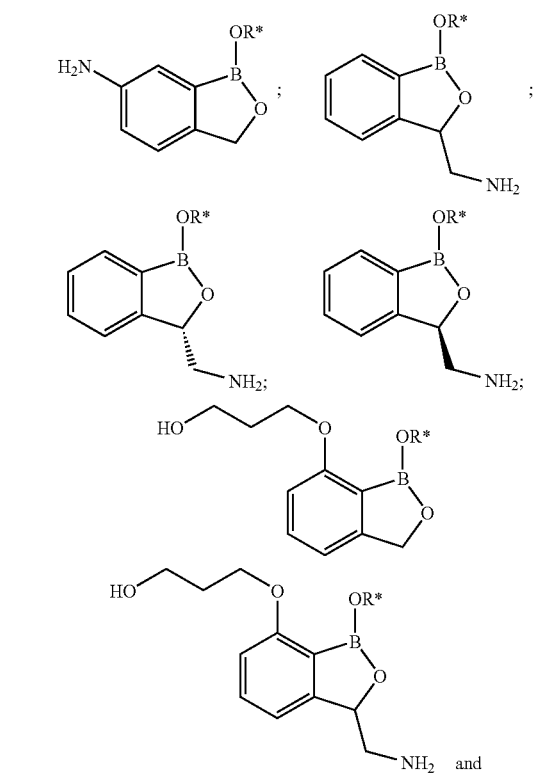

-continued

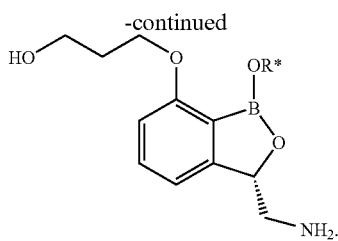

In an exemplary embodiment, the compound is a member selected from

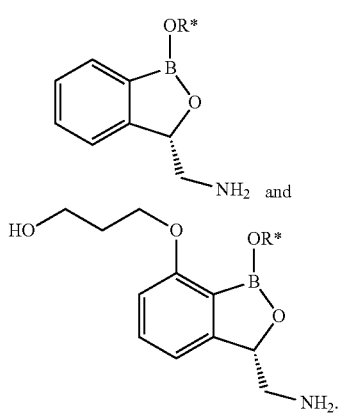

In another exemplary embodiment, R* is H.

IX. Methods of Nail Penetration

It is believed that poor penetration of the active agent through the hoof or nail plate and/or excessive binding to keratin, (the major protein in nails and hair) are the reasons for the poor efficacy of 8% ciclopirox w/w in commercial lacquer and other topical treatments that have failed in clinical trials. In mild cases of onychomycosis, the pathogenic fungi reside in the nail plate only. In moderate to severe cases the pathogenic fungi establish a presence in the nail plate and in the nail bed. If the infection is cleared from the nail plate but not from the nail bed, the fungal pathogen can re-infect the nail plate. Therefore, to effectively treat onychomycosis, the infection must be eliminated from the nail plate and the nail bed. To do this, the active agent must penetrate and disseminate substantially throughout the nail plate and nail bed.

It is believed that in order for an active agent to be effective once disseminated throughout the infected area, it must be bioavailable to the fungal pathogen and cannot be so tightly bound to keratin that the drug cannot inhibit growth or kill the infecting fungi.

An understanding of the morphology of the nail plate suggests certain physicochemical properties of an active agent that would facilitate penetration of the nail plate. The desired physicochemical properties are described throughout. The tested compounds of the present invention are able to penetrate the nail plate and were also active against *Trichophyton rubrum* and *mentagrophytes* and other species. In addition, the tested compounds are also active against *Trichophyton rubrum* in the presence of 5% keratin powder.

In an exemplary embodiment, the invention provides a method of killing or inhibiting growth of a microorganism present in a human nail unit, wherein said human nail unit comprises a nail plate. The method comprising contacting a dorsal layer of the nail plate with a compound of the invention capable of penetrating the nail plate, traveling through the nail plate to a nail bed underlying said nail plate, and contacting said microorganism, under conditions sufficient for said compound to penetrate said nail plate. In this embodiment, the compound has a molecular weight of between about 100 Da and about 200 Da, a log P value of between about 1.0 and about 2.6, a water solubility greater than about 0.1 mg/mL octanol/saturated water, and an MIC of less than 16 μg/mL against said microorganism, thereby killing or inhibiting the growth of said microorganism. In another exemplary embodiment, the compound of the invention has a structure which is a member selected from

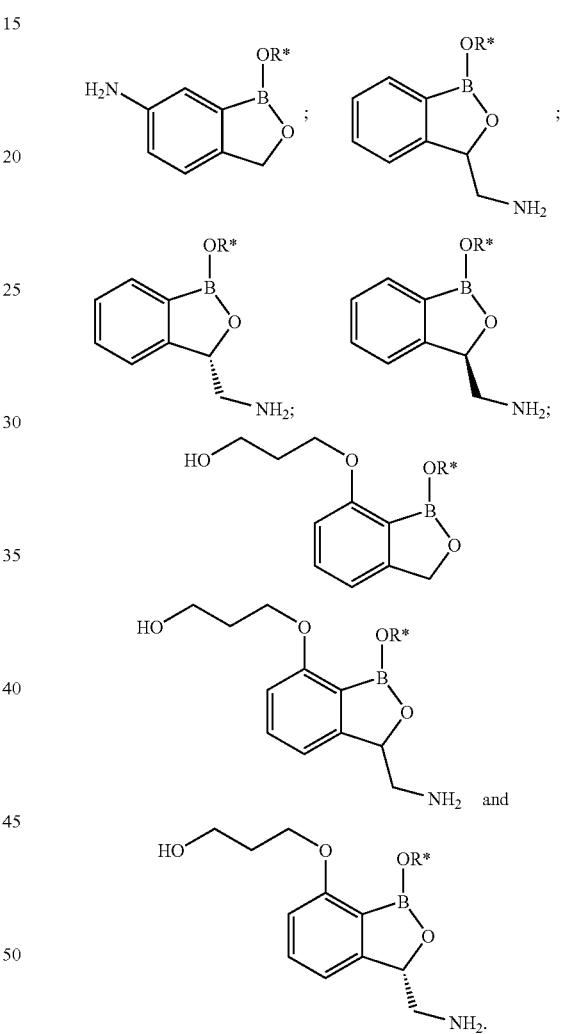

In an exemplary embodiment, the compound is a member selected from

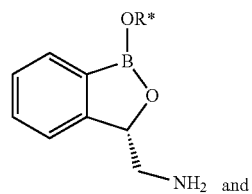

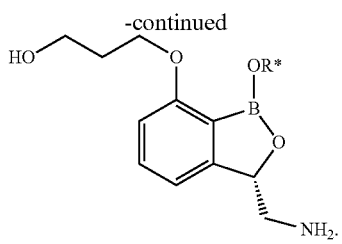

In another exemplary embodiment, R* is H.

In another exemplary embodiment, the invention provides a method of treating a disease caused by a microorganism present in a human nail unit, wherein said human nail unit comprises a nail plate, said method comprising: contacting a dorsal layer of the nail plate with a compound of the invention capable of penetrating the nail plate, traveling through the nail plate to a nail bed underlying said nail plate, and contacting said microorganism, under conditions sufficient for said compound to penetrate said nail plate and to treat said disease. In this embodiment, the compound has a molecular weight of between about 100 Da and about 200 Da; a log P value of between about 1.0 and about 2.6; a water solubility greater than about 0.1 mg/mL octanol/saturated water, and an MIC of less than 16 µg/mL against said microorganism, thereby treating said disease. In an exemplary embodiment, the compound is described herein.

In another aspect, the invention provides a method of delivering a compound from the dorsal layer of the nail plate to the nail bed. This method comprises contacting the cell with a compound of the invention capable of penetrating the nail plate, under conditions sufficient to penetrate the nail. The compound has a molecular weight of between about 100 and about 200 Da. The compound also has a log P value of between about 1.0 and about 2.6. The compound additionally has a water solubility between about 0.1 mg/mL and 1 g/mL octanol/saturated water, thereby delivering said compound.

In a preferred embodiment, the physicochemical properties of the compound of the invention, described by quantities predictive for migration of the compound through the nail plate, including, but not limited to, molecular weight, log P and solubility in water, and the like, are effective to provide substantial penetration of the nail plate.

Compounds with a molecular weight of less than 200 Da penetrate the nail plate in a manner superior to the commercially available treatment for onychomycosis. In one embodiment of the present invention the compound has a molecular weight of between 130 and 200. In another embodiment of this invention, the compound has a molecular weight of from about 140 to about 200 Da. In another embodiment of this invention, the compound has a molecular weight of from about 170 to about 200 Da. In another embodiment of this invention, the compound has a molecular weight of from about 155 to about 190 Da. In another embodiment of this invention, the compound has a molecular weight of from about 165 to about 185 Da. In another embodiment of this invention, the compound has a molecular weight of from about 145 to about 170 Da. In yet another embodiment the molecular weight is either 151.93 or 168.39 Da.

In one embodiment of the present invention the compound has a log P value of between about −3.5 to about 2.5. In another exemplary embodiment, the compound has a log P value of from about −1.0 to about 2.5. In another exemplary embodiment, the compound has a log P value of from about −1.0 to about 2.0. In another exemplary embodiment, the compound has a log P value of from about −0.5 to about 2.5.

In another exemplary embodiment, the compound has a log P value of from about −0.5 to about 1.5. In another exemplary embodiment, the compound has a log P value of from about 0.5 to about 2.5. In another exemplary embodiment, the compound has a log P value of from about 1.0 to about 2.5. In yet another exemplary embodiment, the compound has a log P value of 1.9 or 2.3.

Also contemplated by the present invention is a compound with a log P value less then 2.5, with a molecular weight less than 200 Da, that are still able to penetrate the nail plate.

In one embodiment of the present invention the compound has a water solubility between about 0.1 mg/mL to 1 g/mL in octanol saturated water. In one embodiment of the present invention the compound has a water solubility of between 0.1 mg/mL and 100 mg/mL. In another embodiment of this invention, the compound has a water solubility of from about 0.1 mg/mL and 10 mg/mL. In another embodiment of this invention, the compound has a water solubility of from about 0.1 mg/mL and 1 mg/mL. In another embodiment of this invention, the compound has a water solubility of from about 5 mg/mL and 1 g/mL. In another embodiment of this invention, the compound has a water solubility of from about 10 mg/mL and 500 g/mL. In another embodiment of this invention, the compound has a water solubility of from about 80 mg/mL and 250 mg/mL.

In an exemplary embodiment, the present invention provides a compound with a log P value selected from a range above, with a molecular weight selected from a range above, that are still able to penetrate the nail plate.

In an exemplary embodiment, the present invention provides a compound with a molecular weight selected from a range above, with a water solubility selected from a range above, that are still able to penetrate the nail plate.

In an exemplary embodiment, the present invention provides a compound with a log P selected from a range above, with a water solubility selected from a range above, that are still able to penetrate the nail plate.

In an exemplary embodiment, the present invention provides a compound with a molecular weight selected from a range above, with a log P selected from a range above, and with a water solubility selected from a range above, that are still able to penetrate the nail plate.

Penetration of the nail by the active ingredient may be effected by the polarity of the formulation. However, the polarity of the formulation is not expected have as much influence on nail penetration as some of the other factors, such as the molecular weight or the log P of the active ingredient. The presence of penetration enhancing agents in the formulation is likely to increase penetration of the active agent when compared to similar formulations containing no penetration enhancing agent.

Some examples of molecules with optimal physicochemical properties are given in the table below.

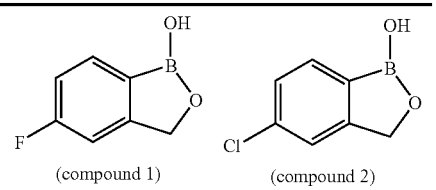

| Structure: | (compound 1) | (compound 2) |
|---|---|---|
| Formula: | $C_7H_6BFO_2$ | $C_7H_6BClO_2$ |
| Molecular weight (Da): | 151.93 | 168.39 |

| | | |
|---|---|---|
| Plasma protein binding (%): | 66 | 83 |
| LogP: | 1.9 | 2.3 |
| Water solubility (µg/mL): | >100 | >100 |

Compound 3 below is an example of a compound similar in molecular weight to ciclopirox, and like ciclopirox, penetrates the nail plate poorly.

Structure:

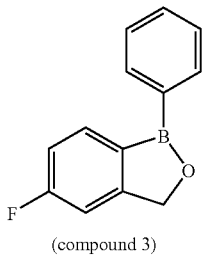 [SMILES: Fc1ccc2c(c1)COB2c1ccccc1]

(compound 3)

| | |
|---|---|
| Formula: | C$_{13}$H$_{10}$BFO |
| Molecular weight (Da): | 212.03 |
| Plasma protein binding (%): | 100 |
| cLogP: | 3.55 |
| Water solubility (µg/mL): | not determined |

In a preferred embodiment the topical formulations including a compound of the invention has a total molecular weight of less than 200 Da, has a Log P of less than 2.5, and a minimum inhibitory concentration against *Trichophyton rubrum* that is substantially unchanged in the presence of 5% keratin.

The efficacy coefficient (defined as flux over MIC) of a compound also informs one of skill regarding whether the compound may be effective in killing a microorganism, inhibiting the growth of a microorganism, or treating a disease which is caused by a microorganism present in a human nail unit, wherein said human nail unit comprises a nail plate. The method comprises: contacting a dorsal layer of the nail plate with a compound of the invention capable of penetrating the nail plate, traveling through the nail plate to a nail bed underlying said nail plate, and contacting said microorganism, under conditions sufficient for the compound to penetrate said nail plate and to treat said disease, wherein the compound has an efficacy coefficient above 10.

In an exemplary embodiment, the compound has an efficacy coefficient between about 10 and about 1000. In an exemplary embodiment, the compound has an efficacy coefficient between about 30 and about 100. In an exemplary embodiment, the compound has an efficacy coefficient between about 100 and about 500. In an exemplary embodiment, the compound has an efficacy coefficient between about 25 and about 200.

The methods provided in this aspect of the invention are useful in the penetration of nails and hoofs, as well as the treatment of ungual and periungual conditions.

X Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof, or a combination thereof. In another aspect, the pharmaceutical formulation includes: (a) a pharmaceutically acceptable excipient; and (b) a compound described herein, or a salt, hydrate or solvate thereof, or a combination thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

In another exemplary embodiment, the invention is a pharmaceutical formulation comprising: (a) a pharmaceutically acceptable excipient; and (b) a compound having a structure which is a member selected from:

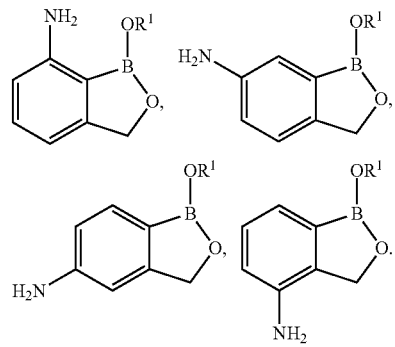

In another exemplary embodiment, the invention is a pharmaceutical formulation comprising: (a) a pharmaceutically acceptable excipient; and (b) a compound having a structure which is a member selected from

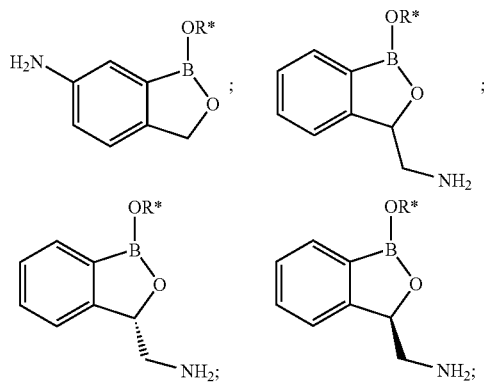

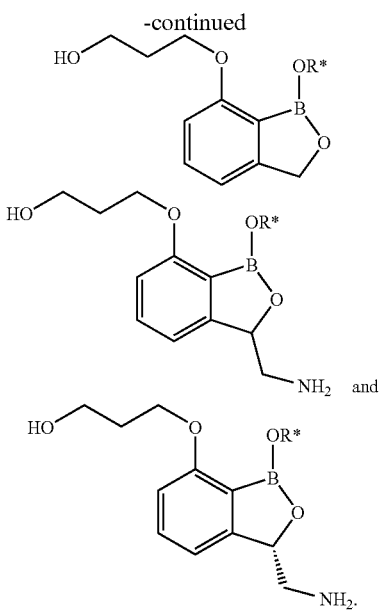

In an exemplary embodiment, the compound is a member selected from

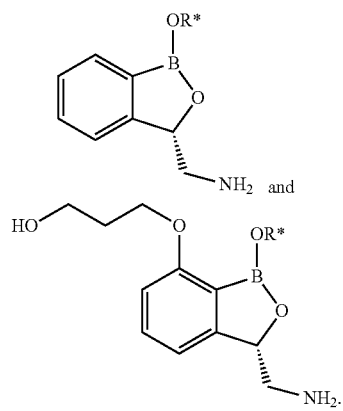

In another exemplary embodiment, R* is H.

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation of the invention is administered orally. In an exemplary embodiment, the pharmaceutical formulation of the invention is administered intravenously.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity. Penetration of the blood brain barrier of a compound in humans may be predicted from the brain levels of laboratory animals that receive the compound intravenously.

Serum protein binding may be predicted from albumin binding assays. Such assays are described in a review by Oravcova, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

The amount of the composition required for use in treatment will vary not only with the particular compound selected but also with the route of administration, the nature of the condition being treated and the age and condition of the patient and will ultimately be at the discretion of the attendant physician or clinician.

In an exemplary embodiment, the pharmaceutical formulation excipient comprises ethanol and the pharmaceutical formulation compound is a member selected from

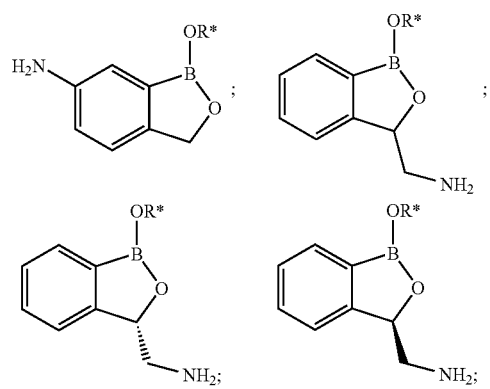

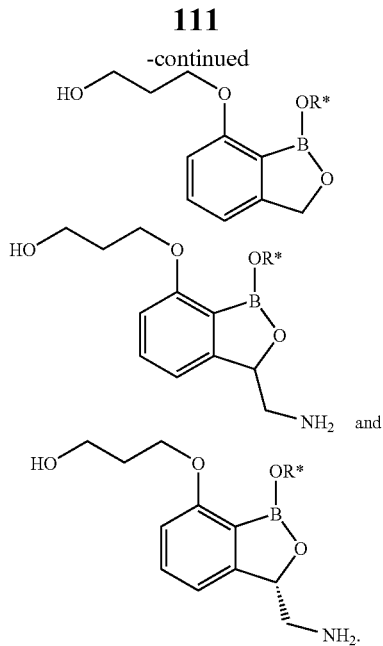

In an exemplary embodiment, the compound is a member selected from

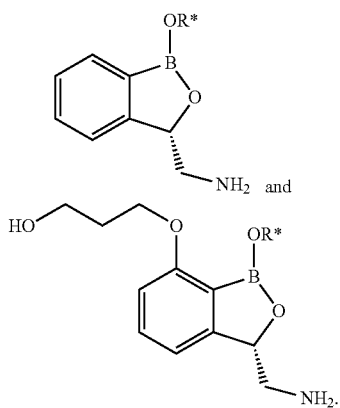

In another exemplary embodiment, R* is H. In another exemplary embodiment, the pharmaceutical formulation excipient comprises propylene glycol and the pharmaceutical formulation compound is a member selected from

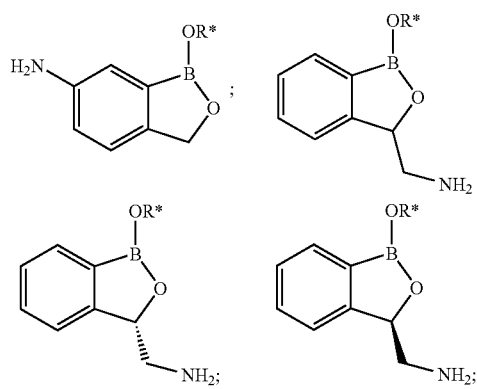

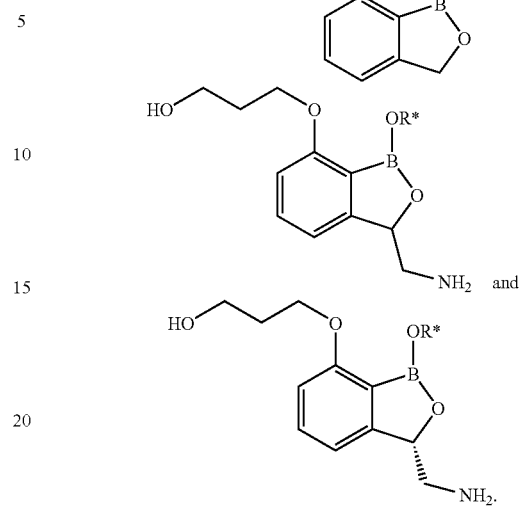

In an exemplary embodiment, the compound is a member selected from

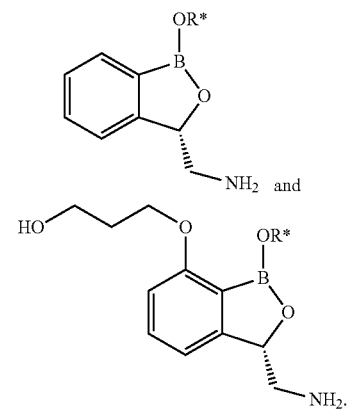

In another exemplary embodiment, R* is H. In an exemplary embodiment the pharmaceutical formulation comprises: about propylene glycol:ethanol 1:4, with 1:10 wt/volume of a compound which is a member selected from -continued

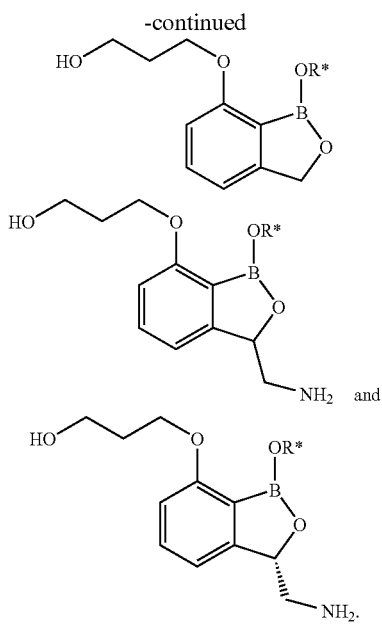

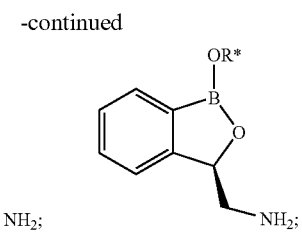

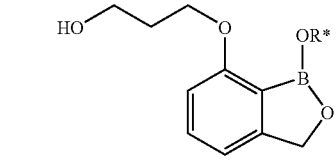

In an exemplary embodiment, the compound is a member selected from

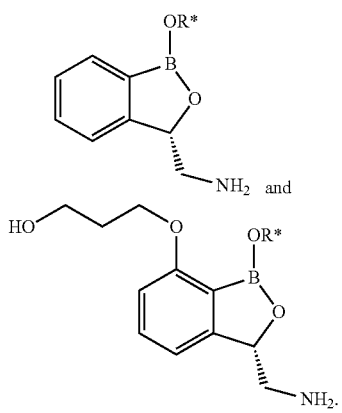

In another exemplary embodiment, R* is H. In an exemplary embodiment the pharmaceutical formulation comprises: about 70% ethanol; about 20% poly(vinyl methyl ether-alt-maleic acid monobutyl ester); about 10% of a compound which is a member selected from

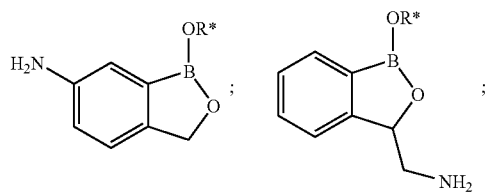

-continued

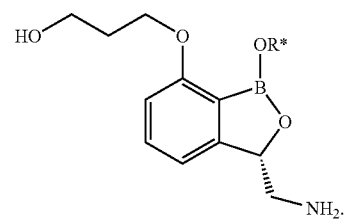

In an exemplary embodiment, the compound is a member selected from

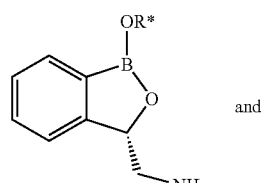

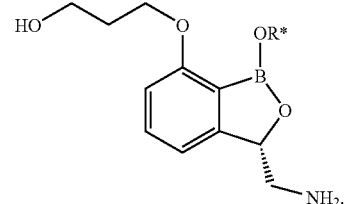

In another exemplary embodiment, R* is H. In an exemplary embodiment the pharmaceutical formulation comprises: about 56% ethanol; about 14% water; about 15% poly(2-hydroxyethyl methacrylate); about 5% dibutyl sebacate; about 10% of a compound which is a member selected from

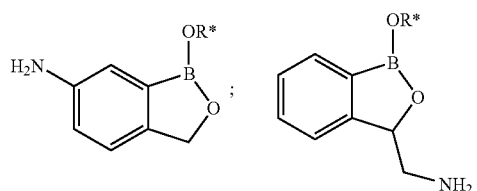
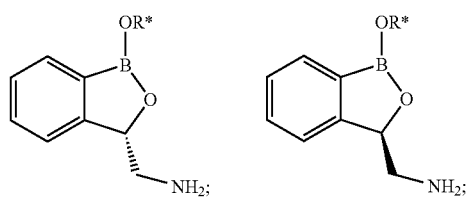
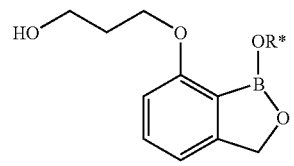
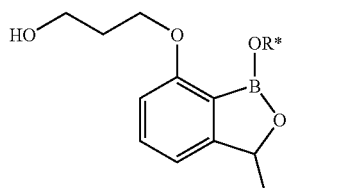
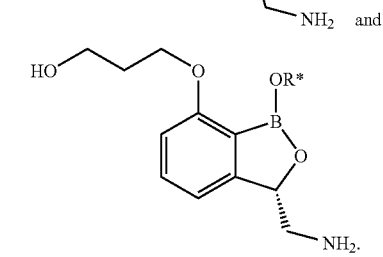

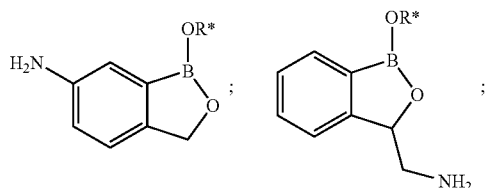
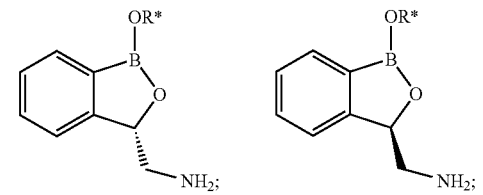
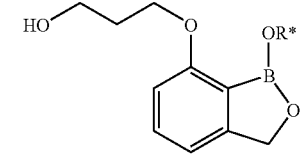
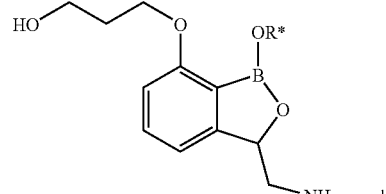
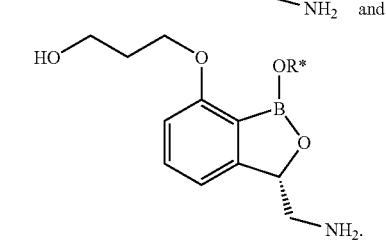

In an exemplary embodiment, the compound is a member selected from

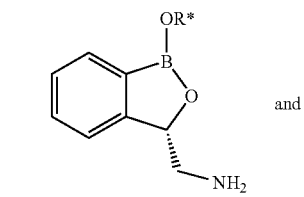

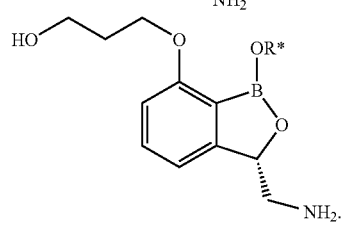

In another exemplary embodiment, R* is H. In an exemplary embodiment the pharmaceutical formulation comprises: about 55% ethanol; about 15% ethyl acetate; about 15% poly(vinyl acetate); about 5% dibutyl sebacate; about 10% of a compound which is a member selected from In an exemplary embodiment, the compound is a member selected from

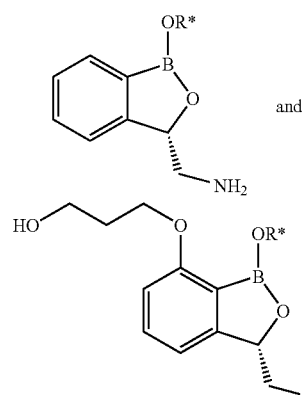

In another exemplary embodiment, R* is H. In another exemplary embodiment, a compound which is a member selected from

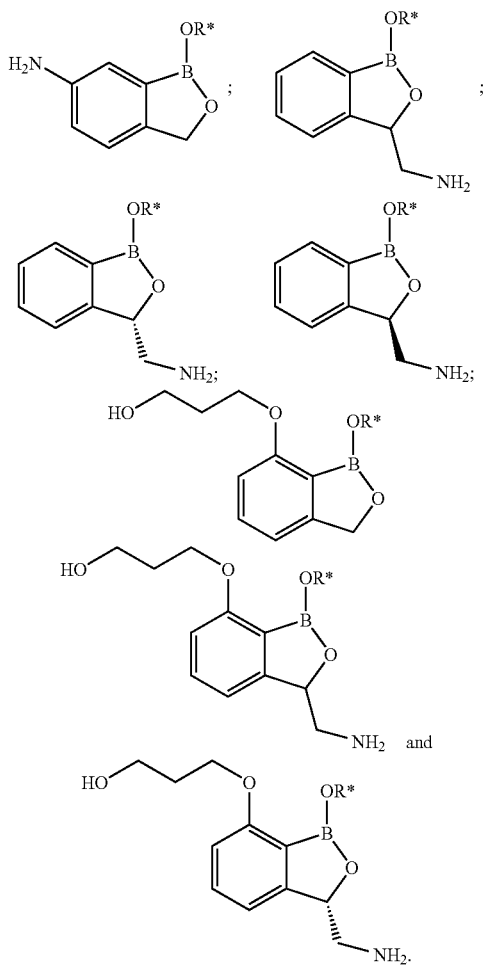

is present in a pharmaceutical formulation in a concentration which is a member selected from 1%, 2.5%, 5%, 7.5%, 10% and 15% w/v. In another exemplary embodiment, the pharmaceutical formulation is a lacquer.

In an exemplary embodiment, the pharmaceutical formulation excipient comprises ethanol and the pharmaceutical formulation compound is a compound described herein. In another exemplary embodiment, the pharmaceutical formulation excipient comprises propylene glycol and the pharmaceutical formulation compound is a compound described herein. In an exemplary embodiment the pharmaceutical formulation comprises: about 20% propylene glycol; about 70% ethanol; about 10% of a compound described herein. In an exemplary embodiment the pharmaceutical formulation comprises: about 70% ethanol; about 20% poly(vinyl methyl ether-alt-maleic acid monobutyl ester); about 10% of a compound described herein. In an exemplary embodiment the pharmaceutical formulation comprises: about 56% ethanol; about 14% water; about 15% poly(2-hydroxyethyl methacrylate); about 5% dibutyl sebacate; about 10% of a compound described herein. In an exemplary embodiment the pharmaceutical formulation comprises: about 55% ethanol; about 15% ethyl acetate; about 15% poly(vinyl acetate); about 5% dibutyl sebacate; about 10% of a compound described herein. In another exemplary embodiment, a compound described herein is present in a pharmaceutical formulation in a concentration which is a member selected from 1%, 2.5%, 5%, 7.5%, 10% and 15% w/v. In another exemplary embodiment, the pharmaceutical formulation is a lacquer.

X. a) Topical Formulations

In a preferred embodiment, the methods of the invention can be employed through the topical application of the compounds described herein. In another exemplary embodiment, the compound is a member selected from

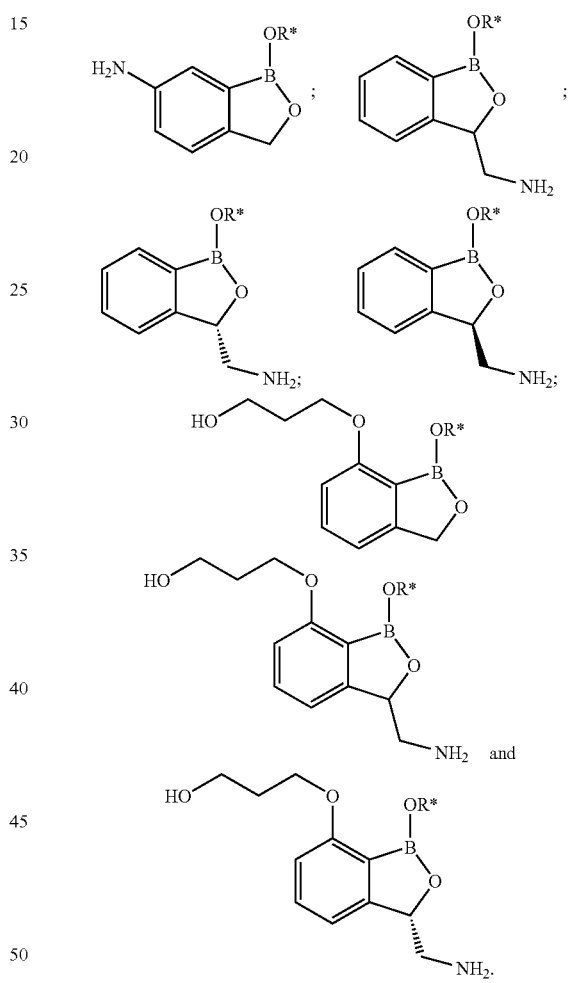

In an exemplary embodiment, the compound is a member selected from

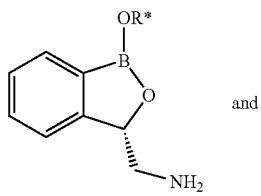

-continued

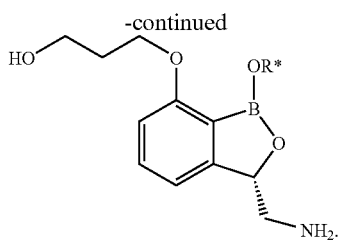

In another exemplary embodiment, R* is H.

The compositions of the present invention comprises fluid or semi-solid vehicles that may include but are not limited to polymers, thickeners, buffers, neutralizers, chelating agents, preservatives, surfactants or emulsifiers, antioxidants, waxes or oils, emollients, sunscreens, and a solvent or mixed solvent system. The solvent or mixed solvent system is important to the formation because it is primarily responsible for dissolving the drug. The best solvent or mixed solvent systems are also capable of maintaining clinically relevant levels of the drug in solution despite the addition of a poor solvent to the formulation. The topical compositions useful in the subject invention can be made into a wide variety of product types. These include, but are not limited to, lotions, creams, gels, sticks, sprays, ointments, pastes, foams, mousses, and cleansers. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in Remington: The Science and Practice of Pharmacy, supra. The formulation can be selected to maximize delivery to a desired target site in the body.

Lotions, which are preparations that are to be applied to the skin, nail, hair, claw or hoof surface without friction, are typically liquid or semi-liquid preparations in which finely divided solid, waxy, or liquid are dispersed. Lotions will typically contain suspending agents to produce better dispersions as well as compounds useful for localizing and holding the active agent in contact with the skin, nail, hair, claw or hoof, e.g., methylcellulose, sodium carboxymethyl-cellulose, or the like.

Creams containing the active agent for delivery according to the present invention are viscous liquid or semisolid emulsions, either oil-in-water or water-in-oil. Cream bases are water-washable, and contain an oil phase, an emulsifier and an aqueous phase. The oil phase is generally comprised of petrolatum or a fatty alcohol, such as cetyl- or stearyl alcohol; the aqueous phase usually, although not necessarily, exceeds the oil phase in volume, and generally contains a humectant. The emulsifier in a cream formulation, as explained in Remington: The Science and Practice of Pharmacy, supra, is generally a nonionic, anionic, cationic or amphoteric surfactant.

Gel formulations can also be used in connection with the present invention. As will be appreciated by those working in the field of topical drug formulation, gels are semisolid. Single-phase gels contain organic macromolecules distributed substantially uniformly throughout the carrier liquid, which is typically aqueous, but also may be a solvent or solvent blend.

Ointments, which are semisolid preparations, are typically based on petrolatum or other petroleum derivatives. As will be appreciated by the ordinarily skilled artisan, the specific ointment base to be used is one that provides for optimum delivery for the active agent chosen for a given formulation, and, preferably, provides for other desired characteristics as well, e.g., emolliency or the like. As with other carriers or vehicles, an ointment base should be inert, stable, nonirritating and non-sensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to Remington: The Science and Practice of Pharmacy, supra, for further information.

Useful formulations of the invention also encompass sprays. Sprays generally provide the active agent in an aqueous and/or alcoholic solution which can be misted onto the skin, nail, hair, claw or hoof for delivery. Such sprays include those formulated to provide for concentration of the active agent solution at the site of administration following delivery, e.g., the spray solution can be primarily composed of alcohol or other like volatile liquid in which the drug or active agent can be dissolved. Upon delivery to the skin, nail, hair, claw or hoof, the carrier evaporates, leaving concentrated active agent at the site of administration.

The topical pharmaceutical compositions may also comprise suitable solid or gel phase carriers. Examples of such carriers include but are not limited to calcium carbonate, calcium phosphate, various sugars, starches, cellulose derivatives, gelatin, and polymers such as polyethylene glycols.

The topical pharmaceutical compositions may also comprise a suitable emulsifier which refers to an agent that enhances or facilitates mixing and suspending oil-in-water or water-in-oil. The emulsifying agent used herein may consist of a single emulsifying agent or may be a nonionic, anionic, cationic or amphoteric surfactant or blend of two or more such surfactants; preferred for use herein are nonionic or anionic emulsifiers. Such surface-active agents are described in "McCutcheon's Detergent and Emulsifiers," North American Edition, 1980 Annual published by the McCutcheon Division, MC Publishing Company, 175 Rock Road, Glen Rock, N.J. 07452, USA.

Preferred for use herein are high molecular weight alcohols such as cetearyl alcohol, cetyl alcohol, stearyl alcohol, emulsifying wax, glyceryl monostearate. Other examples are ethylene glycol distearate, sorbitan tristearate, propylene glycol monostearate, sorbitan monooleate, sorbitan monostearate (SPAN 60), diethylene glycol monolaurate, sorbitan monopalmitate, sucrose dioleate, sucrose stearate (CRODESTA F-160), polyoxyethylene lauryl ether (BRIJ 30), polyoxyethylene (2) stearyl ether (BRIJ 72), polyoxyethylene (21) stearyl ether (BRIJ 721), polyoxyethylene monostearate (Myij 45), polyoxyethylene sorbitan monostearate (TWEEN 60), polyoxyethylene sorbitan monooleate (TWEEN 80), polyoxyethylene sorbitan monolaurate (TWEEN 20) and sodium oleate. Cholesterol and cholesterol derivatives may also be employed in externally used emulsions and promote w/o emulsions.

Especially suitable nonionic emulsifying agents are those with hydrophile-lipophile balances (HLB) of about 3 to 6 for w/o system and 8 to 18 for o/w system as determined by the method described by Paul L. Lindner in "Emulsions and Emulsion", edited by Kenneth Lissant, published by Dekker, New York, N.Y., 1974, pages 188-190. More preferred for use herein are one or more nonionic surfactants that produce a system having HLB of about 8 to about 18.

Examples of such nonionic emulsifiers include but are not limited to "BRIJ 72", the trade name for a polyoxyethylene (2) stearyl ether having an HLB of 4.9; "BRIJ 721", the trade name for a polyoxyethylene (21) stearyl ether having an HLB of 15.5, "Brij 30", the trade name for polyoxyethylene lauryl ether having an HLB of 9.7; "Polawax", the trade name for emulsifying wax having an HLB of 8.0; "Span 60", the trade name for sorbitan monostearate having an HLB of 4.7; "Crodesta F-160", the trade name for sucrose stearate" having an HLB of 14.5. All of these materials are available from Ruger Chemicals Inc.; Croda; ICI Americas, Inc.; Spectrum Chemicals; and BASF. When the topical formulations of the present invention contain at least one emulsifying agent, each emulsifying agent is present in amount from about 0.5 to about 2.5 wt %, preferably 0.5 to 2.0%, more preferably 1.0% or 1.8%. Preferably the emulsifying agent comprises a mixture of steareth 21 (at about 1.8%) and steareth 2 (at about 1.0%).

The topical pharmaceutical compositions may also comprise suitable emollients. Emollients are materials used for the prevention or relief of dryness, as well as for the protection of the skin, nail, hair, claw or hoof. Useful emollients include, but are not limited to, cetyl alcohol, isopropyl myristate, stearyl alcohol, and the like. A wide variety of suitable emollients are known and can be used herein. See e.g., Sagarin, Cosmetics, Science and Technology, 2nd Edition, Vol. 1, pp. 32-43 (1972), and U.S. Pat. No. 4,919,934, to Deckner et al., issued Apr. 24, 1990, both of which are incorporated herein by reference in their entirety. These materials are available from Ruger Chemical Co, (Irvington, N.J.).

When the topical formulations of the present invention contain at least one emollient, each emollient is present in an amount from about 0.1 to 15%, preferably 0.1 to about 3.0, more preferably 0.5, 1.0, or 2.5 wt %. Preferably the emollient is a mixture of cetyl alcohol, isopropyl myristate and stearyl alcohol in a 1/5/2 ratio. The emollient may also be a mixture of cetyl alcohol and stearyl alcohol in a 1/2 ratio.

The topical pharmaceutical compositions may also comprise suitable antioxidants, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4, 5-trihydroxybutyrophenone, 4-hydroxymethyl-2,6-di-tert-butylphenol, erythorbic acid, gum guaiac, propyl gallate, thiodipropionic acid, dilauryl thiodipropionate, tert-butylhydroquinone and tocopherols such as vitamin E, and the like, including pharmaceutically acceptable salts and esters of these compounds. Preferably, the antioxidant is butylated hydroxytoluene, butylated hydroxyanisole, propyl gallate, ascorbic acid, pharmaceutically acceptable salts or esters thereof, or mixtures thereof. Most preferably, the antioxidant is butylated hydroxytoluene. These materials are available from Ruger Chemical Co, (Irvington, N.J.).

When the topical formulations of the present invention contain at least one antioxidant, the total amount of antioxidant present is from about 0.001 to 0.5 wt %, preferably 0.05 to about 0.5 wt %, more preferably 0.1%.

The topical pharmaceutical compositions may also comprise suitable preservatives. Preservatives are compounds added to a pharmaceutical formulation to act as an antimicrobial agent. Among preservatives known in the art as being effective and acceptable in parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. See, e.g., Wallhausser, K.-H., Develop. Biol. Standard, 24:9-28 (1974) (S. Krager, Basel). Preferably, the preservative is selected from methylparaben, propylparaben and mixtures thereof. These materials are available from Inolex Chemical Co (Philadelphia, Pa.) or Spectrum Chemicals.

When the topical formulations of the present invention contain at least one preservative, the total amount of preservative present is from about 0.01 to about 0.5 wt %, preferably from about 0.1 to 0.5%, more preferably from about 0.03 to about 0.15. Preferably the preservative is a mixture of methylparaben and proplybarben in a 5/1 ratio. When alcohol is used as a preservative, the amount is usually 15 to 20%.

The topical pharmaceutical compositions may also comprise suitable chelating agents to form complexes with metal cations that do not cross a lipid bilayer. Examples of suitable chelating agents include ethylene diamine tetraacetic acid (EDTA), ethylene glycol-bis(beta-aminoethyl ether)-N,N,N', N'-tetraacetic acid (EGTA) and 8-Amino-2-[(2-amino-5-methylphenoxy)methyl]-6-methoxyquinoline-N,N,N',N'-tetraacetic acid, tetrapotassium salt (QUIN-2). Preferably the chelating agents are EDTA and citric acid. These materials are available from Spectrum Chemicals.

When the topical formulations of the present invention contain at least one chelating agent, the total amount of chelating agent present is from about 0.005% to 2.0% by weight, preferably from about 0.05% to about 0.5 wt %, more preferably about 0.1% by weight.

The topical pharmaceutical compositions may also comprise suitable neutralizing agents used to adjust the pH of the formulation to within a pharmaceutically acceptable range. Examples of neutralizing agents include but are not limited to trolamine, tromethamine, sodium hydroxide, hydrochloric acid, citric acid, and acetic acid. Such materials are available from are available from Spectrum Chemicals (Gardena, Calif.).

When the topical formulations of the present invention contain at least one neutralizing agent, the total amount of neutralizing agent present is from about 0.1 wt to about 10 wt %, preferably 0.1 wt % to about 5.0 wt %, and more preferably about 1.0 wt %. The neutralizing agent is generally added in whatever amount is required to bring the formulation to the desired pH.

The topical pharmaceutical compositions may also comprise suitable viscosity increasing agents. These components are diffusible compounds capable of increasing the viscosity of a polymer-containing solution through the interaction of the agent with the polymer. CARBOPOL ULTREZ 10 may be used as a viscosity-increasing agent. These materials are available from Noveon Chemicals, Cleveland, Ohio.

When the topical formulations of the present invention contain at least one viscosity increasing agent, the total amount of viscosity increasing agent present is from about 0.25% to about 5.0% by weight, preferably from about 0.25% to about 1.0 wt %, and more preferably from about 0.4% to about 0.6% by weight.

The topical pharmaceutical compositions may also comprise suitable nail penetration enhancers. Examples of nail penetration enhancers include mercaptan compounds, sulfites and bisulfites, keratolytic agents and surfactants. Nail penetration enhancers suitable for use in the invention are described in greater detail in Malhotra et al., J. Pharm. Sci., 91:2, 312-323 (2002), which is incorporated herein by reference in its entirety.

The topical pharmaceutical compositions may also comprise one or more suitable solvents. The ability of any solid substance (solute) to dissolve in any liquid substance (solvent) is dependent upon the physical properties of the solute and the solvent. When solutes and solvents have similar physical properties the solubility of the solute in the solvent will be the greatest. This gives rise to the traditional understanding that "like dissolves like." Solvents can be characterized in one extreme as non-polar, lipophilic oils, while in the other extreme as polar hydrophilic solvents. Oily solvents dissolve other non-polar substances by Van der Wals interactions while water and other hydrophilic solvents dissolve polar substances by ionic, dipole, or hydrogen bonding interactions. All solvents can be listed along a continuum from the least polar, i.e. hydrocarbons such as decane, to the most polar solvent being water. A solute will have its greatest solubility in solvents having equivalent polarity. Thus, for drugs having minimal solubility in water, less polar solvents will provide improved solubility with the solvent having polarity nearly equivalent to the solute providing maximum solubility. Most drugs have intermediate polarity, and thus experience maximum solubility in solvents such as propylene glycol or ethanol, which are significantly less polar than water. If the drug has greater solubility in propylene glycol (for example 8% (w/w)) than in water (for example 0.1% (w/w)), then addition of water to propylene glycol should decrease the maximum amount of drug solubility for the solvent mixture compared with pure propylene glycol. Addition of a poor solvent to an excellent solvent will decrease the maximum solubility for the blend compared with the maximum solubility in the excellent solvent.

When compounds are incorporated into topical formulations the concentration of active ingredient in the formulation may be limited by the solubility of the active ingredient in the chosen solvent and/or carrier. Non-lipophilic drugs typically display very low solubility in pharmaceutically acceptable solvents and/or carriers. For example, the solubility of some compounds in the invention in water is less than 0.00025% wt/wt. The solubility of the same compounds in the invention can be less than about 2% wt/wt in either propylene glycol or isopropyl myristate. In one embodiment of the present invention, diethylene glycol monoethyl ether (DGME) is the solvent used to dissolve the compounds of the invention. The compounds in the invention useful in the present formulation are believed to have a solubility of from about 10% wt/wt to about 25% wt/wt in DGME. In another embodiment a DGME water cosolvent system is used to dissolve the compounds of the invention. The solvent capacity of DGME drops when water is added; however, the DGME/water cosolvent system can be designed to maintain the desired concentration of from about 0.1% to about 5% wt/wt active ingredient. Preferably the active ingredient is present from about 0.5% to about 3% wt/wt, and more preferably at about 1% wt/wt, in the as-applied topical formulations. Because DGME is less volatile than water, as the topical formulation evaporates upon application, the active agent becomes more soluble in the cream formulation. This increased solubility reduces the likelihood of reduced bioavailability caused by the drug precipitating on the surface of the skin, nail, hair, claw or hoof.

Liquid forms, such as lotions suitable for topical administration or suitable for cosmetic application, may include a suitable aqueous or nonaqueous vehicle with buffers, suspending and dispensing agents, thickeners, penetration enhancers, and the like. Solid forms such as creams or pastes or the like may include, for example, any of the following ingredients, water, oil, alcohol or grease as a substrate with surfactant, polymers such as polyethylene glycol, thickeners, solids and the like. Liquid or solid formulations may include enhanced delivery technologies such as liposomes, microsomes, microsponges and the like.

Additionally, the compounds can be delivered using a sustained-release system, such as semipermeable matrices of solid hydrophobic polymers containing the therapeutic agent. Various sustained-release materials have been established and are well known by those skilled in the art.

Topical treatment regimens according to the practice of this invention comprise applying the composition directly to the skin, nail, hair, claw or hoof at the application site, from one to several times daily.

Formulations of the present invention can be used to treat, ameliorate or prevent conditions or symptoms associated with bacterial infections, acne, inflammation and the like.

In an exemplary embodiment, the pharmaceutical formulation includes a simple solution. In an exemplary embodiment, the simple solution includes an alcohol. In an exemplary embodiment, the simple solution includes alcohol and water. In an exemplary embodiment, the alcohol is ethanol, ethylene glycol, propanol, polypropylene glycol, isopropanol or butanol. In another exemplary embodiment, the simple solution is a member selected from about 10% polypropylene glycol and about 90% ethanol; about 20% polypropylene glycol and about 80% ethanol; about 30% polypropylene glycol and about 70% ethanol; about 40% polypropylene glycol and about 60% ethanol; about 50% polypropylene glycol and about 50% ethanol; about 60% polypropylene glycol and about 40% ethanol; about 70% polypropylene glycol and about 30% ethanol; about 80% polypropylene glycol and about 20% ethanol; about 90% polypropylene glycol and about 10% ethanol.

In an exemplary embodiment, the pharmaceutical formulation is a lacquer. Please see Remington's, supra, for more information on the production of lacquers.

In an exemplary embodiment, the compound is present in said pharmaceutical formulation in a concentration of from about 0.5% to about 15%. In an exemplary embodiment, the compound is present in said pharmaceutical formulation in a concentration of from about 0.1% to about 12.5%. In an exemplary embodiment, the compound is present in said pharmaceutical formulation in a concentration of from about 1% to about 10%. In an exemplary embodiment, the compound is present in said pharmaceutical formulation in a concentration of from about 1% to about 5%. In an exemplary embodiment, the compound is present in said pharmaceutical formulation in a concentration of from about 0.5% to about 5%. In an exemplary embodiment, the compound is present in said pharmaceutical formulation in a concentration of from about 0.5% to about 7.5%. In an exemplary embodiment, the compound is present in said pharmaceutical formulation in a concentration of from about 5% to about 7.5%. In an exemplary embodiment, the compound is present in said pharmaceutical formulation in a concentration of from about 2% to about 8%. In an exemplary embodiment, the compound is present in said pharmaceutical formulation in a concentration of from about 4% to about 9%.

X. b) Additional Active Agents

The following are examples of the cosmetic and pharmaceutical agents that can be added to the topical pharmaceutical formulations of the present invention. The following agents are known compounds and are readily available commercially.

Anti-inflammatory agents include, but are not limited to, bisabolol, mentholatum, dapsone, aloe, hydrocortisone, and the like.

Vitamins include, but are not limited to, Vitamin B, Vitamin E, Vitamin A, Vitamin D, and the like and vitamin derivatives such as tazarotene, calcipotriene, tretinoin, adapalene and the like.

Anti-aging agents include, but are not limited to, niacinamide, retinol and retinoid derivatives, AHA, Ascorbic acid, lipoic acid, coenzyme Q 10, beta hydroxy acids, salicylic acid, copper binding peptides, dimethylaminoethyl (DAEA), and the like.

Sunscreens and or sunburn relief agents include, but are not limited to, PABA, jojoba, aloe, padimate-O, methoxycinnamates, proxamine HCl, lidocaine and the like. Sunless tanning agents include, but are not limited to, dihydroxyacetone (DHA).

Psoriasis-treating agents and/or acne-treating agents include, but are not limited to, salicylic acid, benzoyl peroxide, coal tar, selenium sulfide, zinc oxide, pyrithione (zinc and/or sodium), tazarotene, calcipotriene, tretinoin, adapalene and the like.

Agents that are effective to control or modify keratinization, including without limitation: tretinoin, tazarotene, and adapalene.

The compositions comprising an compound/active agent of the invention, and optionally at least one of these additional agents, are to be administered topically. In a primary application, this leads to the compounds of the invention and any other active agent working upon and treating the skin, nail, hair, claw or hoof. Alternatively, any one of the topically applied active agents may also be delivered systemically by transdermal routes.

In such compositions an additional cosmetically or pharmaceutically effective agent, such as an anti-inflammatory agent, vitamin, anti-aging agent, sunscreen, and/or acne-treating agent, for example, is usually a minor component (from about 0.001% to about 20% by weight or preferably from about 0.01% to about 10% by weight) with the remainder being various vehicles or carriers and processing aids helpful for forming the desired dosing form.

X. c) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat.* B677: 1-27). Compound half-life is inversely proportional to the frequency of dosage of a compound. In vitro half-lives of compounds may be predicted from assays of microsomal half-life as described by Kuhnz and Gleschen (Drug Metabolism and Disposition, (1998) volume 26, pages 1120-1127).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

X. d) Administration

For any compound used in the method of the invention, the therapeutically effective dose can be estimated initially from cell culture assays, as disclosed herein. For example, a dose can be formulated in animal models to achieve a circulating concentration range that includes the $EC_{50}$ (effective dose for 50% increase) as determined in cell culture, i.e., the concentration of the test compound which achieves a half-maximal inhibition of bacterial cell growth. Such information can be used to more accurately determine useful doses in humans.

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Dosage amount and interval can be adjusted individually to provide plasma levels of the active moiety that are sufficient to maintain bacterial cell growth inhibitory effects. Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m²/day.

The amount of the compound in a formulation can vary within the full range employed by those skilled in the art. Typically, the formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention provides a compound having a structure according to the formula:

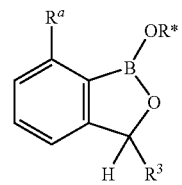

wherein R* is a member selected from H and a negative charge; $R^3$ is a member selected from H, cyano, substituted or unsubstituted nitroalkyl and substituted or unsubstituted aminoalkyl; $R^a$ is a member selected from H and —$YR^5$; wherein Y is a member selected from O and S; $R^5$ is a member selected from H, substituted or unsubstituted alkyl and substituted or unsubstituted heteroalkyl; with the proviso that $R^a$ and $R^3$ cannot both be H; with the proviso that $R^a$ and R*, together with the atoms to which they are attached, are optionally combined to form a 6- to 10-membered substituted or unsubstituted heterocycloalkyl ring; and with the proviso that when $R^3$ is H, $R^a$ does not have a structure which is a member selected from: unsubstituted benzyloxy, —$OCH_2COOH$, methoxy, ethoxy, with the proviso that when $R^a$ is H, $R^3$ is not cyano, or a salt thereof.

In an exemplary embodiment, according to the above paragraph, having a structure according to the following formula:

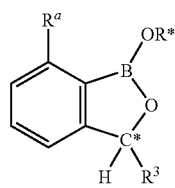

wherein C* is a carbon atom with the proviso that when $R^3$ is not H, C* is a stereocenter which has a configuration which is a member selected from (R) and (S).

In an exemplary embodiment, according to any of the above paragraphs, $R^3$ is-$(CR^{20}R^{21})_nNR^{22}R^{23}$ in which n is an integer selected from 1 to 10; each $R^{20}$ and each $R^{21}$ is a member independently selected from H, $R^{26}$, $OR^{26}$, $NR^{26}R^{27}$, $SR^{26}$, —$S(O)R^{26}$, —$S(O)_2R^{26}$, —$S(O)_2NR^{26}R^{27}$, —$C(O)R^{27}$, —$C(O)OR^{27}$, —$C(O)NR^{26}R^{27}$; $R^{22}$ and $R^{23}$ are members independently selected from H, —$S(O)R^{28}$, —$S(O)_2R^{28}$, —$S(O)_2NR^{28}R^{29}$, —$C(O)R^{28}$, —$C(O)OR^{28}$, —$C(O)NR^{28}R^{29}$, nitro, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; wherein each $R^{26}$, each $R^{27}$, each $R^{28}$ and each $R^{29}$ is a member independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, n is an integer selected from 1 to 5.

In an exemplary embodiment, according to any of the above paragraphs, n is 1.

In an exemplary embodiment, according to any of the above paragraphs, $R^{20}$ is substituted or unsubstituted alkyl.

In an exemplary embodiment, according to any of the above paragraphs, $R^{20}$ is unsubstituted alkyl.

In an exemplary embodiment, according to any of the above paragraphs, $R^{20}$ is $C_1$-$C_4$ unsubstituted alkyl.

In an exemplary embodiment, according to any of the above paragraphs, $R^{20}$ is methyl.

In an exemplary embodiment, according to any of the above paragraphs, $R^{21}$ is H.

In an exemplary embodiment, according to any of the above paragraphs, $R^{23}$ is H.

In an exemplary embodiment, according to any of the above paragraphs, $R^3$ is a member selected from cyano and —$CH_2NO_2$.

In an exemplary embodiment, according to any of the above paragraphs, $R^{22}$ is a member selected from —$C(O)R^{28}$ and —$C(O)OR^{28}$.

In an exemplary embodiment, according to any of the above paragraphs, $R^{28}$ is a member selected from substituted or unsubstituted alkyl, substituted or unsubstituted heteroalkyl and substituted or unsubstituted aryl.

In an exemplary embodiment, according to any of the above paragraphs, $R^{28}$ is a member selected from —$(CR^{30}R^{31})_mR^{32}$, wherein $R^{32}$ is a member selected from substituted or unsubstituted aryl, —$NR^{33}R^{34}$ and $OR^{33}$ wherein m is an integer selected from 0 to 10; each $R^{33}$ and each $R^{34}$ is a member independently selected from H, nitro, halogen, cyano, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, $R^{28}$ is a member selected from

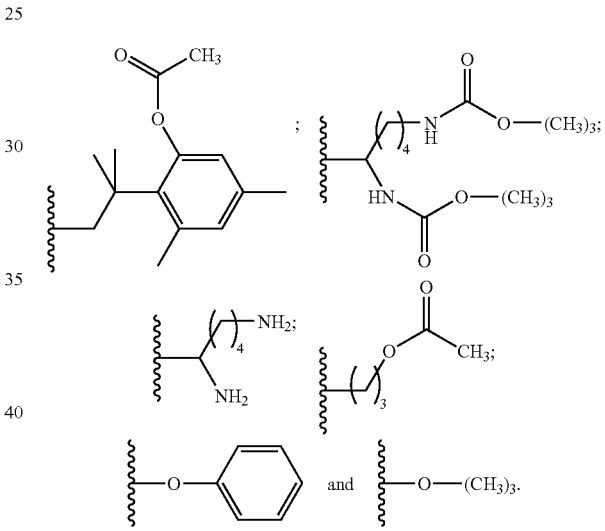

In an exemplary embodiment, according to any of the above paragraphs, $R^5$ is:

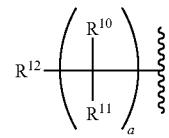

wherein a is a member selected from 1 to 10; each $R^{10}$ and each $R^{11}$ is a member selected from H, substituted or unsubstituted alkyl, OH and $NH_2$; $R^{12}$ is a member selected from H, $R^7$, halogen, cyano, amidino, $OR^7$, $NR^7R^8$, $SR^7$, —$N(R^7)S(O)_2R^8$, —$C(O)R^7$, —$C(O)OR^7$, —$C(O)NR^7R^8$; wherein each $R^7$ and each $R^8$ is a member independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, a is an integer selected from 1 to 5.

In an exemplary embodiment, according to any of the above paragraphs, a is an integer selected from 2 to 4.

In an exemplary embodiment, according to any of the above paragraphs, each $R^{10}$ and each $R^{11}$ is a member selected from H, substituted or unsubstituted alkyl, OH and $NH_2$.

In an exemplary embodiment, according to any of the above paragraphs, each $R^{10}$ and each $R^{11}$ is a member selected from H, hydroxyalkyl and $NH_2$.

In an exemplary embodiment, according to any of the above paragraphs, at least one $R^{10}$ or $R^{11}$ is a member selected from hydroxyalkyl and $NH_2$.

In an exemplary embodiment, according to any of the above paragraphs, each $R^{10}$ and each $R^{11}$ is H.

In an exemplary embodiment, according to any of the above paragraphs, $R^{12}$ is a member selected from H, cyano, amidino, $-N(R^7)S(O)_2R^8$, $OR^7$, $NR^7R^8$, $-C(O)OR^7$, $-C(O)NR^7R^8$; each $R^7$ and each $R^8$ is a member independently selected from H substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, each $R^7$ and each $R^8$ is a member independently selected from H, $-C(O)R^9$, $-C(O)NHR^9$, substituted or unsubstituted $C_1$-$C_4$ alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; wherein $R^9$ is substituted or unsubstituted $C_1$-$C_4$ alkyl.

In an exemplary embodiment, according to any of the above paragraphs, at least one member selected from $R^7$ and $R^8$ is a member independently selected from $-C(O)R^9$ and $-C(O)NHR^9$; wherein $R^9$ is substituted or unsubstituted $C_1$-$C_4$ alkyl.

In an exemplary embodiment, according to any of the above paragraphs, $R^{12}$ is a member selected from OH, $NH_2$, methyl, ethyl, $-NHS(O)_2CH_3$, cyano, $-NHC(O)CH_3$, $-NHC(O)NHCH_2CH_3$, $-C(O)NH_2$, $-C(O)OH$, 4-(methoxy)phenyl, benzyl, $-NHC(O)OCH_2Ph$, $-C(O)NHCH_2CH_2OH$ and $-C(NH_2)(NH)$.

In an exemplary embodiment, according to any of the above paragraphs, when $R^{12}$ comprises $OR^7$, said $R^7$ comprises a hydroxy-protecting group; and when $R^{12}$ comprises $NR^7R^8$, at least one of said $R^7$ or $R^8$ comprises an amino-protecting group.

In an exemplary embodiment, according to any of the above paragraphs, $R^3$ is a member selected from H, $-CH_2NH_2$ and $-CH_2NO_2$; and $R^{12}$ is a member selected from OH, $NH_2$, methyl, ethyl, $-NHS(O)_2CH_3$, cyano, $-NHC(O)CH_3$, $-NHC(O)NHCH_2CH_3$, $-C(O)NH_2$, $-C(O)OH$, 4-(methoxy)phenyl, benzyl, $-NHC(O)OCH_2Ph$, $-C(O)NHCH_2CH_2OH$ and $-C(NH_2)(NH)$.

In an exemplary embodiment, according to any of the above paragraphs, $R^3$ is a member selected from H, $-CH_2NH_2$ and $-CH_2NO_2$; and $R^a$ is a member selected from H, $-O(CH_2)_3NH_2$, $-O(CH_2)_3OH$, $-OCH_2CH_3$, $-O(CH_2)_3NHS(O)_2CH_3$, $-O(CH_2)_3CN$, $-O(CH_2)_3NHC(O)CH_3$, $-O(CH_2)_3NHCH_3$, $-O(CH_2)_3OCH_3$, $-O(CH_2)_4OH$, $-OCH_3$, $-O(CH_2)_3NHC(O)NHCH_2CH_3$, $-O(CH_2)_3C(O)NH_2$, $-O(CH_2)_3C(O)OH$, $-O(CH_2)_4NH_2$, $-O(CH_2)_2NH_2$, $-OCH_2CH_2CH(NH_2)CH_2OH$, $-OCH_2Ph(4-methoxy)$, $-O(CH_2)_4OCH_2Ph$, $-O(CH_2)_3NHC(O)OCH_2Ph$, $-OCH_2C(O)NH(CH_2)_2OH$, $-O(CH_2)_3NHC(O)CH_3$, $-O(CH_2)_3C(NH_2)(NH)$, $-C(O)OCH_3$, $-OCH_2C(O)OH$ and $-OCH_2CH(CH_2OH)(CH_2)OH$.

In an exemplary embodiment, according to any of the above paragraphs, when $R^3$ is H, $R^a$ is a member selected from $-O(CH_2)_3NH_2$, $-O(CH_2)_3NHS(O)_2CH_3$, $-O(CH_2)_3CN$, $-O(CH_2)_3NHC(O)CH_3$, $-O(CH_2)_3NHCH_3$, $-O(CH_2)_4OH$, $-O(CH_2)_3NHC(O)NHCH_2CH_3$, $-O(CH_2)_3C(O)NH_2$, $-O(CH_2)_3C(O)OH$, $-O(CH_2)_4NH_2$, $-O(CH_2)_2NH_2$, $-OCH_2CH_2CH(NH_2)CH_2OH$, $-OCH_2Ph(4-methoxy)$, $-O(CH_2)_4OCH_2Ph$, $-OCH_2C(O)NH(CH_2)_2OH$ and $-OCH_2CH(CH_2OH)(CH_2)OH$; when $R^3$ is $-CH_2NH_2$, $R^a$ is a member selected from H, $-O(CH_2)_3OH$, $-OCH_2CH_3$, $-O(CH_2)_3OCH_3$, $-OCH_3$, $-O(CH_2)_4NH_2$, $-O(CH_2)_3NHS(O)_2CH_3$, $-O(CH_2)_3NHC(O)OCH_2Ph$, $-O(CH_2)_3NHC(O)CH_3$, $-O(CH_2)_3NH_2$; and when $R^3$ is $-CH_2NO_2$, $R^a$ is a member selected from $-O(CH_2)_3CN$ and $-OCH_2CH_3$.

In an exemplary embodiment, according to any of the above paragraphs, when $R^3$ is H, $R^a$ is a member selected from $-O(CH_2)_3NH_2$, $-O(CH_2)_3NHS(O)_2CH_3$, $-O(CH_2)_3CN$, $-O(CH_2)_3NHC(O)CH_3$, $-O(CH_2)_3NHCH_3$, $-O(CH_2)_4OH$, $-O(CH_2)_3NHC(O)NHCH_2CH_3$, $-O(CH_2)_3C(O)NH_2$, $-O(CH_2)_3C(O)OH$, $-O(CH_2)_4NH_2$, $-O(CH_2)_2NH_2$, $-OCH_2CH_2CH(NH_2)CH_2OH$; when $R^3$ is $-CH_2NH_2$, $R^a$ is a member selected from H, $-O(CH_2)_3OH$, $-OCH_2CH_3$, $-O(CH_2)_3OCH_3$, $-OCH_3$.

In an exemplary embodiment, according to any of the above paragraphs, when $R^3$ is H, $R^a$ is a member selected from $-O(CH_2)_3NH_2$, $-O(CH_2)_3CN$, $-O(CH_2)_3NHC(O)CH_3$, $-O(CH_2)_3NHCH_3$; and when $R^3$ is $-CH_2NH_2$, $R^a$ is a member selected from H, $-O(CH_2)_3OH$, and $-OCH_2CH_3$.

In an exemplary embodiment, according to any of the above paragraphs, the a structure which is a member selected from

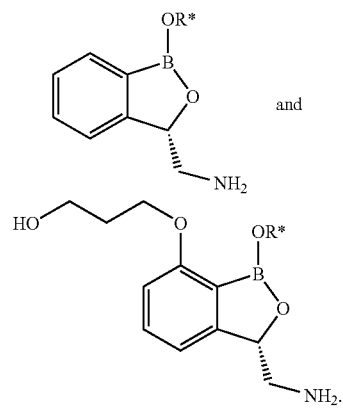

In an exemplary embodiment, according to any of the above paragraphs, the invention provides a compound having a structure according to a formula which is a member selected from:

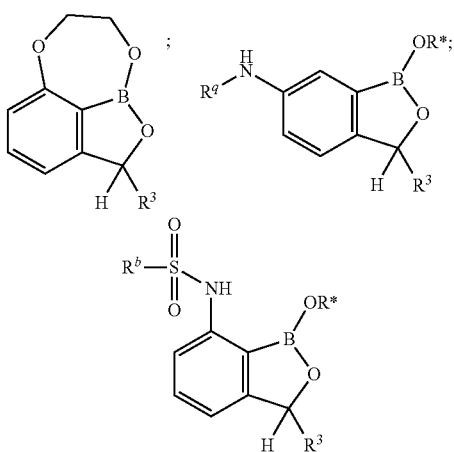

R* is a member selected from H and a negative charge; $R^q$ is a member selected from H and —$SO_2$—$R^b$; $R^b$ is a member selected from unsubstituted phenyl and unsubstituted pyridinyl; $R^3$ is a member selected from H, cyano, substituted or unsubstituted nitroalkyl and substituted or unsubstituted aminoalkyl; or a salt thereof.

In an exemplary embodiment, according to any of the above paragraphs, having a structure according to a formula which is a member selected from:

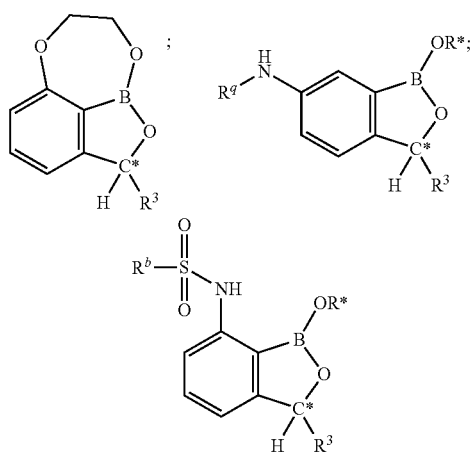

wherein C* is a carbon atom; with the proviso that when $R^3$ is not H, C* is a stereocenter which has a configuration which is a member selected from (R) and (S).

In an exemplary embodiment, according to any of the above paragraphs, $R^3$ is a member selected from H, —$CH_2NH_2$ and —$CH_2NO_2$.

In an exemplary embodiment, according to any of the above paragraphs, R* is H.

In an exemplary embodiment, according to any of the above paragraphs, wherein $R^3$ is not H, and the C* stereocenter is in a (S) configuration.

In an exemplary embodiment, according to any of the above paragraphs, wherein $R^3$ is —$CH_2NH_2$.

In an exemplary embodiment, according to any of the above paragraphs, said alkyl is a member selected from linear alkyl and branched alkyl, and wherein said heteroalkyl is a member selected from linear heteroalkyl and branched heteroalkyl.

In an exemplary embodiment, according to any of the above paragraphs, the invention provides a composition comprising: a) a first stereoisomer of the compound described herein, wherein $R^3$ is not H; b) at least one additional stereoisomer of the first stereoisomer; wherein the first stereoisomer is present in an enantiomeric excess of at least 80% relative to said at least one additional stereoisomer.

In an exemplary embodiment, according to any of the above paragraphs, said enantiomeric excess is at least 92%.

In an exemplary embodiment, according to any of the above paragraphs, the C* stereocenter of the first stereoisomer is in a (S) configuration.

In an exemplary embodiment, according to any of the above paragraphs, $R^3$ is —$CH_2NH_2$.

In an exemplary embodiment, according to any of the above paragraphs, the invention provides a composition comprising a compound described herein, wherein $R^3$ is not H and the C* stereocenter is in a (S) configuration, and said composition is substantially free of the enantiomer of the compound.

In an exemplary embodiment, according to any of the above paragraphs, the invention provides a composition comprising a compound described herein, wherein the composition is substantially free of the enantiomer of the compound.

In an exemplary embodiment, according to any of the above paragraphs, the invention provides a combination comprising a compound described herein, or a pharmaceutically acceptable salt thereof, together with at least one other therapeutically active agent.

In an exemplary embodiment, according to any of the above paragraphs, the combination is a unit dosage form.

In an exemplary embodiment, according to any of the above paragraphs, the invention provides a pharmaceutical formulation comprising: a) a compound described herein, or a pharmaceutically acceptable salt thereof, and b) a pharmaceutically acceptable excipient.

In an exemplary embodiment, according to any of the above paragraphs, the pharmaceutical formulation is a unit dosage form.

In an exemplary embodiment, according to any of the above paragraphs, the invention provides a method of inhibiting an enzyme, comprising: contacting the enzyme with the compound described herein, thereby inhibiting the enzyme.

In an exemplary embodiment, according to any of the above paragraphs, the invention provides a method of inhibiting an enzyme, comprising: contacting the enzyme with a pharmaceutical formulation described herein, thereby inhibiting the enzyme.

In an exemplary embodiment, according to any of the above paragraphs, the enzyme is a t-RNA synthetase which comprises an editing domain. In an exemplary embodiment, according to any of the above paragraphs, the enzyme is a leucyl t-RNA synthetase.

In an exemplary embodiment, according to any of the above paragraphs, the invention provides a method of killing and/or preventing the growth of a microorganism, comprising: contacting the microorganism with an effective amount of the compound described herein, thereby killing and/or preventing the growth of the microorganism.

In an exemplary embodiment, according to any of the above paragraphs, the invention provides a method of killing and/or preventing the growth of a microorganism, comprising: contacting the microorganism with an effective amount of the pharmaceutical formulation described herein, thereby killing and/or preventing the growth of the microorganism.

In an exemplary embodiment, according to any of the above paragraphs, the microorganism is a bacterium.

In an exemplary embodiment, according to any of the above paragraphs, the invention provides a method of treating and/or preventing a disease in an animal, comprising: administering to the animal a therapeutically effective amount of a compound described herein, or a pharmaceutically-acceptable salt thereof, thereby treating and/or preventing the disease.

In an exemplary embodiment, according to any of the above paragraphs, the invention provides a method of treating and/or preventing a disease in an animal, comprising: administering to the animal a therapeutically effective amount of a pharmaceutical formulation described herein, or a pharmaceutically-acceptable salt thereof, thereby treating and/or preventing the disease.

In an exemplary embodiment, according to any of the above paragraphs, the disease is pneumonia.

In an exemplary embodiment, according to any of the above paragraphs, the animal is a human.

In an exemplary embodiment, according to any of the above paragraphs, the salt is a pharmaceutically acceptable salt.

The invention is further illustrated by the Examples that follow. The Examples are not intended to define or limit the scope of the invention.

EXAMPLES

All solvents used were commercially available and were used without further purification. Reactions were typically run using anhydrous solvents under an inert atmosphere of $N_2$.

$^1$H, $^{13}$C, and $^{19}$F NMR spectra were recorded at 400 MHz for proton, 100 MHz for carbon-13, and 376 MHz for fluorine-19 on a Varian 300 MercuryPlus station with an Oxford AS400 Spectrometer equipped with a Varian 400 ATB PFG probe. All deuterated solvents typically contained 0.03% to 0.05% v/v tetramethylsilane, which was used as the reference signal (set at δ 0.00 for both $^1$H and $^{13}$C).

Compounds are named using ChemDraw 7.0 or their catalogue name if commercially available.

Mass spectra were recorded on a Waters MS consisting of an Alliance 2795 (LC) and Waters Micromass ZQ detector at 120° C. The mass spectrometer was equipped with an electrospray ion source (ESI) operated in a positive or negative mode. The mass spectrometer was scanned between m/z=100-1000 with a scan time of 0.3 s.

Elemental Analysis for C, H and N composition was performed using a Costech Instrument Elemental Combustion System ECS4010 with a helium flow of 100 mL/min (14 psi), oxygen 20 mL/min (10 psi), air 25 psi and purge of 50 mL/min. The reported analyses are an average of two runs.

HPLC analyses were performed on a Water 600 Controller system with a Waters 717 Plus Autosampler and a Waters 2996 Photodiode Array Detector. The column used was an ACE $C_{18}$, 5 μm, 4.6×150 mm. A linear gradient was applied, starting at 95% A (A: 0.1% $H_3PO_4$ in water) and ending at 90% B (B: MeCN) over 6 min and then maintained at 90% B until the 10 min mark. The column was then re-equilibrated over 3 min to 95:5 with a total run time of 20 min. The column temperature was at rt with the flow rate of 1.0 mL/min. The Diode Array Detector was scanned from 200-400 nm. For high purity samples requiring baseline subtraction, a linear gradient was applied, starting at 99% A (A: 0.1% $H_3PO_4$ in water) and ending at 90% B (B: MeCN) over 15 min. The column was then re-equilibrated over 3 min to 99% A with a total run time of 23 min. The column temperature was at rt with the flow rate of 1.0 mL/min. The Diode Array Detector was scanned from 200-400 nm. A blank MeOH sample was run immediately prior to the sample of which purity was to be determined: this was then subtracted to obtain the baseline subtracted chromatogram.

Thin layer chromatography (TLC) was performed on Alugram® (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), vanillin (generated by dissolving about 1 g vanillin in 100 mL 10% $H_2SO_4$), potassium permanganate (generated by dissolving 1.5 g $KMnO_4$ and 10 g $K_2CO_3$ in 1.25 mL NaOH and 200 mL $H_2O$), ninhydrin (available commercially from Aldrich), or Magic Stain (generated by thoroughly mixing 25 g $(NH_4)_6Mo_7O_{24}.4H_2O$, 5 g $(NH_4)_2Ce(IV)(NO_3)_6$ in 450 mL $H_2O$ and 50 mL conc $H_2SO_4$) to visualize the compound. Flash chromatography was preformed using typically 40-63 μm (230-400 mesh) silica gel from Silicycle following analogous techniques to those disclosed by Still et al. Typical solvents used for flash chromatography or thin layer chromatography (TLC) were mixtures of $CHCl_3$/MeOH, $CH_2Cl_2$/MeOH, EtOAc/MeOH and hexane/EtOAc. Reverse phase flash chromatography were performed on a Biotage® using a Biotage $C_{18}$ cartridges and a $H_2O$/MeOH gradient (typically eluting from 5% MeOH/$H_2O$ to 90% MeOH/$H_2O$).

Preparative chromatography was performed on either a Waters Prep LC 4000 System using a Waters 2487 Diode Array or on a Waters LC Module 1 plus. The column used were either a Waters×Terra Prep $C_{18}$, 5 μm, 30×100 mm, Phenomenex Luna $C_{18}$, 5 μm, 21.6×250 mm, or a Phenomenex Gemini $C_{18}$, 5 μm, 100×30 mm. Narrow gradients with MeCN/$H_2O$ (water containing either 0.1% TFA, 0.1% AcOH, 0.1% $HCO_2H$ or 0.1% $NH_4OAc$) were used to elute the compound at a flow rate of approximately 20 mL/min and a total run time between 20-30 min.

For enantiomeric excess determination, e.g. A2 and A49, chiral HPLC analysis was performed on a Waters 600 Controller and Multisolvent Delivery System using a Waters 717+ Autosampler and a Waters 996 Photodiode Array Detector with a Crownpak CR(+) column, eluting with 85:15 pH 1 perchloric acid in $H_2O$/MeOH mobile phase. The pH 1 perchloric acid was generated by adding 16.3 g of 70% perchloric acid to 1 L of distilled $H_2O$.

Starting materials used were either available from commercial sources or prepared according to literature procedures and had experimental data in accordance with those reported. 6-aminobenzo[c][1,2]oxaborol-1(3H)-ol (C50), for example, can be synthesized according to the methods described in U.S. Pat. Pubs. US20060234981 and US20070155699.

Example 1

3-Aminomethyl-3H-benzo[c][1,2]oxaborol-1-ol) hydrochloride (A1) 3-Nitromethyl-3H-benzo[c][1,2]oxaborol-1-ol

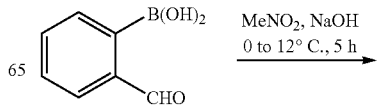

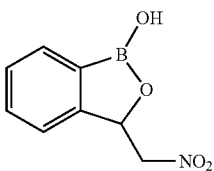

2-formylphenylboronic acid (3 g, 20.0 mmol) was added to solution of sodium hydroxide (850 mg, 1.05 eq) in 10 mL of water at 10° C. To this suspension was added nitromethane (1.1 mL, 1 eq) and then warmed to room temperature with stirring. After 30 minutes, the reaction was cooled in an ice bath and acidified with 3M HCl. A white precipitate was filtered and air dried to 3.2 g (82.9%) of 3-(nitromethyl)benzo[c][1,2]oxaborol-1(3H)-ol.

m.p. 122-127° C. $^1$H NMR 300 MHz (DMSO-$d_6$) δ 9.48 (s, 1H), 7.71-7.74 (d, J=6.9 Hz, 1H), 7.47-7.54 (m, 2H) 7.39 (t, J=7.65 Hz, 1H) 5.73-7.78 (dd, J=2.7, J=9.0 Hz, 1H), 5.30-5.35 (dd, J=3.0, J=13.5 Hz, 1H), 4.52-4.59 (dd, J=13.5, J=9.3 Hz, 1H). MS ESI (−) 192 [M−H].

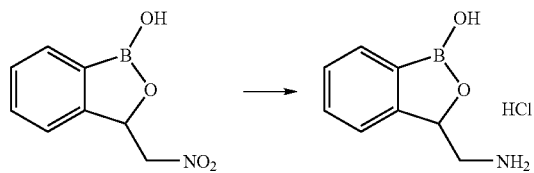 [SMILES: O=[N+]([O-])CC1OB(O)c2ccccc21 ; NCC1OB(O)c2ccccc21 ; Cl]

Synthesis of 3-Aminomethyl-3H-benzo[c][1,2]oxaborol-1-ol) hydrochloride (A1) using 10% palladium on carbon 3-(nitromethyl)benzo[c][1,2]oxaborol-1(3H)-ol (0.5 g, 2.59 mmol) was dissolved in absolute ethanol and flushed with $N_2$. A catalytic amount of 10% palladium on carbon was added and the reaction mixture flushed with $H_2$ 3× via balloon. Stirred under an atmosphere of $H_2$ for 24 hrs then filtered through celite, added 2 mL of water and concentrated in vacuo to a grey solid. This material was dissolved in a minimum amount of absolute ethanol, neutralized with concentrated hydrochloric acid, then ether was added to precipitate the title compound as a white solid. Air dried to 295 mg (57.1%).

m.p. 201-205° C. $^1$H NMR 300 MHz (DMSO-$d_6$) δ 9.59 (bs, 1H), 8.33 (bs, 3H), 7.81-7.83 (d, J=7.5 Hz, 1H), 7.35-7.50 (m, 3H), 5.34-5.37 (d, J=10.2 Hz, 1H), 3.46 (m, 1H), 2.71 (m, 1H). MS ESI (−) 162 [M−H], ESI (+) 164 [M+H].

Synthesis of 3-Aminomethyl-3H-benzo[c][1,2]oxaborol-1-ol) hydrochloride (A1) using Raney Nickel To a solution of 3-(nitromethyl)benzo[c][1,2]oxaborol-1 (3H)-ol (965 mg, 5 mmol) in ethanol (30 mL) were added ammonia (2M solution in ethanol, 18 mL, 36 mmol) and Raney 2800 Nickel (⅓ teaspoon of a slurry in water). The reaction mixture was subjected to hydrogenation at 45 atmospheres for 2 h at rt. The resulting mixture was filtered through Celite and the filtrate was concentrated in vacuo yielding the crude amine. The amine was dissolved in dioxanes (10 mL) and HCl (4M in dioxanes, 5 mL, 20 mmol) was added. After 1 h, the suspension was concentrated and the resulting solid was washed with hexanes followed by ether yielding 3-(aminomethyl)benzo[c][1,2]oxaborol-1(3H)-ol hydrochloride (917 mg, 4.6 mmol, 92% yield) as a white solid.

Recrystallization of 3-(aminomethyl)benzo[c][1,2]oxaborol-1(3H)-ol hydrochloride 3-(aminomethyl)benzo[c][1,2]oxaborol-1(3H)-ol hydrochloride (1.0 g) was taken up in hot water (3 mL) then hot acetonitrile (about 25 to 30 mL) was added until the milky suspension remains. The milky solution was allowed to cool to room temperature where a further 70-80 mL of acetonitrile was added. After 30 minutes the fluffy white suspension was filtered off and washed with $CH_2Cl_2$ to yield 680 mg clean 3-(aminomethyl)benzo[c][1,2]oxaborol-1(3H)-ol hydrochloride.

Synthesis of 3-Aminomethyl-3H-benzo[c][1,2]oxaborol-1-ol) hydrochloride (A1) using palladium hydroxide 3-(nitromethyl)benzo[c][1,2]oxaborol-1(3H)-ol (25 g, 130 mmol) was dissolved in acetic acid and placed into a 500 mL Parr flask. 4 g of 20 wt % palladium hydroxide on carbon was added and the reaction mixture flushed 3× with $H_2$ gas. Charged to 50 psi $H_2$ and shaken for 36 hrs then filtered free of catalyst and evaporated in vacuo. This residue was dissolved in 100 mL of dichloromethane and acidified with 50 mL 4M HCl in dioxane to precipitate crude hydrochloride salt. Addition of 30 mL methyl tert-butylether precipitates residual product. Crude was recrystallized by dissolving in 1:2 $H_2O$/ACN at 60° C. then adding ACN until saturation point is reached. Cooling to rt yielded 13 g of 3-(aminomethyl)benzo[c][1,2]oxaborol-1(3H)-ol hydrochloride as fine white crystals (50.3%).

Considerations for Choosing Catalyst

Synthesis of 3-(nitromethyl)benzo[c][1,2]oxaborol-1 (3H)-ol can be accomplished under a variety of hydrogenation conditions. Catalytic hydrogenation with 10% Pd/C under balloon is highly variable and in some cases was unsuccessful. Generally, higher pressures of hydrogen are necessary to drive the reduction to completion. It was discovered that the nitro moiety forms a complex with the boron atom and it is speculated that this complicates the reduction to amine. Using ammonia as a co-solvent disrupts this complex and facilitates the reduction at atmospheric or elevated pressure. Using Raney-nickel as the catalyst has the advantage of dramatically accelerating the reaction time, but is highly pyrophoric and needs to be kept moist to avoid fire hazard. Large scale (25 g) reductions have been achieved in a Parr apparatus with palladium hydroxide catalyst and acetic acid as solvent. This methodology provides good yields and strikes a balance between the speed of Raney-nickel and the ease of use of palladium on carbon.

(R)-3-Aminomethyl-3H-benzo[c][1,2]oxaborol-1-ol) hydrochloride (A60) 2-Bromo-1-(2-bromophenyl) ethanone

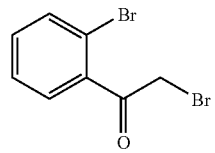

1

Ref—*Chem. Pharm. Bull.*, 1992, 40(5), 1170-1176. Bromine (12.6 mL, 0.246 mol, 1.0 eq) was added slowly to 2'-bromoacetophenone (48.9 g, 0.246 mol, 1.0 eq) in diethyl ether (250 mL) at room temperature and stirred for 2 hours. Water (500 mL) was added and the reaction mixture was stirred until the orange colour faded. The phases were separated and the aqueous layer was extracted with diethyl ether (3×250 mL). The combined organic phases were washed with brine (250 mL), dried over MgSO$_4$, filtered and concentrated under reduced pressure to give (1) as an orange oil (65 g, 95%).

TLC, (20% Et$_2$O : petrol) R$_f$=0.61; δ$_H$ (300 MHz, CDCl$_3$) 7.62 (1H, dd, J=7.7, 1.2 Hz), 7.49-7.31 (3H, m), 4.49 (2H, s).

(R)-2-Bromo-1-(2-bromophenyl)ethanol

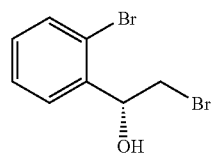

2

(R)-(+)-2-Methyl-CBS-oxazaborolidine (10.3 mL, 1.0 M in toluene, 10.3 mmol, 0.11 eq) was added to a stirred solution of (1) (26.0 g, 93.5 mmol, 1.0 eq) in THF (250 mL). The reaction mixture was cooled to −10° C. where BH$_3$.THF (112 mL, 1.0 M in THF, 112.3 mmol, 1.20 eq) was added over 4 hours. The reaction mixture was stirred for a further 45 minutes at −10° C. before the addition of methanol (130 mL). The reaction mixture was concentrated under reduced pressure. The resultant residue was subjected to flash column chromatography (10% Et$_2$O: petrol ether) to provide the product (2) as a pale yellow oil (25.1 g, 96%).

TLC, (10% Et$_2$O : petrol) R$_f$=0.20; δ$_H$ (300 MHz, CDCl$_3$) 7.40 (1H, d, J=7.78 Hz), 7.32 (1H, d, J=7.9 Hz), 7.15 (1H, t, J=7.5 Hz), 6.97 (1H, t, J=7.6 Hz), 5.05 (1H, td, J=8.6, 3.0 Hz), 3.56 (1H, dd, J=10.5, 2.6 Hz), 3.20 (1H, dd, J=10.5, 8.8 Hz), 3.01-2.92 (1H, m).

(R)-2-Azido-1-(2-bromophenyl)ethanol

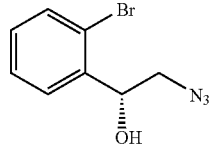

4

Ref—*Tetrahedron: Asymmetry* 2005, 16, 3633-3639. Sodium azide (3.5 g, 54.4 mmol, 1.05 eq) was added to a solution of (2) (14.5 g, 51.8 mmol, 1.00 eq) in DMF (55 mL) at room temperature. The reaction mixture was then heated to 80° C. for 24 hours. Water (150 mL) was added and this solution was then extracted with diethyl ether (3×150 mL). The combined organic phases were washed with brine (50 mL), dried over MgSO$_4$, filtered and concentrated under reduced pressure. The residue was subjected to flash column chromatography (15% Et$_2$O : petrol ether) to yield (4) as a yellow oil (9.5 g, 76%).

TLC, (15% Et$_2$O : petrol) R$_f$=0.36; δ$_H$ (300 MHz, CDCl$_3$) 7.64 (1H, dd, J=7.8, 1.4 Hz,), 7.56 (1H, dd, J=7.9, 1.1 Hz), 7.40 (1H, dt, J=7.6, 0.8 Hz), 7.21 (1H, dt, J=7.7, 1.7 Hz), 5.28 (1H, d, J=8.0 Hz), 3.60 (1H, dd, J=12.7, 2.8 Hz), 3.37 (1H, dd, J=12.7, 8.2 Hz), 2.68 (1H, bs).

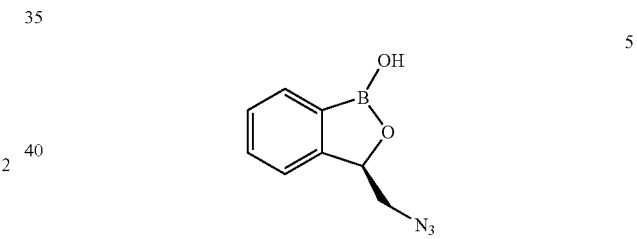

5

To a solution of (4) (9.3 g, 38.4 mmol, 1.00 eq) in toluene (300 mL) was added triisopropyl borate (13.3 mL, 57.6 mmol, 1.50 eq). The reaction flask had a Dean and Stark condenser attached and the reaction mixture was refluxed to remove approximately 300 mL of liquid. The dark reaction mixture was cooled to room temperature where THF (250 mL) was added and then cooled to −78° C. n-Butyl lithium (17.7 mL, 2.5 M in hexanes, 44.2 mmol, 1.15 eq) was added dropwise to the reaction mixture at −78° C. and then stirred for 30 minutes at this temperature. The reaction mixture was then allowed to warm to room temperature where it was stirred for 3 hours before being quenched with 6 M HCl (30 mL). The reaction mixture was concentrated under reduced pressure and the resulting residue was subjected to flash column chromatography (20% Et$_2$O : petrol ether to 30% Et$_2$O : petrol ether) to give the product (5) as a viscous yellow oil (4.9 g, 67%).

TLC, (40% Et$_2$O : petrol) R$_f$=0.47; δ$_H$ (300 MHz, DMSO) 9.39 (1H, s), 7.74 (1H, d, J=7.1 Hz), 7.47 (2H, s), 7.43-7.33 (1H, m), 5.35 (1H, dd, J=5.8, 2.8 Hz), 3.83 (1H, dd, J=13.1, 2.9 Hz), 3.49 (1H, dd, J=13.1, 6.2 Hz).

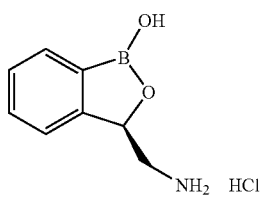

6

To a solution of (5) (2.75 g, 14.6 mmol, 1.0 eq) in methanol (150 mL) was added triphenylphosphine (3.82 g, 14.6 mmol, 1.0 eq) and this was stirred for 3 hours at room temperature. Concentrated HCl (7.0 mL) was added and the reaction mixture was stirred for a further 2 hours before being concentrated to dryness under reduced pressure. Dichloromethane was added and this was extracted with 2 M HCl (5×10 mL). The combined aqueous layers were washed with dichloromethane (10 mL) before being concentrated under reduced pressure. The residue was then recrystalised from hot water/acetonitrile (3 mL water/50-80 mL acetonitrile per gram of compound) to give the product (6) as a white solid (1.2 g, 41%).

m.p. 224-228° C.; $[\alpha]_D^{27}=-47.5°$ (c 1.9, $H_2O$); $\delta_H$ (300 MHz, DMSO+$D_2O$) 7.76 (1H, d, J=7.0 Hz), 7.58-7.36 (3H, m), 5.31 (1H, d, J=9.0 Hz), 3.47 (1H, d, J=13.2 Hz), 2.73 (1H, dd, J=12.8, 10.0 Hz); $\delta_C$ (75.5 MHz, $CDCl_3$) 131.67, 131.22, 128.63, 122.05, 77.06, 44.11; HRMS (ESI): calcd. for $C_9H_{13}BNO_2$ $[M+CH_2]^+$ 178.1039, found 178.1036.

(S)-3-Aminomethyl-3H-benzo[c][1,2]oxaborol-1-ol) hydrochloride (A2) (S)-2-Bromo-1-(2-bromophenyl)ethanol

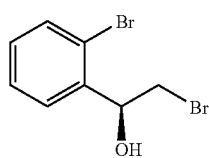

7

(S)-(-)-2-Methyl-CBS-oxazaborolidine (15.8 mL, 1.0 M in toluene, 15.8 mmol, 0.11 eq) was added to a stirred solution of (1) (40.0 g, 143 mmol, 1.0 eq) in THF (400 mL). The reaction mixture was cooled to −10° C. where $BH_3$.THF (172 mL, 1.0 M in THF, 172 mmol, 1.20 eq) was added over 4 hours. The reaction mixture was stirred for a further 45 minutes at −10° C. before the addition of methanol (180 mL). The reaction mixture was concentrated under reduced pressure. The resultant residue was subjected to flash column chromatography (10% $Et_2O$ : petrol ether) to provide the product (7) as a colourless oil (37.3 g, 93%).

TLC, (10% $Et_2O$ : petrol) $R_f$=0.25; $\delta_H$ (300 MHz, $CDCl_3$) 7.62 (1H, dd, J=7.8, 1.4 Hz), 7.54 (1H, dd, J=7.9, 1.0 Hz), 7.37 (1H, dt, J=7.6, 0.9 Hz), 7.19 (1H, dt, J=7.7, 1.5 Hz), 5.26 (1H, td, J=8.8, 3.0 Hz), 3.80 (1H, dd, J=10.5, 2.8 Hz), 3.42 (1H, dd, J=10.5, 8.9 Hz), 2.89-2.84 (1H, m).

(S)-2-Azido-1-(2-bromophenyl)ethanol

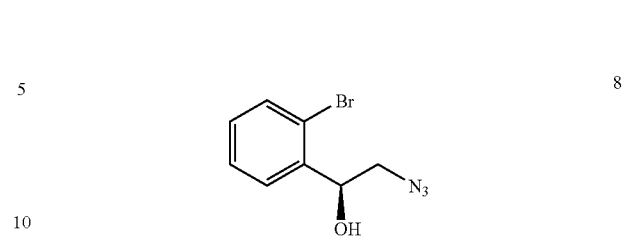

8

Ref—*Tetrahedron: Asymmetry* 2005, 16, 3633-3639. Sodium azide (9.7 g, 149.5 mmol, 1.2 eq) was added to a solution of (7) (35.0 g, 124.5 mmol, 1.0 eq) in DMF (140 mL) at room temperature. The reaction mixture was then heated to 80° C. for 24 hours. Water (450 mL) was added and this solution was then extracted with diethyl ether (3×500 mL). The combined organic phases were washed with brine (100 mL), dried over $MgSO_4$, filtered and concentrated under reduced pressure. The residue was subjected to flash column chromatography (15% $Et_2O$ : petrol ether) to yield (8) as an orange oil (24.3 g, 80%).

TLC, (10% $Et_2O$ : petrol) $R_f$=0.18; $\delta_H$ (300 MHz, $CDCl_3$) 7.60 (1H, dd, J=7.8, 1.4 Hz,), 7.52 (1H, dd, J=7.9, 1.1 Hz), 7.36 (1H, dt, J=7.6, 0.8 Hz), 7.17 (1H, dt, J=7.7, 1.7 Hz), 5.28-5.19 (1H, m), 3.55 (1H, dd, J=12.7, 2.8 Hz), 3.33 (1H, dd, J=12.7, 8.2 Hz), 2.94 (1H d, J=3.5 Hz).

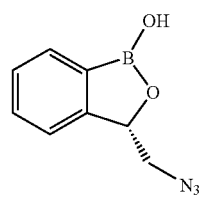

9

To a solution of (8) (23 g, 94.6 mmol, 1.00 eq) in toluene (460 mL) was added triisopropyl borate (32 mL, 142.0 mmol, 1.50 eq). The reaction flask had a Dean and Stark condenser attached and the reaction mixture was refluxed to remove approximately 450 mL of liquid. The dark reaction mixture was cooled to room temperature where THF (400 mL) was added and then cooled to −78° C. n-Butyl lithium (43.5 mL, 2.5 M in hexanes, 108.8 mmol, 1.15 eq) was added dropwise to the reaction mixture at −78° C. and then stirred for 30 minutes at this temperature. The reaction mixture was then allowed to warm to room temperature where it was stirred for 3 hours before being quenched with 6 M HCl (70 mL). The reaction mixture was concentrated under reduced pressure and the resulting residue was subjected to flash column chromatography (20% $Et_2O$ : petrol ether to 30% $Et_2O$ : petrol ether) to give the product (9) as a viscous orange oil (6.1 g, 34%).

TLC, (30% $Et_2O$ : petrol) $R_f$=0.34; $\delta_H$ (300 MHz, DMSO) 9.39 (1H, s), 7.74 (1H, d, J=7.1 Hz), 7.52-7.43 (2H, m), 7.43-7.33 (1H, m), 5.35 (1H, dd, J=5.8, 2.8 Hz), 3.83 (1H, dd, J=13.1, 2.8 Hz), 3.49 (1H, dd, J=13.1, 6.2 Hz).

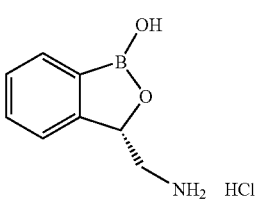

To a solution of azide (9) (1.0 g, 5.3 mmol, 1.0 eq) in acetonitrile (50 mL) was added triphenylphosphine (2.7 g, 10.5 mmol, 2.0 eq) and then concentrated HCl (1 mL, 10.5 mmol, 2.0 eq). The orange solution was stirred for 18 hours and then filtered. The precipitate was washed with dichloromethane to yield the product (10) as a white solid (680 mg, 65%).

m.p. 227-230° C.; $[\alpha]_D^{27}$=+48.6° (c 2.0, $H_2O$); $\delta_H$ (300 MHz, DMSO+$D_2O$) 7.76 (1H, d, J=6.9 Hz), 7.57-7.35 (3H, m), 5.31 (1H, d, J=8.1 Hz), 3.47 (1H, d, J=13.4 Hz), 2.72 (1H, dd, J=12.8, 9.9 Hz); $\delta_C$ (75.5 MHz, $CDCl_3$) 152.39, 131.63, 131.23, 128.59, 122.07, 77.09, 44.11; HRMS (ESI): calcd. for $C_8H_{11}BNO_2$ $[M+H]^+$ 164.0882, found 164.0868.

Alternative synthesis for (S)-3-Aminomethyl-3H-benzo[c][1,2]oxaborol-1-ol)hydrochloride (A2)

3-Nitromethyl-3H-benzo[c][1,2]oxaborol-1-ol

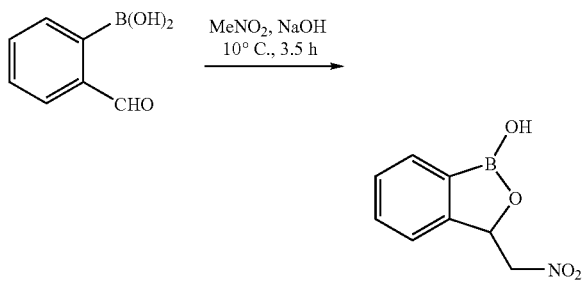

2-Formylphenylboronic acid (25 g, 0.167 mol) was added to a cooled solution of sodium hydroxide (7.0 g, 0.175 mol, 1.05 eq) in 83 mL of water at 10° C. Nitromethane (10.17 g, 1 eq) was added to this solution and then warmed to room temperature with stirring. This mixture was stirred for 3.5 hours. The reaction was then cooled in an ice bath and acidified with 3M HCl to a pH of 2. A white precipitate was collected and filtered, washed with water and air dried to obtain 28 g (87%) of 3-(nitromethyl)benzo[c][1,2]oxaborol-1(3H)-ol (off-white solid).

Synthesis of 3-Aminomethyl-3H-benzo[c][1,2]oxaborol-1-ol) hydrochloride (A1) using palladium hydroxide

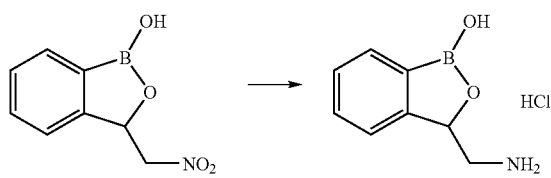 [SMILES: O=[N+]([O-])CC1OB(O)c2ccccc21 ; NCC1OB(O)c2ccccc21 ; Cl]

3-(Nitromethyl)benzo[c][1,2]oxaborol-1(3H)-ol (20 g, 103 mmol) was dissolved in glacial acetic acid (200 mL) and placed into a 500 mL Parr flask. The flask was purged with $N_2$ for 20 minutes. 4.2 g of 20 wt % palladium hydroxide on carbon (Pearlman's catalyst) was added and the reaction mixture was flushed with hydrogen 3× and hydrogenated at 45-55 psi for 36 hours. The mixture was filtered through Celite to remove the catalyst. The acetic acid solvent was then evaporated under vacuum at 40-50° C., leaving a crude oil. The crude oil was dissolved in 250 mL of dichloromethane and cooled to 0-5° C. HCl gas was then bubbled through the solution for 25 minutes. Ether (150 mL) was added to further precipitate a yellow solid which was subsequently filtered, washed with ether and rotovapped to dryness. 7.8 g of a yellow solid (37%) was obtained.

(1-Hydroxy-1,3-dihydro-benzo[c][1,2]oxaborol-3-ylmethyl)-carbamic acid tert-butyl ester (Boc-A1)

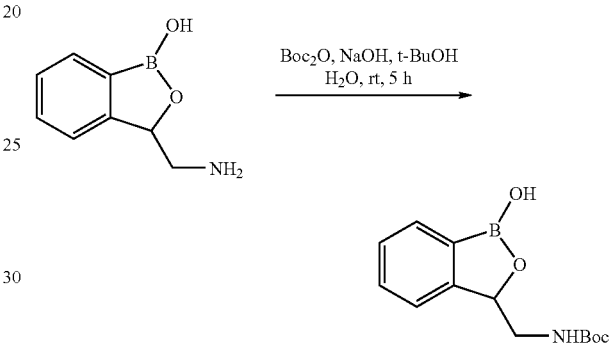

Crude amine (7.4 grams, 0.037 moles) was suspended in 40 ml of tert-butanol at rt. KOH (5.4 grams, 0.82 moles) in 50 mL of water was added. The suspension was cooled with an ice bath and then solid $BOC_2O$ (8.51 grams, 0.039 moles) was added portion wise over 10 minutes. The reaction mixture was stirred at rt for 24 hours. 150 mL of dichloromethane was then added. The organic layer which formed was then separated and the aqueous layer was extracted twice with 100 mL of dichloromethane. The extracts were combined, dried over $MgSO_4$, filtered and evaporated. Purification by flash silica gel chromatography using dichloromethane/Methanol 95:5 yielded 4.4 grams (45% yield).

$^1$H NMR (400 MHz, DMSO-$d_6$) δ (ppm): 9.20 (s, 1H), 7.72 (d, J=7.0 Hz, 1H), 7.46 (t, J=7.2 Hz, 1H), 7.42-7.31 (m, 2H), 7.00 (t, J=5.5 Hz, 1H), 5.13 (dd, J=6.8, 4.5 Hz, 1H), 3.45-3.29 (m, 1H), 3.05 (ddd, J=13.7, 6.6, 6.2 Hz, 1H), 1.37 (s, 9H); MS (ESI): m/z=262 (M−1, negative); HPLC purity: 99.20% (MaxPlot 200-400 nm); Anal. Calcd for $C_{13}H_{18}BNO_4$: C 59.35%; H 6.90%; N 5.32%. Found, %: C 59.37%; H 7.14%; N 5.58%.

(S)-(1-Hydroxy-1,3-dihydro-benzo[c][1,2]oxaborol-3-ylmethyl)-carbamic acid tert-butyl ester (BocA2)

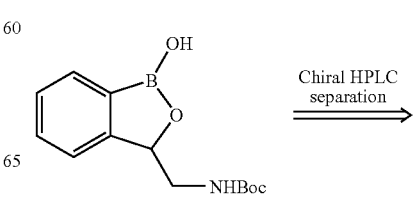

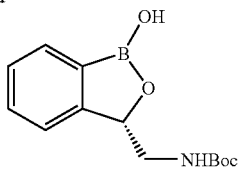

2.1 g of BocA1 was resolved via chiral HPLC using CHIRALPAK AY column and 10% ethanol/hexane as eluent @ 25° C. UV detection was monitored at 265 nm. Two peaks (BocA2 and BocA60) were collected and evaporated to yellow oils. Analysis of the pooled fractions using a CHIRALPAK AY 4.6 mm ID×250 mm analytical column and same mobile phase showed BocA2 [910 mg (86.7% yield)] with a retention time of 3.998 min. and a 99.8% ee. BocA60 [600 mg (57.1% yield)] had a retention time of 4.889 min and a 97.5% ee.

(S)-3-Aminomethyl-3H-benzo[c][1,2]oxaborol-1-ol) hydrochloride (A2)

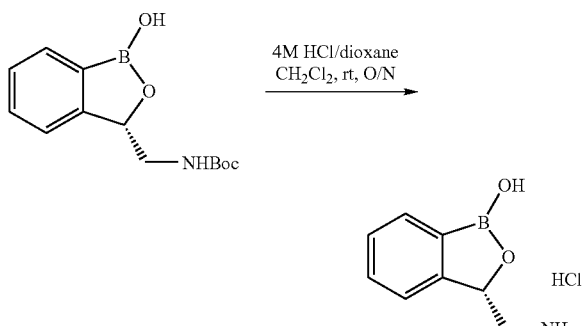

BocA2 (910 mg) was dissolved in EtOAc (200 mL), treated with conc HCl and sonicated for 3 hrs until a precipitate began to form. The reaction was cooled to −10° C. overnight and then filtered. An off-white solid was collected and air dried to 340 mg. This material was re-crystallized from aqueous acetonitrile to yield 242 mg of white solid after drying.

MP 214-216° C.; $^1$H NMR 300 MHz (DMSO-d$_6$) δ 9.59 (bs, 1H), 8.33 (bs, 3H), 7.81-7.83 (d, J=7.5 Hz, 1H), 7.35-7.50 (m, 3H), 5.34-5.37 (d, J=10.2 Hz, 1H), 3.46 (m, 1H), 2.71 (m, 1H); MS ESI (−) 162 [M−H], ESI (+) 164 [M+H]; [α]D31=+71.0° (c 2.0, H$_2$O) [Absolute Configuration (S)]

Pyridine-2-sulfonic acid (1-hydroxy-1,3-dihydro-benzo[c][1,2]oxaborol-6-yl)-amide (A3)

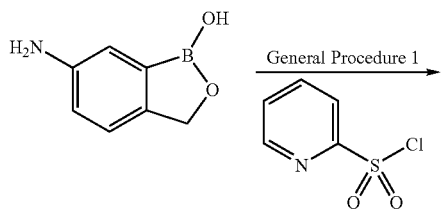

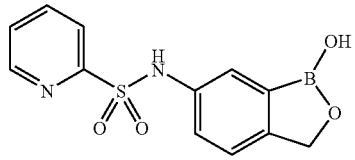

General Procedure 1: C50 (0.843 g, 5.66 mmol), MeCN (20 mL), K$_2$CO$_3$ (3.13 g, 22.6 mmol), and pyridine-2-sulfonyl chloride (1.21 g, 5.66 mmol). The reaction was restarted with NMM (0.249 mL, 22.6 mmol) to consume all the C50. Purification: precipitation from acidic H$_2$O. A3 was isolated as a light-cream solid: yield 462 mg (28%).

mp 252-255° C.; $^1$H NMR (400 MHz, DMSO-d$_6$) δ (ppm): 10.50 (s, 1H), 9.18 (s, 1H), 8.70 (ddd, J=4.7, 2.0, 1.2 Hz, 1H), 8.03 (td, J=7.8, 1.6 Hz, 1H), 7.91 (dt, J=7.8, 1.2 Hz, 1H), 7.62 (ddd, J=7.8, 4.7, 1.2 Hz, 1H), 7.50 (bs, 1H), 7.26-7.20 (m, 2H), 4.87 (s, 2H); MS (ESI) m/z=291 (M+1, positive); HPLC purity: 95.63% (MaxPlot 200-400 nm), 95.50% (220 nm), 95.02% (254 nm); Anal. Calcd for C$_{12}$H$_{11}$BN$_2$O$_4$S: C, 49.68%; H, 3.82%; N, 9.66%. Found: C, 50.13%; H, 3.89%; N, 9.88%.

Pyridine-3-sulfonic acid (1-hydroxy-1,3-dihydro-benzo[c][1,2]oxaborol-6-yl)-amide (A4)

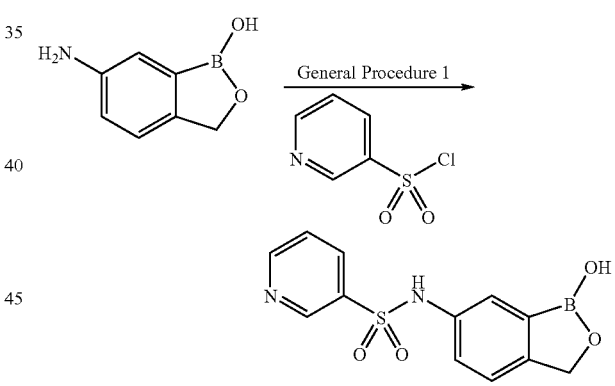

General Procedure 1: C50 (0.800 g, 5.37 mmol), MeCN (30 mL), K$_2$CO$_3$ (3.13 g, 22.6 mmol), and pyridine-3-sulfonyl chloride (1.21 g, 5.66 mmol). The reaction was restarted with NMM (0.249 mL, 22.6 mmol) to consume all the C50. Purification: precipitation from H$_2$O, flash chromatography (95:5 CH$_2$Cl$_2$/MeOH), then precipitation from H$_2$O. A4 was isolated as a light yellow solid: yield 343 mg (22%).

mp 197-199° C.; $^1$H NMR (400 MHz, DMSO-d$_6$) δ (ppm): 10.46 (s, 1H), 9.22 (s, 1H), 8.56 (dd, J=2.3, 0.8 Hz, 1H), 8.77 (dd, J=5.1, 1.6 Hz, 1H), 8.07 (ddd, J=8.2, 2.3, 1.6 Hz, 1H), 7.59 (ddd, J=8.2, 5.1, 0.8 Hz, 1H), 7.49 (d, J=2.0 Hz, 1H), 7.29 (dd, J=8.2, 0.8 Hz, 1H), 7.18 (dd, J=8.2, 2.3 Hz, 1H), 4.89 (s, 2H); MS (ESI) m/z=291 (M+1, positive); HPLC purity: 98.87% (MaxPlot 200-400 nm), 98.30% (220 nm), 97.33% (254 nm); Anal. Calcd for C$_{12}$H$_{11}$BN$_2$O$_4$S.0.33H$_2$O: C, 48.68%; H, 3.97%; N, 9.46%. Found: C, 48.76%; H, 3.83%; N, 9.89%.

4-(3-Aminomethyl-1-hydroxy-1,3-dihydro-benzo[c][1,2]oxaborol-7-yloxy)-butyramide acetate salt (A5)

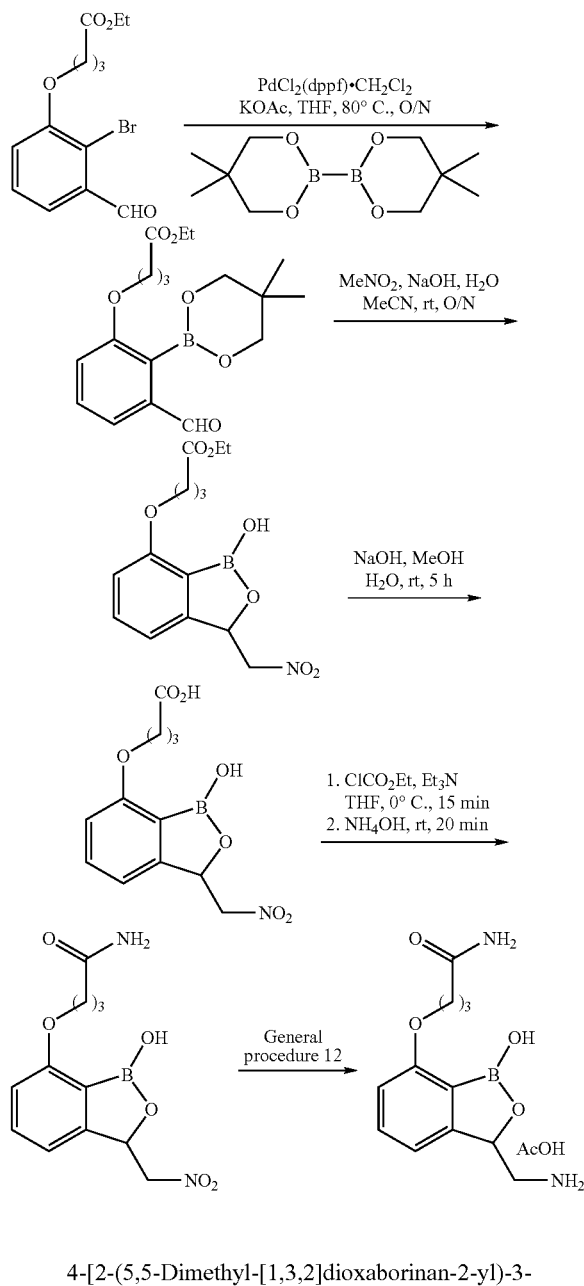

4-[2-(5,5-Dimethyl-[1,3,2]dioxaborinan-2-yl)-3-formyl-phenoxy]-butyric acid ethyl ester

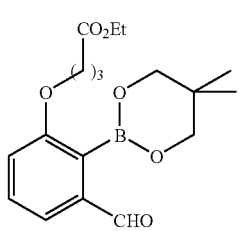

A mixture of 4-(2-bromo-3-formyl-phenoxy)-butyric acid ethyl ester (5.50 g, 17.5 mmol), bis(neopentyl glucolato) diboron (6.80 g, 30.1 mmol), PdCl$_2$(dppf)·CH$_2$Cl$_2$ (1.30 g, 1.79 mmol), and KOAc (5.30 g, 54.1 mmol) in anhydrous THF (600 mL) was heated with stirring at 80° C. (bath temp) O/N under an atmosphere of N2. The mixture was then filtered through Celite and concentrated in vacuo to approximately one quarter of the original volume. The resulting precipitate was isolated by filtration. The precipitate was washed with THF and EtOAc and the combined filtrate was concentrated in vacuo to give an oily residue which was used directly in the next reaction without further purification.

$^1$H NMR (400 MHz, CDCl$_3$) δ (ppm): 9.95 (s, 1H), 7.47-7.39 (m, 2H), 7.09-7.07 (m, 1H), 4.14 (q, J=7.2 Hz, 2H), 4.09-4.01 (m, 2H), 3.83 (s, 3H), 3.66 (s, 3H), 2.53 (t, J=8.0 Hz, 2H), 2.19-2.07 (m, 2H), 1.32-1.22 (m, 3H), 0.98 (s, 6H).

4-(1-Hydroxy-3-nitromethyl-1,3-dihydro-benzo[c][1,2]oxaborol-7-yloxy)-butyric acid ethyl ester

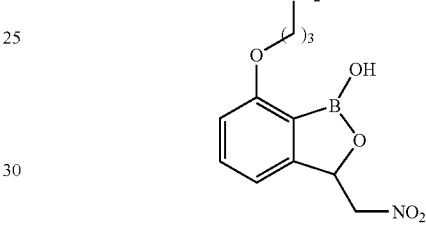

MeNO$_2$ (1.3 mL, 25 mmol) was added dropwise to a stirred solution of crude 4-[2-(5,5-dimethyl-[1,3,2]dioxaborinan-2-yl)-3-formyl-phenoxy]-butyric acid methyl ester (9.4 g), NaOH (1.0 g, 25 mmol) and H$_2$O (35 mL) in MeCN (90 mL) at rt. The mixture was stirred at rt O/N and then acidified (pH 2) using 4 M HCl. The THF was removed in vacuo and the aqueous layer was extracted with EtOAc. The organic layer was washed with brine, dried (MgSO$_4$), and concentrated in vacuo. The residue was purified by flash chromatography (10% to 30% EtOAc in hexane) to give the title compound as a yellow oil: yield 2.52 g (45% over 2 steps).

$^1$H NMR (400 MHz, DMSO-d$_6$) δ (ppm): 9.04 (s, 1H), 7.46-7.42 (m, 1H), 7.07-7.05 (m, 1H), 6.88-6.86 (m, 1H), 5.87 (d, J=8.2 Hz, 1H), 5.69 (dd, J=9.2, 2.5 Hz, 1H), 5.29 (dd, J=13.3, 2.7 Hz, 1H), 4.14-3.94 (m, 5H), 2.55-2.44 (m, 2H), 2.02-1.88 (m, 2H), 1.16 (t, J=7.2 Hz, 3H); MS (ESI) m/z=322 (M−1, negative).

4-(1-Hydroxy-3-nitromethyl-1,3-dihydro-benzo[c][1,2]oxaborol-7-yloxy)-butyric acid

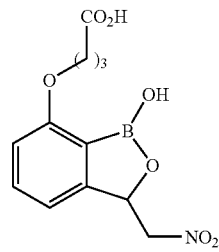

A mixture of 4-(1-hydroxy-3-nitromethyl-1,3-dihydro-benzo[c][1,2]oxaborol-7-yloxy)-butyric acid ethyl ester (2.51 g, 7.78 mmol), 10% NaOH (17 mL), and 1:1 MeOH/H$_2$O (70 mL) was stirred at rt for 5 h. The MeOH was removed in vacuo and the remaining aqueous layer was acidified to pH 1 using 2 M HCl. The aqueous layer was then extracted with EtOAc. The organic fractions were washed with brine, dried (MgSO$_4$), and concentrated in vacuo to give the title compound as a pale yellow foam: yield 1.85 g (81%).

$^1$H NMR (400 MHz, DMSO-d$_6$) δ (ppm): 12.08 (bs, 1H), 9.01 (bs, 1H), 7.46-7.41 (m, 1H), 7.06-7.04 (m, 1H) 6.89-6.87 (m, 1H), 5.70 (dd, J=7.0, 2.3 Hz, 1H), 5.30 (dd, J=13.3, 2.3 Hz, 1H), 4.55 (dd, J=13.6, 4.2 Hz, 1H), 4.03 (t, J=6.6 Hz, 2H), 2.40 (t, J=7.5 Hz, 2H), 1.95-1.89 (m, 2H); MS (ESI) m/z=296 (M+1, positive).

4-(1-Hydroxy-3-nitromethyl-1,3-dihydro-benzo[c][1,2]oxaborol-7-yloxy)-butyramide

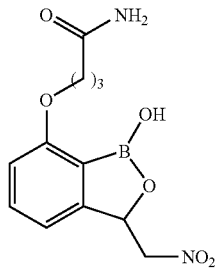

Ethyl chloroformate (80 μL, 0.83 mmol) was added dropwise to a solution of Et$_3$N (0.35 mL, 4.7 mmol) and 4-(1-hydroxy-3-nitromethyl-1,3-dihydro-benzo[c][1,2]oxaborol-7-yloxy)-butyric acid (111 mg, 0.38 mmol) in THF (4 mL) at 0° C. (bath temp). The mixture was stirred at 0° C. (bath temp) for 15 min and then 28% NH$_4$OH (0.5 mL) was added dropwise at 0° C. (bath temp). The mixture was allowed to warm to rt over 20 min. The precipitate was isolated by filtration and washed with THF and H$_2$O to give the title compound as a light yellow solid: yield 52 mg (45%).

$^1$H NMR (400 MHz, DMSO-d$_6$) δ (ppm): 7.43-7.39 (m, 1H), 7.33 (bs, 1H), 7.04-7.02 (m, 1H), 6.86-6.84 (m, 1H), 6.61 (bs, 1H), 5.67 (d, J=9.0 Hz, 1H), 5.26 (dd, J=13.7, 2.7 Hz, 1H), 4.52 (dd, J=13.5, 9.2 Hz, 1H), 4.00 (t, J=6.2 Hz, 2H), 2.22 (t, J=7.0 Hz, 2H), 1.93-1.90 (m, 2H); MS (ESI) m/z=295 (M+1, positive).

4-(3-Aminomethyl-1-hydroxy-1,3-dihydro-benzo[c][1,2]oxaborol-7-yloxy)-butyramide, acetate salt (A5)

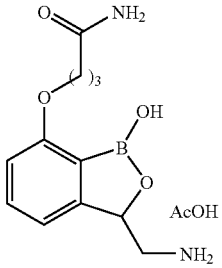

A mixture of 4-(1-hydroxy-3-nitromethyl-1,3-dihydro-benzo[c][1,2]oxaborol-7-yloxy)-butyramide (50 mg, 0.17 mmol), Raney Ni (~20 mg), 2 M NH$_3$ in EtOH (1 mL), and EtOH (100 mL) was shaken under an atmosphere of H$_2$ (42 psi) for 4.5 h at rt. The mixture was filtered through a bed of Celite and the filtrate was concentrated in vacuo. 3 N HCl in MeOH (1 mL) was added immediately to the residue and the resulting mixture was concentrated in vacuo. The residue was then purified by preparative HPLC (AcOH). The title compound was isolated as a white lyophilizate: yield 5 mg (111%).

$^1$H NMR (400 MHz, DMSO-d$_6$+D$_2$O+HCl) δ (ppm): 8.14 (bs, 1H), 7.49-7.45 (m, 1H), 7.06-7.04 (m, 1H), 6.90-6.88 (m, 1H), 5.27 (d, J=8.2 Hz, 1H), 4.04-4.01 (m, 2H), 2.81-2.76 (m, 1H), 2.25 (t, J=7.0 Hz, 2H), 1.98-1.94 (m, 2H); MS (ESI) m/z=265 (M+1, positive).

(1-Hydroxy-1,3-dihydro-benzo[c][1,2]oxaborol-7-yloxy)-acetic acid (A6)

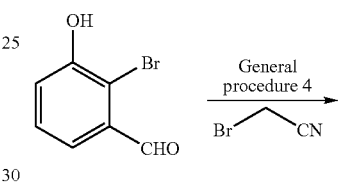

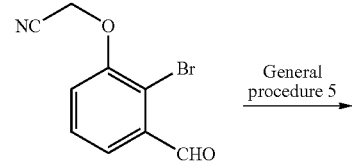

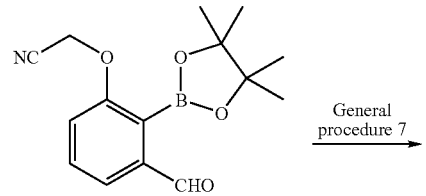

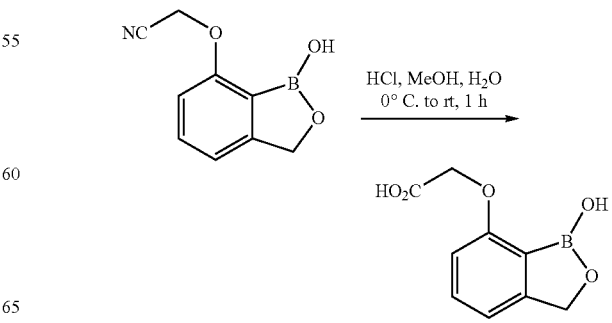

(2-Bromo-3-formyl-phenoxy)-acetonitrile

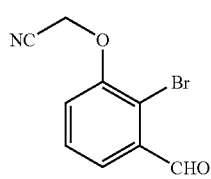

General procedure 4: 2-bromo-3-hydroxy-benzaldehyde (20.1 g, 0.10 mol), BrCH$_2$CN (8.7 mL, 0.13 mol), K$_2$CO$_3$ (20.73 g, 0.15 mol), and DMF (60 mL). Purification: precipitation from EtOAc to give the title compound as white crystals (16.2 g), the filtrate was concentrated and the residue purified by flash chromatography (EtOAc/hexane 1:3) to give additional 3.68 g: yield 19.88 g (83%).

$^1$H NMR (400 MHz, CDCl$_3$) δ (ppm): 10.41 (s, 1H), 7.77-7.60 (m, 1H), 7.47 (t, J=7.6 Hz, 1H), 7.34-7.19 (m, 1H), 4.91 (s, 2H).

3-Formyl-2-(4,4,5,5-tetramethyl-[1,3,2]dioxaborolan-2-yl)-phenoxy]-acetonitrile

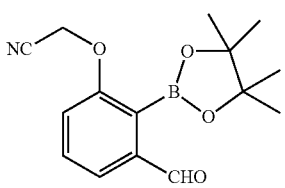 [SMILES: CC1(C)OB(c2c(C=O)cccc2OCC#N)OC1(C)C]

General procedure 5: (2-bromo-3-formyl-phenoxy)-acetonitrile (14.4 g, 60.0 mmol), B$_2$pin$_2$ (30.47 g, 0.12 mol), KOAc (17.68 g, 0.18 mol), PdCl$_2$(dppf).CH$_2$Cl$_2$ (3.51 g, 4.8 mmol), and dioxane (150 mL). Purification: flash chromatography (20% then 40% EtOAc in hexane) to give the title compound as a light yellow solid: yield 11.38 g (66%).

$^1$H NMR (400 MHz, CDCl$_3$) δ (ppm): 9.97 (s, 1H), 7.60-7.56 (m, 2H), 7.22-7.17 (m, 1H), 4.78 (s, 2H), 1.47 (s, 12H).

1-Hydroxy-1,3-dihydro-benzo[c][1,2]oxaborol-7-yloxy)-acetonitrile

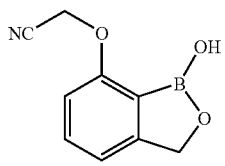

General procedure 7: 3-formyl-2-(4,4,5,5-tetramethyl-[1,3,2]dioxaborolan-2-yl)-phenoxy]-acetonitrile (1.02 g, 4.0 mmol), NaBH$_4$ (182 mg, 4.8 mmol), and MeOH (10 mL). Purification: flash chromatography (2% MeOH in CH$_2$Cl$_2$). Title compound was isolated as a white solid: yield 260 mg (34%).

$^1$H NMR (400 MHz, DMSO-d$_6$) δ (ppm): 9.11 (s, 1H), 7.51 (t, J=7.8 Hz, 1H), 7.11 (d, J=7.4 Hz, 1H), 6.97 (d, J=8.2 Hz, 1H), 5.25 (s, 2H), 4.97 (s, 2H); MS (ESI): m/z=188 (M−1, negative).

(1-Hydroxy-1,3-dihydro-benzo[c][1,2]oxaborol-7-yloxy)-acetic acid (A 6)

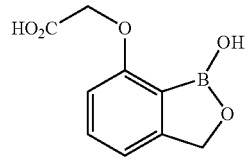 [SMILES: O=C(O)COc1cccc2c1B(O)OC2]

HCl (g) was bubbled through a solution of 1-hydroxy-1,3-dihydro-benzo[c][1,2]oxaborol-7-yloxy)-acetonitrile (132 mg, 0.67 mmol) in 4:1 MeOH/H$_2$O (25 mL) at 0° C. (bath temp) for 5 min. The reaction mixture was stirred at 0° C. (bath temp) for 10 min and then at rt for 1 h. The MeOH was removed in vacuo and the aqueous layer was adjusted to pH 6 using sat. NaHCO$_3$. The resulting precipitate was isolated by filtration and washed with Et$_2$O to give A6 as a white solid: yield 105 mg (76%).

mp 258-260° C.; $^1$H NMR (400 MHz, DMSO-d$_6$) δ (ppm): 7.35 (t, J=7.6 Hz, 1H), 6.97 (d, J=7.0 Hz, 1H), 6.77 (d, J=7.8 Hz, 1H), 5.10 (s, 2H), 4.70-4.50 (m, 1H), 4.40-4.00 (m, 3H); MS (ESI): m/z=207 (M−1, negative); HPLC purity 95.52% (MaxPlot) and 92.77% (220 nm).

2-(1-Hydroxy-1,3-dihydro-benzo[c][1,2]oxaborol-7-yloxy)-N-(2-hydroxy-ethyl)-acetamide (A7)

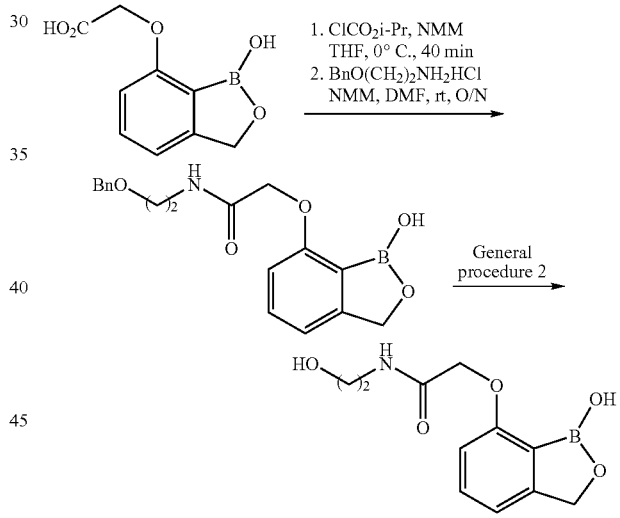

N-(2-Benzyloxy-ethyl)-2-(1-hydroxy-1,3-dihydro-benzo[c][1,2]oxaborol-7-yloxy)-acetamide

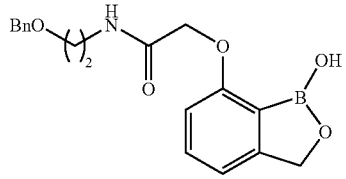 [SMILES: O=C(COc1cccc2c1B(O)OC2)NCOCc1ccccc1]

Isobutylchloroformate (250 mg, 1.83 mmol) was added to a solution of NMM (184 mg, 1.82 mmol) and A6 (190 mg, 0.91 mmol) in anhydrous THF (10 mL) at 0° C. (bath temp) under N$_2$. The reaction mixture was stirred at 0° C. (bath temp) for 40 min. A mixture of 2-benzyloxyethylamine hydrochloride (171 mg, 0.91 mmol) and NMM (92 mg, 0.91 mmol) in DMF (5 mL) was added. The mixture was stirred at 0° C. (bath temp) for 20 min and then at rt O/N. The mixture was concentrated in vacuo and the residue was dissolved in EtOAc (100 mL). The organic layer was washed with H₂O (2×30 mL) then brine, dried (Na₂SO₄), and concentrated in vacuo to give the title compound: yield 260 mg (84%).

¹HNMR (400 MHz, CDCl₃) δ (ppm): 7.44 (m, 1H), 7.37-7.18 (m, 5H), 7.06-6.94 (m, 1H), 6.78-6.66 (m, 1H), 5.28 (bs, 1H), 5.03 (bs, 2H), 4.60 (bs, 2H), 4.49 (bs, 2H), 3.60 (bs, 4H).

2-(1-Hydroxy-1,3-dihydro-benzo[c][1,2]oxaborol-7-yloxy)-N-(2-hydroxy-ethyl)-acetamide (A7)

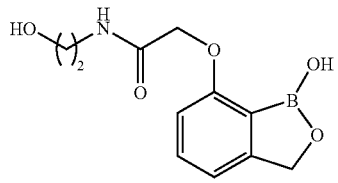

General Procedure 2: N-(2-benzyloxy-ethyl)-2-(1-hydroxy-1,3-dihydro-benzo[c][1,2]oxaborol-7-yloxy)-acetamide (0.26 g, 0.76 mmol), glacial AcOH (20 mL), and 20% Pd(OH)₂/C (50% weight-wet) (50 mg). Purification: preparative HPLC (0.1% AcOH) followed by dissolution in a mixture of H₂O (5 mL), MeOH (1 mL), and 2 N HCl (2 drops), filtration, and lyophilization of the filtrate: yield 55 mg (29%).

mp 248-249° C.; ¹H NMR {400 MHz, DMSO-d₆+D₂O (0.01 mL)} δ (ppm): 9.00 (s, 1H), 7.96 (bs, 1H), 7.43 (t, J=7.8 Hz, 1H), 7.02 (d, J=7.6 Hz, 1H), 6.84 (d, J=8.2 Hz, 1H), 4.95 (s, 2H), 4.73 (t, J=5.3 Hz, 1H), 4.56 (s, 2H), 3.44 (t, J=5.9 Hz, 2H), 3.23 (t, J=6.1 Hz, 2H); MS (ESI) m/z=250 (M−1, negative); HPLC purity: 98.14% (MaxPlot) and 96.08% (220 nm).

7,8-Dihydro-2H-1,69-trioxa-9a-bora-benzo[cd]azulene (A8)

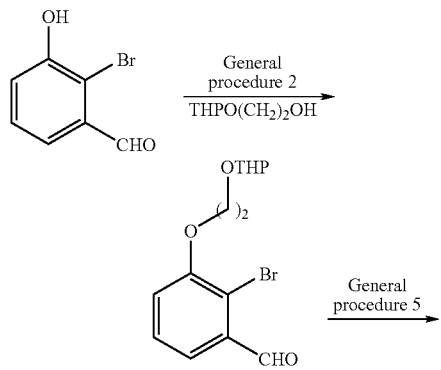

2-Bromo-3-[2-(tetrahydro-pyran-2-yloxy)-ethoxy]-benzaldehyde

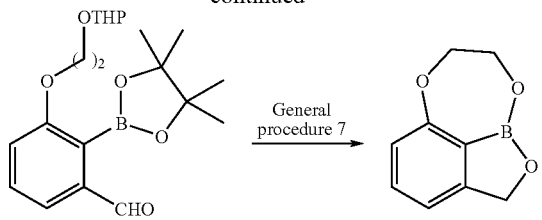

General procedure 3: 2-bromo-3-hydroxy-benzaldehyde (7.04 g; 35 mmol), 2-(tetrahydro-pyran-2-yloxy)-ethanol (5.0 mL; 35 mmol), PPh₃ (9.18 g; 35 mmol), anhydrous THF (200 mL), and DIAD (6.9 mL; 35 mmol). Purification: flash chromatography (hexane then 5% EtOAc/hexane): yield 7.22 g (66%).

¹H NMR (400 MHz, DMSO-d₆) δ (ppm): 10.41 (s, 1H), 7.49 (d, J=7.2 Hz, 1H), 7.32-7.25 (m, 6H), 7.08 (d, J=8.0 Hz, 1H), 4.54 (s, 2H), 4.16 (t, J=6.0 Hz, 2H), 3.74 (t, J=5.8 Hz, 2H), 2.19-2.14 (m, 2H).

3-[2-(Tetrahydro-pyran-2-yloxy)-ethoxy]-2-(4,4,5,5-tetramethyl-[/, 3, 2]dioxaborolan-2-yl)-benzaldehyde

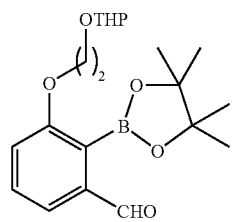

General procedure 5: 2-bromo-3-[2-(tetrahydro-pyran-2-yloxy)-ethoxy]-benzaldehyde (6.0 g, 19 mmol), KOAc (5.65 g, 57.5 mmol), B₂pin₂ (6.35 g, 25 mmol), PdCl₂(dppf).CH₂Cl₂ (0.70 g, 0.96 mmol), and anhydrous DMF (70 mL). Purification: flash chromatography (hexane then 30% EtOAc/hexane): yield 2.07 g (29%).

¹H NMR (400 MHz, CDCl₃) δ (ppm): 9.92 (s, 1H), 7.53-7.33 (m, 2H), 7.11 (d, J=7.9 Hz, 1H), 4.65 (bs, 1H), 4.17-3.71 (m, 2H), 3.59-3.38 (m, 1H), 1.90-1.40 (m, 6H), 1.43 (s, 12H), 1.40-1.29 (m, 2H).

153

7,8-Dihydro-2H-1,6,9-trioxa-9a-bora-benzo[cd]azulene (A8)

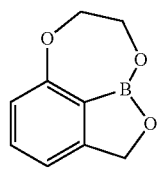

General procedure 7: 3-[2-(tetrahydro-pyran-2-yloxy)-ethoxy]-2-(4,4,5,5-tetramethyl-[1,3,2]dioxaborolan-2-yl)-benzaldehyde (0.93 g, 2.58 mmol), $NaBH_4$ (195 mg, 5.16 mmol), and anhydrous MeOH (5 mL). Purification: flash chromatography (20% EtOAc/hexane): yield 230 mg (51%).

$^1$H NMR (400 MHz, $CDCl_3$) δ (ppm): 7.40 (t, J=7.8 Hz, 1H), 6.96 (d, J=7.3 Hz, 1H), 6.84 (d, J=8.2 Hz, 1H), 5.15 (d, J=3.5 Hz, 2H), 4.62 (d, J=12.9 Hz, 1H), 4.38 (bs, 2H), 4.21 (d, J=9.7 Hz, 1H); MS (ESI) m/z=177 (M+1, positive); HPLC purity 99.36% (MaxPlot) and 95.84% (220 nm).

4-(1-Hydroxy-1,3-dihydro-benzo[c][1,2]oxaborol-7-yloxy)-butyric acid (A9)

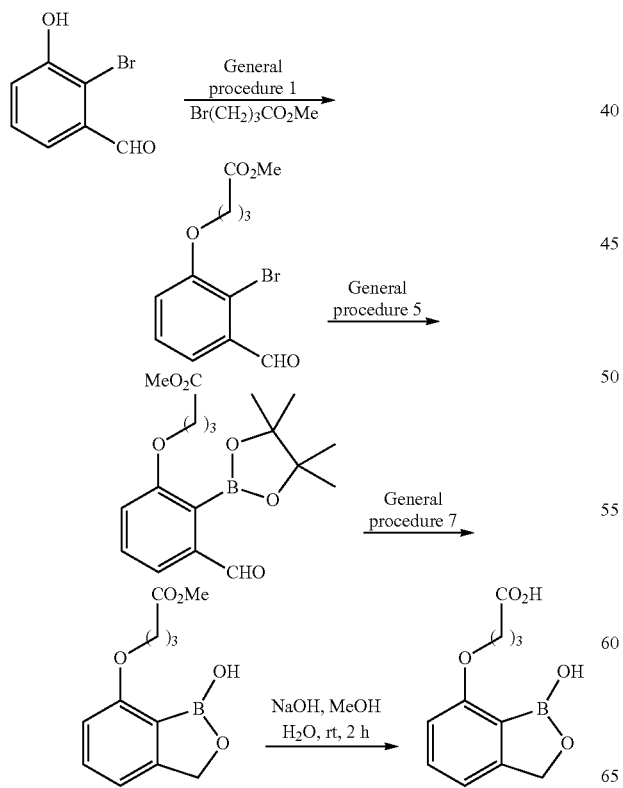

154

4-(2-bromo-3-formyl-phenoxy)-butyric acid ethyl ester

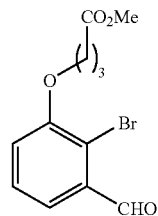

General procedure 1: 2-bromo-3-hydroxy-benzaldehyde (0.30 g, 1.5 mmol), ethyl 4-bromobutyrate (0.30 g, 1.5 mmol), $K_2CO_3$ (0.42 g, 3.0 mmol), and DMF (5 mL). Purification: flash chromatography (2:8 EtOAc/hexane). The title compound was isolated as a red liquid: yield 0.23 g (50%).

$^1$H NMR (400 MHz, $CDCl_3$) δ (ppm): 10.44 (s, 1H) 7.52 (d, J=7.8 Hz, 1H) 7.36 (t, J=8.0 Hz, 1H) 7.12 (d, J=7.8 Hz, 1H) 4.20-4.02 (m, 4H) 2.61 (m, 2H) 2.2 (dq, J=6.8, 6.6 Hz, 2H) 1.27 (t, J=7.2 Hz, 3H); MS (ESI) m/z=317 (M+1, positive).

3-[3-formyl-2-(4,4,5,5-tetramethyl-[1,3,2]dioxaborolan-2-yl)-phenoxy]-propionic acid ethyl ester General procedure 5: 4-(2-bromo-3-formyl-phenoxy)-butyric acid ethyl ester (0.20 g, 6.3 mmol), $B_2pin_2$ (0.177 g, 6.9 mmol), $PdCl_2(dppf)\cdot CH_2Cl_2$ (0.025 g, 0.25 mmol), KOAc (0.185 g, 18.9 mmol), and 1,4-dioxane (5 mL). Purification: flash chromatography (1:5 EtOAc/hexane). The title compound was isolated as a white solid: yield 0.13 g (57%).

$^1$H NMR (400 MHz, $CDCl_3$) δ (ppm): 9.94 (s, 1H), 7.56-7.33 (m, 2H), 7.07 (d, J=8.2 Hz, 1H), 4.14 (q, J=7.2 Hz, 2H), 4.04 (t, J=6.1 Hz, 2H), 2.55 (t, J=7.4 Hz, 2H), 2.24-1.96 (m, 2H), 1.46 (s, 12H), 1.25 (t, J=7.0 Hz, 3H); MS (ESI) m/z=361 (M−1, negative).

3-(1-hydroxy-1,3-dihydro-benzo[c][1,2]oxaborol-7-yloxy-propionic acid ethyl ester

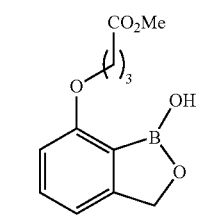

General procedure 7: 3-[3-formyl-2-(4,4,5,5-tetramethyl-[1,3,2]dioxaborolan-2-yl)-phenoxy]-propionic acid ethyl ester (2.2 g, 6.0 mmol), NaBH$_4$ (0.40 g, 10 mmol), and MeOH (25 mL). Purification: flash chromatography (1:10 EtOAc/hexane). The title compound was isolated as a yellow liquid: yield 0.6 g (40%).

$^1$H NMR (400 MHz, CDCl$_3$) δ (ppm): 8.7 (s, 1H), 7.44-7.40 (m, 1H), 6.90 (d, J=7.6 Hz, 1H), 6.78 (d, J=7.2 Hz, 1H), 4.91 (s, 2H), 4.11 (t, J=6.7 Hz, 4H), 2.46 (t, J=7.3 Hz, 2H), 2.10-1.96 (m, 2H), 1.22 (t, J=7.1 Hz, 3H); MS (ESI) m/z=296 (M+1, positive).

3-(1-Hydroxy-1,3-dihydro-benzo[c][1,2]oxaborol-7-yloxy-propionic acid (A9)

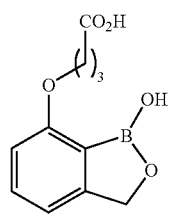

10% NaOH (2 mL) was added dropwise to a solution of 3-(1-hydroxy-1,3-dihydro-benzo[c][1,2]oxaborol-7-yloxy-propionic acid ethyl ester (0.20 g, 0.75 mmol) in 1:1 MeOH/H$_2$O (4 mL) at 0° C. The mixture was then allowed to warm to rt and was stirred for 2 h. The MeOH was then removed in vacuo and H$_2$O (3 mL) was added. The mixture was adjusted to pH 3 and then extracted with EtOAc. The organic phase was washed with H$_2$O (5 mL) then brine (5 mL), dried, and concentrated to give A9 as a white powder: yield 0.15 g (85%).

$^1$H NMR (400 MHz, CDCl$_3$) δ (ppm): 11.35 (s, 1H), 9.08 (s, 1H), 7.44 (t, J=7.1 Hz, 1H), 6.96 (d, J=7.1 Hz, 1H), 6.85 (d, J=7.2 Hz, 1H), 4.92 (s, 2H), 4.12 (t, J=7.0 Hz, 2H), 2.36 (t, J=7.0 Hz, 2H) 1.95-1.86 (m, 2H); MS (ESI) m/z=237 (M+1, positive); HPLC purity: 95.81% (MaxPlot 200-400 nm), 95.20% (220 nm).

4-(1-Hydroxy-1,3-dihydro-benzo[c][1,2]oxaborol-7-yloxy)-butyramide (A10)

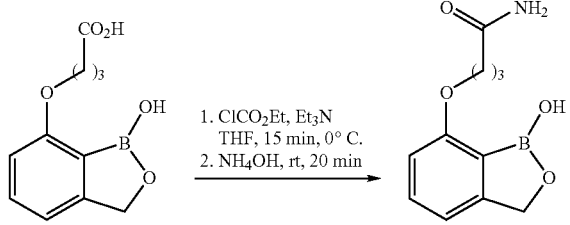

Ethyl chloroformate (80 μL, 0.84 mmol) was added dropwise to a solution of A9 (105 mg, 0.44 mmol) and Et$_3$N (0.32 mL, 2.3 mmol) in anhydrous THF (4 mL) at 0° C. (bath temp). The solution was stirred at 0° C. (bath temp) for 15 min and then 28% NH$_4$OH (0.5 mL) was added resulting in the formation of a white precipitate. The suspension was stirred for a further 20 min at rt. The solid was isolated by filtration and then dissolved in H$_2$O and lyophilized to give A10 (48 mg, 46%) as a white solid. $^1$H NMR (400 MHz, DMSO-d$_6$) δ (ppm): 7.40-7.36 (m, 3H), 7.26 (s, 1H), 7.13 (s, 1H), 6.92-6.90 (m, 1H), 6.79-6.77 (m, 1H), 4.89 (s, 2H), 4.01 (t, J=6.3 Hz, 2H), 2.22 (t, J=7.0 Hz, 2H), 1.92-1.88 (m, 2H); MS (ESI) m/z=236 (M+1, positive); HPLC purity: 95.14% (MaxPlot 200-400 nm), 95.19% (220 nm).

7-(3-Amino-propoxy)-3H-benzo[c][1,2]oxaborol-1-ol acetate salt (A11)

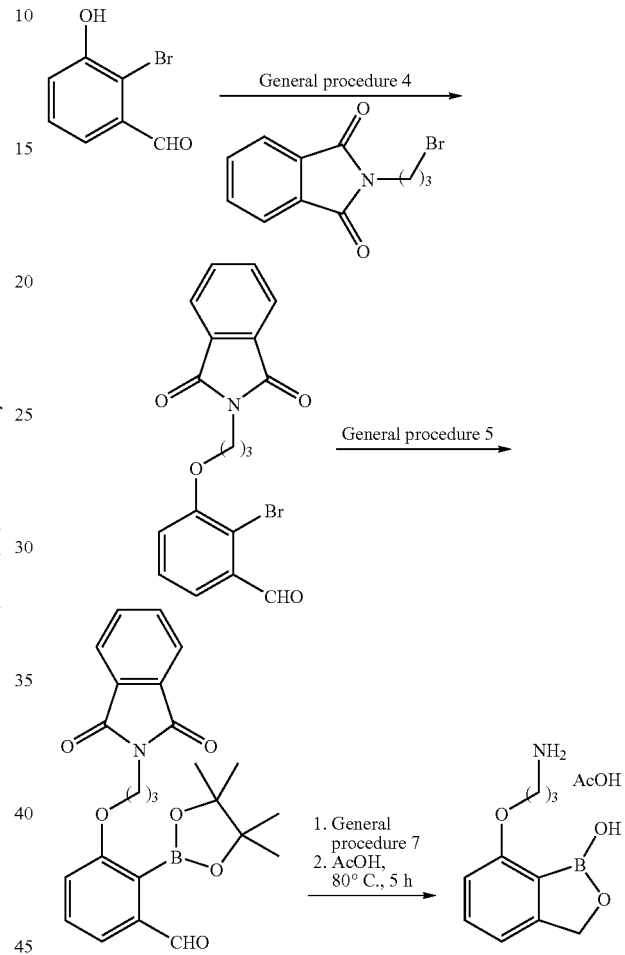

2-Bromo-3-[3-(1,3-dioxo-1,3-dihydro-isoindol-2-yl)-propoxy]-benzaldehyde

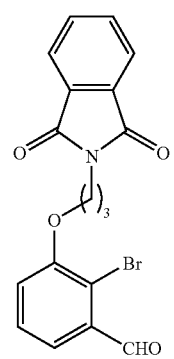

General Procedure 4: 2-bromo-3-hydroxy-benzaldehyde (10.05 g, 50.0 mmol), 2-(3-bromo-propyl)-isoindole-1,3-dione (16.1 g, 60.0 mmol), Cs$_2$CO$_3$ (40.7 g, 0.125 mol) and DMF (100 mL): yield 13.93 g (72%).

$^1$H NMR (400 MHz, DMSO-d$_6$) δ (ppm): 10.22 (s, 1H), 7.89-7.73 (m, 4H), 7.46 (t, J=7.8 Hz, 1H), 7.40-7.33 (m, 2H), 4.16 (t, J=5.7 Hz, 2H), 3.81 (t, J=6.4 Hz, 2H), 2.11 (quin, J=6.1 Hz, 2H); MS (ESI): m/z=388 (M+1, positive); HPLC purity: 94.74% (MaxPlot 200-400 nm), 95.36% (220 nm), 94.50% (254 nm).

3-[3-(1,3-Dioxo-1,3-dihydro-isoindol-2-yl)-propoxy]-2-(4,4,5,5-tetramethyl-[1,3,2]dioxaborolan-2-yl)-benzaldehyde

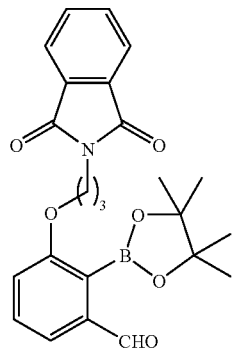

General procedure 5: 2-bromo-3-[3-(1,3-dioxo-1,3-dihydro-isoindol-2-yl)-propoxy]-benzaldehyde (2.42 g, 6.23 mmol), B$_2$pin$_2$ (3.16 g, 12.5 mmol), KOAc (1.85 g, 18.7 mmol), PdCl$_2$(dppf).CH$_2$Cl$_2$ (0.137 g, 0.187 mmol), and DMSO (25 mL). Purification: flash chromatography [3:1 to 2:1 hexane/EtOAc (sample pre-absorbed onto silica 51 g)]: yield 1.43 g (53%)—some pinacol contamination. Compound was used without further purification.

$^1$H NMR (400 MHz, DMSO-d$_6$) δ (ppm): 9.90 (s, 1H), 7.89-7.76 (m, 4H), 7.63-7.46 (m, 2H), 7.24 (d, J=7.9 Hz, 1H), 4.03 (t, J=6.0 Hz, 2H), 3.74 (t, J=7.0 Hz, 2H), 2.15-1.93 (m, 2H), 1.34 (s, 12H); MS (ESI): m/z=436 (M+1, positive); HPLC purity: 97.71% (MaxPlot 200-400 nm), 97.49% (220 nm), 98.20% (254 nm).

7-(3-Amino-propoxy)-3H-benzo[c][1,2]oxaborol-1-ol acetate salt (A11)

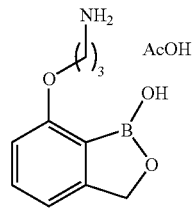

General procedure 7: 3-[3-(1,3-dioxo-1,3-dihydro-isoindol-2-yl)-propoxy]-2-(4,4,5,5-tetramethyl-[1,3,2]dioxaborolan-2-yl)-benzaldehyde (1.77 g, 4.07 mmol), NaBH$_4$ (0.769 g, 20.3 mmol), i-PrOH (37 mL), and H$_2$O (6.2 mL). After 16 h, AcOH (4.3 mL) was slowly added and the mixture heated to 80° C. (bath temp) for 5 h. After cooling to rt the volatiles were removed in vacuo. EtOH and Et$_2$O were added and the mixture filtered. The filtrate was concentrated in vacuo and the residue dissolved in H$_2$O. The aqueous layer was washed with Et$_2$O and then lyophilized. Purification by preparative HPLC (0.1% AcOH) gave A11 as a white lyophilizate: yield 0.140 g (13%).

$^1$H NMR (400 MHz, DMSO-d$_6$) δ (ppm): 7.22 (t, J=7.6 Hz, 1H), 6.80 (d, J=7.0 Hz, 1H), 6.66 (d, J=7.8 Hz, 1H), 4.81 (s, 2H), 4.31 (bs, 2H), 2.79 (t, J=5.9 Hz, 2H), 1.91-1.82 (m, 2H), 1.80 (s, 3H); MS (ESI): m/z=208 (M+1, positive); HPLC purity: 99.19% (MaxPlot 200-400 nm), 98.46% (220 nm).

7-(3-Amino-propoxy)-3H-benzo[c][1,2]oxaborol-1-ol hydrochloride (A11)

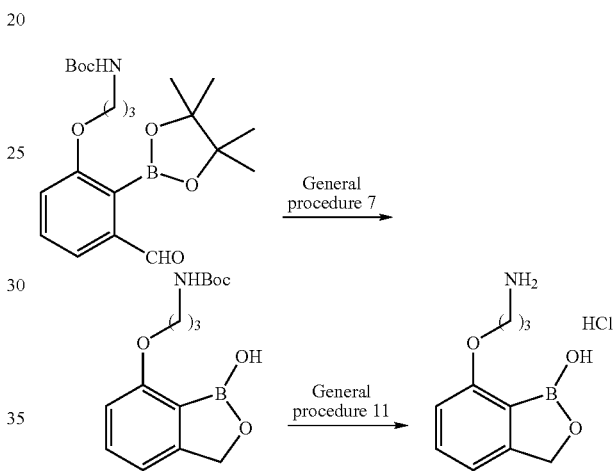

[3-(1-Hydroxy-1,3-dihydro-benzo[c][1,2]oxaborol-7-yloxy)-propyl]-carbamic acid tert-butyl ester

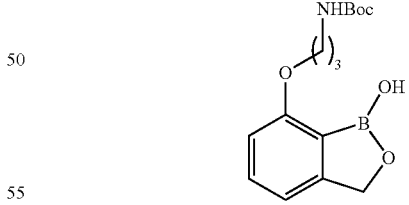

General procedure 7: {3-[3-formyl-2-(4,4,5,5-tetramethyl-[1,3,2]dioxaborolan-2-yl)-phenoxy]-propyl}-carbamic acid tert-butyl ester (3.38 g, 8.33 mmol), absolute EtOH (65 mL), and NaBH$_4$ (0.451 g, 11.9 mmol). Purification: crystallization (1:2 EtOH/H$_2$O). The title compound was isolated as a white solid: yield 1.18 g (46%).

$^1$H NMR (400 MHz, DMSO-d$_6$) δ (ppm): 8.65 (s, 1H), 7.40 (t, J=7.8 Hz, 1H), 6.9 (d, J=7.4 Hz, 1H), 6.90-6.84 (m, 1H), 6.8 (d, J=8.2 Hz, 1H), 4.91 (s, 2H), 4.04 (t, J=6.3 Hz, 2H), 3.16-3.01 (m, 2H), 1.83 (t, J=6.5 Hz, 2H), 1.37 (s, 9H).

7-(3-Amino-propoxy)-3H-benzo[c][1,2]oxaborol-1-ol hydrochloride (A11)

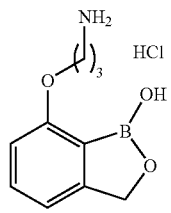

General procedure 11: [3-(1-hydroxy-1,3-dihydro-benzo[c][1,2]oxaborol-7-yloxy)-propyl]-carbamic acid tert-butyl ester (0.50 g, 1.6 mmol) and 4 N HCl in dioxane (10 mL) was stirred at rt O/N. Purification: trituration with EtOAc. A11 was isolated as a white solid: yield 0.39 g (98%).

$^1$H NMR (400 MHz, DMSO-$d_6$) δ (ppm): 7.83 (bs, 1H), 7.44 (t, J=7.8 Hz, 1H), 6.98 (d, J=7.4 Hz, 1H), 6.83 (d, J=8.2 Hz, 1H), 4.94 (s, 2H), 4.15 (t, J=5.7 Hz, 2H), 3.03 (t, J=6.8 Hz, 2H), 2.14-1.92 (m, 2H).

N-[3-(1-Hydroxy-1,3-dihydro-benzo[c][1,2]oxaborol-7-yloxy)-propyl]-acetamide (A12)

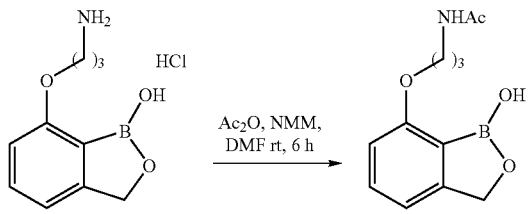

NMM (0.114 mL, 1.04 mmol) was added to a solution of A11 (0.120 g, 0.493 mmol) in DMF (1.0 mL) at 0° C. (bath temp). After 1 h, Ac$_2$O (56 µL, 0.59 mmol) was added and the mixture warmed to rt and stirred for 6 h. H$_2$O (5 mL) was added and the mixture extracted with EtOAc (50 mL). The aqueous layer was acidified to pH 5 using a 2 N HCl and extracted with EtOAc (50 mL). The combined organic fractions were washed with brine (10 mL), dried (Na$_2$SO$_4$), and concentrated in vacuo. The residue was precipitated from 1:1 EtOH/H$_2$O to give the title compound as a white solid: yield 45 mg (37%).

$^1$H NMR (400 MHz, DMSO-$d_6$) δ (ppm): 8.75 (bs, 1H), 7.84 (bs, 1H), 7.39 (t, J=7.8 Hz, 1H), 6.93 (d, J=7.4 Hz, 1H), 6.79 (d, J=8.2 Hz, 1H), 4.91 (s, 2H), 4.03 (t, J=5.9 Hz, 2H), 3.20 (q, J=6.2 Hz, 3H), 1.90-1.80 (m, 2H), 1.79 (s, 3H); MS (ESI): m/z=248 (M−1, negative); HPLC purity: 99.12% (MaxPlot 200-400 nm), 97.88% (220 nm).

7-(3-Methylamino-propoxy)-3H-benzo[c][1,2]oxaborol-1-ol hydrochloride (A13)

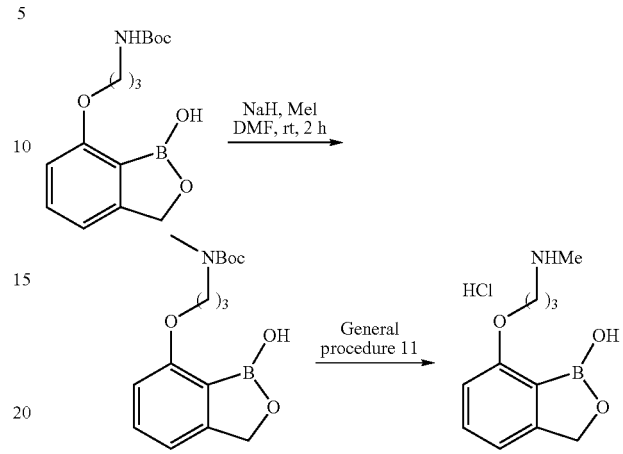

[3-(1-Hydroxy-1,3-dihydro-benzo[c][1,2]oxaborol-7-yloxy)-propyl]-methyl-carbamic acid tert-butyl ester NaH (60% dispersion in mineral oil, 0.082 g, 2.05 mmol) was added portionwise to a solution of [3-(1-hydroxy-1,3-dihydro-benzo[c][1,2]oxaborol-7-yloxy)-propyl]-carbamic acid tert-butyl ester (0.212 g, 0.690 mmol) and MeI (1.03 mL, 2.07 mmol) in anhydrous DMF (5 mL) at 0° C. The reaction was then stirred at rt for 2 h. The mixture was cooled to 0° C., acidified to pH 6 using a sat. NH$_4$Cl, and then extracted with EtOAc. The organic fractions were dried (Na$_2$SO$_4$) and concentrated in vacuo. The residue was purified by flash chromatography (40% EtOAc/hexane) to give the title compound as a colorless oil: yield 0.17 g (77%).

$^1$H NMR (400 MHz, CDCl$_3$) (mixture of rotomers) δ (ppm): 7.40 (t, J=7.6 Hz, 1H), 6.93 (d, J=7.0 Hz, 1H), 7.40 (t, J=7.6 Hz, 1H), 6.93 (d, J=7.0 Hz, 1H), 6.72 (d, J=8.2 Hz, 0.5H), 6.64 (d, J=7.4 Hz, 0.5H), 5.10 (s, 1H), 5.04 (s, 1H), 4.07 (bs, 1H), 3.75 (t, J=6.5 Hz, 1H), 3.46 (bs, 1H), 3.06 (bs, 1H), 2.88 (s, 1.5H), 2.66 (bs, 1.5H), 2.00 (bs, 1H), 1.44 (d, J=17.6 Hz, 12H); MS (ESI): m/z=322 (M+1, positive).

7-(3-Methylamino-propoxy)-3H-benzo[c][1,2]ox-aborol-1-ol hydrochloride (A13)

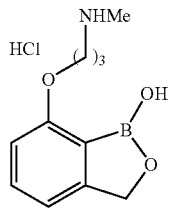

General procedure 11: [3-(1-hydroxy-1,3-dihydro-benzo[c][1,2]oxaborol-7-yloxy)-propyl]-methyl-carbamic acid tert-butyl ester (0.160 g, 0.498 mmol) and 4 N HCl in dioxane (10 mL). A13 was isolated as a white solid lyophilizate: yield 90 mg (70%).

$^1$H NMR (400 MHz, DMSO-$d_6$) δ (ppm): 8.74 (bs, 2H), 7.44 (t, J=7.8 Hz, 1H), 6.99 (d, J=7.4 Hz, 1H), 6.84 (d, J=8.2 Hz, 1H), 4.95 (s, 2H), 4.15 (t, J=5.5 Hz, 2H), 3.11 (t, J=6.4 Hz, 2H), 2.57 (s, 3H), 2.10 (t, J=6.1 Hz, 2H); MS (ESI): m/z=222 (M+1, positive); HPLC purity: 99.52% (MaxPlot 200-400 nm), 98.59% (220 nm).

1-Ethyl-3-[3-(1-hydroxy-1,3-dihydro-benzo[c][1,2]oxaborol-7-yloxy)-propyl]-urea (A14)

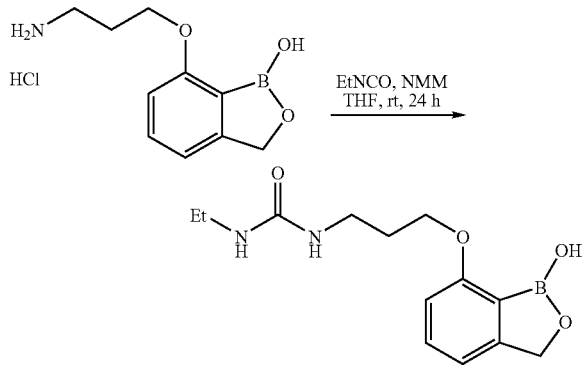

Ethyl isocyanate (0.081 mL, 1.04 mmol) was added to a suspension of NMM (0.170 mL, 1.56 mmol) and A11 (0.126 g, 0.518 mmol) in THF (5 mL) at rt. The mixture was stirred O/N and then DMF (3 mL) was added. The cloudy solution was then stirred for an additional 24 h. The mixture was acidified to pH 4 using 2 N HCl and then extracted with EtOAc. The organic layer was dried (Na$_2$SO$_4$) and concentrated in vacuo. The residue was purified by preparative HPLC to give A14 as a light yellow solid: yield 45 mg (31%).

$^1$H NMR (400 MHz, DMSO-$d_6$) δ (ppm): 8.80 (s, 1H), 7.41 (t, J=7.8 Hz, 1H), 6.94 (d, J=7.4 Hz, 1H), 6.81 (d, J=8.2 Hz, 1H), 6.01-5.80 (m, 1H), 5.80-5.58 (m, 1H), 4.04 (t, J=6.1 Hz, 2H), 3.16 (q, J=6.2 Hz, 2H), 3.07-2.91 (m, 2H), 1.91-1.72 (m, 2H), 0.97 (t, J=7.0 Hz, 3H); MS (ESI): m/z=279 (M+1, positive); HPLC purity: 95.99% (MaxPlot 200-400 nm), 94.68% (220 nm).

N-[3-(1-Hydroxy-1,3-dihydro-benzo[c][1,2]ox-aborol-7-yloxy)-propyl]-methanesulfonamide (A15)

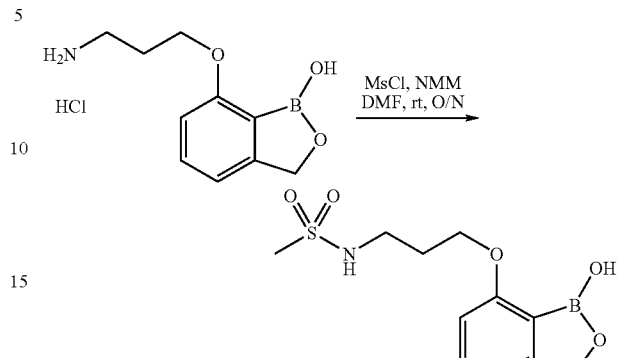

NMM (0.190 mL, 1.75 mmol) was added to a solution of methanesulfonyl chloride (0.081 mL, 1.05 mmol) and A11 (0.170 g, 0.700 mmol) in DMF (3 mL) at rt. The mixture was stirred O/N then H$_2$O was added and the mixture extracted with EtOAc. The organic layer was washed with brine, dried (Na$_2$SO$_4$), and concentrated in vacuo. The residue was purified by flash chromatography (50% EtOAc/hexane, then 5% MeOH/EtOAc). The residue was crystallized from EtOAc and washed with Et$_2$O to give A15 as white crystals: yield 60 mg (30%).

mp 135-140° C.; $^1$H NMR (400 MHz, DMSO-$d_6$) δ (ppm): 8.74 (s, 1H), 7.41 (t, J=7.6 Hz, 1H), 7.01 (bs, 1H), 6.95 (d, J=7.4 Hz, 1H), 6.82 (d, J=8.2 Hz, 1H), 4.92 (s, 2H), 4.09 (t, J=6.1 Hz, 2H), 3.14 (d, J=5.5 Hz, 2H), 2.89 (s, 3H), 1.99-1.84 (m, 2H); MS (ESI): m/z=284 (M−1, negative); HPLC purity: 98.27% (MaxPlot 200-400 nm), 98.37% (220 nm).

4-(1-Hydroxy-1,3-dihydro-benzo[c][1,2]oxaborol-7-yloxy)-butyronitrile (A16)

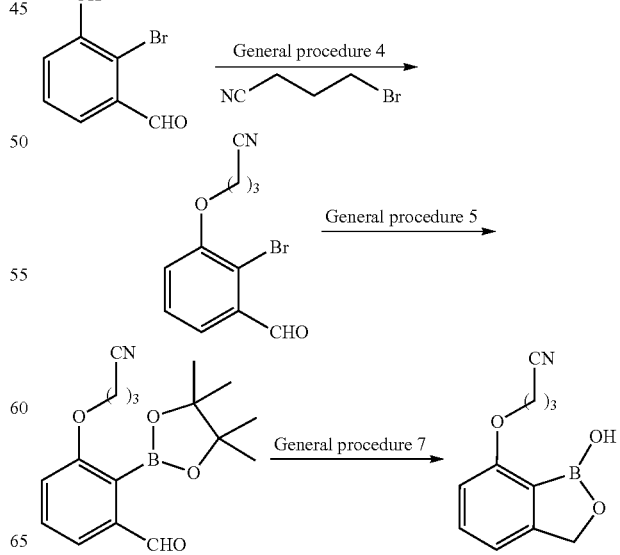

4-(2-Bromo-3-formyl-phenoxy)-butyronitrile

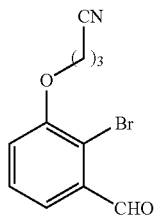

General procedure 4: 2-bromo-3-hydroxy-benzaldehyde (5.0 g, 25 mmol), 4-bromo-butyronitrile (2.95 mL, 29.8 mmol), $Cs_2CO_3$ (12.15 g, 37.30 mmol), and DMF (50 mL): yield 3.94 g (59%).

$^1$H NMR (400 MHz, $CDCl_3$) δ (ppm): 10.43 (s, 1H), 7.56 (dd, J=7.8, 1.6 Hz, 1H), 7.39 (t, J=8.0 Hz, 1H), 7.16-7.10 (m, 1H), 4.20 (t, J=5.5 Hz, 2H), 2.73 (t, J=7.0 Hz, 2H), 2.30-2.21 (m, 2H).

4-[3-Formyl-2-(4,4,5,5-tetramethyl-[1,3,2]dioxaborolan-2-yl)-phenoxy]-butyronitrile

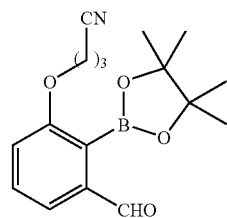

General procedure 5: 4-(2-bromo-3-formyl-phenoxy)-butyronitrile (3.94 g, 14.69 mmol), $B_2pin_2$ (4.47 g, 17.63 mmol), KOAc (5.76 g, 58.76 mmol), $PdCl_2(dppf)\cdot CH_2Cl_2$ (0.537 g, 0.73 mmol), and dioxane (100 mL). Purification: flash chromatography (20% EtOAc in hexane). The title compound was isolated as a white foam: yield 1.4 g (30%).

$^1$H NMR (400 MHz, $CDCl_3$) δ (ppm): 9.96 (s, 1H), 7.54-7.47 (m, 1H), 7.46-7.41 (m, 1H), 7.09 (d, J=7.0 Hz, 1H), 4.13 (t, J=5.7 Hz, 2H), 2.63 (t, J=7.2 Hz, 2H), 2.20-2.11 (m, 2H), 1.49-1.40 (m, 12H).

4-(1-Hydroxy-1,3-dihydro-benzo[c][1,2]oxaborol-7-yloxy)-butyronitrile (A16)

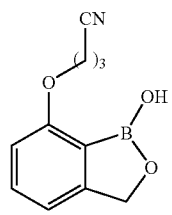

General procedure 7: 4-[3-formyl-2-(4,4,5,5-tetramethyl-[1,3,2]dioxaborolan-2-yl)-phenoxy]-butyronitrile (1.40 g, 4.44 mmol), $NaBH_4$ (219 mg, 5.77 mmol), and MeOH (10 mL). A16 was isolated as a light orange solid: yield 600 mg (62%).

$^1$H NMR (400 MHz, DMSO-$d_6$) δ (ppm): 8.69 (s, 1H), 7.39 (dd, J=7.4 Hz, 1H), 6.95 (d, J=7.4 Hz, 1H), 6.82 (d, J=8.2 Hz, 1H), 4.90 (s, 2H), 4.08 (t, J=5.9 Hz, 2H), 2.68 (t, J=7.2 Hz, 2H), 2.13-1.91 (m, 2H); MS (ESI): m/z=216 (M−1, negative); HPLC purity: 99.37% (MaxPlot 200-400 nm), 98.27% (220 nm).

7-(4-Amino-butoxy)-3H-benzo[c][1,2]oxaborol-1-ol hydrochloride (A17)

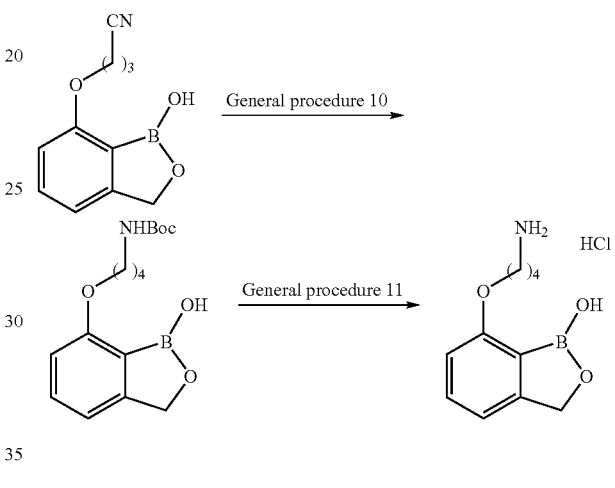

[4-(1-Hydroxy-1,3-dihydro-benzo[c][1,2]oxaborol-7-yloxy)-butyl]-carbamic acid tert-butyl ester

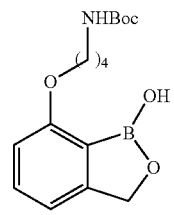

General procedure 10: A16 (600 mg, 2.76 mmol), $NiCl_2\cdot 6H_2O$ (65 mg, 0.276 mmol), $NaBH_4$ (540 mg, 19.32 mmol), and $Boc_2O$ (1.20 g, 5.52 mmol) in MeOH (50 mL). Purification: flash chromatography (30% EtOAc in hexane). The title compound was isolated as a white foam: yield 200 mg (22%).

$^1$H NMR (400 MHz, $CDCl_3$) δ (ppm): 7.51-7.34 (m, 1H), 7.02-6.84 (m, 1H), 6.73 (d, J=8.2 Hz, 1H), 5.05 (s, 2H), 4.13-3.99 (m, 2H), 3.30-3.12 (m, 2H), 1.97-1.77 (m, 2H), 1.77-1.61 (m, 2H), 1.45 (s, 9H); MS (ESI): m/z=320 (M−1, negative).

7-(4-Amino-butoxy)-3H-benzo[c][1,2]oxaborol-1-ol hydrochloride (A17)

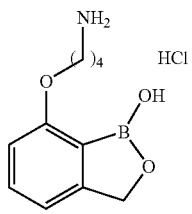

General procedure 11: [4-(1-hydroxy-1,3-dihydro-benzo[c][1,2]oxaborol-7-yloxy)-butyl]-carbamic acid tert-butyl ester (200 mg, 0.62 mmol) and 1 M HCl in Et$_2$O (4 mL). A17 was isolated as a white solid: yield 72 mg (45%).

mp 140-141° C.; $^1$H NMR (400 MHz, DMSO-d$_6$) δ (ppm): 8.74 (s, 1H), 7.80 (bs, 3H), 7.41 (t, J=7.8 Hz, 1H), 6.95 (d, J=7.8 Hz, 1H), 6.82 (d, J=8.2 Hz, 1H), 4.93 (s, 2H), 4.11-3.99 (m, 2H), 2.97-2.78 (m, 2H), 1.95-1.52 (m, 4H); MS (ESI): m/z=222 (M+1, positive); HPLC purity: 97.72% (MaxPlot 200-400 nm), 96.62% (220 nm).

7-(2-Amino-ethoxy)-3H-benzo[c][1,2]oxaborol-1-ol hydrochloride (A18)

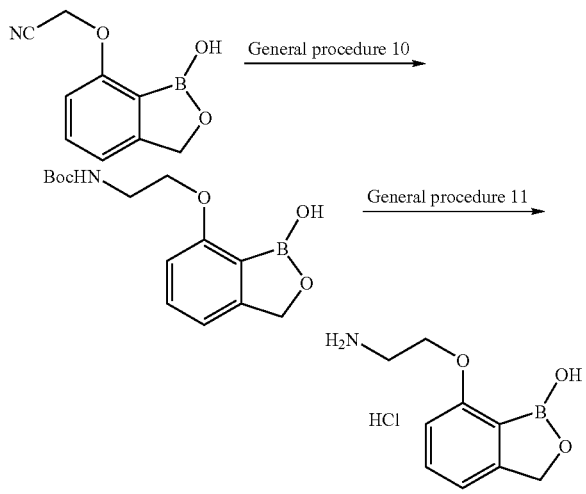

General procedure 10: (1-hydroxy-1,3-dihydro-benzo[c][1,2]oxaborol-7-yloxy)-acetonitrile (360 mg, 1.90 mmol), NiCl$_2$.6H$_2$O (90 mg, 0.38 mmol), NaBH$_4$ (505 mg, 13.3 mmol), and Boc$_2$O (829 mg, 3.8 mmol) in MeOH (20 mL). Purification: flash chromatography (30% EtOAc in hexane). The title compound was isolated as a white foam: yield 100 mg (18%).

$^1$H NMR (400 MHz, DMSO-d$_6$) δ (ppm): 8.32 (s, 1H), 7.39 (t, J=7.8 Hz, 1H), 7.14 (bs, 1H), 6.94 (d, J=7.4 Hz, 1H), 6.79 (d, J=8.2 Hz, 1H), 4.90 (s, 2H), 3.99-3.82 (m, 2H).

7-(2-Amino-ethoxy)-3H-benzo[c][1,2]oxaborol-1-ol hydrochloride (A18)

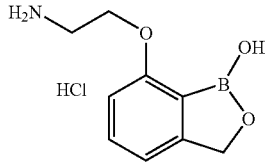 [SMILES: NCCOc1cccc2c1B(O)OC2 ; Cl]

General procedure 11: [2-(1-hydroxy-1,3-dihydro-benzo[c][1,2]oxaborol-7-yloxy)-ethyl]-carbamic acid tert-butyl ester (100 mg, 0.34 mmol.), 1 M HCl in Et$_2$O (2 mL), and CH$_2$Cl$_2$ (2 mL). A18 was isolated as a white solid: yield 58 mg (74%).

mp 217-218° C.; $^1$H NMR (400 MHz, DMSO-d$_6$) δ (ppm): 8.65 (bs, 1H), 8.08-7.97 (m, 3H), 7.44 (t, J=7.8 Hz, 1H), 7.01 (d, J=7.4 Hz, 1H), 6.86 (d, J=8.2 Hz, 1H), 4.92 (s, 2H), 4.20 (t, J=3.90 Hz, 2H), 3.26-3.20 (m, 2H); MS (ESI): m/z=194 (M+1, positive); HPLC purity: 97.69% (MaxPlot 200-400 nm), 96.84% (220 nm).

4-(1-Hydroxy-1,3-dihydro-benzo[c][1,2]oxaborol-7-yloxy)-butyramidine (A19)

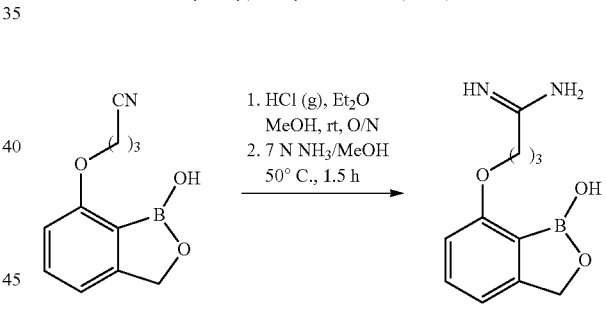

HCl (g) was bubbled through a solution of 4-(1-hydroxy-1,3-dihydro-benzo[c][1,2]oxaborol-7-yloxy)-butyronitrile (300 mg, 1.38 mmol) in MeOH (20 mL) and Et$_2$O (10 mL) for 1 h at 0° C. (bath temp). The mixture was left O/N in a closed system and was then concentrated in vacuo to give the title compound as a white solid: yield 310 mg. This was used in the next step without further purification or characterization.

A mixture of 4-(1-hydroxy-1,3-dihydro-benzo[c][1,2]oxaborol-7-yloxy)-butyrimidic acid methyl ester hydrochloride (310 mg crude), 7 M NH$_3$ in MeOH (10 mL) and MeOH (5 mL) was heated to 50° C. (bath temp) in a sealed tube for 1.5 h. The mixture was cooled and concentrated in vacuo. Purification by preparative HPLC (0.1% NH$_4$OH) gave A19: yield 35 mg (11% over 2 steps).

$^1$H NMR (400 MHz, CD$_3$OD-d$_4$) δ (ppm): 7.08 (t, J=7.6 Hz, 1H), 6.70 (d, J=7.0 Hz, 1H), 6.62 (d, J=7.8 Hz, 1H), 4.81 (s, 2H), 4.04 (t, J=5.5 Hz, 2H), 2.73 (t, J=7.0 Hz, 2H), 2.13 (quin, J=6.2 Hz, 2H); MS (ESI): m/z=235 (M+1, positive); HPLC purity: 86.89% (MaxPlot 200-400 nm), 86.19% (220 nm).

7-(3-Hydroxypropoxy)benzo[c][1,2]oxaborol-1(3H)-ol [A20]

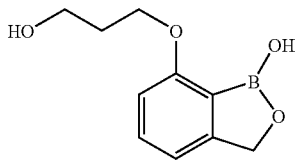 [SMILES: OCCCOc1cccc2c1B(O)OC2]

To a solution of 2-bromo-3-hydroxybenzaldehyde (5.18 g, 25.0 mmol) and 2-(3-bromopropoxy)tetrahydro-2H-pyran (5.1 mL, 30 mmol) in DMF (60 mL) was added sodium hydride (1.20 g, 30.0 mmol) at 0° C. under nitrogen atmosphere, and the mixture was stirred at room temperature for overnight. The reaction was quenched with water, and the mixture was extracted with ethyl acetate. The organic layer was washed with water twice and brine, and dried on anhydrous sodium sulfate. The solvent was removed under reduced pressure, and the residue was purified by silica gel column chromatography (9:1 to 3:1 hexane/ethyl acetate) to give 2-bromo-3-[3-(tetrahydropyran-2-yloxy)propoxy]benzaldehyde (8.75 g, quantitative).

To a solution of the compound obtained above (8.75 g, 25.0 mmol) in methanol (60 mL) was added sodium borohydride (475 mg, 12.5 mmol) at 0° C., and the mixture was stirred for 15 min. The reaction was quenched with acetone and water, and the mixture was extracted with ethyl acetate. The organic layer was washed with brine, and dried on anhydrous sodium sulfate. The solvent was removed under reduced pressure. To a solution of the residue in dichloromethane (100 mL) were added 3,4-dihydro-2H-pyran (3.40 mL, 37.5 mmol) and camphorsulfonic acid (116 mg, 2 mol %), and the mixture was stirred at room temperature for overnight. Sodium carbonate (1 g) was added and the mixture was poured into chloroform and water. The organic layer was washed with brine, and dried on anhydrous sodium sulfate. The solvent was removed under reduced pressure and the residue was purified by silica gel column chromatography (9:1 hexane/ethyl acetate) to give 2-(2-(2-bromo-3-((tetrahydro-2H-pyran-2-yloxy)methyl)phenoxy)ethoxy)tetrahydro-2H-pyran (9.98 g, 93%).

To a solution of the compound obtained above (9.98 g, 23.3 mmol) in tetrahydrofuran (50 mL) were added n-butyllithium (1.6 mol/L in hexanes; 18 mL) and triisopropyl borate (8.0 mL, 35 mmol) at −78° C. under nitrogen atmosphere, and the mixture was allowed to warm to room temperature and stirred for overnight. Then hydrochloric acid (6 mol/L, 10 mL) was added, and the mixture was stirred for 30 min at room temperature. The mixture was poured into ethyl acetate and water. The organic layer was washed with brine, and dried on anhydrous sodium sulfate. The solvent was removed under reduced pressure and the residue was purified by silica gel column chromatography (7:3 to 6:4 hexane/ethyl acetate) to give 7-(3-Hydroxypropoxy)benzo[c][1,2]oxaborol-1(3H)-ol (2.06 g, 43%).

$^1$H-NMR (300 MHz, DMSO-$d_6$+$D_2O$) δ (ppm) 1.84 (quint, J=6.2 Hz, 2H), 3.55 (t, J=6.2 Hz, 2H), 4.07 (t, J=6.2 Hz, 2H), 4.89 (s, 2H), 6.79 (d, J=8.2 Hz, 1H), 6.91 (d, J=7.3, 1H), 7.38 (t, J=7.8 Hz, 1H).

7-(4-Benzyloxy-butoxy)-3H-benzo[c][1,2]oxaborol-1-ol (A21)

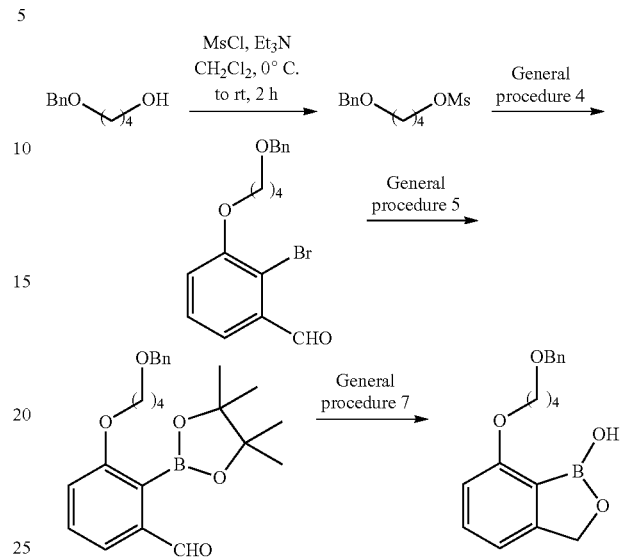

Methanesulfonic acid 4-benzyloxy-butyl ester

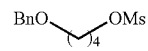

MsCl (2.48 mL, 32.1 mmol) was added slowly to a solution of 4-benzyloxy-butan-1-ol (5.26 g, 29.2 mmol) and Et$_3$N (6.1 mL, 43 mmol) in CH$_2$Cl$_2$ (100 mL) at 0° C. (bath temp). The reaction mixture was stirred at rt for 2 h and then quenched with H$_2$O (100 mL). The aqueous layer was extracted with CH$_2$Cl$_2$, dried (MgSO$_4$), and concentrated in vacuo to give the title compound as a colorless liquid: yield 7.5 g (99%).

$^1$H NMR (400 MHz, CDCl$_3$) δ (ppm): 7.39-7.25 (m, 5H), 4.50 (s, 2H), 4.26 (t, J=6.5 Hz, 2H), 3.52 (t, J=6.1 Hz, 2H), 2.98 (s, 3H), 1.92-1.84 (m, 2H), 1.78-1.69 (m, 2H).

3-(4-Benzyloxy-butoxy)-2-bromo-benzaldehyde

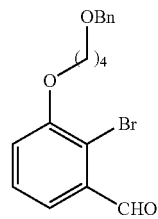

General procedure 4: 2-bromo-3-hydroxy-benzaldehyde (4.86 g, 24.2 mmol), methanesulfonic acid 4-benzyloxy-butyl ester (7.5 g, 29 mmol), Cs₂CO₃ (11.82 g, 36.3 mmol) and DMF (100 mL). The title compound was isolated as a viscous liquid: yield 6.4 g (73%).

¹H NMR (400 MHz, CDCl₃) δ (ppm): 10.44 (s, 1H), 7.51 (d, J=7.8 Hz, 1H), 7.38-7.24 (m, 6H), 7.09 (d, J=8.2 Hz, 1H), 4.53 (s, 2H), 4.09 (t, J=6.1 Hz, 2H), 3.59 (t, J=6.2 Hz, 2H), 2.03-1.95 (m, 2H), 1.93-1.82 (m, 2H).

3-(4-Benzyloxy-butoxy)-2-(4,4,5,5-tetramethyl-[1,3,2]dioxaborolan-2-yl)-benzaldehyde

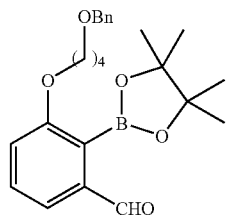

General procedure 5: 3-(4-benzyloxy-butoxy)-2-bromo-benzaldehyde (6.4 g, 17 mmol), B₂pin₂ (8.94 g, 35.2 mmol), KOAc (6.91 g, 70.4 mmol), PdCl₂(dppf).CH₂Cl₂ (0.64 g, 0.88 mmol), and dioxane (200 mL). Purification: flash chromatography (20% EtOAc in hexane). The title compound was isolated as a white foam: yield 4.0 g (55%).

¹H NMR (400 MHz, CDCl₃) δ (ppm): 9.92 (s, 1H), 7.44 (t, J=7.8 Hz, 1H), 7.39-7.24 (m, 6H), 7.04 (d, J=8.2 Hz, 1H), 4.50 (s, 2H), 3.99 (t, J=6.2 Hz, 2H), 3.52 (t, J=6.1 Hz, 2H), 1.96-1.75 (m, 4H), 1.44 (s, 12H).

7-(4-Benzyloxy-butoxy)-3H-benzo[c][1,2]oxaborol-1-ol (A21)

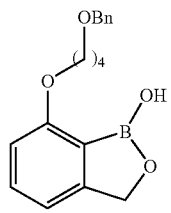

General procedure 7: 3-(4-benzyloxy-butoxy)-2-(4,4,5,5-tetramethyl-[1,3,2]dioxaborolan-2-yl)-benzaldehyde (2.0 g, 4.8 mmol), NaBH₄ (239 mg, 6.3 mmol), and MeOH (10 mL). Purification: flash chromatography (30% EtOAc in hexane): yield 650 mg (43%).

¹H NMR (400 MHz, DMSO-d₆) δ (ppm): 8.66 (s, 1H), 7.43-7.22 (m, 6H), 6.91 (d, J=7.4 Hz, 1H), 6.77 (d, J=8.2 Hz, 1H), 4.89 (s, 2H), 4.44 (s, 2H), 4.03 (t, J=6.3 Hz, 2H), 3.48 (t, J=6.1 Hz, 2H), 1.85-1.61 (m, 4H); MS (ESI): m/z=313 (M+1, positive); HPLC purity: 93.49% (MaxPlot 200-400 nm), 92.07% (220 nm).

7-(4-Hydroxy-butoxy)-3H-benzo[c][1,2]oxaborol-1-ol (A22)

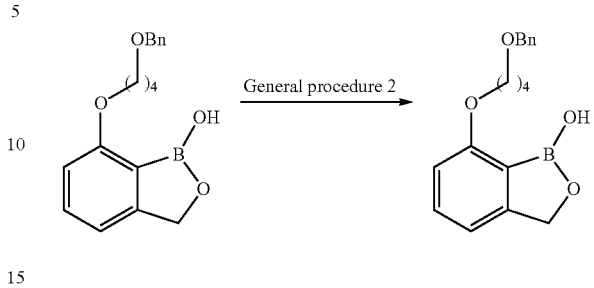

General procedure 2: H₂ (50 psi), A21 (600 mg, 1.92 mmol), Pd(OH)₂ (600 mg), and AcOH (20 mL). Purification: flash chromatography (50% EtOAc in hexane). A22 was isolated as a white solid: yield 90 mg (21%).

mp 141-142° C.; ¹H NMR (400 MHz, DMSO-d₆) δ (ppm): 8.68 (bs, 1H), 7.52-7.29 (m, 1H), 6.92 (d, J=7.4 Hz, 1H), 6.80 (d, J=7.4 Hz, 1H), 4.91 (s, 2H), 4.55-4.35 (m, 1H), 4.12-3.95 (m, 2H), 3.54-3.54 (m, 2H), 1.91-1.67 (m, 2H), 1.63-1.50 (m, 2H); MS (ESI): m/z=221 (M−1, negative); HPLC purity: 95.71% (MaxPlot 200-400 nm), 93.02% (220 nm).

(3S)-7-(3-Amino-4-hydroxy-butoxy)-3H-benzo[c][1,2]oxaborol-1-ol hydrochloride (A23)

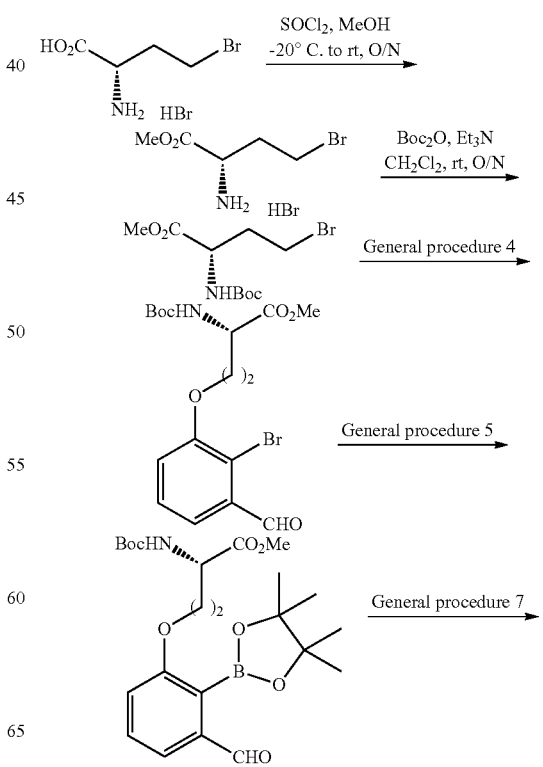

-continued

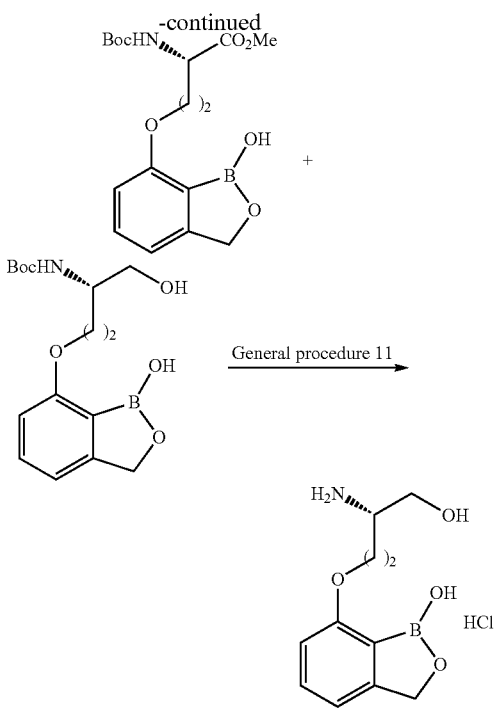

General procedure 11

(2S)-2-Amino-4-bromo-butyric acid methyl ester hydrobromide

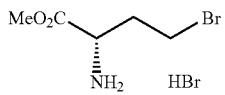

SOCl$_2$ (7.0 mL) was added slowly to MeOH (100 mL) at −20° C. (bath temp), and stirred for 30 min. 2-Amino-4-bromo-butyric acid hydrobromide (5.0 g, 19 mmol) was then added and the reaction mixture was stirred O/N at rt. Concentration in vacuo gave the title compound as a viscous liquid which become solid on standing: yield 5.2 g (99%).

$^1$H NMR (400 MHz, DMSO-d$_6$) δ (ppm): 8.57 (bs, 3H), 4.11 (t, J=6.2 Hz, 1H), 3.75 (s, 3H), 3.71-3.53 (m, 2H), 2.40-2.22 (m, 2H).

(2S)-4-Bromo-2-tert-butoxycarbonylamino-butyric acid methyl ester

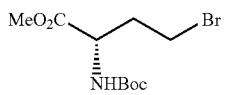

Et$_3$N (6.5 mL, 47 mmol) followed by Boc$_2$O (4.09 g, 18.8 mmol) were added to a solution of 2-amino-4-bromo-butyric acid methyl ester hydrobromide (5.2 g, 19 mmol) in CH$_2$Cl$_2$ (100 mL) at rt. The reaction mixture was stirred O/N at rt and then quenched with H$_2$O (100 mL). The aqueous layer was extracted with CH$_2$Cl$_2$, dried (MgSO$_4$), and concentrated in vacuo. The residue was purified by flash chromatography (20% EtOAc in hexane) to give the title compound as a colorless liquid: yield 3.1 g (56%).

$^1$H NMR (400 MHz, CDCl$_3$) δ (ppm): 5.19-5.00 (m, 1H), 4.51-4.37 (m, 1H), 3.77 (s, 3H), 3.44 (t, J=7.0 Hz, 2H), 2.47-2.32 (m, 1H), 2.27-2.13 (m, 1H), 1.45 (s, 9H).

(2S)-4-(2-Bromo-3-formyl-phenoxy)-2-tert-butoxycarbonylamino-butyric acid methyl ester

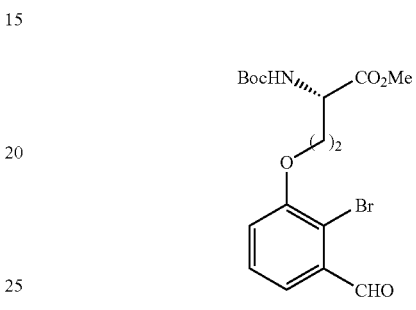

General procedure 4: 2-bromo-3-hydroxy-benzaldehyde (2.31 g, 11.5 mmol), 4-bromo-2-tert-butoxycarbonylamino-butyric acid methyl ester (3.1 g, 10 mmol), Cs$_2$CO$_3$ (5.11 g, 15.7 mmol), and DMF (100 mL). Purification: flash chromatography (20% EtOAc in hexane). The title compound was isolated as a viscous liquid: yield 3.01 g (69%)

$^1$H NMR (400 MHz, CDCl$_3$) δ (ppm): 10.43 (s, 1H), 7.54 (d, J=8.2 Hz, 1H), 7.37 (t, J=7.8 Hz, 1H), 7.10 (d, J=8.2 Hz, 1H), 5.74-5.60 (m, 1H), 4.58 (t, J=8.6 Hz, 1H), 4.25-4.03 (m, 2H), 3.77 (s, 3H), 2.53-2.26 (m, 2H), 1.44 (s, 9H).

(2S)-2-tert-Butoxycarbonylamino-4-[3-formyl-2-(4,4,5,5-tetramethyl-[1,3,2]-dioxaborolan-2-yl)-phenoxy]-butyric acid methyl ester

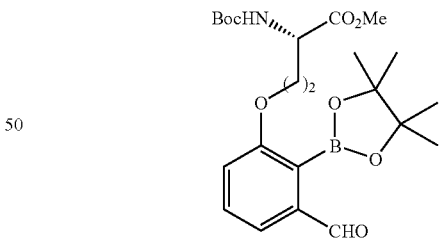

General procedure 5: (2S)-4-(2-bromo-3-formyl-phenoxy)-2-tert-butoxycarbonylamino-butyric acid methyl ester (3.01 g, 7.23 mmol), B$_2$pin$_2$ (3.67 g, 14.5 mmol), KOAc (2.83 g, 28.9 mmol), PdCl$_2$(dppf).CH$_2$Cl$_2$ (0.37 g, 0.51 mmol) in dioxane (50 mL). Purification: flash chromatography (10% EtOAc in hexane). The title compound was isolated as a white foam: yield 1.2 g (35%).

$^1$H NMR (400 MHz, CDCl$_3$) δ (ppm): 9.96 (s, 1H), 7.51-7.39 (m, 2H), 7.09 (d, J=7.8 Hz, 1H), 5.32 (d, J=9.4 Hz, 1H), 4.49-4.39 (m, 1H), 4.17-3.99 (m, 2H), 3.75 (s, 3H), 2.45-2.31 (m, 1H), 2.21-2.10 (m, 1H), 1.45 (s, 12H), 1.42 (s, 9H).

173

(3S)-[3-(1-Hydroxy-1,3-dihydro-benzo[c][1,2]ox-aborol-7-yloxy)-J-hydroxy-methyl-propyl]-carbamic acid tert-butyl ester

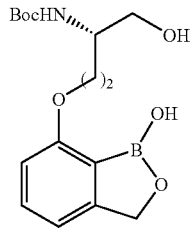

General procedure 7: (2S)-2-tert-Butoxycarbonylamino-4-[3-formyl-2-(4,4,5,5-tetramethyl-[1,3,2]-dioxaborolan-2-yl)-phenoxy]-butyric acid methyl ester (1.10 g, 2.3 mmol), NaBH$_4$ (113 mg, 2.99 mmol), and MeOH (25 mL). Purification: flash chromatography (10%-50% EtOAc/hexane): yield 70 mg (9%).

$^1$H NMR (400 MHz, DMSO-d$_6$) δ (ppm): 8.59 (bs, 1H), 7.38 (t, J=7.6 Hz, 1H), 6.91 (d, J=7.4 Hz, 1H), 6.77 (d, J=7.8 Hz, 1H), 6.63 (d, J=8.2 Hz, 1H), 4.89 (s, 2H), 4.70 (t, J=4.9 Hz, 1H), 4.10-3.96 (m, 2H), 3.64-3.52 (m, 1H), 3.41-3.35 (m, 1H), 2.02-1.90 (m, 1H), 1.82-1.67 (m, 1H), 1.33 (s, 9H); MS (ESI): m/z=336 (M−1, negative).

(3S)-7-(3-Amino-4-hydroxy-butoxy)-3H-benzo[c][1,2]oxaborol-1-ol hydrochloride; (A23)

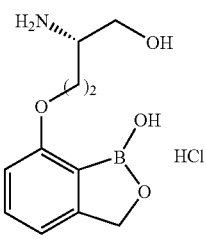

General procedure 11: (3S)-[3-(1-hydroxy-1,3-dihydro-benzo[c][1,2]oxaborol-7-yloxy)-1-hydroxy-methyl-propyl]-carbamic acid tert-butyl ester (70 mg, 0.21 mmol) in 4 N HCl dioxane (2 mL). A23 was isolated as a white solid lyophilizate: yield 35 mg (61%).

$^1$H NMR (400 MHz, DMSO-d$_6$) δ (ppm): 8.89 (s, 1H), 7.90 (bs, 3H), 7.42 (t, J=7.8 Hz, 1H), 6.96 (d, J=7.4 Hz, 1H), 6.82 (d, J=8.2 Hz, 1H), 5.34 (bs, 1H), 4.92 (s, 2H), 4.24-4.03 (m, 2H), 3.70-3.60 (m, 1H), 3.57-3.47 (m, 1H), 2.06-1.94 (m, 2H); MS (ESI): m/z=238 (M+1, positive); HPLC purity: 94.91% (MaxPlot 200-400 nm), 94.63% (220 nm).

174

7-(2-Benzyloxy-ethoxy)-3H-benzo[c][1,2]oxaborol-1-ol (A24)

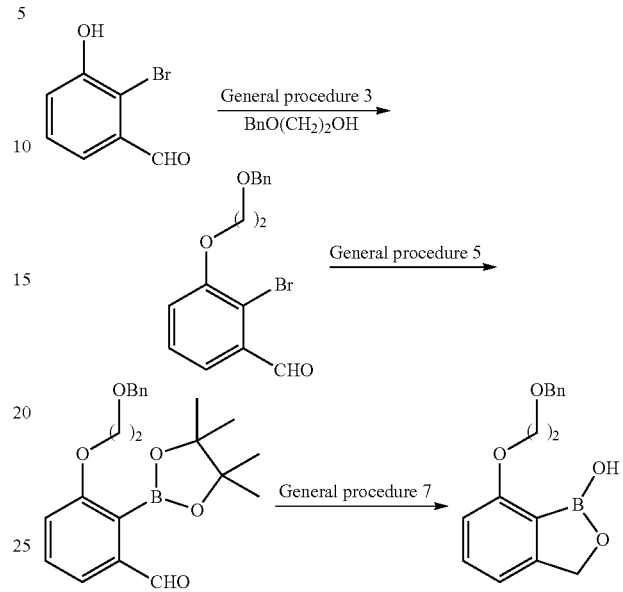

3-(3-Benzyloxy-ethoxy)-2-bromo-benzaldehyde

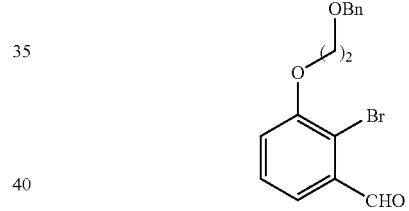

General Procedure 3: 2-bromo-3-hydroxy-benzaldehyde (7.0 g, 35 mmol), 2-benzyloxy-ethanol (5.0 mL, 35 mmol), PPh$_3$ (9.2 g, 35 mmol), anhydrous THF (200 mL), and DIAD (6.9 mL, 35 mmol). Purification: flash chromatography (hexane then 5% EtOAc/hexane): yield 7.6 g (65%).

$^1$H NMR (400 MHz, CDCl$_3$) δ (ppm): 10.44 (s, 1H), 7.53 (d, J=7.9 Hz, 1H), 7.44-7.26 (m, 6H), 7.15 (d, J=7.9 Hz, 1H), 4.70 (s, 2H), 4.26 (t, J=4.7 Hz, 2H), 3.93 (t, J=4.7 Hz, 2H).

3-(3-Benzyloxy-ethoxy)-2-(4,4,5,5-tetramethyl-[1,3,2]dioxaborolan-2-yl)-benzaldehyde

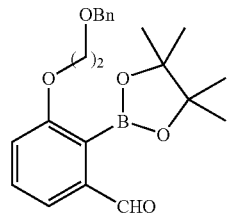

General procedure 5: 3-(3-benzyloxy-ethoxy)-2-bromo-benzaldehyde (7.2 g, 23 mmol), KOAc (6.3 g, 64 mmol), B$_2$pin$_2$ (10.9 g, 43 mmol), PdCl$_2$(dppf).CH$_2$Cl$_2$ (0.79 g, 1.1 mmol), and anhydrous DMF (50 mL). Purification: flash chromatography (hexane then 30% EtOAc/hexane): yield 4.93 g (60%).

$^1$H NMR (400 MHz, CDCl$_3$) δ (ppm): 9.91 (s, 1H), 7.49-7.24 (m, 7H), 7.09 (d, J=8.20 Hz, 1H), 4.57 (s, 2H), 4.18 (t, J=5.0 Hz, 2H), 3.84 (t, J=5.0 Hz, 2H), 1.43 (s, 12H)

7-(2-Benzyloxy-ethoxy)-3H-benzo[c][1,2]oxaborol-1-ol (A24)

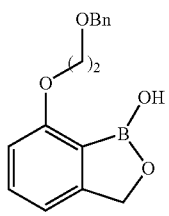

General procedure 7: 3-(3-benzyloxy-ethoxy)-2-(4,4,5,5-tetramethyl-[1,3,2]dioxaborolan-2-yl)-benzaldehyde (0.76 g, 2.0 mmol), NaBH$_4$ (38 mg, 1.0 mmol), and MeOH (5 mL). Purification: flash chromatography (30% EtOAc in hexane): yield 0.55 g (96%).

$^1$H NMR {400 MHz, DMSO-d$_6$+D$_2$O (0.01 mL)} δ (ppm): 8.80 (s, 1H), 7.40-7.20 (m, 6H), 6.97 (d, J=7.4 Hz, 1H), 6.80 (d, J=7.4 Hz, 1H), 4.85 (s, 2H), 4.60 (s, 2H), 4.25-4.18 (m, 2H), 3.80-3.72 (m, 2H); MS (ESI) m/z=283 (M−1, negative); HPLC purity 96.23% (MaxPlot) and 95.11% (220 nm).

7-(4-Methoxy-benzyloxy)-3H-benzo[c][1,2]oxaborol-1-ol (A25)

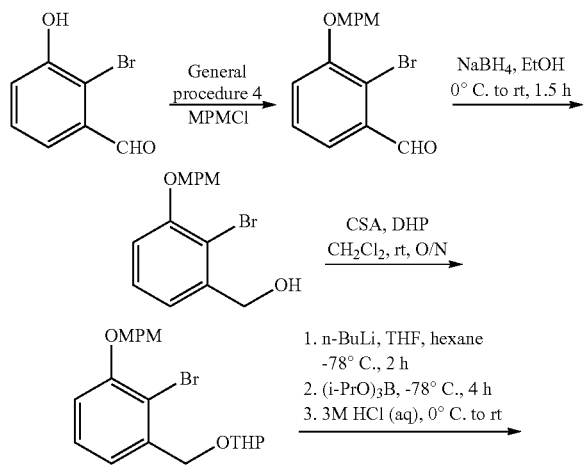

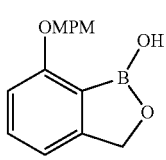

2-Bromo-3-(4-methoxy-benzyloxy)-benzaldehyde

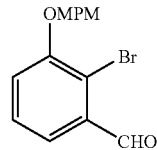

General procedure 4: 2-bromo-3-hydroxy-benzaldehyde (1.0 g, 7.2 mmol) K$_2$CO$_3$ (1.09 g, 7.95 mmol), 1-chloromethyl-4-methoxy-benzene (1.03 mL, 7.95 mmol), and DMSO (14 mL) at 50° C. (bath temp) O/N. Purification: flash chromatography (25% EtOAc in hexane). The title compound was isolated as a white solid: yield 1.59 g (96%).

$^1$H NMR (400 MHz, CDCl$_3$) δ (ppm): 10.42 (s, 1H), 7.49 (d, J=1.6 Hz, 1H), 7.39 (d, J=9.0 Hz, 2H), 7.16 (s, 1H), 7.02-6.84 (m, 3H), 5.11 (s, 2H), 3.80 (s, 3H); MS (ESI)/z=323 (M+1, positive).

[2-Bromo-3-(4-ethoxy-benzyloxy)-phenyl]-methanol

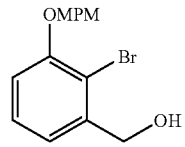

NaBH$_4$ (0.38 g, 10 mmol) was added to a solution of 2-bromo-3-(4-methoxy-benzyloxy)-benzaldehyde (1.59 g, 4.95 mmol) in EtOH (15 mL) at 0° C. (bath temp). The mixture was stirred at 0° C. (bath temp) for 1.5 h and then concentrated in vacuo. H$_2$O (10 mL) was added and the aqueous layer was extracted with EtOAc (2×50 mL). The organic fractions were washed with brine (20 mL), dried (Na$_2$SO$_4$), and concentrated in vacuo to give the title compound as white solid: yield 1.50 g (94%).

$^1$H NMR (400 MHz, CDCl$_3$) δ (ppm): 7.40 (d, J=8.6 Hz, 2H), 7.26 (s, 1H), 7.10 (d, J=9.0 Hz, 1H), 6.98-6.84 (m, 3H), 5.10 (s, 2H), 4.78 (d, J=6.6 Hz, 2H), 3.83 (bs, 3H).

2-[2-Bromo-3-(4-methoxy-benzyloxy)-benzyloxy]-tetrahydro-pyran

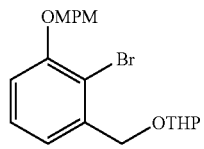

DHP (0.67 mL, 7.4 mmol) and CSA (30 mg, 0.12 mmol) were added to a solution of [2-bromo-3-(4-methoxy-benzyloxy)-phenyl]-methanol (2.0 g, 6.1 mmol) in CH$_2$Cl$_2$ (15 mL). The resulting mixture was stirred at rt O/N. 4 Å Molecular sieves (1.0 g) was added and mixture was stirred for 1 h. Sat. NaHCO$_3$ was added and mixture was extracted with CHCl$_3$ (2×50 mL). The organic fractions were washed with H$_2$O (2×25 mL) then brine (50 mL), dried (Na$_2$SO$_4$), and concentrated in vacuo. The residue was purified by flash chromatography (25% EtOAc in hexane) to give the title compound as yellow oil: yield 1.30 g (96%).

$^1$H NMR (400 MHz, CDCl$_3$) δ (ppm): 7.40 (d, J=9.0 Hz, 2H), 7.32-7.19 (m, 1H), 7.15 (dd, J=7.8, 1.2 Hz, 1H), 6.96-6.81 (m, 3H), 5.08 (s, 2H), 4.94-4.73 (m, 2H), 4.62 (d, J=13.3 Hz, 1H), 4.12-3.86 (m, 1H), 3.81 (s, 3H), 3.65-3.42 (m, 1H), 1.99-1.44 (m, 6H).

7-(4-Methoxy-benzyloxy)-3H-benzo[c][1,2]oxaborol-1-ol (A25)

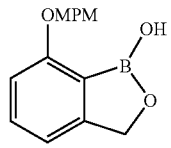

2.5 M n-BuLi in hexane (1.53 mL, 3.83 mmol) was added dropwise to a solution of 2-[2-bromo-3-(4-methoxy-benzyloxy)-benzyloxy]-tetrahydro-pyran (1.3 g, 3.2 mmol) in THF (14 mL) under N$_2$ at −78° C. (bath temp). The mixture was stirred at −78° C. (bath temp) for 2 h then triisopropyl borate (0.90 mL, 3.8 mmol) was added slowly and stirred at −78° C. (bath temp) for 4 h. The mixture was allowed to warm up to 0° C. (bath temp) and then acidified with 3 M HCl to pH 5. The mixture was stirred for 3 h and the resulting precipitate was isolated by filtration and washed with 1:9 CH$_2$Cl$_2$/Et$_2$O to give A25 as a yellow solid: yield 0.10 g (12%).

$^1$H NMR 400 MHz (DMSO-d$_6$) δ (ppm): 8.81 (s, 1H), 7.48-7.28 (m, 3H), 6.96-6.91 (m, 3H), 6.87 (d, J=8.2 Hz, 1H), 5.12 (s, 2H), 4.93 (s, 2H), 3.75 (s, 3H); MS (ESI) m/z=271 (M+1, positive); HPLC purity: 97.79% (220 nm).

3H-Benzo[c][1,2]oxaborole-1,7-diol (A26)

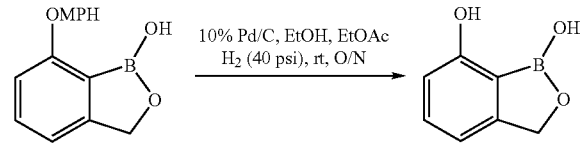

A mixture of A25 (0.65 g, 2.40 mmol) 10% Pd/C (1:1 w/w) and 2:1 EtOAc/EtOH (30 mL) was shaken under an atmosphere of H$_2$ (40 psi) O/N. The mixture was filtered through Celite and the filtrate was concentrated in vacuo. The residue was purified by reverse phase preparative HPLC and lyophilized to yield the title compound as white solid: yield 20 mg, (6%).

$^1$H NMR (400 MHz, DMSO-d$_6$) δ (ppm): 9.39 (bs, 1H), 8.69 (bs, 1H), 7.25 (t, J=8.2 Hz, 1H), 6.77 (d, J=6.2 Hz, 1H), 6.63 (d, J=6.6 Hz, 1H), 4.85 (bs, 2H); MS (ESI) m/z=149 (M−1, negative); HPLC purity: 94.82% (220 nm), (254 nm).

2,6-Diamino-hexanoic acid (1-hydroxy-1,3-dihydro-benzo[c][1,2]oxaborol-3-ylmethyl)-amide hydrochloride (A27)

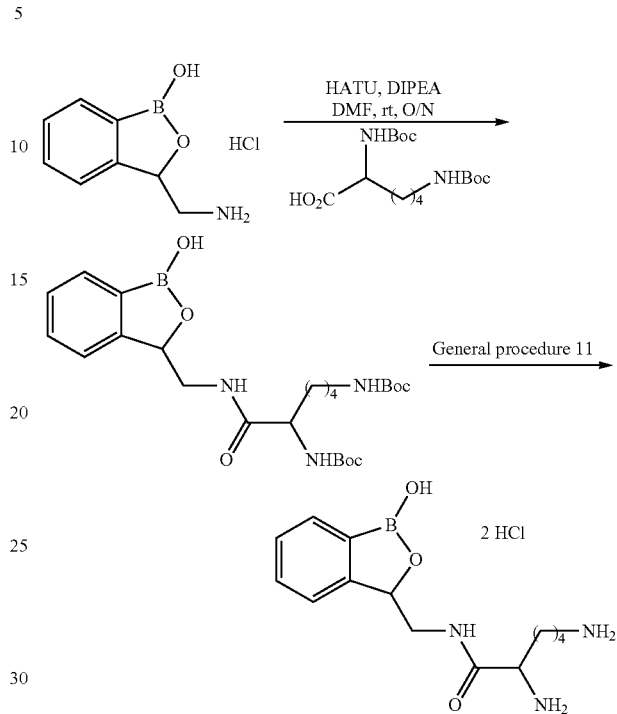

{5-tert-Butoxycarbonylamino-5-[(1-hydroxy-1,3-dihydro-benzo[c][1,2]oxaborol-3-ylmethyl)-carbamoyl]-pentyl}-carbamic acid tert-butyl ester

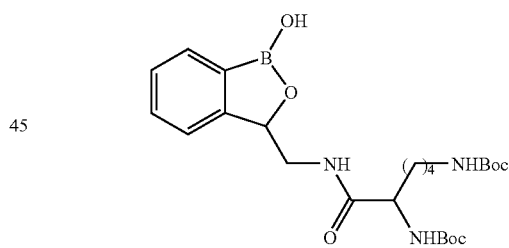

DIPEA (0.96 mL, 5.5 mmol), HATU (1.05 g, 2.76 mmol) and A1 (0.50 g, 2.5 mmol) were added sequentially to a solution of 2,6-bis-tert-butoxycarbonylamino-hexanoic acid (0.79 g, 2.3 mmol) in DMF (10 mL) at rt. The bath was removed and the solution was stirred at rt O/N. The mixture was concentrated in vacuo and the residue was taken up in EtOAc, washed with H$_2$O (3×30 mL), dried (Na$_2$SO$_4$), and concentrated in vacuo. The residue was purified by flash chromatography (2% MeOH in EtOAc) to give the title compound: yield 0.67 g (55%).

$^1$H NMR (400 MHz, DMSO-d$_6$) δ (ppm): 9.24 (d, J=7.8 Hz, 1H), 7.95 (q, J=6.8 Hz, 1H), 7.71 (t, J=6.5 Hz, 1H), 7.50-7.28 (m, 3H), 6.89-6.60 (m, 2H), 5.23-5.06 (m, 1H), 3.94-3.73 (m, 2H), 3.60-3.47 (m, 1H), 3.47-3.37 (m, 1H), 2.85 (dd, J=15.4, 5.7 Hz, 3H), 1.37 (s, 18H).

2,6-Diamino-hexanoic acid (1-hydroxy-1,3-dihydro-benzo[c][1,2]oxaborol-3-ylmethyl)-amide hydrochloride (A27)

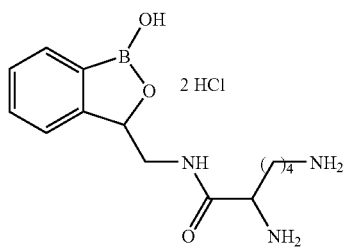

General procedure 11: {5-tert-butoxycarbonylamino-5-[(1-hydroxy-1,3-dihydro-benzo[c][1,2]oxaborol-3-ylmethyl)-carbamoyl]-pentyl}-carbamic acid tert-butyl ester (0.66 g, 1.3 mmol) and 1 M HCl in Et$_2$O (25 mL). A27 was isolated as a white solid: yield 0.33 g (69%).

$^1$H NMR (400 MHz, DMSO-d$_6$) δ (ppm): 9.36 (bs, 1H), 8.68-8.50 (m, 1H), 8.13 (bs, 6H), 7.81 (dd, J=7.2, 4.1 Hz, 1H), 7.55-7.29 (m, 3H), 5.30-5.13 (m, 1H), 3.90-3.61 (m, 2H), 3.54-3.43 (m, 1H), 3.13 (dd, J=18.4, 7.0 Hz, 1H), 2.75 (t, J=7.6 Hz, 1H), 2.63 (t, J=7.6 Hz, 1H), 1.81-1.47 (m, 2H), 1.46-1.25 (m, 3H); MS (ESI): m/z=292 (M+1, positive); HPLC purity: 97.80% (MaxPlot 200-400 nm), 97.62% (220 nm).

Acetic acid 2-{2-[(1-hydroxy-1,3-dihydro-benzo[c][1,2]oxaborol-3-ylmethyl)-carbamoyl]-1,1-dimethyl-ethyl}-3,5-dimethyl-phenyl ester (A27a)

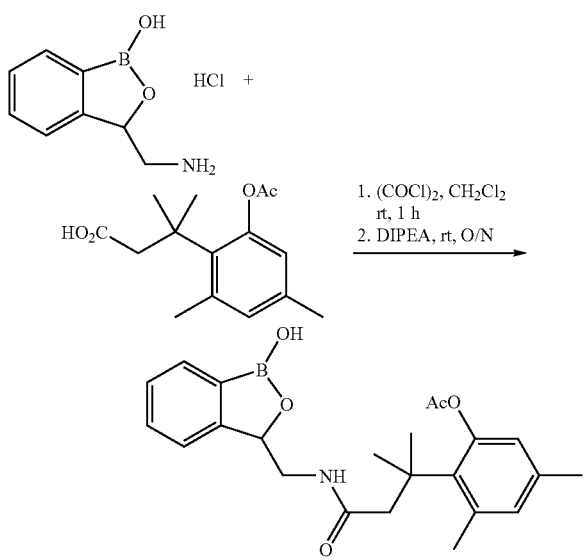

Oxalyl chloride (0.50 mL, 5.7 mmol) was added to an ice-cold solution of 3-(2-acetoxy-4,6-dimethyl-phenyl)-3-methyl-butyric acid (1.00 g, 3.60 mmol) (produced according to the procedure in Kent, L.; Amsberry, A.; Gerstenberger, E.; Borchardt, R. T.; Pharm. Res., 1991, 8, 455-460 and Michalis, G.; Nicolaou, C.-S. Y.; Borchardt, R. T.; J. Org. Chem., 1996, 61, 8636-8641) in anhydrous CH$_2$Cl$_2$ (15 mL) at rt. The mixture was stirred for 1 h and then the excess oxalyl chloride was removed in vacuo. The residue was dissolved in anhydrous CH$_2$Cl$_2$ (15 mL) and cooled to 0° C. (bath temp). DIPEA (2.0 mL, 10 mmol) and A1 (0.70 g, 3.6 mmol) were added and the reaction mixture was stirred at rt for 12 h. The mixture was then diluted with brine (50 mL) and extracted with CH$_2$Cl$_2$ (2×50 mL). The combined organic layers were washed with H$_2$O then brine, dried (NaSO$_4$), and concentrated in vacuo. The product was purified by flash chromatography (EtOAc/MeOH) to give (A27a) yield 0.50 g (24%).

$^1$H NMR (400 MHz, DMSO-d$_6$) δ (ppm): 9.22 (s, 1H), 7.88 (t, J=5.7 Hz, 1H), 7.73-7.69 (m, 1H), 7.47-7.41 (m, 1H), 7.38-7.31 (m, 4H), 6.77 (d, J=2.0 Hz, 1H), 6.57 (d, J=2.0 Hz, 1H), 5.09 (dd, J=6.8, 4.1 Hz, 1H), 3.50-3.41 (m, 1H), 3.19 (m, 1H), 2.53 (s, 2H), 2.45 (s, 3H), 2.25 (s, 3H), 2.16 (s, 3H), 1.36 (d, J=5.1 Hz, 6H); MS (ESI) m/z=410 (M+1, positive); HPLC purity: 97.73% (MaxPlot 200-400 nm), 96.90% (220 nm); Anal. Calcd for C$_{23}$H$_{28}$BNO$_5$: C, 67.50%; H, 6.90%; N, 3.42%. Found: C, 67.65%; H, 6.91%; N, 3.28%.

Acetic acid 3-[(1-hydroxy-1,3-dihydro-benzo[c][1,2]oxaborol-3-ylmethyl)-carbamoyl]-propyl ester (A28)

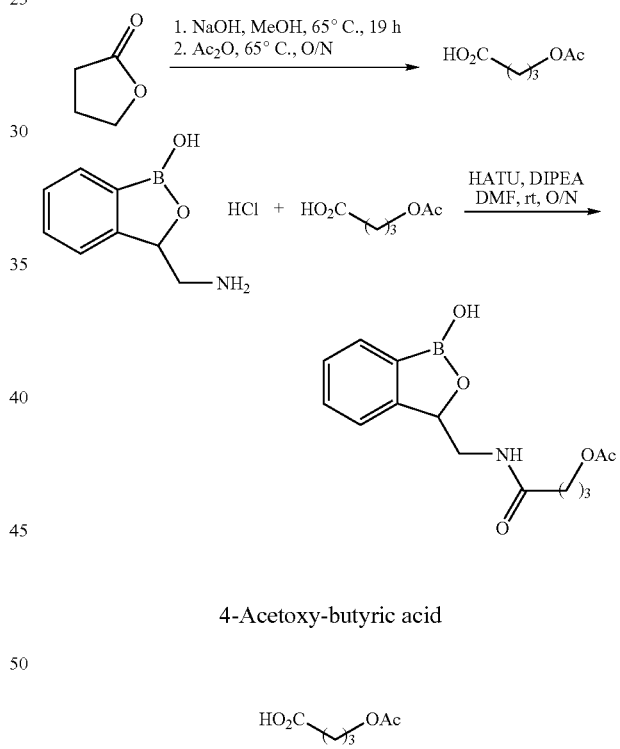

4-Acetoxy-butyric acid

A mixture of dihydro-furan-2-one (5.2 g, 60 mmol) and NaOH (2.9 g, 73 mmol) in MeOH (50 mL) was refluxed for 19 h. The solution was cooled and concentrated to give a glassy powder which was used in the next step without purification. The crude mass was dissolved in excess of Ac$_2$O (100 mL) and heated at 65° C. (bath temp) O/N. The mixture was concentrated in vacuo and the residue dissolved in Et$_2$O. The organic layer was washed with H$_2$O and the concentrated in vacuo to give the title compound as a colorless oil: yield 0.92 g (111%).

$^1$H NMR (400 MHz, CDCl$_3$) δ (ppm): 4.14 (t, J=6.1 Hz, 2H), 2.69-2.37 (m, 2H), 2.06 (s, 3H), 2.05-1.97 (m, 2H).

Acetic acid 3-[(1-hydroxy-1,3-dihydro-benzo[c][1,2]oxaborol-3-ylmethyl)-carbamoyl]-propyl ester (A28)

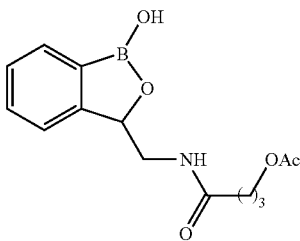

DIPEA (1.27 mL, 7.28 mmol), HATU (1.32 g, 3.48 mmol) and A1 (0.63 g, 3.2 mmol) were added to a solution of 4-acetoxy-butyric acid (0.38 g, 2.6 mmol) in DMF (10 mL) at 0° C. The cooling bath was removed and the solution was stirred at rt for 19 h. The mixture was concentrated in vacuo and the residue was dissolved in EtOAc. The organic layer was washed with sequentially with 1 N NaHSO$_4$ (2×20 mL), H$_2$O, and brine. The organic layer was then dried (Na$_2$SO$_4$), and concentrated in vacuo. The gummy white residue was purified by flash chromatography (EtOAc) to give A28 as a solid: yield 0.39 g (42%).

$^1$H NMR (400 MHz, DMSO-d$_6$) δ (ppm): 9.23 (s, 1H), 8.09 (t, J=5.5 Hz, 1H), 7.70 (d, J=7.4 Hz, 1H), 7.54-7.16 (m, 3H), 5.19-4.98 (m, 1H), 3.90 (t, J=6.6 Hz, 2H), 3.62-3.45 (m, 1H), 3.24-3.05 (m, 1H), 2.13 (t, J=7.4 Hz, 2H), 1.97 (s, 3H), 1.71 (qd, J=7.1, 6.8 Hz, 2H); MS (ESI): m/z=292 (M+1, positive); HPLC purity: 99.28% (MaxPlot 200-400 nm), 98.21% (220 nm).

(1-Hydroxy-1,3-dihydro-benzo[c][1,2]oxaborol-3-ylmethyl)-carbamic acid phenyl ester (A29)

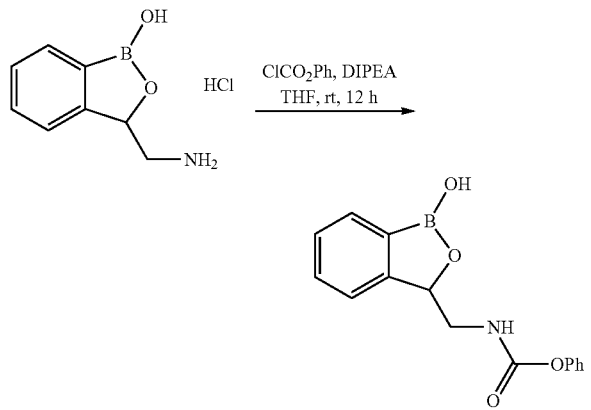

A mixture of A1 (0.50 g, 2.5 mmol), DIPEA (0.50 mL, 2.5 mmol) and phenyl chloroformate (0.50 mL, 2.5 mmol) in anhydrous THF was stirred at rt for 12 h. The mixture was then diluted with brine (50 mL) and extracted with EtOAc (2×50 mL). The combined organic layers were washed with H$_2$O then brine, dried (Na$_2$SO$_4$), and concentrated in vacuo. The residue was purified by flash chromatography (8:2 hexane/EtOAc) to give A29: yield 0.27 g (20%).

$^1$H NMR (400 MHz, DMSO-d$_6$) δ (ppm): 9.25 (s, 1H), 7.98 (t, J=5.3 Hz, 1H), 7.73 (d, J=7.4 Hz, 1H), 7.53-7.29 (m, 5H), 7.18 (t, J=7.4 Hz, 1H), 7.02 (d, J=7.8 Hz, 2H), 5.28-5.15 (m, 1H), 3.59-3.45 (m, 1H), 3.27-3.13 (m, 1H); MS (ESI) m/z=284 (M+1, positive); HPLC purity: 99.31% (MaxPlot 200-400 nm), 99.31% (220 nm).

3-Aminomethyl-6-(2-hydroxy-ethoxy)-3H-Benzo[c][1,2]oxaborol-1-ol acetate salt (A30)

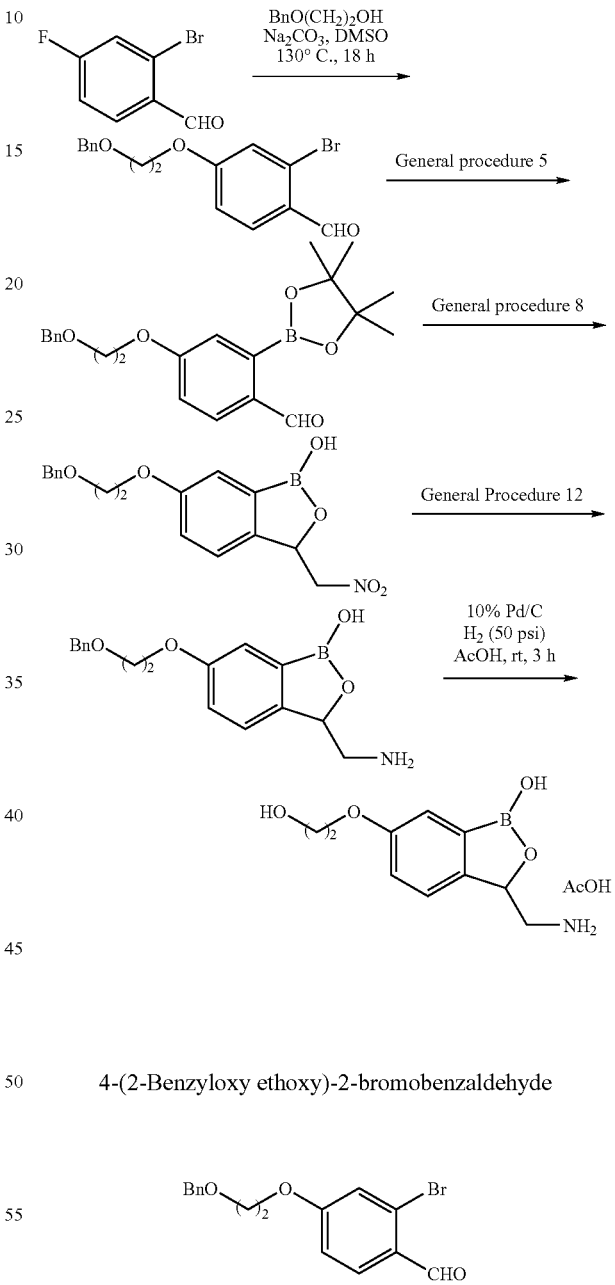

4-(2-Benzyloxy ethoxy)-2-bromobenzaldehyde

A mixture of 2-bromo-4-fluoro-benzaldehyde (32.0 g, 157 mmol), Na$_2$CO$_3$ (85.5 g, 788 mmol), and 2-benzyloxy ethanol (24.0 g, 158 mmol) in anhydrous DMSO (300 mL) were heated under N$_2$ at 130° C. (bath temp) for 18 h. The reaction mixture cooled to rt, diluted with H$_2$O (100 mL), and extracted with EtOAc The organic layer was washed with H$_2$O then brine, dried (MgSO$_4$), and concentrated in vacuo The residue was purified by flash chromatography (hexane to 10% EtOAc in hexane) to give the title compound as a viscous liquid: yield 11.8 g (22%).

$^1$H NMR (400 MHz, CDCl$_3$) δ (ppm): 10.22 (s, 1H), 7.88 (d, J=8.6 Hz, 1H), 7.45-7.29 (m, 5H), 7.17 (d, J=2.3 Hz, 1H), 6.96 (dd, J=8.8, 2.2 Hz, 1H), 4.63 (s, 2H), 4.32-4.14 (m, 2H), 3.92-3.78 (m, 2H); MS (ESI): m/z=334 (M+1, positive).

4-(2-Benzyloxy-ethoxy)-2-(4,4,5,5-tetramethyl-[1,3,2]dioxaborolan-2-yl)-benzaldehyde

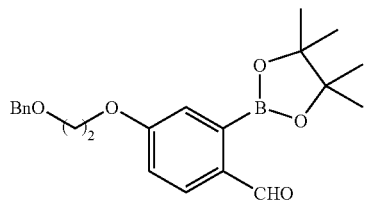

General procedure 5: 4-(2-benzyloxy ethoxy)-2-bromobenzaldehyde (1.37 g, 4.10 mmol) B$_2$pin$_2$ (1.56 g, 6.15 mmol), KOAc (1.20 g, 12.3 mmol), PdCl$_2$(dppf).CH$_2$Cl$_2$ (240 mg, 8 mol %) and anhydrous 1,4-dioxane (13 mL). Purification: flash chromatography (hexane to 20% EtOAc in hexane). The title compound was isolated as a white solid: yield 900 mg (70%).

$^1$H NMR (400 MHz, CDCl$_3$) δ (ppm): 10.37 (s, 1H), 7.93 (d, J=8.6 Hz, 1H), 7.47-7.28 (m, 6H), 7.05 (dd, J=8.6, 2.3 Hz, 1H), 4.64 (s, 2H), 4.25 (t, J=4.7 Hz, 2H), 3.85 (t, J=4.7 Hz, 2H), 1.39 (s, 12H); MS (ESI): m/z=383 (M+1, positive).

6-(2-Benzyloxy-ethoxy)-3-nitromethyl-3H-Benzo[c][1,2]oxaborol-1-ol

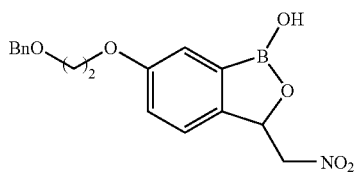

General procedure 8: 4-(2-benzyloxy-ethoxy)-2-(4,4,5,5-tetramethyl-[1,3,2]dioxaborolan-2-yl)-benzaldehyde (900 mg, 2.35 mmol), MeNO$_2$ (172 mg, 2.82 mmol), NaOH (113 mg, 2.82 mmol), and H$_2$O (3 mL). Purification: flash chromatography (10% EtOAc/hexane to 40% EtOAc). The title compound was isolated as a brown liquid: yield 300 mg (38%).

$^1$H NMR (400 MHz, DMSO-d$_6$) δ (ppm): 9.45 (bs, 1H), 7.43 (d, J=8.6 Hz, 1H), 7.38-7.18 (m, 6H), 7.10 (dd, J=8.6, 2.3 Hz, 1H), 5.70 (dd, J=9.2, 2.5 Hz, 1H), 5.29 (dd, J=13.5, 2.5 Hz, 1H), 4.61-4.38 (m, 3H), 4.23-4.06 (m, 2H), 3.88-3.68 (m, 3H) MS (ESI): m/z=342 (M−1, negative).

3-Aminomethyl-6-(2-benzyloxy-ethoxy)-3H-Benzo[c][1,2]oxaborol-1-ol

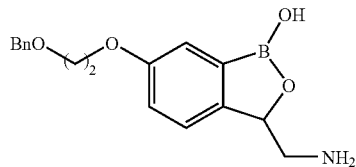

General procedure 12: 6-(2-benzyloxy-ethoxy)-3-nitromethyl-3H-benzo[c][1,2]oxaborol-1-ol (500 mg, 16.0 mmol), Raney Ni (1.1 g, 2 equiv w/w) and 2 M NH$_3$ EtOH (12 mL): yield 438 mg (96%).

$^1$H NMR (400 MHz, DMSO-d$_6$) δ (ppm): 8.28 (bs, 3H), 7.44-7.33 (m, 2H), 7.33-7.17 (m, 5H), 7.07 (d, J=2.3 Hz, 1H), 5.27 (d, J=7.4 Hz, 1H), 4.51 (s, 2H), 4.18-4.02 (m, 2H), 3.81-3.63 (m, 2H), 2.64-2.60 (m, 1H); MS (ESI): m/z=314 (M+1, positive).

3-Aminomethyl-6-(2-hydroxy-ethoxy)-3H-benzo[c][1,2]oxaborol-1-ol, acetate salt (A30)

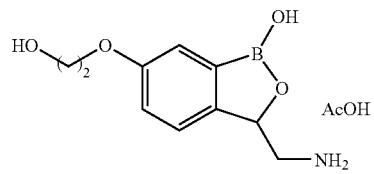

A mixture of 3-aminomethyl-6-(2-benzyloxy-ethoxy)-3H-benzo[c][1,2]oxaborol-1-ol (334 mg, 1.06 mmol), 10% Pd/C (330 mg, 1 equiv w/w), and AcOH (15 mL) was shaken under an atmosphere of H$_2$ (50 psi) at rt for 3 h. The mixture was filtered through a pad of Celite and washed with EtOH. The filtrate was concentrated in vacuo and the residue was triturated with Et$_2$O. The solid was purified by preparative HPLC (AcOH) to give A30 as a white solid: yield 50 mg (17%).

$^1$H NMR (400 MHz, DMSO-d$_6$) δ (ppm): 7.30 (bs, 1H), 7.22 (bs, 1H), 7.02 (bs, 1H), 4.98 (bs, 1H), 3.98 (bs, 2H), 3.71 (bs, 2H), 2.98-2.96 (m, 1H), 2.65-2.63 (m, 1H), 1.87 (s, 3H); MS (ESI): m/z=224 (M+1, positive); HPLC purity: 98.29% (MaxPlot 200-400 nm), 96.81% (220 nm).

3-Aminomethyl-6-(2-hydroxy-propoxy)-3H-Benzo[c][1,2]oxaborol-1-ol acetate salt (A31)

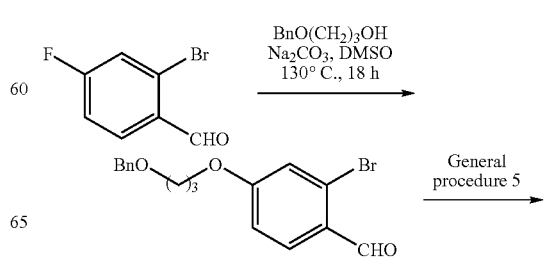

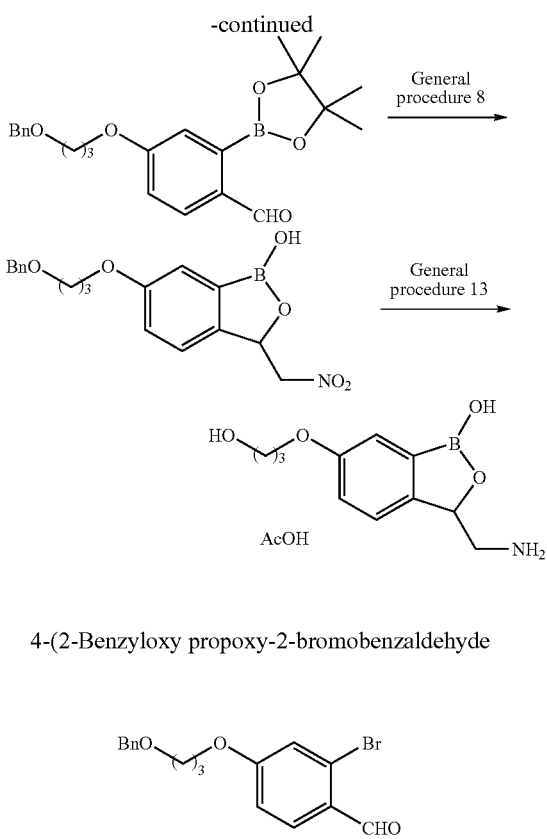

4-(2-Benzyloxy propoxy-2-bromobenzaldehyde

A mixture of 2-bromo-4-fluoro-benzaldehyde (30.0 g, 148 mmol), Na2CO3 (78.31 g, 738.8 mmol) and 2-benzyloxy propanol (24.56 g, 147.8 mmol) in anhydrous DMSO (300 mL) was heated with stirring at 130° C. (bath temp) for 72 h under $N_2$. The reaction mixture was cooled to rt and diluted with $H_2O$ and extracted with EtOAc. The organic layer was washed with $H_2O$ then brine, dried (MgSO$_4$), and concentrated in vacuo. The residue was purified by flash chromatography (hexane to 30% EtOAc in hexane) to give the title compound: yield 3.84 g (7%).

$^1$H NMR (400 MHz, CDCl$_3$) δ (ppm): 10.22 (s, 1H), 7.88 (d, J=8.6 Hz, 1H), 7.42-7.20 (m, 5H), 7.12 (d, J=2.3 Hz, 1H), 6.92 (dd, J=8.8, 2.2 Hz, 1H), 4.52 (s, 2H), 4.16 (t, J=6.2 Hz, 2H), 3.65 (t, J=6.1 Hz, 2H), 2.10 (q, J=6.2 Hz, 2H).

4-(2-Benzyloxy-propoxy)-2-(4,4,5,5-tetramethyl-[/, 3, 2]dioxaborolan-2-yl)-benzaldehyde

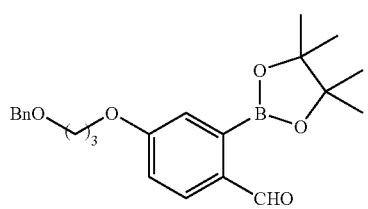

General procedure 5: 4-(2-benzyloxy propoxy-2-bromobenzaldehyde (4.84 g, 13.9 mmol), B$_2$pin$_2$ (5.27 g, 20.8 mmol), KOAc (4.08 g, 41.6 mmol), PdCl$_2$(dppf).CH$_2$Cl$_2$ (811 mg, 8 mol %), and 1,4-dioxane (50 mL). Purification: Biotage (gradient from 2% EtOAc/hexane to 20% EtOAc/hexane): yield 4.0 g (70%).

$^1$H NMR (400 MHz, CDCl$_3$) δ (ppm): 10.36 (s, 1H), 7.93 (d, J=8.6 Hz, 1H), 7.43-7.14 (m, 6H), 7.01 (dd, J=8.6, 2.7 Hz, 1H), 4.53 (s, 2H), 4.18 (t, J=6.2 Hz, 2H), 3.66 (t, J=6.1 Hz, 2H), 2.11 (q, J=6.1 Hz, 2H), 1.40 (s, 12H).

6-(2-Benzyloxy-propoxy)-3-nitromethyl-3H-benzo[c][1,2]oxaborol-1-ol

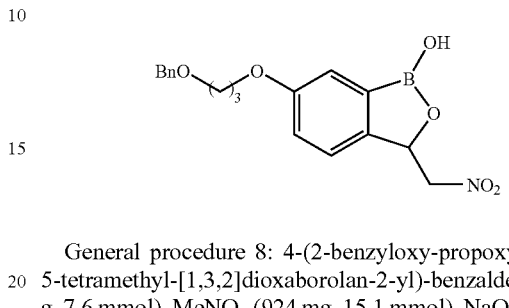

General procedure 8: 4-(2-benzyloxy-propoxy)-2-(4,4,5,5-tetramethyl-[1,3,2]dioxaborolan-2-yl)-benzaldehyde (3.0 g, 7.6 mmol), MeNO$_2$ (924 mg, 15.1 mmol), NaOH (605 mg, 15.1 mmol), and H$_2$O (10 mL). Purification: flash chromatography (10% EtOAc/hexane to 40% EtOAc): yield 820 mg (30%).

$^1$H NMR (400 MHz, DMSO-d$_6$) δ (ppm): 9.46 (bs, 1H), 7.45 (d, J=8.2 Hz, 1H), 7.41-7.18 (m, 6H), 7.09 (dd, J=8.6, 2.3 Hz, 1H), 5.71 (dd, J=9.2, 2.5 Hz, 1H), 5.31 (dd, J=13.3, 2.7 Hz, 1H), 4.58-4.40 (m, 3H), 4.08 (t, J=6.2 Hz, 2H), 3.60 (t, J=6.2 Hz, 2H), 2.08-1.94 (m, 2H).

3-Aminomethyl-6-(2-hydroxy-propoxy)-3H-benzo[c][1,2]oxaborol-1-ol acetate salt (A31)

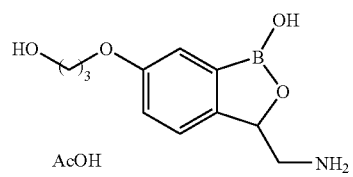

General procedure 13: 6-(2-benzyloxy-propoxy)-3-nitromethyl-3H-benzo[c][1,2]oxaborol-1-ol (820 mg, 2.29 mmol), 20% Pd(OH)$_2$ (850 mg, 1 equiv w/w), and AcOH (40 mL). Purification: preparative HPLC: yield 120 mg (22%).

$^1$H NMR (400 MHz, DMSO-d$_6$) δ (ppm): 7.32 (d, J=8.2 Hz, 1H), 7.22 (s, 1H), 7.02 (d, J=7.8 Hz, 1H), 4.98 (bs, 1H), 4.04 (t, J=6.2 Hz, 2H), 3.56 (t, J=6.2 Hz, 2H), 3.03-2.85 (m, 1H), 2.61 (dd, J=12.9, 7.0 Hz, 1H), 1.89 (s, 3H), 1.97-1.67 (m, 2H); MS (ESI): m/z=238 (M+1, positive); HPLC purity: 97.44% (MaxPlot 200-400 nm), 97.77% (220 nm).

6-Amino-3-aminomethyl-3H-benzo[c][1,2]oxaborol-1-ol hydrochloride (A32)

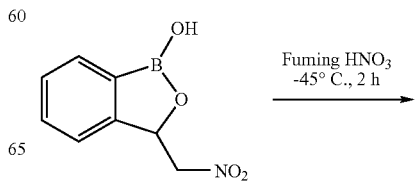

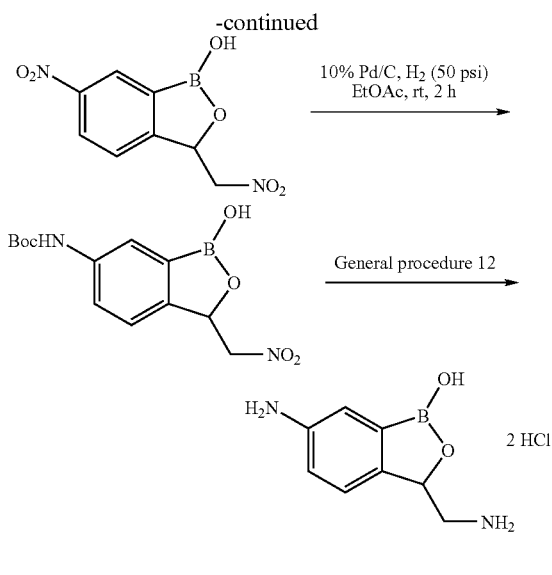

6-Nitro-3-nitromethyl-3H-benzo[c][1,2]oxaborol-1-ol

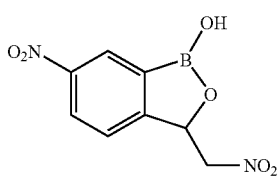 [SMILES: O=[N+]([O-])CC1OB(O)c2cc([N+](=O)[O-])ccc21]

3-Nitromethyl-3H-benzo[c][1,2]oxaborol-1-ol (20.0 g, 104 mmol) was added in small portions with stirring over 2 h to fuming HNO₃ (200 mL) at −45° C. (bath temp). The cold reaction mixture was then poured into crushed ice and allowed to warm to rt. The aqueous phase was extracted with EtOAc. The EtOAc phase was concentrated in vacuo and the residue was poured into crushed ice. The precipitate was filtered and washed with H₂O. The solid was dissolved in EtOAc, dried (Na₂SO₄), and concentrated in vacuo to yield the title compound: yield (14.3 g, 58%).

¹H NMR (400 MHz, DMSO-d₆): δ 9.87 (bs, 1H), 8.57 (s, 1H), 8.40 (dd, J=8.4, 2.4 Hz, 1H), 7.85 (d, J=8.0 Hz, 1H), 5.92 (dd, J=8.0, 2.8 Hz, 1H), 5.42 (dd, J=13.6, 2.8 Hz, 1H), 4.82 (dd, J=13.6, 8.0 Hz, 1H); MS (ESI) m/z=237 (M−1, negative).

(1-Hydroxy-3-nitromethyl-1,3-dihydro-benzo[c][1,2]
oxaborol-6-yl)-carbamic acid tert-butyl ester

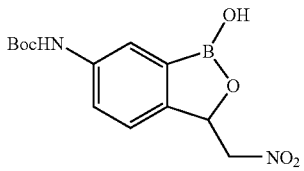 [SMILES: CC(C)(C)OC(=O)Nc1ccc2c(c1)B(O)OC2C[N+](=O)[O-]]

A mixture of 6-nitro-3-nitromethyl-3H-benzo[c][1,2]oxaborol-1-ol (2.38 g, 10 mmol), 10% Pd/C (250 mg), and (Boc)₂O (10.9 g, 50 mmol) in EtOAc (50 mL) was shaken under an atmosphere of H₂ (50 psi) at rt for 1 h. The reaction mixture was filtered through Celite and the filtrate was concentrated in vacuo. The crude product was purified by Biotage flash chromatography (gradient of increasing MeOH in CH₂Cl₂): yield 2.0 g (65%).

¹H NMR (400 MHz, DMSO-d₆): δ 9.47 (s, 1H), 9.43 (s, 1H), 7.88 (s, 1H), 7.49 (dd, J=8.0, 2.0 Hz, 1H), 7.37 (d, J=8.4 Hz, 1H), 5.69 (dd, J=8.8, 2.8 Hz, 1H), 5.26 (dd, J=14.0, 3.2 Hz, 1H), 4.49 (dd, J=13.6, 9.2 Hz, 1H), 1.44 (s, 9H); MS (ESI) m/z=307 (M−1, negative).

6-Amino-3-aminomethyl-3H-benzo[c][1,2]oxaborol-
1-ol hydrochloride (A32)

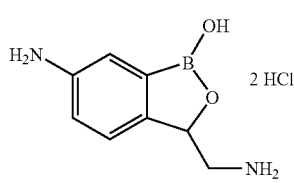 [SMILES: NCC1OB(O)c2cc(N)ccc21 ; "2 HCl"]

General procedure 12: (1-hydroxy-3-nitromethyl-1,3-dihydro-benzo[c][1,2]oxaborol-6-yl)-carbamic acid tert-butyl ester (1.25 g, 4.06 mmol), Raney Ni slurry in H₂O (1 teaspoon), 2 M NH₃ in EtOH (14.21 mL, 28.42 mmol), and EtOH (20 mL). The residue was dissolved in dioxane (30 mL) and MeOH (few drops) mixture and 4 N HCl in dioxane (10 mL, 40 mmol) was added and stirred for 16 h at rt. The precipitate was filtered and washed with CH₂Cl₂, dried to yield 900 mg crude compound. The crude was dissolved in hot H₂O and MeCN was added. During addition solution was separated into two layers. MeOH was added to the solution to make clear solution and excess CH₃CN was added. The precipitate was allowed to settle down and the liquid was decanted and fresh MeCN was added and repeated the same procedure to give A32 as a pale yellow solid: yield 400 mg (39%).

mp 190-200° C. (dec.); ¹H NMR (400 MHz, DMSO-d₆): δ (ppm): 8.29 (bs, 3H), 7.79 (d, J=2.0 Hz, 1H), 7.62 (d, J=8.4 Hz, 1H), 7.49 (dd, J=8.0, 2.0 Hz, 1H), 5.40 (dd, J=8.8, 2.8 Hz, 1H), 3.51-3.49 (m, 1H), 2.84-2.77 (m, 1H); MS (ESI) m/z=163 (M+1, positive); HPLC 93.40% (MaxPlot 200-400 nm), 96% (220 nm).

N-(3-Aminomethyl-1-hydroxy-1,3-dihydro-benzo[c]
[1,2]oxaborol-6-yl)-benzenesulfonamide, hydrochloride (A33)

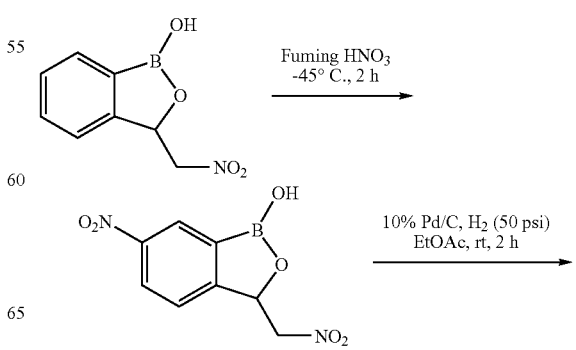

189

-continued

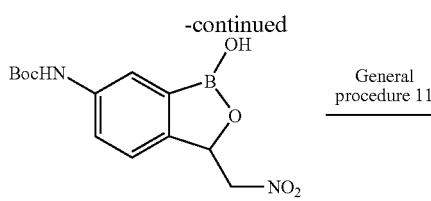
General procedure 11

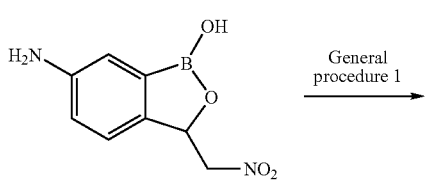
General procedure 1

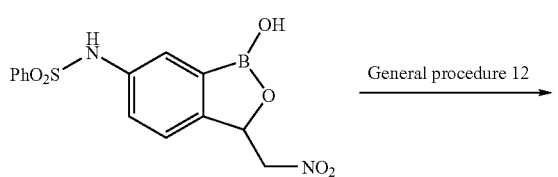
General procedure 12

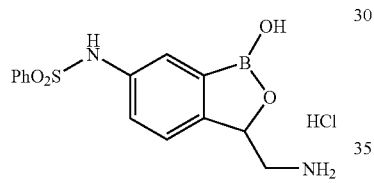

6-Nitro-3-nitromethyl-3H-benzo[c][1,2]oxaborol-1-ol

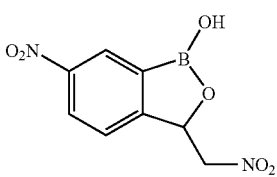 [SMILES: O=[N+]([O-])CC1OB(O)c2cc([N+](=O)[O-])ccc21]

3-Nitromethyl-3H-benzo[c][1,2]oxaborol-1-ol (20.0 g, 104 mmol) was added in small portions with stirring over 2 h to fuming HNO₃ (200 mL) at −45° C. (bath temp). The cold reaction mixture was then poured into crushed ice and allowed to warm to rt. The aqueous phase was extracted with EtOAc. The EtOAc phase was concentrated in vacuo and the residue was poured into crushed ice. The precipitate was filtered and washed with H₂O. The solid was dissolved in EtOAc, dried (Na₂SO₄), and concentrated in vacuo to yield the title compound: yield (14.3 g, 58%).

$^1$H NMR (400 MHz, DMSO-d$_6$): δ 9.87 (bs, 1H), 8.57 (s, 1H), 8.40 (dd, J=8.4, 2.4 Hz, 1H), 7.85 (d, J=8.0 Hz, 1H), 5.92 (dd, J=8.0, 2.8 Hz, 1H), 5.42 (dd, J=13.6, 2.8 Hz, 1H), 4.82 (dd, J=13.6, 8.0 Hz, 1H); MS (ESI) m/z=237 (M−1, negative).

190

(1-Hydroxy-3-nitromethyl-1,3-dihydro-benzo[c][1,2]oxaborol-6-yl)-carbamic acid tert-butyl ester

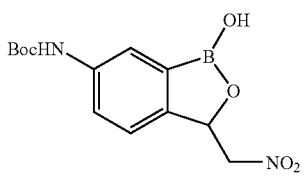 [SMILES: CC(C)(C)OC(=O)Nc1ccc2c(c1)B(O)OC2C[N+](=O)[O-]]

A mixture of 6-nitro-3-nitromethyl-3H-benzo[c][1,2]oxaborol-1-ol (2.38 g, 10 mmol), 10% Pd/C (250 mg), and (Boc)₂O (10.9 g, 50 mmol) in EtOAc (50 mL) was shaken under an atmosphere of H₂ (50 psi) at rt for 1 h. The reaction mixture was filtered through Celite and the filtrate was concentrated in vacuo. The crude product was purified by Biotage flash chromatography (gradient of increasing MeOH in CH₂Cl₂): yield 2.0 g (65%).

$^1$H NMR (400 MHz, DMSO-d$_6$): δ 9.47 (s, 1H), 9.43 (s, 1H), 7.88 (s, 1H), 7.49 (dd, J=8.0, 2.0 Hz, 1H), 7.37 (d, J=8.4 Hz, 1H), 5.69 (dd, J=8.8, 2.8 Hz, 1H), 5.26 (dd, J=14.0, 3.2 Hz, 1H), 4.49 (dd, J=13.6, 9.2 Hz, 1H), 1.44 (s, 9H); MS (ESI) m/z=307 (M−1, negative).

6-Amino-3-nitromethyl-3H-benzo[c][1,2]oxaborol-1-ol

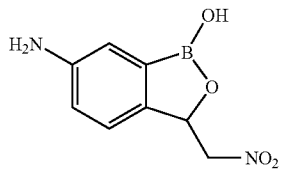

General procedure 11: (1-hydroxy-3-nitromethyl-1,3-dihydro-benzo[c][1,2]oxaborol-6-yl)-carbamic acid tert-butyl ester (2.0 g, 6.5 mmol) and 4 N HCl in dioxane (16 mL). The reaction mixture was concentrated in vacuo and to the residue was neutralized (pH 7) with sat. NaHCO₃. The reaction mixture was extracted with EtOAc, and the combined organic phase was dried (Na₂SO₄) and concentrated to give the title compound: yield 1.06 g (78%).

$^1$H NMR (400 MHz, DMSO-d$_6$): δ 9.25 (s, 1H), 7.13 (d, J=8.0 Hz, 1H), 6.85 (d, J=1.6 Hz, 1H), 6.68 (dd, J=8.0, 1.6 Hz, 1H), 5.58 (dd, J=9.2, 2.4 Hz, 1H), 5.21-5.16 (m, 3H), 4.36 (dd, J=13.2, 9.6 Hz, 1H); MS (ESI) m/z=309 (M+1, positive).

N-(1-Hydroxy-3-nitromethyl-1,3-dihydro-benzo[c][1,2]oxaborol-6-yl)-benzenesulfonamide

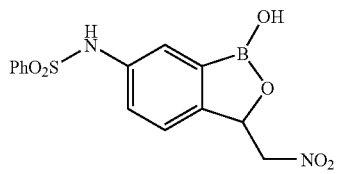

General procedure 1: 6-amino-3-nitromethyl-3H-benzo[c][1,2]oxaborol-1-ol (1.06 g, 5.1 mmol), phenylsulfonyl chloride (0.64 mL, 5.1 mmol), pyridine (1.23 mL, 15.3 mmol), and MeCN (50 mL): yield 1.6 g (90%).

$^1$H NMR (400 MHz, DMSO-$d_6$): δ 10.40 (s, 1H), 9.52 (s, 1H), 7.75 (d, J=8.0 Hz, 2H), 7.61-7.50 (m, 3H), 7.47 (d, J=2.0 Hz, 1H), 7.37 (d, J=8.0 Hz, 1H), 7.19 (dd, J=8.4, 2.4 Hz, 1H), 5.66 (dd, J=8.8, 2.8 Hz, 1H), 5.23 (dd, J=13.2, 2.8 Hz, 1H), 4.48 (dd, J=13.2, 8.8 Hz, 1H); MS (ESI) m/z=347 (M−1, negative).

N-(3-Aminomethyl-1-hydroxy-1,3-dihydro-benzo[c][1,2]oxaborol-6-yl)-benzenesulfonamide, hydrochloride (A33)

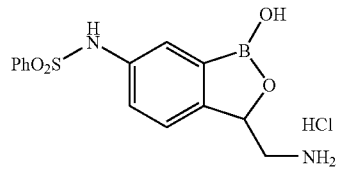

General procedure 12: N-(1-hydroxy-3-nitromethyl-1,3-dihydro-benzo[c][1,2]oxaborol-6-yl)-benzenesulfonamide (1.6 g, 4.6 mmol) Raney Ni slurry in H$_2$O (1.5 teaspoon), 2 M NH$_3$/EtOH (16.1 mL, 32.2 mmol), and EtOH (50 mL). Purification: the residue was dissolved in a mixture of dioxane (30 mL) and MeOH (few drops), and 4 N HCl in dioxane (5.6 mL, 22.4 mmol) was added and stirred for 16 h at rt. The mixture was concentrated and the residue dissolved in MeOH. The solution was added dropwise to Et$_2$O and the precipitate isolated by decanting. The solid was then partially dissolved in H$_2$O and the mixture was filtered. The filtrate was lyophilized to give A33 as a pale yellow solid: yield 150 mg (9%).

$^1$H NMR (400 MHz, DMSO-$d_6$): δ 10.48 (s, 1H), 9.58 (s, 1H), 8.17 (bs, 3H), 7.79 (d, J=8.4 Hz, 2H), 7.63-7.53 (m, 4H), 7.38 (d, J=8.0 Hz, 1H), 7.21 (dd, J=8.0, 2.0 Hz, 1H), 5.25 (dd, J=8.8, 1.6 Hz, 1H), 3.42-3.35 (m, 1H), 2.80-2.70 (m, 1H); MS (ESI) m/z 319 (M+1); HPLC purity: 90% (220 nm).

Pyridine-2-sulfonic acid (3-aminomethyl-1-hydroxy-1,3-dihydro-benzo[c][1,2]oxaborol-6-yl)-amide hydrochloride (A34)

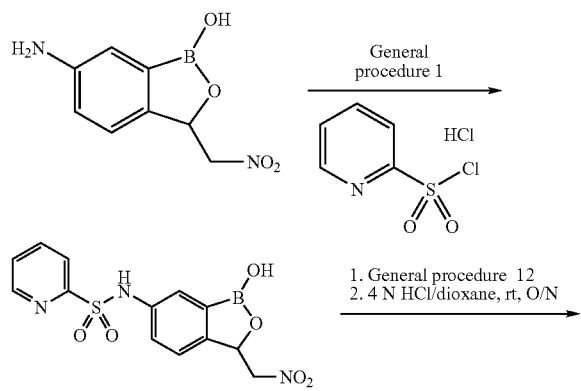

Pyridine-2-sulfonic acid (1-hydroxy-3-nitromethyl-1,3-dihydro-benzo[c][1,2]oxaborol-6-yl)-amide

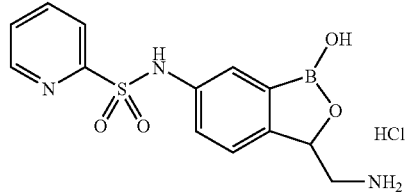

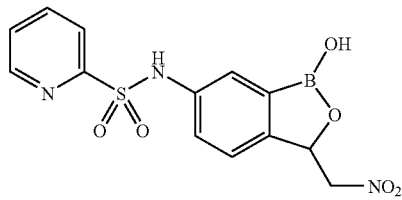 [SMILES: O=[N+]([O-])CC1OB(O)c2cc(NS(=O)(=O)c3ccccn3)ccc21]

General procedure 1: a solution of 2-pyridinesulphonyl chloride hydrochloride (905 mg, 4.23 mmol) and pyridine (0.34 mL, 4.23 mmol) in MeCN (3 mL) was added to 6-amino-3-nitromethyl-3H-benzo[c][1,2]oxaborol-1-ol (0.88 g, 4.23 mmol), pyridine (1.03 mL, 12.7 mmol), and MeCN (50 mL): yield 380 mg (26%).

$^1$H NMR (400 MHz, DMSO-$d_6$): δ 10.67 (s, 1H), 9.53 (s, 1H), 8.71 (d, J=4.8 Hz, 1H), 8.05 (td, J=7.6, 1.6 Hz, 1H), 7.97 (d, J=8.0 Hz, 1H), 7.66-7.63 (m, 1H), 7.51 (d, J=1.6 Hz, 1H), 7.39 (d, J=8.0 Hz, 1H), 7.26 (dd, J=8.0, 2.0 Hz, 1H), 5.68 (dd, J=9.2, 2.4 Hz, 1H), 5.25 (dd, J=13.6, 2.8 Hz, 1H), 4.51 (dd, J=13.6, 9.6 Hz, 1H); MS (ESI) m/z=350 (M−1, negative).

Pyridine-2-sulfonic acid (3-aminomethyl-1-hydroxy-1,3-dihydro-benzo[c][1,2]oxaborol-6-yl)-amide hydrochloride (A34)

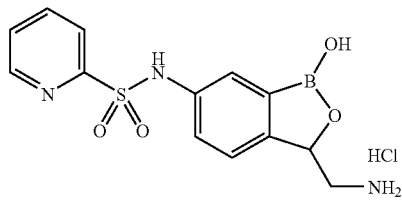 [SMILES: NCC1OB(O)c2cc(NS(=O)(=O)c3ccccn3)ccc21 ; Cl]

General procedure 12: pyridine-2-sulfonic acid (1-hydroxy-3-nitromethyl-1,3-dihydro-benzo[c][1,2]oxaborol-6-yl)-amide (349 mg, 1.0 mmol), Raney Ni slurry in H$_2$O (0.5 teaspoon), 2 M NH$_3$ in EtOH (3.5 mL, 7.0 mmol), and EtOH (10 mL). Purification: the residue was dissolved in a mixture of dioxane (30 mL) and MeOH (few drops) and 4 N HCl in dioxane (5.6 mL, 22.4 mmol) was added and stirred for 16 h at rt The mixture was concentrated and the crude residue dissolved in MeOH. This solution was added dropwise to Et$_2$O and the resulting precipitate was isolated by decanting. The solid was partially dissolved in H$_2$O and the mixture filtered. The filtrate was lyophilized to give A34 as a pale yellow solid: yield 100 mg (31%).

$^1$H NMR (400 MHz, DMSO-d$_6$): δ 10.68 (s, 1H), 9.58 (bs, 1H), 8.71 (d, J=4.4 Hz, 1H), 8.10-8.04 (m, 4H), 7.98 (d, J=7.6 Hz, 1H), 7.67-7.63 (m, 1H), 7.59 (d, J=2.0 Hz, 1H), 7.37 (d, J=8.0 Hz, 1H), 7.26 (dd, J=8.4, 2.4 Hz, 1H), 5.24 (dd, J=9.2, 2.4 Hz, 1H), 3.50-3.25 (m, 1H), 2.78-2.68 (m, 1H); MS (ESI) m/z=320 (M+1, positive); HPLC purity: 88.76% (220 nm).

N-[3-(3-Aminomethyl-1-hydroxy-1,3-dihydro-benzo[c][1,2]oxaborol-7-yloxy)-propyl]-acetamide hydrochloride (A35)

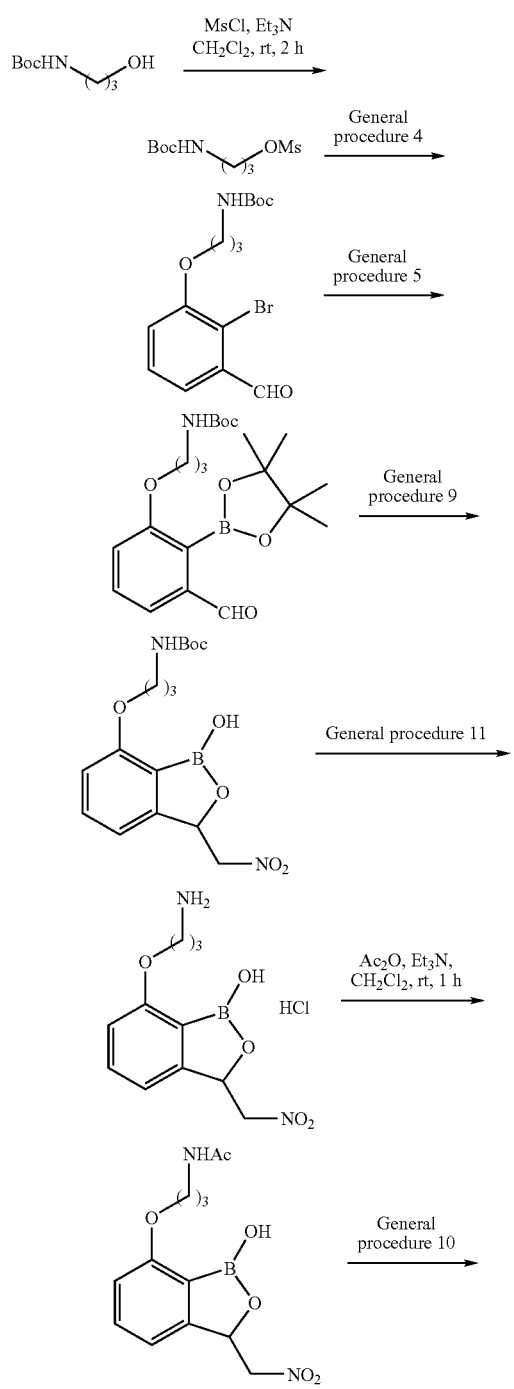

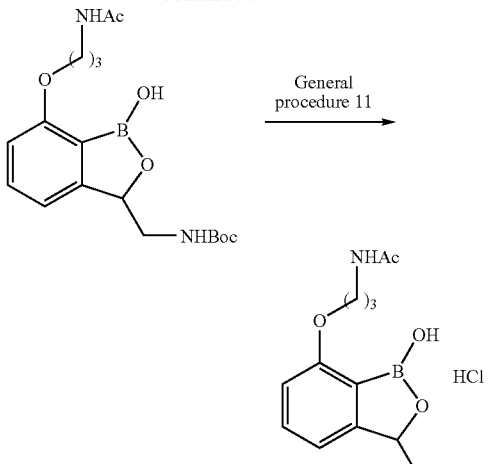

Methanesulfonic acid 3-tert-butoxycarbonylamino-propyl ester

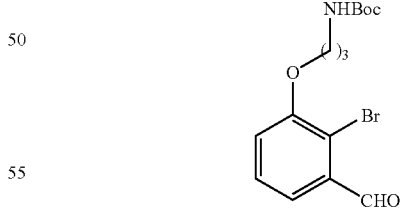

MsCl (6.5 mL, 84 mmol) was added slowly to a solution of Et$_3$N (16.0 mL, 114 mmol) and (3-hydroxy-propyl)-carbamic acid tert-butyl ester (13.4 g, 76.5 mmol) in CH$_2$Cl$_2$ (200 mL) at 0° C. (bath temp). The reaction mixture was stirred at rt for 2 h and then quenched with H$_2$O (100 mL). The aqueous layer was extracted with CH$_2$Cl$_2$ and the organic fractions were then dried (MgSO$_4$) and concentrated in vacuo. The title compound was isolated as a colorless oil: yield 18.9 g (98%).

$^1$H NMR (400 MHz, CDCl$_3$) δ (ppm): 4.73 (bs, 1H), 4.30 (t, J=5.9 Hz, 2H), 3.31-3.24 (m, 2H), 3.04 (s, 3H), 1.94 (t, J=6.1 Hz, 2H), 1.44 (s, 9H).

[3-(2-Bromo-3-formyl-phenoxy)-propyl]-carbamic acid tert-butyl ester

General procedure 4: 2-bromo-3-hydroxy-benzaldehyde (15.0 g, 74.6 mmol), methanesulfonic acid 3-tert-butoxycarbonylamino-propyl ester (18.9 g, 74.6 mmol), Cs$_2$CO$_3$ (36.5 g, 112 mmol), and DMF (300 mL). The title compound was isolated as a viscous liquid: yield 22.0 g (82%).

$^1$H NMR (400 MHz, CDCl$_3$) δ (ppm): 10.43 (s, 1H), 7.53 (dd, J=7.8, 1.6 Hz, 1H), 7.37 (t, J=7.8 Hz, 1H), 7.12 (dd, J=8.2, 1.6 Hz, 1H), 5.16 (bs, 1H), 4.15 (t, J=5.9 Hz, 2H), 3.42 (q, J=6.1 Hz, 2H), 2.13-2.05 (m, 2H), 1.44 (s, 9H).

{3-[3-Formyl-2-(4,4,5,5-tetramethyl-[1,3,2]dioxaborolan-2-yl)-phenoxy]-propyl}-carbamic acid benzyl ester

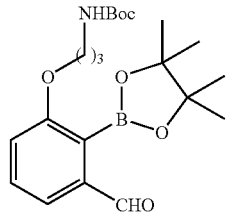

General procedure 5: [3-(2-bromo-3-formyl-phenoxy)-propyl]-carbamic acid tert-butyl ester (22.0 g, 61.4 mmol), B₂pin₂ (31.2 g, 123 mmol), KOAc (24.1 g, 246 mmol), PdCl₂(dppf).CH₂Cl₂ (6.73 g, 9.21 mmol), and dioxane (300 mL). Purification: flash chromatography (20% EtOAc in hexane). The title compound was isolated as a white foam: yield 11.0 g (44%).

¹H NMR (400 MHz, CDCl₃) δ (ppm): 9.95 (s, 1H), 7.48 (t, J=7.8 Hz, 1H), 7.43-7.39 (m, 1H), 7.09 (d, J=8.2 Hz, 1H), 4.76 (bs, 1H), 4.05 (t, J=6.3 Hz, 2H), 3.32 (q, J=6.0 Hz, 2H), 2.03-1.95 (m, 2H), 1.45 (s, 12H), 1.43 (s, 9H).

[3-(1-Hydroxy-3-nitromethyl-1,3-dihydro-benzo[c][1,2]oxaborol-7-yloxy)-propyl]-carbamic acid tert-butyl ester

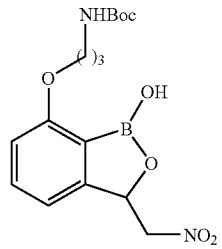

General procedure 9: {3-[3-formyl-2-(4,4,5,5-tetramethyl-[1,3,2]dioxaborolan-2-yl)-phenoxy]-propyl}-carbamic acid benzyl ester (11.0 g, 27.1 mmol), MeNO₂ (2.9 mL, 54 mmol), CTAB (494 mg, 1.35 mmol), 25 mM NaOH (100 mL), and THF (5 mL). Mixture acidified using 1 M NaHSO₃HCl (100 mL): yield 6.0 g (60%).

¹H NMR (400 MHz, DMSO-d₆) δ (ppm): 9.05 (s, 1H), 7.46 (t, J=7.8 Hz, 1H), 7.07 (d, J=7.4 Hz, 1H), 6.94-6.85 (m, 2H), 5.71 (dd, J=9.0, 2.7 Hz, 1H), 5.31 (dd, J=13.3, 2.7 Hz, 1H), 4.55 (dd, J=13.3, 9.4 Hz, 1H), 4.05 (t, J=6.3 Hz, 2H), 3.09 (q, J=6.6 Hz, 2H), 1.83 (quin, J=6.6 Hz, 2H), 1.37 (s, 9H).

7-(3-Amino-propoxy)-3-nitromethyl-3H-benzo[c][1,2]oxaborol-1-ol hydrochloride

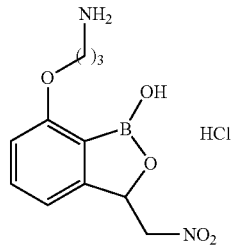

General procedure 11: [3-(1-hydroxy-3-nitromethyl-1,3-dihydro-benzo[c][1,2]oxaborol-7-yloxy)-propyl]-carbamic acid tert-butyl ester (3.0 g, 8.2 mmol) and 4 M HCl in dioxane (20 mL). Purification: trituration with Et₂O. The title compound was isolated as a white solid 2.32 g (93%).

¹H NMR (400 MHz, DMSO-d₆) δ (ppm): 9.24 (bs, 1H), 7.91 (bs, 3H), 7.47 (t, J=7.8 Hz, 1H), 7.10 (d, J=7.4 Hz, 1H), 6.90 (d, J=8.2 Hz, 1H), 5.72 (dd, J=9.2, 2.5 Hz, 1H), 5.31 (dd, J=13.5, 2.9 Hz, 1H), 4.54 (dd, J=13.5, 9.2 Hz, 1H), 4.13 (t, J=5.9 Hz, 2H), 3.06-2.94 (m, 2H), 2.02 (quin, J=5.9 Hz, 2H).

N-[3-(1-Hydroxy-3-nitromethyl-1,3-dihydro-benzo[c][1,2]oxaborol-7-yloxy)-propyl]-acetamide

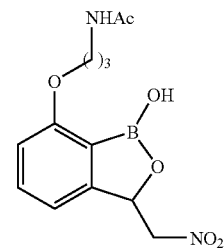

Ac₂O (1.16 mL, 12.3 mmol) was added slowly to a solution of Et₃N (2.33 mL, 16.5 mmol) and 7-(3-amino-propoxy)-3-nitromethyl-3H-benzo[c][1,2]oxaborol-1-ol hydrochloride (1.69 g, 76.5 mmol) in CH₂Cl₂ (50 mL) at 0° C. (bath temp). The reaction mixture was stirred at rt for 1 h and then quenched with H₂O (50 mL). The mixture was extracted with CH₂Cl₂ and the organic fraction was dried (MgSO₄) and concentrated in vacuo to give the title compound as a viscous liquid: yield 1.29 g (75%).

¹H NMR (400 MHz, DMSO-d₆) δ (ppm): 9.13 (s, 1H), 7.89-7.78 (m, 1H), 7.45 (t, J=7.8 Hz, 1H), 7.06 (d, J=7.4 Hz, 1H), 6.88 (d, J=8.2 Hz, 1H), 5.70 (dd, J=9.6, 2.5 Hz, 1H), 5.29 (dd, J=13.3, 2.7 Hz, 1H), 4.54 (dd, J=13.7, 9.4 Hz, 1H), 4.04 (t, J=6.6 Hz, 2H), 3.23-3.15 (m, 2H), 2.20 (s, 3H), 1.82 (t, J=6.5 Hz, 2H); MS (ESI): m/z=307 (M−1, negative).

197

7-(3-Acetylamino-propoxy)-1-hydroxy-1,3-dihydro-benzo[c][1,2]oxaborol-3-ylmethyl]-carbamic acid tert-butyl ester

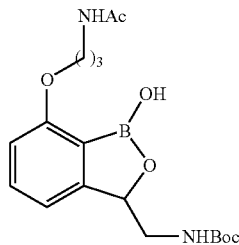

General procedure 10: N-[3-(1-hydroxy-3-nitromethyl-1,3-dihydro-benzo[c][1,2]oxaborol-7-yloxy)-propyl]-acetamide (1.29 g, 4.18 mmol), NiCl$_2$.6H$_2$O (995 mg, 4.18 mmol), NaBH$_4$ (953 mg, 25.2 mmol), Boc$_2$O (1.82 g, 8.36 mmol), and MeOH (100 mL). Purification: flash chromatography (5% MeOH in CH$_2$Cl$_2$). The title compound was isolated as a white foam: yield 600 mg (38%).

$^1$H NMR (400 MHz, DMSO-d$_6$) δ (ppm): 8.81 (s, 1H), 7.86 (t, J=5.5 Hz, 1H), 7.40 (t, J=7.8 Hz, 1H), 7.01-6.90 (m, 2H), 6.84 (d, J=8.2 Hz, 1H), 5.11-5.04 (m, 1H), 4.05 (t, J=6.1 Hz, 2H), 3.22 (q, J=6.4 Hz, 2H), 3.10-2.96 (m, 1H), 1.88-1.81 (m, 2H), 1.80 (s, 3H), 1.37 (s, 9H); MS (ESI): m/z=377 (M−1, negative).

N-[3-(3-Aminomethyl-1-hydroxy-1,3-dihydro-benzo[c][1,2]oxaborol-7-yloxy)-propyl]-acetamide hydrochloride (A35)

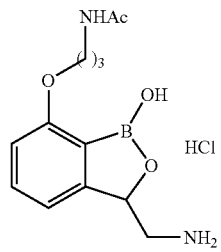

General procedure 11: [7-(3-acetylamino-propoxy)-1-hydroxy-1,3-dihydro-benzo[c][1,2]oxaborol-3-ylmethyl]-carbamic acid tert-butyl ester (600 mg, 1.58 mmol), 1 M HCl in Et$_2$O (3 mL), and CH$_2$Cl$_2$ (5 mL). Purification: trituration with Et$_2$O followed by preparative HPLC. A35 was isolated as a white solid: yield 35 mg (7%).

$^1$H NMR (400 MHz, DMSO-d$_6$+1 drop conc. HCl) δ (ppm): 8.32 (bs, 3H), 7.42 (t, J=7.8 Hz, 1H), 7.01 (d, J=7.4 Hz, 1H), 6.85 (d, J=8.2 Hz, 1H), 5.28 (dd, J=9.0, 2.3 Hz, 1H), 4.01 (t, J=6.3 Hz, 2H), 3.45-3.32 (m, 1H), 3.18 (t, J=5.8 Hz, 2H), 2.78-2.63 (m, 1H), 1.84-1.76 (m, 5H); MS (ESI): m/z=279 (M+1, positive); HPLC purity: 99.03% (MaxPlot 200-400 nm), 97.82% (220 nm).

198

3-Aminomethyl-7-(3-amino-propoxy)-3H-benzo[c][1,2]oxaborol-1-ol trifluoroacetate salt (A36)

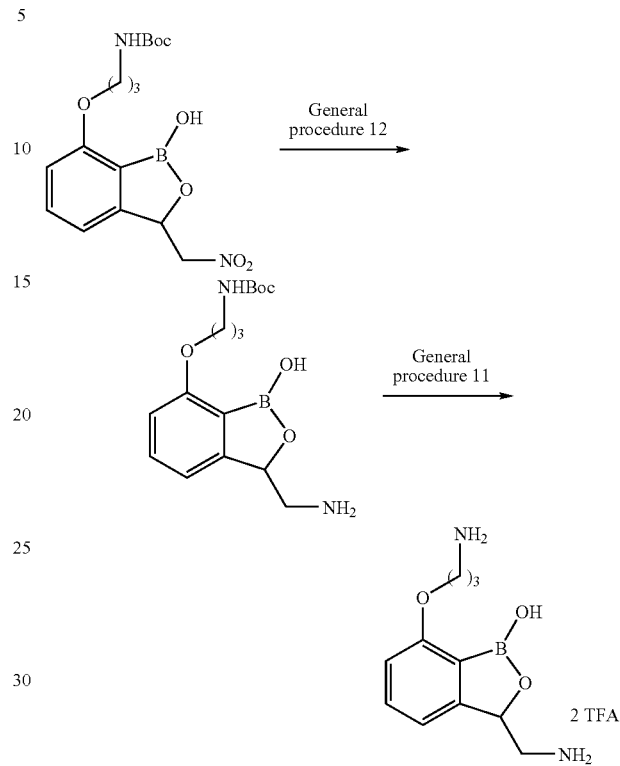

[3-(3-Aminomethyl-1-hydroxy-1,3-dihydro-benzo[c][1,2]oxaborol-7-yloxy)-propyl]-carbamic acid tert-butyl ester

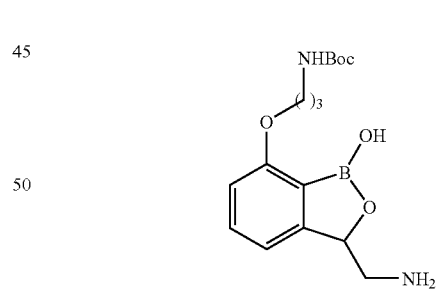

General procedure 12: [3-(1-hydroxy-3-nitromethyl-1,3-dihydro-benzo[c][1,2]oxaborol-7-yloxy)-propyl]-carbamic acid tert-butyl ester (1.0 g, 2.7 mmol), Raney Ni (2.0 g, 2 equiv w/w), 2 M NH$_3$ in EtOH (5 mL), and absolute EtOH (20 mL): yield 800 mg (88%).

MS (ESI): m/z=337 (M+1, positive).

3-Aminomethyl-7-(3-amino-propoxy)-3H-benzo[c][1,2]oxaborol-1-ol, TFA salt (A36)

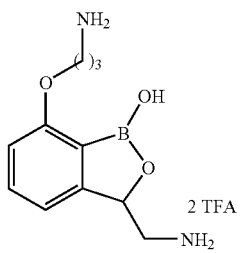

General procedure 11: [3-(3-aminomethyl-1-hydroxy-1,3-dihydro-benzo[c][1,2]oxaborol-7-yloxy)-propyl]-carbamic acid tert-butyl ester (700 mg, 2.08 mmol) and 4 N HCl in 1,4-dioxane (10 mL) was stirred at rt for 18 h. Purification: preparative HPLC (TFA): yield 159 mg (14%).

mp 136-138° C.; $^1$H NMR (400 MHz, DMSO-d$_6$) δ (ppm): 9.11 (bs, 1H), 8.13 (bs, 3H), 7.90 (bs, 3H), 7.50 (t, J=7.8 Hz, 1H), 7.09 (d, J=7.4 Hz, 1H), 6.92 (d, J=8.2 Hz, 1H), 5.28 (d, J=7.0 Hz, 1H), 4.26-4.04 (m, 2H), 3.04 (d, J=5.1 Hz, 2H), 2.82 (bs, 1H), 2.17-1.94 (m, 2H); $^{19}$F NMR (376 MHz, DMSO-d$_6$) δ (ppm): −74.08 (s); MS (ESI): m/z=237 (M+1, positive); HPLC purity: 98.44% (MaxPlot 200-400 nm), 94.39% (220 nm).

3-Aminomethyl-7-(3-methoxy-propoxy)-3H-benzo[c][1,2]oxaborol-1-ol hydrochloride (A38)

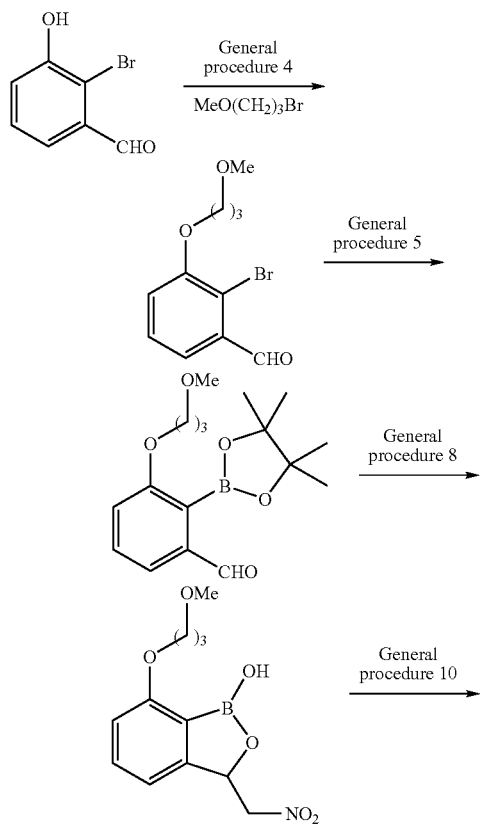

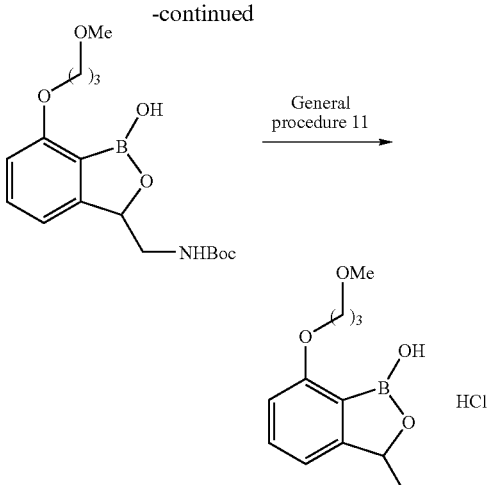

2-Bromo-3-(3-methoxy-propoxy)-benzaldehyde

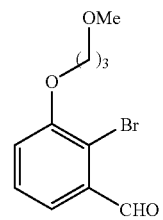

General procedure 4: 2-bromo-3-hydroxy-benzaldehyde (10.0 g, 49.7 mmol), Cs$_2$CO$_3$ (32.41 g, 99.42 mmol), 1-bromo-3-methoxy propane (7.61 g, 49.7 mmol), and anhydrous DMF (100 mL). Reaction conditions: 60° C. (bath temp) for 20 h. The title compound was isolated as a colorless liquid: yield 10.5 g (77%).

$^1$H NMR (400 MHz, CDCl$_3$) δ (ppm): 10.54 (s, 1H), 7.51 (d, J=6.2 Hz, 1H), 7.35 (t, J=7.8 Hz, 1H), 7.14 (d, J=8.2 Hz, 1H), 4.17 (t, J=6.1 Hz, 2H), 3.64 (t, J=6.1 Hz, 2H), 3.37 (s, 3H), 2.13 (qd, J=6.1, 5.9 Hz, 2H).

3-(3-Methoxy-propoxy)-2-(4,4,5,5-tetramethyl-[1,3,2]dioxaborolan-2-yl)-benzaldehyde

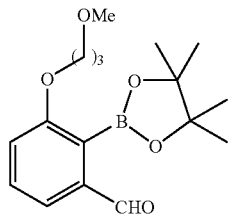

General procedure 5: 2-bromo-3-(3-methoxy-propoxy)-benzaldehyde (13.44 g, 49.22 mmol), B$_2$pin$_2$ (18.74 g, 73.83 mmol), KOAc (14.49 g, 147.66 mmol), PdCl$_2$(dppf).CH$_2$Cl$_2$ (2.88 g, 8 mol %), and anhydrous 1,4-dioxane (130 mL). Purification: flash chromatography (hexane to 20% EtOAc). The title compound was isolated as a white solid: yield 7.04 g (50%).

$^1$H NMR (400 MHz, CDCl$_3$) δ (ppm): 9.94 (s, 1H), 7.59-7.45 (m, 1H), 7.45-7.32 (m, 1H), 7.09 (d, J=8.2 Hz, 1H), 4.08 (t, J=6.2 Hz, 2H), 3.56 (t, J=6.2 Hz, 2H), 3.34 (s, 3H), 2.06 (qd, J=6.2 Hz, 2H), 1.45 (s, 12H).

7-(3-ethoxy-propoxy)-3-nitro ethyl-3H-Benzo[c][1,2]oxaborol-1-ol

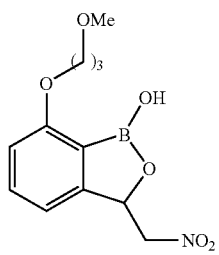

General procedure 8: 3-(3-methoxy-propoxy)-2-(4,4,5,5-tetramethyl-[1,3,2]dioxaborolan-2-yl)-benzaldehyde (7.04 g, 22.0 mmol), MeNO$_2$ (4.03 g, 66.0 mmol), NaOH (880 mg, 22.1 mmol), and H$_2$O (30 mL). Purification: flash chromatography (hexane to 20% EtOAc/hexane): yield 4.8 g (78%).

$^1$H NMR (400 MHz, DMSO-d$_6$) δ (ppm): 9.03 (s, 1H), 7.44 (t, J=7.8 Hz, 1H), 7.05 (d, J=7.4 Hz, 1H), 6.87 (d, J=8.2 Hz, 1H), 5.69 (dd, J=9.2, 2.5 Hz, 1H), 5.28 (dd, J=13.3, 2.7 Hz, 1H), 4.54 (dd, J=13.5, 9.2 Hz, 1H), 4.06 (t, J=6.2 Hz, 2H), 3.47 (t, J=6.2 Hz, 2H), 3.22 (s, 3H), 2.04-1.86 (m, 2H); MS (ESI): m/z=280 (M−1, negative).

[1-Hydroxy-7-(3-ethoxy-proxy)-1,3-dihydro-benzo[c][1,2]oxaborole-3-ylmethyl]-carbamic acid tert-butyl ester

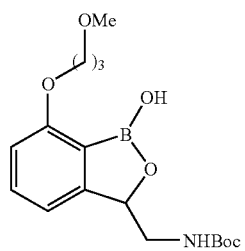

General procedure 10: 7-(3-methoxy-propoxy)-3-nitromethyl-3H-benzo[c][1,2]oxaborol-1-ol (1.30 g, 4.62 mmol), Boc$_2$O (2.01 g, 9.25 mmol), NiCl$_2$.6H$_2$O (1.32 g, 5.55 mmol), NaBH$_4$ (1.04 g, 27.5 mmol), and anhydrous MeOH (10 mL). The crude residue was used directly in the next reaction without further purification.

3-Aminomethyl-7-(3-methoxy-propoxy)-3H-benzo[c][1,2]oxaborol-1-ol hydrochloride (A38)

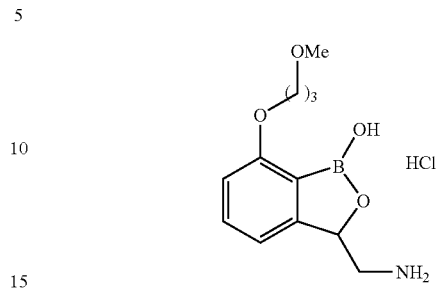

General procedure 11: [1-hydroxy-7-(3-methoxy-proxy)-1,3-dihydro-benzo[c][1,2]oxaborole-3-ylmethyl]-carbamic acid tert-butyl ester (2.0 g, 5.5 mmol) and 4 N HCl in 1,4-dioxane (20 mL). Purification: preparative HPLC: yield 540 mg (37% over 2 steps).

$^1$H NMR (400 MHz, DMSO-d$_6$) δ (ppm): 8.85 (s, 1H), 8.29 (bs, 3H), 7.44 (t, J=7.8 Hz, 1H), 7.03 (d, J=7.8 Hz, 1H), 6.87 (d, J=7.8 Hz, 1H), 5.30 (dd, J=8.6, 2.3 Hz, 1H), 4.06 (t, J=6.2 Hz, 2H), 3.48 (t, J=6.2 Hz, 2H), 3.22 (s, 3H), 2.76-2.74 (m, 1H), 1.94 (q, J=6.2 Hz, 2H); MS (ESI): m/z=252 (M+1, positive); HPLC purity: 98.90% (MaxPlot 200-400 nm), 97.04 (220 nm); Anal. Calcd for C$_{12}$H$_{19}$BClNO$_4$: C, 50.12%; H, 6.66%; N, 4.87% Found: C, 50.30%; H, 6.63%; N, 5.21%.

C-(7,8-Dihydro-2H-1,6,9-trioxa-9a-bora-benzo[cd]azulen-2-yl)-methylamine acetate salt (A39)

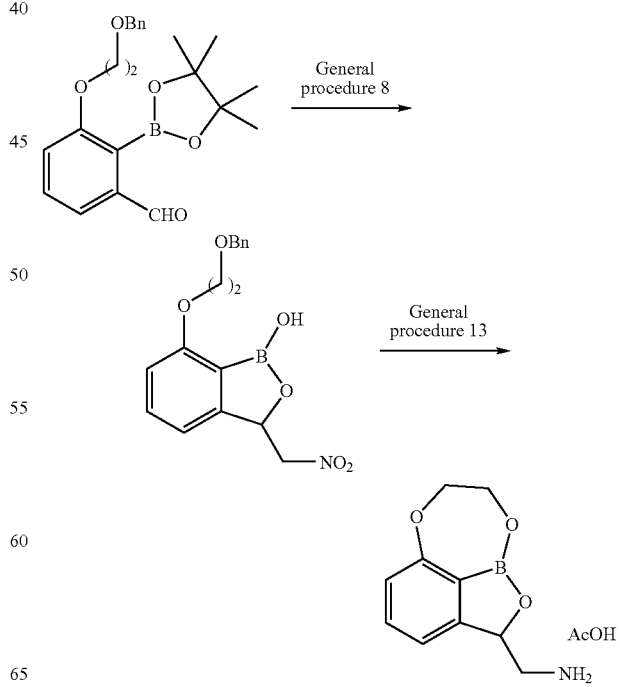

7-(3-Benzyloxy-ethoxy)-3-nitromethyl-3H-benzo[c][1,2]oxaborol-1-ol

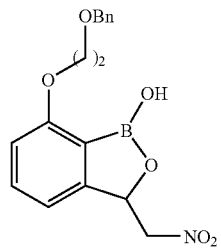

General procedure 8: 3-(2-benzyloxy-ethoxy)-2-(4,4,5,5-tetramethyl-[1,3,2]dioxaborolan-2-yl)-benzaldehyde (1.15 g, 30 mmol), MeNO$_2$ (0.39 mg, 6 mmol), NaOH (50 mg, 0.15 mmol), THF (5 mL) and H$_2$O (50 mL). Purification: flash chromatography (10% EtOAc/hexane to 30% EtOAc/hexane): yield 3.7 g (61%).

$^1$H NMR {400 MHz, DMSO-d$_6$+D$_2$O (0.01 mL)} δ (ppm): 7.49 (t, J=7.8 Hz, 1H), 7.34-7.25 (m, 5H), 7.08 (d, J=7.6 Hz, 1H), 6.92 (d, J=8.0 Hz, 1H), 5.71 (d, J=6.4 Hz, 1H), 5.30 (d, J=6.4 Hz, 1H), 4.58-4.53 (m, 1H), 4.47 (s, 2H), 4.21 (t, J=6.2 Hz, 2H), 3.80 (t, J=6.0 Hz, 2H); MS (ESI) m/z=342 (M−1, negative); MS (ESI): HPLC purity 97.89% (MaxPlot) and 95.57% (220 nm).

C-(7,8-Dihydro-2H-1,6,9-trioxa-9a-bora-benzo[cd]azulen-2-yl)-methylamine acetate salt (A39)

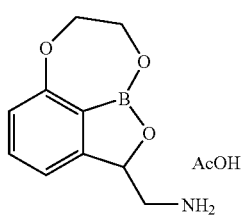

General procedure 13: 7-(3-benzyloxy-propoxy)-3-nitromethyl-3H-benzo[c][1,2]oxaborol-1-ol (0.45 g, 0.013 mol), 20% Pd(OH)$_2$/C (50% weight-wet) (50 mg), and glacial AcOH (30 mL). Purification: preparative HPLC (0.1% AcOH). A39 was isolated as a grey solid with 0.75 mol % AcOH: yield 0.1 g (34%).

mp 69-71° C.; $^1$H NMR {400 MHz, DMSO-d$_6$+D$_2$O (0.01 mL)} δ (ppm): 7.43 (t, J=7.6 Hz, 1H), 7.05 (d, J=7.3 Hz, 1H), 6.84 (d, J=8.2 Hz, 1H), 5.19 (bs, 1H), 4.65 (bs, 1H), 4.40-4.10 (m, 3H), 3.05-2.90 (m, 1H), 2.80-2.60 (m, 1H); MS (ESI) m/z=206 (M+1, positive); HPLC purity: 99.26% (MaxPlot) and 98.26% (220 nm).

4-(1-Hydroxy-3-nitromethyl-1,3-dihydro-benzo[c][1,2]oxaborol-7-yloxy)-butyronitrile (A40)

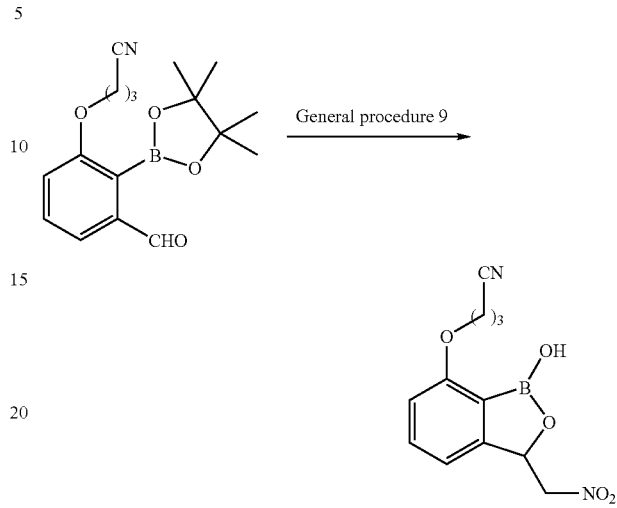

General procedure 9: 4-[3-formyl-2-(4,4,5,5-tetramethyl-[1,3,2]dioxaborolan-2-yl)-phenoxy]-butyronitrile (2.0 g, 6.3 mmol), MeNO$_2$ (0.68 mL, 12 mmol), CTAB (116 mg, 0.32 mmol), 0.025 M NaOH (20 mL), and THF (5 mL). Purification: precipitation: yield 560 mg (32%).

$^1$H NMR (400 MHz, DMSO-d$_6$) δ (ppm): 9.08 (s, 1H), 7.48 (t, J=7.8 Hz, 1H), 7.11 (d, J=7.4 Hz, 1H), 6.93 (d, J=8.2 Hz, 1H), 5.72 (dd, J=9.4, 2.7 Hz, 1H), 5.31 (dd, J=13.2, 2.7 Hz, 1H), 4.65-4.48 (m, 1H), 4.10 (t, J=5.5 Hz, 2H), 2.69 (t, J=7.4 Hz, 2H), 2.04 (quin, 2H); MS (ESI): m/z=275 (M−1, negative); HPLC purity: 97.72% (MaxPlot 200-400 nm), 96.62% (220 nm).

7-(4-Amino-butoxy)-3-aminomethyl-3H-benzo[c][1,2]oxaborol-1-ol hydrochloride (A41)

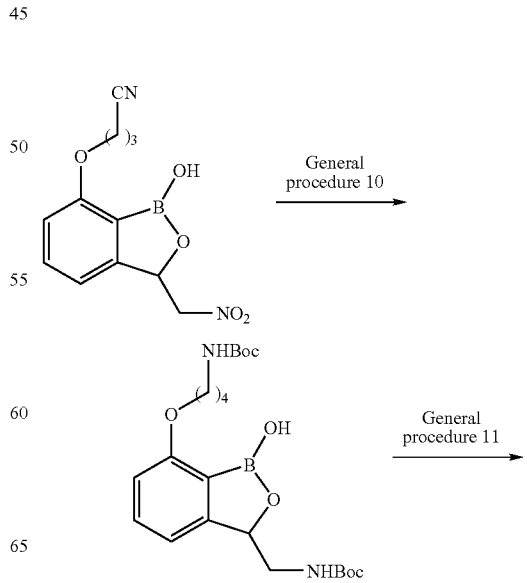

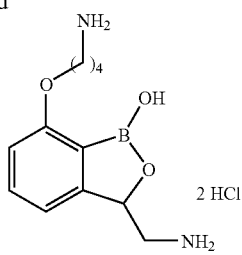

{4-[3-(tert-Butoxycarbonylamino-methyl)-1-hydroxy-1,3-dihydro-benzo[c][1,2]oxaborol-7-yloxy]-butyl}-carbamic acid tert-butyl ester

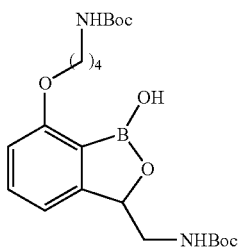

General procedure 10: A40 (490 mg, 1.77 mmol), NiCl₂.6H₂O (632 mg, 2.66 mmol), NaBH₄ (807 mg, 21.3 mmol), Boc₂O (1.54 g, 7.08 mmol), and MeOH (20 mL). Purification: flash chromatography (30% EtOAc in hexane). The title compound was isolated as a white foam: yield 420 mg (53%).

¹H NMR (400 MHz, DMSO-d₆) δ (ppm): 8.76 (s, 1H), 8.73-8.66 (m, 1H), 8.82-8.65 (m, 2H), 7.42-7.33 (m, 1H), 7.43-7.32 (m, 1H), 6.92 (dd, J=17.8, 7.2 Hz, 1H), 6.85-6.76 (m, 1H), 5.21-4.99 (m, 1H), 3.99 (t, J=6.1 Hz, 2H), 3.01-2.89 (m, 2H), 1.73-1.61 (m, 2H), 1.57-1.46 (m, 2H), 1.39-1.29 (m, 18H); MS (ESI): m/z=449 (M−1, negative).

7-(4-Amino-butoxy)-3-aminomethyl-3H-benzo[c][1,2]oxaborol-1-ol hydrochloride (A41)

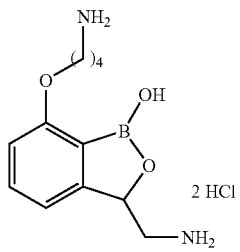

General procedure 11: {4-[3-(tert-butoxycarbonylamino-methyl)-1-hydroxy-1,3-dihydro-benzo[c][1,2]oxaborol-7-yloxy]-butyl}-carbamic acid tert-butyl ester (420 mg, 0.93 mmol) and 1 M HCl in Et₂O (5 mL). Purification: preparative HPLC. A41 was isolated as a white solid: yield 260 mg (86%).

mp 145-146° C.; ¹H NMR (400 MHz, DMSO-d₆) δ (ppm): 8.93 (bs, 1H), 8.23 (bs, 3H), 8.01 (bs, 3H), 7.48 (t, J=7.6 Hz, 1H), 7.07 (d, J=7.4 Hz, 1H), 6.92 (d, J=7.8 Hz, 1H), 5.30 (d, J=7.8 Hz, 1H), 4.21-3.95 (m, 2H), 2.95-2.72 (m, 2H), 1.92-1.60 (m, 4H); MS (ESI): m/z=251 (M+1, positive); HPLC purity: 87.79% (MaxPlot 200-400 nm), 85.7% (220 nm).

3-Aminomethyl-7-(4-hydroxy-butoxy)-3H-benzo[c][1,2]oxaborol-1-ol acetate salt (A42)

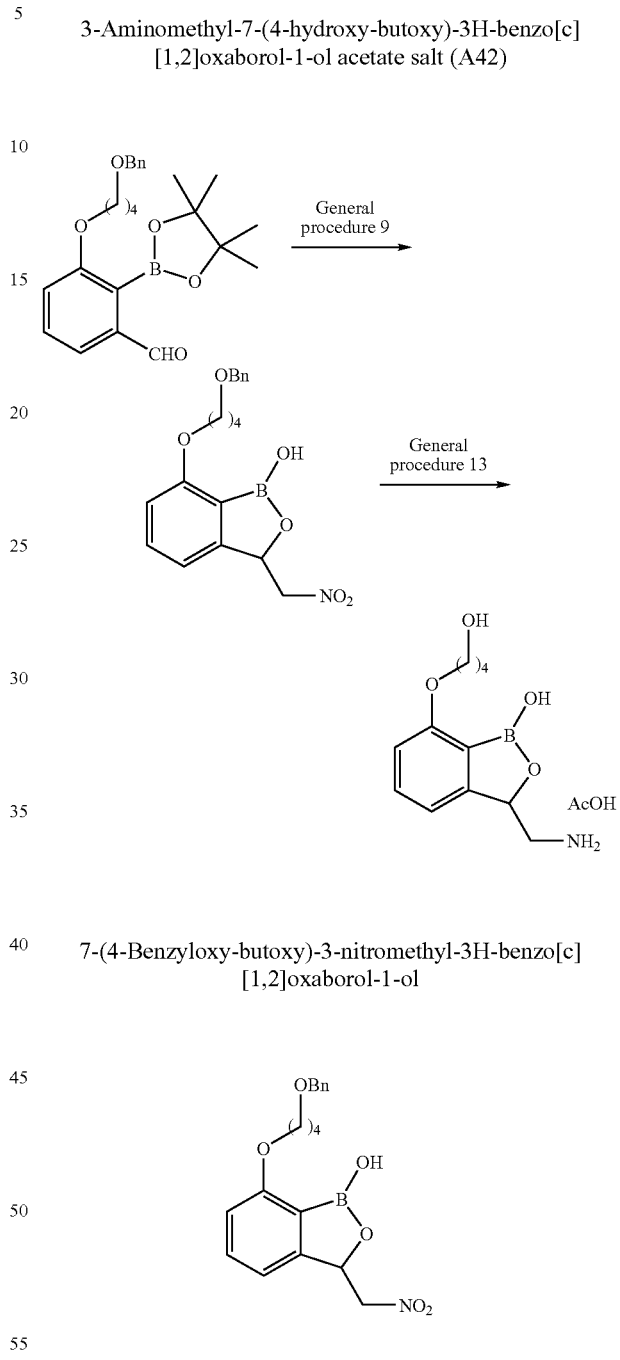

7-(4-Benzyloxy-butoxy)-3-nitromethyl-3H-benzo[c][1,2]oxaborol-1-ol

General procedure 9: 3-(4-benzyloxy-butoxy)-2-(4,4,5,5-tetramethyl-[1,3,2]dioxaborolan-2-yl)-benzaldehyde (2.0 g, 4.8 mmol), MeNO₂ (0.51 mL, 9.6 mmol), CTAB (87 mg, 0.24 mmol), 0.025M NaOH (20 mL), and THF (5 mL). Purification: precipitation to give a white solid: yield 1.2 g (67%).

¹H NMR (400 MHz, DMSO-d₆) δ (ppm): 9.07 (s, 1H), 7.45 (t, J=7.8 Hz, 1H), 7.38-7.24 (m, 5H), 7.06 (d, J=7.4 Hz, 1H), 6.88 (d, J=8.2 Hz, 1H), 5.71 (dd, J=9.6, 2.5 Hz, 1H), 5.31 (dd, J=13.3, 2.7 Hz, 1H), 4.55 (dd, J=13.5, 9.6 Hz, 1H), 4.46 (s, 2H), 4.13-3.97 (m, 2H), 3.56-3.45 (m, 2H), 1.85-1.65 (m, 4H); MS (ESI): m/z=370 (M−1, negative).

3-Aminomethyl-7-(4-hydroxy-butoxy)-3H-benzo[c][1,2]oxaborol-1-ol acetate salt (A42)

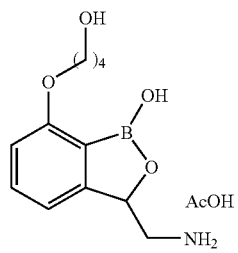

General procedure 13: 7-(4-benzyloxy-butoxy)-3-nitromethyl-3H-benzo[c][1,2]oxaborol-1-ol (1.0 g, 2.7 mmol), Pd(OH)$_2$ (1.0 g), and AcOH (20 mL). Purification: preparative HPLC (0.1% AcOH). A42 was isolated as a white solid: yield 250 mg (33%).

$^1$H NMR (400 MHz, DMSO-d$_6$+1 drop of conc HCl) δ (ppm): 8.38 (bs, 2H), 7.47 (t, J=7.8 Hz, 1H), 7.06 (d, J=7.4 Hz, 1H), 6.90 (d, J=8.2 Hz, 1H), 5.33 (d, J=9.0 Hz, 1H), 4.05 (t, J=6.2 Hz, 1H), 3.49-3.46 (m, J=6.4 Hz, 4H), 2.77-2.62 (m, 1H), 1.98 (s, 3H), 1.78-1.70 (m, 2H), 1.65-1.45 (m, 2H); MS (ESI): m/z=252 (M+1, positive); HPLC purity: 98.13% (MaxPlot 200-400 nm), 96.65% (220 nm).

[3-(3-Aminomethyl-1-hydroxy-1,3-dihydrobenzo[c][1,2]oxaborol-7-yloxy)-propyl]-carbamic acid benzyl ester hydrochloride (A43)

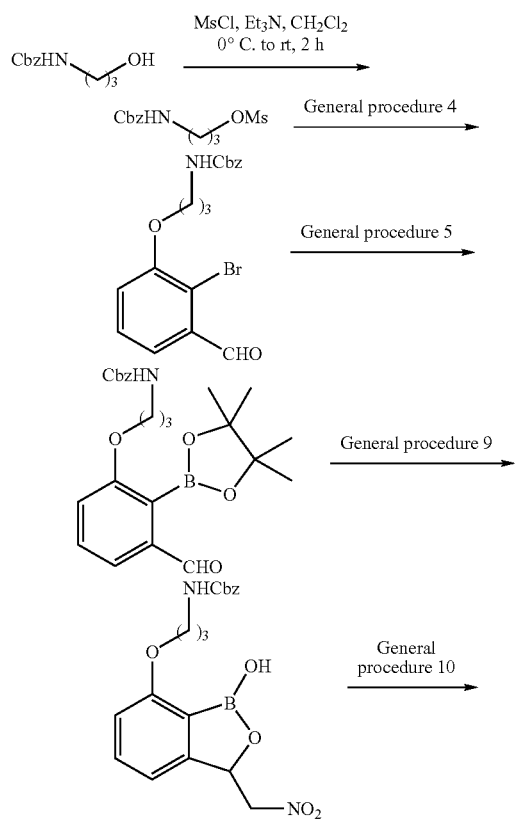

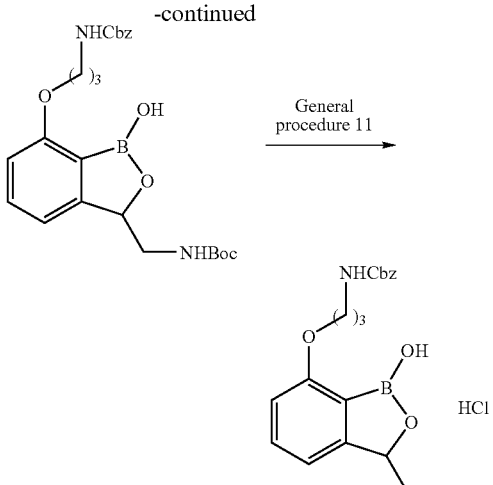

Methanesulfonic acid 3-benzyloxycarbonylamino-propyl ester

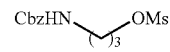

MsCl (2.03 mL, 26.3 mmol) was added slowly to a solution of Et$_3$N (4.9 mL, 36 mmol) and 4-benzyloxy-butan-1-ol (5.0 g, 24 mmol) in CH$_2$Cl$_2$ (100 mL) at 0° C. (bath temp). The reaction mixture was stirred at rt for 2 h and then quenched with H$_2$O (100 mL). The mixture was extracted with CH$_2$Cl$_2$ and the organic layer was dried (MgSO$_4$) and concentrated in vacuo to give the title compound as a colorless liquid: yield 6.58 g (96%).

$^1$H NMR (400 MHz, CDCl$_3$) δ (ppm): 7.43-7.24 (m, 5H), 5.36 (bs, 1H), 5.09 (s, 2H), 4.29 (t, J=5.9 Hz, 2H), 3.39-3.26 (m, 2H), 3.01 (s, 3H), 2.01-1.89 (m, 2H).

[3-(2-Bromo-3-formyl-phenoxy)-propyl]-carbamic acid benzyl ester

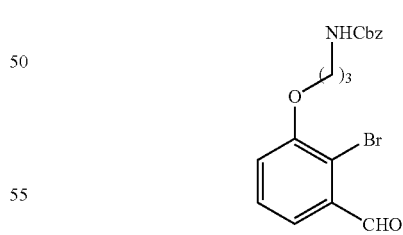

General procedure 4: 2-bromo-3-hydroxy-benzaldehyde (3.81 g, 19 mmol), methanesulfonic acid 3-benzyloxycarbonylamino-propyl ester (6.55 g, 22.8 mmol), Cs$_2$CO$_3$ (9.28 g, 28.5 mmol) and DMF (100 mL). The title compound was isolated as a viscous liquid: yield 6.93 g (93%).

$^1$H NMR (400 MHz, CDCl$_3$) δ (ppm): 10.41 (s, 1H), 7.52 (d, J=8.6 Hz, 1H), 7.41-7.30 (m, 6H), 7.12 (d, J=7.8 Hz, 1H), 5.56 (bs, 1H), 5.11 (s, 2H), 4.20-4.12 (m, 2H), 3.54-3.46 (m, 2H), 2.17-2.07 (m, 2H).

{3-[3-Formyl-2-(4,4,5,5-tetramethyl-[1,3,2]dioxaborolan-2-yl)-phenoxy]-propyl}-carbamic acid benzyl ester

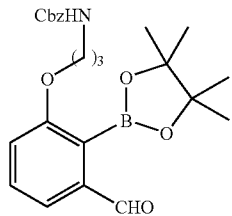

General procedure 5: [3-(2-bromo-3-formyl-phenoxy)-propyl]-carbamic acid benzyl ester (6.9 g, 18 mmol), B$_2$pin$_2$ (8.93 g, 35.2 mmol), KOAc (6.90 g, 70.4 mmol), PdCl$_2$(dppf).CH$_2$Cl$_2$ (0.64 g, 0.87 mmol), and dioxane (200 mL). Purification: flash chromatography (20% EtOAc in hexane). The title compound was isolated as a white foam: yield 1.98 g (26%).

$^1$H NMR (400 MHz, CDCl$_3$) δ (ppm): 9.94 (s, 1H), 7.52-7.31 (m, 7H), 7.07 (d, J=7.8 Hz, 1H), 5.13-5.04 (m, 3H), 4.06 (t, J=5.7 Hz, 2H), 3.41 (q, J=5.9 Hz, 2H), 2.07-2.01 (m, 2H), 1.43 (s, 12H).

[3-(1-Hydroxy-3-nitromethyl-1,3-dihydro-benzo[c][1,2]oxaborol-7-yloxy)-propyl]-carbamic acid benzyl ester

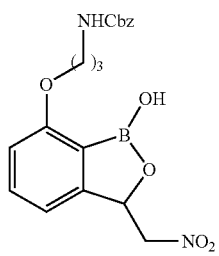

General procedure 9: {3-[3-formyl-2-(4,4,5,5-tetramethyl-[1,3,2]dioxaborolan-2-yl)-phenoxy]-propyl}-carbamic acid benzyl ester (1.98 g, 4.50 mmol), MeNO$_2$ (0.48 mL, 9.0 mmol), CTAB (82 mg, 0.32 mmol), 0.025 M NaOH (20 mL), and THF (5 mL). Purification: precipitation to give a white solid: yield 1.3 g (75%).

$^1$H NMR (400 MHz, DMSO-d$_6$) δ (ppm): 9.06 (s, 1H), 7.50-7.42 (m, 1H), 7.40-7.25 (m, 6H), 7.07 (d, J=7.4 Hz, 1H), 6.88 (d, J=9.4 Hz, 1H), 5.71 (d, J=8.2 Hz, 1H), 5.36-5.25 (m, 1H), 5.01 (s, 2H), 4.61-4.46 (m, 1H), 4.11-3.99 (m, 2H), 3.24-3.14 (m, 2H), 1.93-1.80 (m, 2H).

{3-[3-(tert-Butoxycarbonylamino-methyl)-1-hydroxy-1,3-dihydro-benzo[c][1,2]oxaborol-7-yloxy]-propyl}-carbamic acid benzyl ester

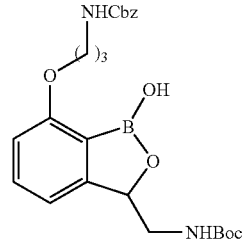

General procedure 10: [3-(1-hydroxy-3-nitromethyl-1,3-dihydro-benzo[c][1,2]oxaborol-7-yloxy)-propyl]-carbamic acid benzyl ester (1.3 g, 3.4 mmol), NiCl$_2$.6H$_2$O (804 mg, 3.38 mmol), NaBH$_4$ (770 mg, 20.3 mmol), Boc$_2$O (1.47 g, 6.76 mmol), and MeOH (20 mL). Purification: flash chromatography (30% EtOAc in hexane). The title compound was isolated as a white foam: yield 300 mg (19%).

$^1$H NMR (400 MHz, DMSO-d$_6$) δ (ppm): 8.73 (s, 1H), 7.43-7.24 (m, 7H), 7.02-6.94 (m, 1H), 6.90 (d, J=7.4 Hz, 1H), 6.80 (d, J=8.6 Hz, 1H), 5.09-5.01 (m, 1H), 4.99 (s, 2H), 4.02 (t, J=5.9 Hz, 2H), 3.20-3.11 (m, 3H), 3.05-2.93 (m, 1H), 1.89-1.78 (m, 2H), 1.35 (s, 9H); MS (ESI): m/z=469 (M−1, negative).

[3-(3-Aminomethyl-1-hydroxy-1,3-dihydrobenzo[c][1,2]oxaborol-7-yloxy)-propyl]-carbamic acid benzyl ester hydrochloride (A43)

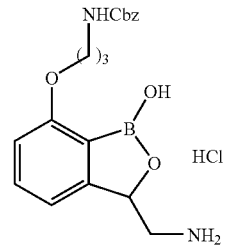

General procedure 11: {3-[3-(tert-butoxycarbonylamino-methyl)-1-hydroxy-1,3-dihydro-benzo[c][1,2]oxaborol-7-yloxy]-propyl}-carbamic acid benzyl ester (300 mg, 0.63 mmol.), 1 M HCl in Et$_2$O (2 mL), and CH$_2$Cl$_2$ (2 mL). Purification: preparative HPLC. A43 was isolated as a white solid 70 mg (29%).

$^1$H NMR (400 MHz, DMSO-d$_6$) δ (ppm): 7.40-7.22 (m, 9H), 7.04 (d, J=7.4 Hz, 1H), 6.87 (d, J=7.8 Hz, 1H), 5.02-4.96 (m, 3H), 4.08-3.98 (m, 2H), 3.23-3.12 (m, 2H), 3.06-2.92 (m, 1H), 2.71-2.60 (m, 1H), 1.92-1.82 (m, 3H); MS (ESI): m/z=371 (M+1, positive); HPLC purity: 97.01% (MaxPlot 200-400 nm), 95.99% (220 nm).

N-[3-(3-Aminomethyl-1-hydroxy-1,3-dihydro-benzo[c][1,2]oxaborol-7-yloxy)-propyl]-methanesulfonamide hydrochloride (A44)

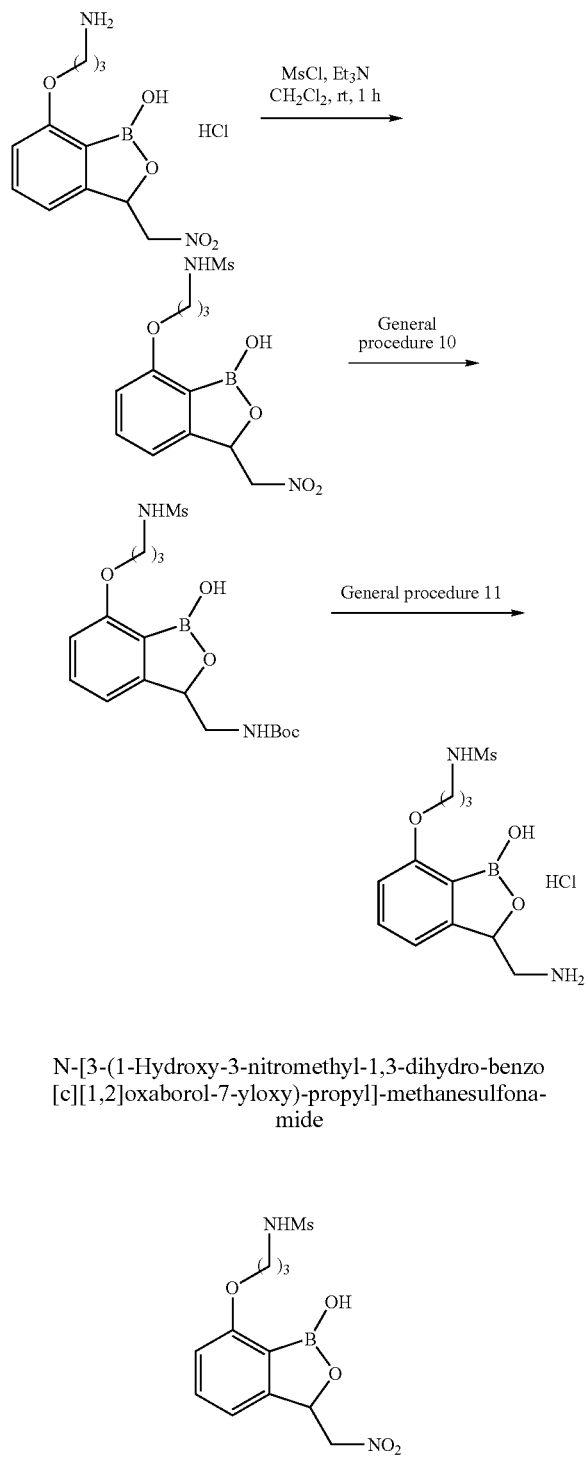

N-[3-(1-Hydroxy-3-nitromethyl-1,3-dihydro-benzo[c][1,2]oxaborol-7-yloxy)-propyl]-methanesulfonamide MsCl (0.99 mL, 13 mmol) was added slowly to a solution of Et$_3$N (2.85 mL, 20.5 mmol) and 7-(3-amino-propoxy)-3-nitromethyl-3H-benzo[c][1,2]oxaborol-1-ol hydrochloride (1.55 g, 5.12 mmol) in CH$_2$Cl$_2$ (50 mL) at 0° C. (bath temp). The reaction mixture was stirred at rt for 1 h and then quenched with H$_2$O (50 mL). The mixture was extracted with CH$_2$Cl$_2$ and the organic fractions were dried (MgSO$_4$) and concentrated in vacuo. The residue was purified by flash chromatography (30% EtOAc in hexane) to give the title compound as a viscous liquid: yield 500 mg (28%).

$^1$H NMR (400 MHz, DMSO-d$_6$) δ (ppm): 7.47 (t, J=7.8 Hz, 1H), 7.12-7.05 (m, 1H), 7.05-6.97 (m, 1H), 6.91 (d, J=7.8 Hz, 1H), 5.71 (dd, J=9.4, 2.7 Hz, 1H), 5.31 (dd, J=13.7, 2.7 Hz, 1H), 4.56 (dd, J=13.5, 9.2 Hz, 1H), 4.10 (t, J=6.1 Hz, 2H), 3.16-3.08 (m, 2H), 2.88 (s, 3H), 1.99-1.86 (m, 2H); MS (ESI): m/z=343 (M−1, negative).

[1-Hydroxy-7-(3-methanesulfonylamino-propoxy)-1,3-dihydro-benzo[c][1,2]oxaborol-3-ylmethyl]-carbamic acid tert-butyl ester

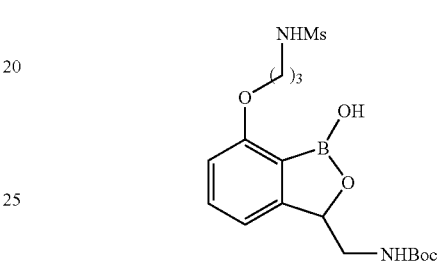

General procedure 10: N-[3-(1-hydroxy-3-nitromethyl-1,3-dihydro-benzo[c][1,2]oxaborol-7-yloxy)-propyl]-methanesulfonamide (500 mg, 1.45 mmol), NiCl$_2$.6H$_2$O (345 mg, 1.45 mmol), NaBH$_4$ (330 mg, 8.7 mmol), Boc$_2$O (632 mg, 2.90 mmol), and MeOH (50 mL). Purification: flash chromatography (5% MeOH in CH$_2$Cl$_2$). The title compound was isolated as a white foam: yield 140 mg (23%).

$^1$H NMR (400 MHz, DMSO-d$_6$) δ (ppm): 8.77 (s, 1H), 7.40 (t, J=7.6 Hz, 1H), 7.07-6.80 (m, 4H), 5.13-5.00 (m, 1H), 4.13-4.03 (m, 2H), 3.21-2.97 (m, 3H), 2.88 (s, 3H), 1.97-1.87 (m, 2H), 1.37 (s, 9H); MS (ESI): m/z=413 (M−1, negative).

N-[3-(3-Aminomethyl-1-hydroxy-1,3-dihydro-benzo[c][1,2]oxaborol-7-yloxy)-propyl]-methanesulfonamide hydrochloride (A44)

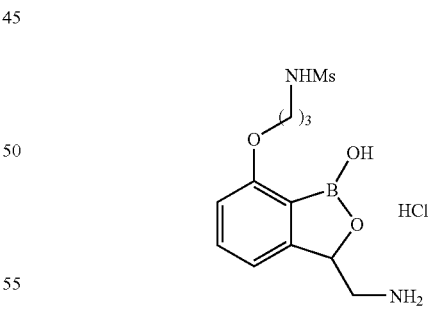

General procedure 11: [1-hydroxy-7-(3-methanesulfonylamino-propoxy)-1,3-dihydro-benzo[c][1,2]oxaborol-3-ylmethyl]-carbamic acid tert-butyl ester (140 mg, 0.33 mmol), 1 M HCl in Et$_2$O (2 mL), and CH$_2$Cl$_2$ (2 mL). Purification: trituration with Et$_2$O followed by preparative HPLC. A44 was isolated as a white solid: yield 30 mg (25%).

$^1$H NMR (400 MHz, DMSO-d$_6$+1 drop conc. HCl) δ (ppm): 8.13 (bs, 3H), 7.46 (t, J=7.6 Hz, 1H), 7.04 (d, J=7.4 Hz, 1H), 6.90 (d, J=8.6 Hz, 1H), 5.26 (d, J=8.6 Hz, 1H), 4.08 (t, J=5.5 Hz, 2H), 3.16-3.07 (m, 3H), 2.87 (s, 3H), 2.84-2.74

(m, 1H), 1.95-1.86 (m, 2H); MS (ESI): m/z=315 (M+1, positive); HPLC purity: 84.60% (MaxPlot 200-400 nm), 82.29% (220 nm).

2-(3-Aminomethyl-1-hydroxy-1,3-dihydro-benzo[c][1,2]oxaborol-7-yloxymethyl)-propane-1,3-diol hydrochloride (A45)

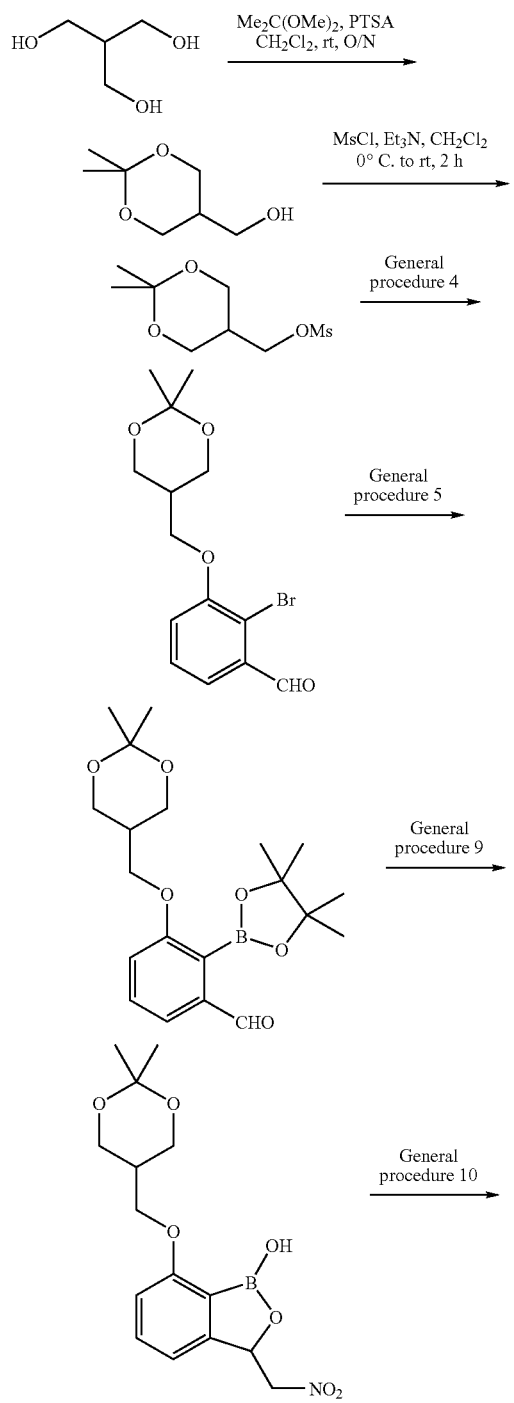

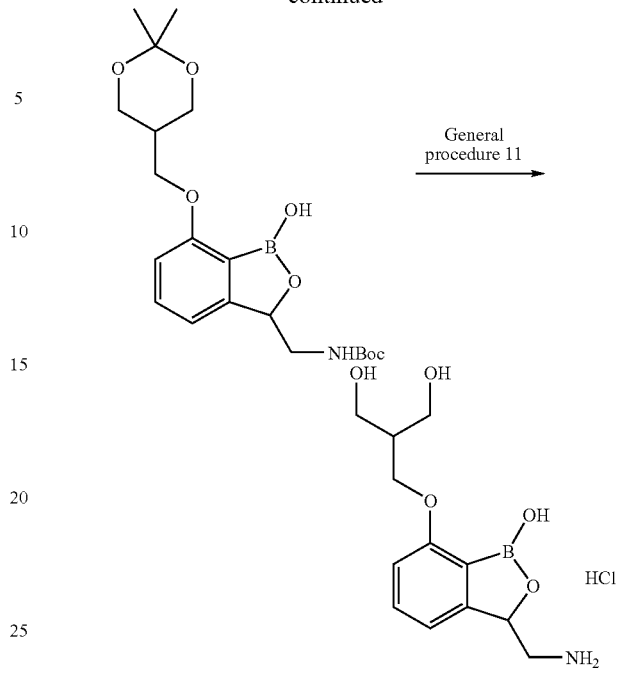

(2,2-Dimethyl-[1,3]dioxan-5-yl)-methanol

A solution of 2,2-dimethoxypropane (5.88 g, 56.5 mmol), 2-methyl-propane-1,3-diol (5.0 g, 47 mmol), and PTSA monohydrate (0.48 g, 2.3 mmol) in THF (100 mL) was stirred O/N at rt. The mixture was concentrated in vacuo to give the title compound as a colorless liquid: yield 6.87 g (99%).

$^1$H NMR (400 MHz, CDCl$_3$) δ (ppm): 4.03 (dd, J=11.7, 3.5 Hz, 2H), 3.84-3.73 (m, 4H), 2.49-2.39 (m, 1H), 1.90-1.80 (m, 1H), 1.45 (s, 3H), 1.40 (s, 3H).

Methanesulfonic acid 2,2-dim ethyl-[1,3]dioxan-5-ylmethyl ester

MsCl (4.4 mL, 56 mmol) was added slowly to a solution of Et$_3$N (9.8 mL, 71 mmol) and (2,2-dimethyl-[1,3]dioxan-5-yl)-methanol (6.87 g, 47.0 mmol) in CH$_2$Cl$_2$ (100 mL) at 0° C. (bath temp). The reaction mixture was stirred at rt for 2 h and then quenched with H$_2$O (100 mL). The mixture was extracted with CH$_2$Cl$_2$ and the organic fractions were dried (MgSO$_4$) and concentrated in vacuo to give the title compound as a colorless liquid: yield 10.02 g (95%).

¹H NMR (400 MHz, CDCl₃) δ (ppm): 4.42 (d, J=7.4 Hz, 2H), 4.13-4.04 (m, 2H), 3.82-3.74 (m, 2H), 3.05 (s, 3H), 2.05-1.95 (m, 1H), 1.46 (s, 3H), 1.40 (s, 3H).

2-Bromo-3-(2,2-dimethyl-[/,3]dioxan-5-ylmethoxy)-benzaldehyde

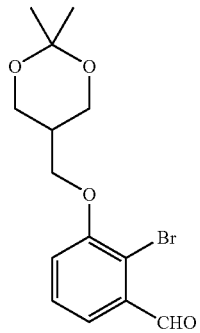 [SMILES: CC1(C)OCC(COc2cccc(C=O)c2Br)CO1]

General procedure 4: 2-bromo-3-hydroxy-benzaldehyde (8.98 g, 44.7 mmol), methanesulfonic acid 2,2-dimethyl-[1,3]dioxan-5-ylmethyl ester (10.02 g, 44.68 mmol), Cs₂CO₃ (21.8 g, 67.0 mmol), and DMF (100 mL). Purification: flash chromatography (20% EtOAc in hexane). The title compound was isolated as a viscous liquid: yield 4.20 g (29%).

¹H NMR (400 MHz, CDCl₃) δ (ppm): 10.43 (s, 1H), 7.53 (d, J=7.4 Hz, 1H), 7.38 (t, J=7.6 Hz, 1H), 7.15 (d, J=8.2 Hz, 1H), 4.26-4.08 (m, 4H), 4.01 (dd, J=11.5, 4.5 Hz, 2H), 2.22 (dt, J=11.2, 5.5 Hz, 1H), 1.50 (s, 3H), 1.45 (s, 3H).

3-(2,2-Dimethyl-[1,3]dioxan-5-ylmethoxy)-2-(4-methyl-[1,3,2]dioxaborolan-2-yl)-benzaldehyde

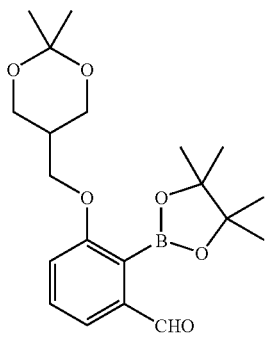 [SMILES: CC1(C)OCC(COc2cccc(C=O)c2B2OC(C)(C)C(C)(C)O2)CO1]

General procedure 5: 2-bromo-3-(2,2-dimethyl-[1,3]dioxan-5-ylmethoxy)-benzaldehyde (4.10 g, 12.5 mmol), B₂pin₂ (6.34 g, 25.0 mmol), KOAc (4.90 g, 50.0 mmol), PdCl₂(dppf).CH₂Cl₂ (0.91 g, 1.3 mmol), and dioxane (200 mL). Purification: flash chromatography (30% EtOAc in hexane). The title compound was isolated as a white foam: yield 2.0 g (42%)

¹H NMR (400 MHz, CDCl₃) δ (ppm): 9.95 (s, 1H), 7.49 (t, J=7.8 Hz, 1H), 7.44-7.38 (m, 1H), 7.13 (d, J=8.2 Hz, 1H), 4.17-4.06 (m, 4H), 3.86 (dd, J=11.9, 4.5 Hz, 2H), 2.12 (d, 1H), 1.27 (s, 15H), 1.24 (s, 3H); MS (ESI): m/z=377 (M+1, positive).

7-(2,2-Dimethyl-[1,3]dioxan-5-ylmethoxy)-3-nitromethyl-3H-benzo[c][1,2]-oxaborol-1-ol

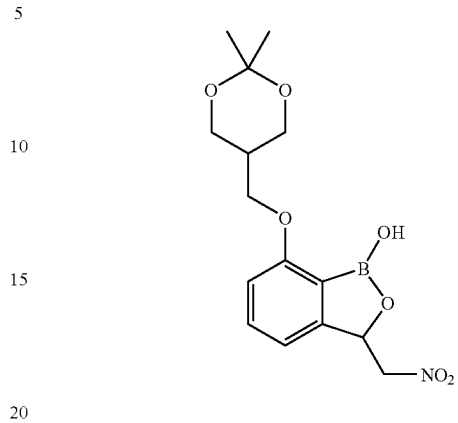

General procedure 9: 3-(2,2-dimethyl-[1,3]dioxan-5-ylmethoxy)-2-(4-methyl-[1,3,2]dioxaborolan-2-yl)-benzaldehyde (2.0 g, 5.3 mmol), MeNO₂ (0.57 mL, 11 mmol), CTAB (97 mg, 0.26 mmol), 0.025 M NaOH (50 mL), and THF (5 mL). Purification: precipitation: yield 0.45 g (25%).

¹H NMR (400 MHz, DMSO-d₆) δ (ppm): 9.09 (s, 1H), 7.47 (t, J=7.8 Hz, 1H), 7.09 (d, J=7.4 Hz, 1H), 6.92 (d, J=8.2 Hz, 1H), 5.71 (d, J=9.0 Hz, 1H), 5.31 (d, J=13.3 Hz, 1H), 4.57 (dd, J=13.7, 9.4 Hz, 1H), 4.07 (d, J=6.6 Hz, 2H), 4.01-3.91 (m, 2H), 3.86-3.75 (m, 2H), 2.08 (m, 1H), 1.35 (s, 3H), 1.33 (s, 3H); MS (ESI): m/z=336 (M−1, negative).

[7-(2,2-Dimethyl-[1,3]dioxan-5-ylmethoxy)-1-hydroxy-1,3-dihydro-benzo[c][1,2]oxaborol-3-ylmethyl]-carbamic acid tert-butyl ester

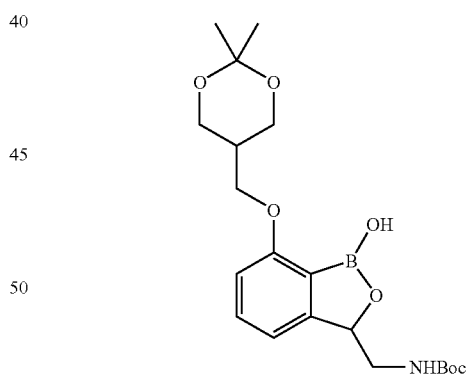

General procedure 10: 7-(2,2-dimethyl-[1,3]dioxan-5-ylmethoxy)-3-nitromethyl-3H-benzo[c][1,2]-oxaborol-1-ol (0.45 g, 1.3 mmol), NiCl₂.6H₂O (317 mg, 1.33 mmol), NaBH₄ (271 mg, 7.98 mmol), Boc₂O (580 mg, 2.66 mmol), and MeOH (30 mL). Purification: flash chromatography (5% MeOH in CH₂Cl₂). The title compound was isolated as a white foam: yield 150 mg (28%).

¹H NMR (400 MHz, DMSO-d₆) δ (ppm): 8.75 (s, 1H), 7.45-7.36 (m, 1H), 6.98-6.91 (m, 2H), 6.85 (d, J=7.8 Hz, 1H), 5.10-5.04 (m, 1H), 4.08-3.93 (m, 4H), 3.80 (dd, J=12.1, 6.6 Hz, 2H), 3.09-2.98 (m, 1H), 2.12-2.06 (m, 1H), 1.37 (s, 9H), 1.35-1.31 (m, 6H).

2-(3-Aminomethyl-1-hydroxy-1,3-dihydro-benzo[c][1,2]oxaborol-7-yloxymethyl)-propane-1,3-diol hydrochloride (A45)

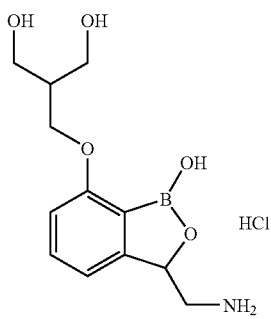 [SMILES: NCC1OB(O)c2c(OCC(CO)CO)cccc21 ; Cl]

General procedure 11: [7-(2,2-dimethyl-[1,3]dioxan-5-yl-methoxy)-1-hydroxy-1,3-dihydro-benzo[c][1,2]oxaborol-3-ylmethyl]-carbamic acid tert-butyl ester (150 mg, 0.37 mmol), 2 N HCl (10 mL), and MeOH (5.0 mL). Purification: preparative HPLC. A45 was isolated as a white solid: yield 80 mg (71%).

$^1$H NMR (400 MHz, DMSO-$d_6$) δ (ppm): 8.29 (bs, 3H), 7.39 (t, J=7.8 Hz, 1H), 6.99 (d, J=7.4 Hz, 1H), 6.83 (d, J=8.2 Hz, 1H), 6.15 (d, J=10.9 Hz, 1H), 5.30-5.23 (m, 1H), 4.01-3.95 (m, 2H), 3.53-3.50 (m, 5H), 2.74-2.63 (m, 1H), 2.01-1.93 (m, 1H); MS (ESI): m/z=250 (M−18, positive); HPLC purity: 96.01% (MaxPlot 200-400 nm), 95.07% (220 nm).

3-Aminomethyl-7-(3-hydroxy-propoxy)-3H-benzo[c][1,2]oxaborol-1-ol hydrochloride (A46)

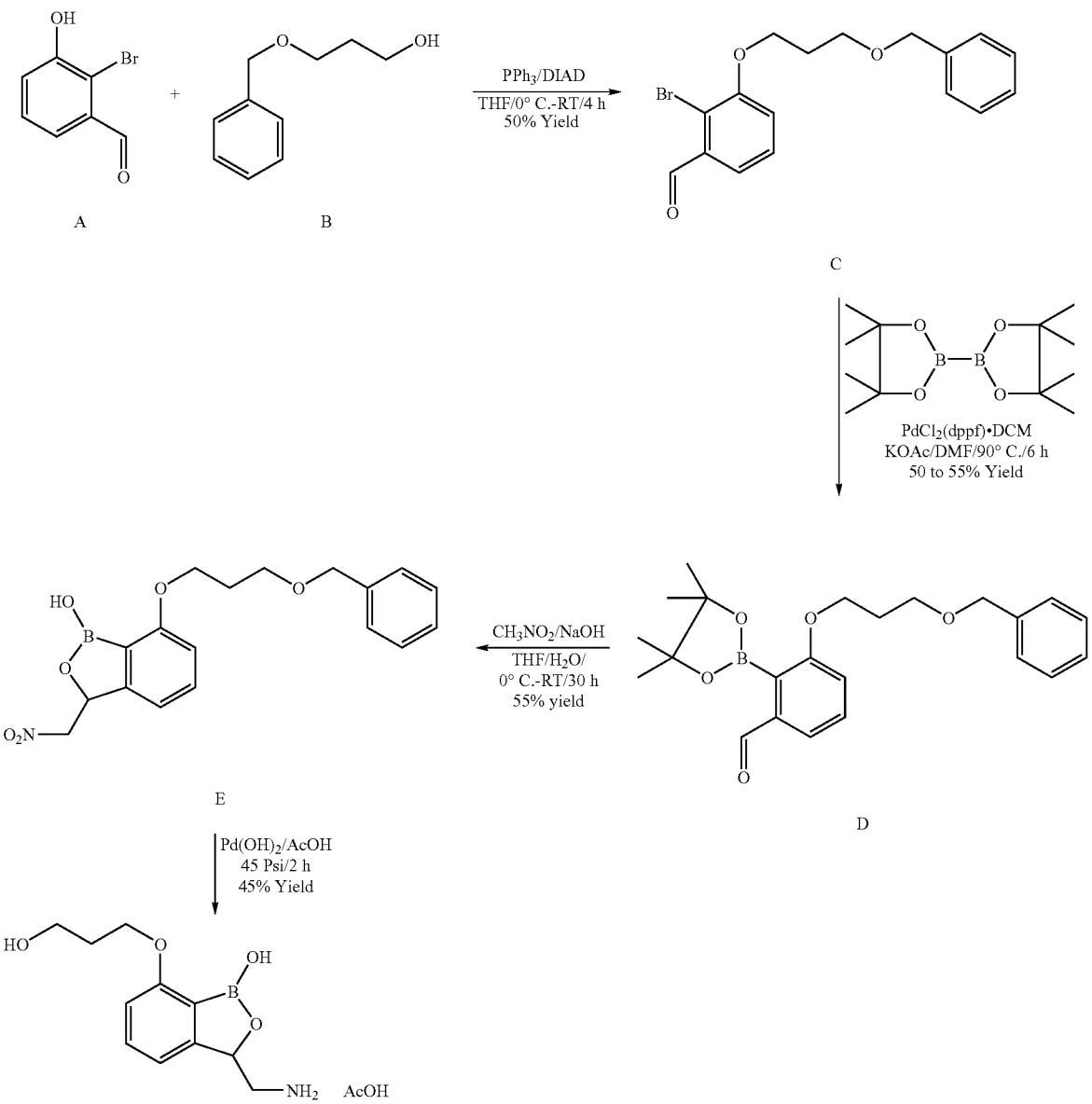

Synthesis of 3-(3-Benzyloxy-propoxy)-2-bromo-benzaldehyde (C)

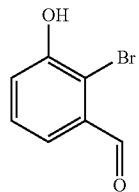

A

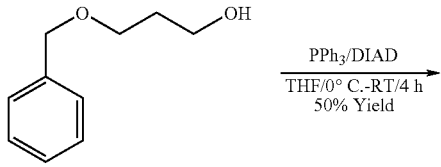

B

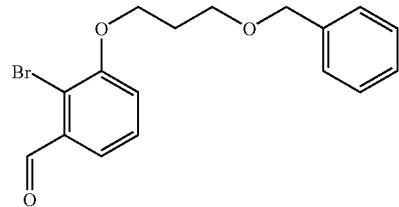

C

To a 5° C. solution of compound A (15.0 g, 0.075 mol), B (12.0 ml, 0.075 mol) and triphenylphosphine (19.6 g, 0.075 mol) in 200 ml of anhydrous THF was added DIAD (14.8 ml, 0.075 mol) drop by drop over a period of 15 minutes. The resulting solution was warmed to room temperature over a period of 5 h and the solvent was evaporated in vacuo. The residue was dissolved in 150 ml of EtOAc and the organic layer washed with water, brine and dried over $Na_2SO_4$, filtered and concentrated in vacuo. The product was purified by silica gel column chromatography (gradient of hexane to 5% EtOAc/hexane) generating 13.0 g (50% yield) of C [3-(3-benzyloxy-propoxy)-2-bromo-benzaldehyde].

$^1$H NMR (400 MHz, DMSO-d$_6$) δ (ppm) 10.41 (s, 1H), 7.49 (d, J=7.2 Hz, 1H), 7.32-7.25 (m, 6H), 7.08 (d, J=8.0 Hz, 1H), 4.54 (s, 2H), 4.16 (t, J=6.0 Hz, 2H), 3.74 (t, J=5.8 Hz, 2H), 2.19-2.14 (m, 2H).

3-(3-Benzyloxy-propoxy)-2-(4,4,5,5-tetramethyl-[1,3,2]dioxaborolan-2-yl)-benzaldehyde (D)

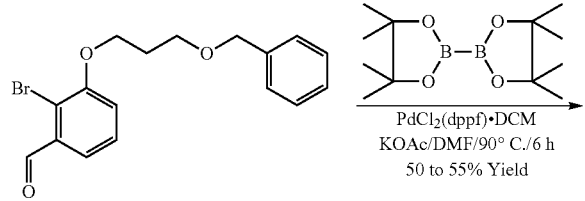

C

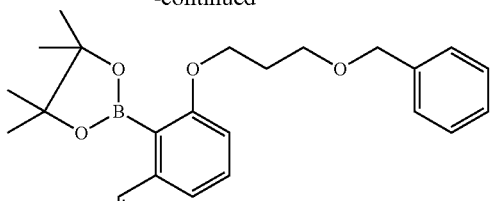

D

Compound C (8.9 g, 0.025 mol), KOAc (7.5 g, 0.076 mol), and bis(pinacolato)diboron (12.9 g, 0.051 mol) were dissolved in 50 ml of dry DMF and degassed for 30 minutes. To this was added PdCl$_2$(dppf).DCM (0.56 g, 0.76 mmol) and the contents were again degassed for 10 minutes and then heated to 90° C. for 4 h. An additional quantity of PdCl$_2$(dppf).DCM (0.2 g, 0.27 mmol) was added and heating was continued for an additional 2 h. The reaction was cooled to RT, filtered through celite and the solvent evaporated in vacuo. The residue was dissolved in DCM, washed with brine and the organic layer dried over Na$_2$SO$_4$, filtered and concentrated in vacuo. The product was purified by silica gel column chromatography (gradient of hexane to 5% EtOAc/hexane) provided 5.4 g (53% yield) of D [3-(3-benzyloxy-propoxy)-2-(4,4,5,5-tetramethyl-[1,3,2]dioxaborolan-2-yl)-benzaldehyde].

$^1$H NMR (400 MHz, DMSO-d$_6$) δ (ppm) 9.91 (s, 1H), 7.43 (t, J=7.8 Hz, 1H), 7.36 (d, J=7.2 Hz, 1H), 7.32-7.27 (m, 5H), 7.06 (d, J=8.4 Hz, 1H), 4.49 (s, 2H), 4.08 (t, J=6.0 Hz, 2H), 3.67 (t, J=6.2 Hz, 2H), 2.11-2.08 (m, 2H), 1.44 (s, 12H). ESI+MS m/z, 397 (M+H)$^+$.

7-(3-Benzyloxy-propoxy)-3-nitromethyl-3H-benzo[c][1,2]oxaborol-1-ol (E)

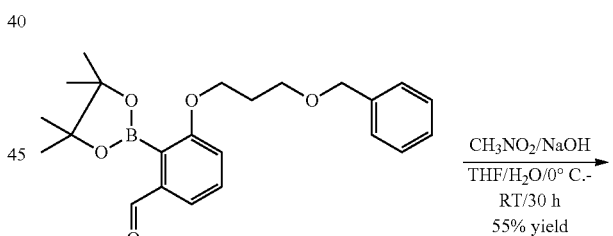

D

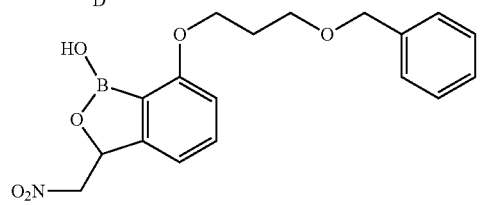

E

To an ice cold solution of NaOH (0.68 g, 0.017 mol) in 10 ml of water was added a solution of compound D (6.8 g, 0.017 mol) dissolved in 5 ml of THF. After 15 minutes, nitromethane (0.93 ml, 0.017 mol) was added drop by drop and the content stirred at RT overnight. The THF was evaporated under reduced pressure and the contents acidified to pH-3 with 2N HCl. The aqueous layer was extracted with EtOAc several times, and the combined ethyl acetate layer was washed with brine, dried over Na$_2$SO$_4$, filtered and concentrated in vacuo. The product was purified by silica gel column chromatography (gradient of 10% EtOAc/hexane to 30% EtOAc/hexane) provided 3.7 g (55% yield) of E [7-(3-Benzyloxy-propoxy)-3-nitromethyl-3H-benzo[c][1,2]oxaborol-1-ol] 3.7 g.

$^1$H NMR (400 MHz, DMSO-d$_6$+D$_2$O (0.01 ml)) δ (ppm) 7.49 (t, J=7.8 Hz, 1H), 7.34-7.25 (m, 5H), 7.08 (d, J=7.6 Hz, 1H), 6.92 (d, J=8.0 Hz, 1H), 5.71 (d, J=6.4 Hz, 1H), 5.23 (dd, J=13.2, 2.4 Hz, 1H), 4.58-4.53 (m, 1H), 4.47 (s, 2H), 4.12 (t, J=6.2 Hz, 2H), 3.63 (t, J=6.0 Hz, 2H), 2.04-2.00 (m, 2H). ESI-MS m/z, 356 [M−H]$^-$. HPLC purity: 97.12% (MaxPlot 200-400 nm).

3-Aminomethyl-7-(3-hydroxy-propoxy)-3H-benzo[c][1,2]oxaborol-1-ol (A46)

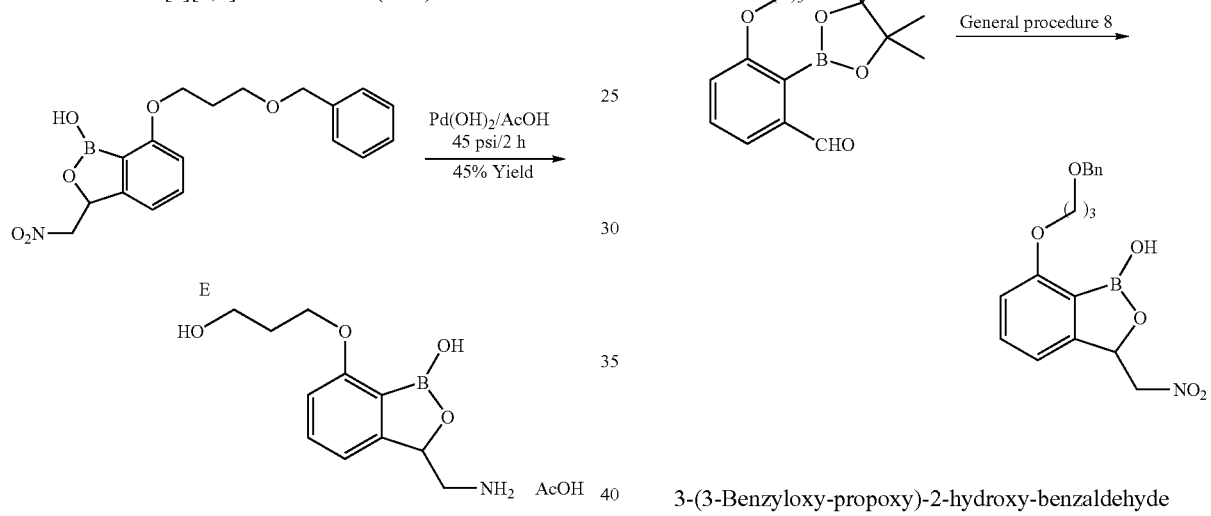

Compound E (6.0 g, 0.016 mol) was dissolved in 50 ml of glacial acetic acid and to it was added Pd(OH)$_2$ on Carbon (20% metal content, 50% weight-wet) (5.2 g) and the content set for hydrogenation in a Parr shaker at 45 psi for 2 h. The reaction was checked for completion and the contents were filtered through Celite. The solvent was evaporated under reduced pressure at ambient temperature to yield a gummy material. To this three times was added 15 ml of dry toluene and evaporated yielding a fluffy solid. Purification was accomplished by preparative HPLC (C18 column, using acetonitrile and 0.1% AcOH/water solution) provided 1.5 g (45% yield) of compound A46 [3-Aminomethyl-7-(3-hydroxy-propoxy)-3H-benzo[c][1,2]oxaborol-1-ol] with 0.33 mol % acetic acid (by HNMR).

$^1$H NMR (400 MHz, DMSO-d$_6$+D$_2$O (0.01 ml)) δ (ppm) 7.52 (t, J=7.8 Hz, 1H), 7.05 (d, J=7.2 Hz, 1H), 6.95 (d, J=8.4 Hz, 1H), 5.29 (dd, J=9.2, 2.4, 1H), 4.12 (t, J=6.2 Hz, 2H), 3.62 (t, J=6.2 Hz, 2H), 3.48 (dd, J=13.2, 2.8 Hz, 1H), 2.80-2.74 (m, 1H), 1.92 (t, J=6.2 Hz, 2H). ESI+MS m/z, 238 [M+H]$^+$. HPLC purity: 95.67% (MaxPlot 200-400 nm) and 96.22% (220 single wavelength).

7-(3-Benzyloxy-propoxy)-3-nitromethyl-3H-benzo[c][1,2]oxaborol-1-ol (A47)

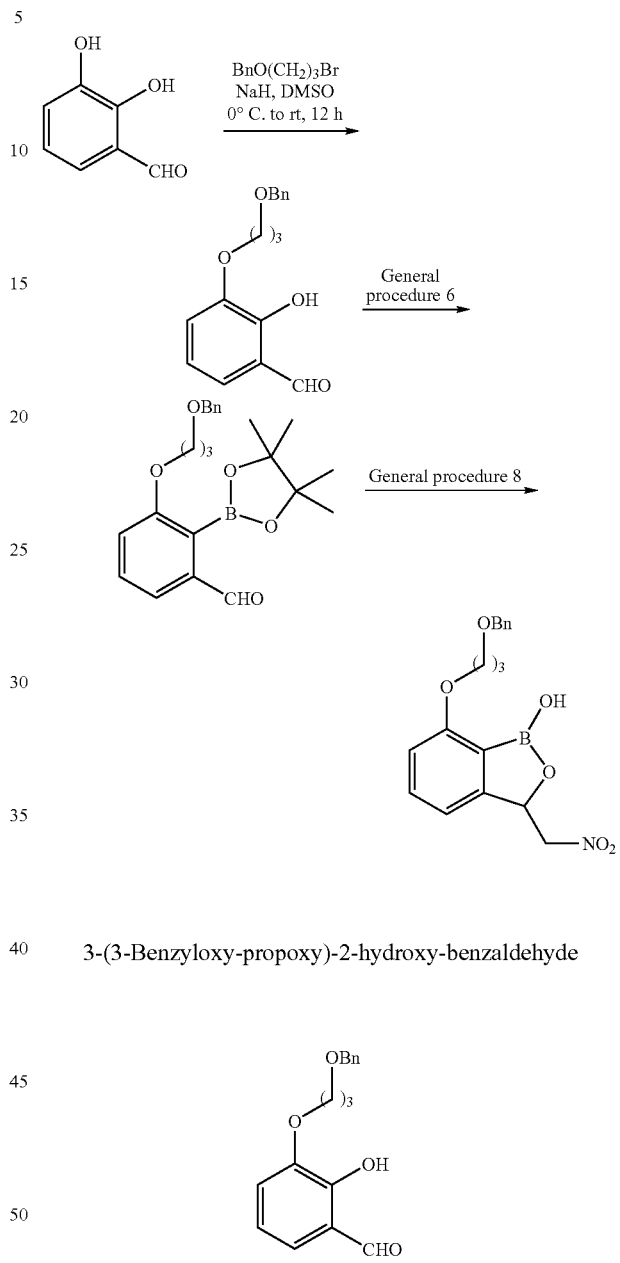

3-(3-Benzyloxy-propoxy)-2-hydroxy-benzaldehyde

NaH (2.95 g, 72.4 mmol) was added to an ice-cold solution of 2,3-dihydroxybenzaldehyde (5.0 g, 36 mmol) in anhydrous DMSO (45 mL). Benzyl-3-bromopropyl ether (6.45 mL, 36.2 mmol) was then added and the mixture was stirred at rt for 12 h. The mixture was neutralized using 1 N HCl and then extracted with EtOAc. The organic fraction was washed with H$_2$O and concentrated in vacuo. The residue was purified by flash chromatography (8:2 hexane/EtOAc) to give the title compound as a brown oil: yield 8.40 g (81%).

$^1$H NMR (400 MHz, CDCl$_3$) δ (ppm): 9.93 (s, 1H), 7.36-7.23 (m, 6H), 7.20-7.16 (m, 2H), 6.98-6.91 (m, 1H), 4.53 (s, 2H), 4.19 (t, J=6.2 Hz, 2H), 3.70 (t, J=6.1 Hz, 2H), 2.19-2.16 (m, 2H).

3-(3-Benzyloxy-propoxy)-2-(4,4,5,5-tetramethyl-[/, 3, 2]dioxaborolan-2-yl)-benzaldehyde

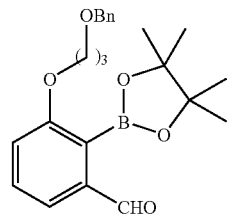

General procedure 6: 3-(3-benzyloxy-propoxy)-2-hydroxy-benzaldehyde (7.6 g, 26 mmol), pyridine (3.42 mL, 42.5 mmol), Tf$_2$O (4.60 mL, 27.9 mmol), and CH$_2$Cl$_2$ (200 mL): yield 8.60 g (77%).

$^1$H NMR (400 MHz, CDCl$_3$) δ (ppm): 10.23 (s, 1H), 7.54-7.47 (m, 1H), 7.43 (t, J=8.0 Hz, 1H), 7.36-7.22 (m, 6H), 4.52 (s, 2H), 4.23 (t, J=6.3 Hz, 2H), 3.71 (t, J=6.1 Hz, 2H), 2.21-2.17 (m, 2H).

General procedure 5: trifluoro-methanesulfonic acid 2-(3-benzyloxy-propoxy)-6-formyl-phenyl ester (8.0 g, 19 mmol), B$_2$pin$_2$ (9.71 g, 38.2 mmol), KOAc (5.71 g, 57.4 mmol), PdCl$_2$(dppf).CH$_2$Cl$_2$ (1.39 g, 1.89 mmol), and anhydrous dioxane (160 mL). Purification: flash chromatography (9:1 hexane/EtOAc): yield 4.80 g (43%)-some pinacol contamination, used without further purification.

$^1$H NMR (400 MHz, CDCl$_3$) δ (ppm): 9.93 (s, 1H), 7.46 (t, J=7.8 Hz, 1H), 7.41-7.36 (m, 1H), 7.35-7.24 (m, 5H), 7.08 (d, J=7.8 Hz, 1H), 4.50 (s, 2H), 4.10 (t, J=6.3 Hz, 2H), 3.67 (t, J=6.3 Hz, 2H), 2.11 (quin, J=6.2 Hz, 2H), 1.43 (s, 12H).

7-(3-Benzyloxy-propoxy)-3-nitromethyl-3H-benzo[c][1,2]oxaborol-1-ol (A47)

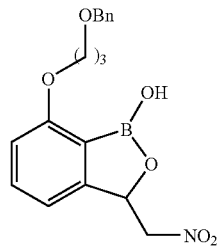

General procedure 8: 3-(3-benzyloxy-propoxy)-2-(4,4,5,5-tetramethyl-[1,3,2]dioxaborolan-2-yl)-benzaldehyde (36 g, 91 mmol), MeNO$_2$ (16.6 g, 273 mmol), NaOH (3.64 g, 83 mmol), H$_2$O (180 mL), and THF (50 mL). Purification: flash chromatography (1:1 hexane/EtOAc). A47 was isolated as a light yellow oil: yield 15.9 g (50%).

$^1$H NMR (400 MHz, DMSO-d$_6$) δ (ppm): 9.05 (s, 1H), 7.44 (t, J=7.8 Hz, 1H), 7.35-7.20 (m, 5H), 7.06 (d, J=7.4 Hz, 1H), 6.88 (d, J=8.2 Hz, 1H), 5.70 (dd, J=9.4, 2.3 Hz, 1H), 5.29 (dd, J=13.7, 2.7 Hz, 1H), 4.53 (dd, J=13.3, 9.4 Hz, 1H), 4.45 (s, 2H), 4.11 (t, J=6.1 Hz, 2H), 3.60 (t, J=6.3 Hz, 2H), 2.04-1.91 (m, 2H); MS (ESI): m/z=356 (M−1, negative); HPLC purity: 99.35% (MaxPlot 200-400 nm), 97.32% (220 nm).

Alternative synthesis of 3-Aminomethyl-7-(3-hydroxy-propoxy)-3H-benzo[c][1,2]oxaborol-1-ol hydrochloride (A46)

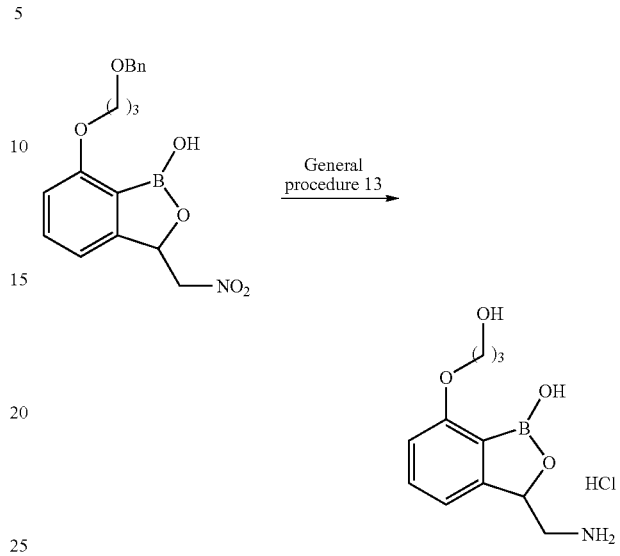

General procedure 13: A47 (0.50 g, 1.4 mmol), 20% Pd(OH)$_2$/C (0.5 g, 1:1 w/w), AcOH (20 mL), and H$_2$O (0.24 mL). The filtrate was concentrated and treated with 4 N HCl to give the title compound as a colorless solid: yield 0.22 g (47%).

$^1$H NMR (400 MHz, DMSO-d$_6$) δ (ppm): 7.42 (t, J=7.8 Hz, 1H), 6.97-6.90 (m, 1H), 6.86 (d, J=8.2 Hz, 1H), 5.20 (dd, J=9.2, 2.5 Hz, 1H), 4.02 (t, J=6.2 Hz, 2H), 3.54 (t, J=6.2 Hz, 2H), 3.40 (dd, J=13.3, 2.7 Hz, 1H), 2.68 (dd, J=13.1, 9.2 Hz, 1H), 1.88-1.78 (m, 2H); MS (ESI): m/z=238 (M+1, positive).

[1-Hydroxy-7-(3-hydroxy-propoxy)-1,3-dihydro-benzo[c][1,2]oxaborol-3-ylmethyl]-carbamic acid tert-butyl ester (A48)

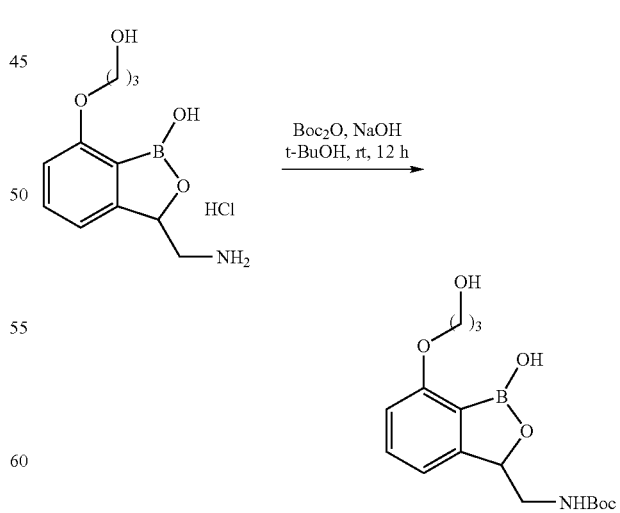

A solution of NaOH (0.13 g, 3.2 mmol) in H$_2$O (3.0 mL) was added to a solution of A46 (0.40 g, 1.5 mmol) in tert-butanol (2.0 mL) at 5-10° C. (bath temp) and then stirred for 20 min. Boc$_2$O (0.31 g, 1.4 mmol) was added at 5-10° C. (bath temp) and then the mixture was allowed to warm to rt and stirred for 5 h. The reaction mixture was diluted with brine (50 mL) and extracted with CH$_2$Cl$_2$ (2×50 mL). The organic fractions were combined, washed with H$_2$O (2×50 mL) then brine (50 mL), dried (Na$_2$SO$_4$), and concentrated in vacuo. The brown sticky residue was purified by reverse phase preparative HPLC (AcOH) to give (after lyophilization) A48 as a white lyophilizate: yield 151 mg (65%).

$^1$H NMR (400 MHz, DMSO-d$_6$) δ (ppm): 7.47-7.26 (m, 1H), 6.88 (d, J=7.4 Hz, 1H), 6.79 (d, J=7.8 Hz, 1H), 5.00 (bs, 1H), 4.01 (t, J=6.1 Hz, 2H), 3.55 (t, J=6.1 Hz, 2H), 3.65-3.47 (m, 2H), 3.38 (d, J=13.7 Hz, 1H), 3.02 (dd, J=13.1, 6.1 Hz, 1H), 1.24 (s, 9H); MS (ESI): m/z=336 (M+1, positive); HPLC purity: 98.48% (MaxPlot 200-400 nm), 98.01% (220 nm).

(S)-3-Aminomethyl-7-(3-hydroxy-propoxy)-3H-benzo[c][1,2]oxaborol-1-ol hydrochloride (A49)

(3-Benzyloxy)-1-bromo-propane (2)

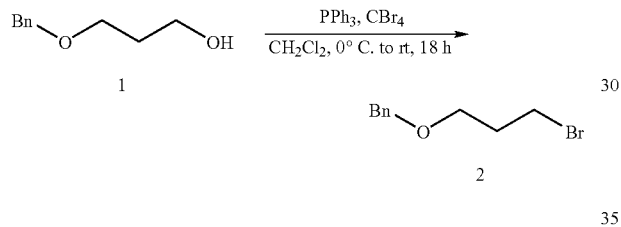

A solution of 1 (160 g, 962.58 mmol) and triphenylphosphine (277.72 g, 1.1 eq, 1058.83 mmol) was dissolved in dichloromethane (800 mL) and cooled to 0° C. (ice/water). A solution of carbon tetrabromide (351.16 g, 1.1 eq, 1058.83 mmol) in dichloromethane (200 mL) was added dropwise and the mixture was left to stir at rt for 18 h. The dichloromethane solvent was evaporated to obtain a white solid. The solid was treated with an excess of hexanes, stirred for 1 h, filtered off and the solvent was evaporated to yield a crude product. The crude product was purified by silica gel column chromatography using 5-10% ethyl acetate and hexane to obtain 2 (199 g, 91%) as a colorless liquid.

3-(3-Benzyloxy-propoxy)-2-hydroxy-benzaldehyde (4)

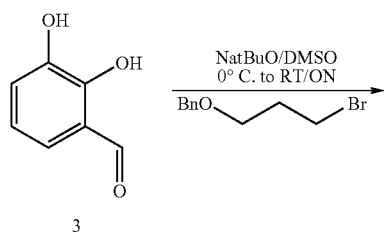

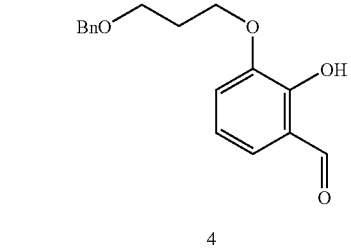

To a solution of aldehyde 3 (27.47 g, 1 eq, 198.88 mmol) in 0.5 L of anhydrous DMSO was added sodium tertiary-butoxide (42.3 g, 2.2 eq, 440.31 mmol) portionwise. The reaction mixture was stirred at rt for 30 minutes. A brown color solution was formed. The reaction mixture was cooled to 0° C. and added bromide (56 g, 1.2 eq, 244.41 mmol) dropwise. The mixture was stirred at rt O/N. 90% of aldehyde 3 was converted to product. The reaction mixture was acidified to pH-3 and then extracted into EtOAc and washed with water. The organic layer was concentrated, the product was purified on silica gel column (EtOAc:hexane 80:20), to yield as compound 4 (48 g, 84.31% yield) (viscous oil).

Trifluoro-methanesulfonic acid 2-(3-benzyloxy-propoxy)-6-formyl-phenyl ester (5)

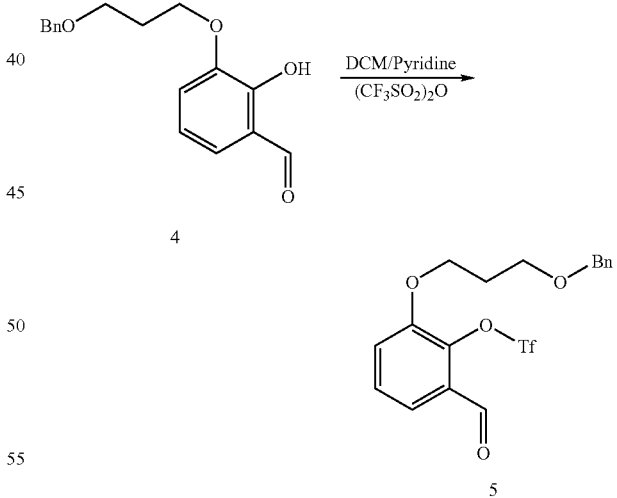

To an ice cold solution of 4 (48 g, 1.0 eq, 167.72 mmol) in 200 mL of dry DCM was added pyridine (22 mL, 1.62 eq, 272.11 mmol). To the reaction mixture trifluoromethanesulfonic anhydride (33 mL, 1.16 eq, 196.14 mol) was added drop by drop. The mixture was stirred for 3 h at 0° C. The mixture was quenched with 500 mL of 1N HCl. The compound was then extracted into DCM (300 mL) and passed through a small silica gel column and concentrated to give compound 5 (57 g, 82% yield) as a pale yellow thick oil.

3-(3-Benzyloxy-propoxy)-2-(4,4,5,5-tetramethyl-[1,3,2]dioxaborolan-2-yl)-benzaldehyde (6)

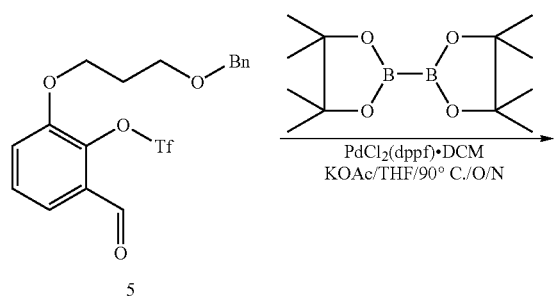

Compound 5 (65 g, 1.0 eq, 155.5 mmol), bis(pinacolato)diboron (86.9 g, 2.2 eq, 342.11 mmol), KOAc (45.7 g, 3.0 eq, 466.5 mmol) were mixed together and 600 mL of dioxane was added. The mixture was degassed with N₂ for 30 minutes and PdCl₂(dppf).DCM (5.7 g, 0.05 eq, 7.77 mmol) was added. The resulting slurry was heated to 90° C. overnight. The solvent was evaporated, EtOAc was added and then filtered through a pad of Celite. The organic layer was then washed with water (2×150 mL) and the solvent was evaporated. Column chromatography using 15% EtOAc/hexanes gave compound 6 (37.1 g, 61% yield).

7-(3-Benzyloxy-propoxy)-3-nitromethyl-3H-benzo[c][1,2]oxaborol-1-ol (A47)

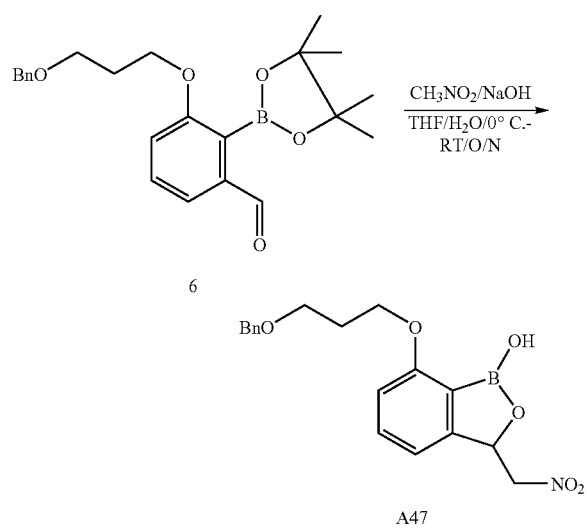

A solution of compound 6 (36 g, 1.0 eq, 90.91 mmol) in 50 mL of THF was cooled to 0° C. Nitromethane (16.6 g, 3.0 eq, 272.72 mmol) was added, followed by an aqueous solution of NaOH (3.64 g in 180 mL of H₂O). The reaction mixture was stirred at room temperature overnight. The starting material disappeared. The cyclization was afforded by adding 1N HCl until the solution was acidified and then extracted into EtOAc. The EtOAc was evaporated and the mixture was triturated with water and decanted. Column chromatography using 50% EtOAc/hexanes gave compound A47 (15.9 g, 50% yield).

(R) and (S) 7-(3-Benzyloxy-propoxy)-3-nitromethyl-3H-benzo[c][1,2]oxaborol-1-ol

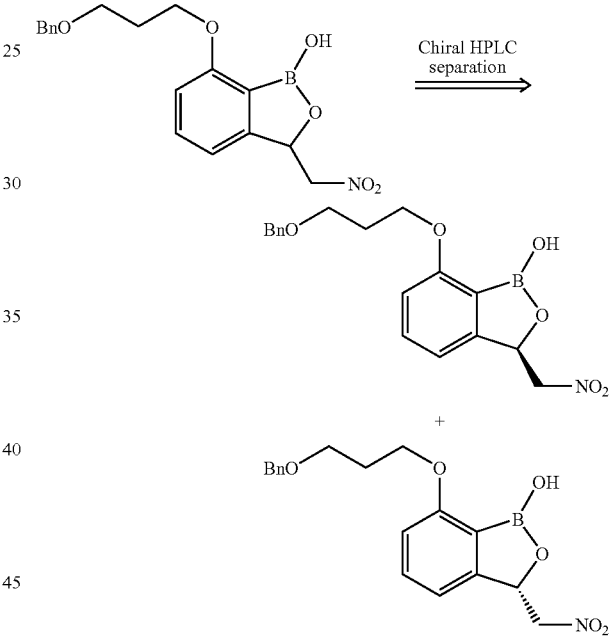

4.82 g of (A47) was resolved via chiral HPLC using CHIRALPAK ADH column and CO₂:methanol (86:14) as eluent (25° C. UV detection was monitored at 230 nm. Two peaks, (S)-7-(3-Benzyloxy-propoxy)-3-nitromethyl-3H-benzo[c][1,2]oxaborol-1-ol and (R)-7-(3-Benzyloxy-propoxy)-3-nitromethyl-3H-benzo[c][1,2]oxaborol-1-ol were collected and evaporated to yellow oils. Analysis of the pooled fractions using a CHIRALPAK ADH 4.6 mm ID×250 mm analytical column and the same mobile phase provided the (S) enantiomer [0.7 g (29% yield)] with a retention time of 6.11 min and a 98.2% ee. The (R) enantiomer [1.0 g (41% yield)] had a retention time of 8.86 min and a 99.6% ee.

(S)-3-Aminomethyl-7-(3-hydroxy-propoxy)-3H-benzo[c][1,2]oxaborol-1-ol (A49)

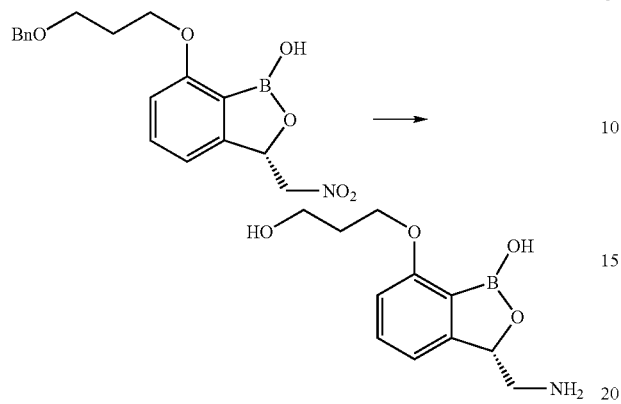

(A47) (550 mg, 1.57 mmol) was dissolved in 15 mL of glacial acetic acid. 280 mg of 20 wt % palladium hydroxide on carbon (Pearlman's catalyst) was added and the reaction mixture was flushed with hydrogen 3× and hydrogenated at 55 psi for 3.5 hours. The mixture was filtered through Celite to remove catalyst and rinsed with methanol. Acetic acid was evaporated to obtain the crude product. HPLC purification gave 128 mg of the acetate salt of (A49). The acetate salt was treated with 10 mL of 2N HCl and stirred for 3 hours. The material was lyophilized overnight to obtain 93 mg of the hydrochloride salt of (A49) (Yield 22%).

$^1$H NMR (400 MHz, DMSO-d$_6$) δ (ppm): 7.48 (t, J=7.8 Hz, 1H), 7.05 (d, J=7.4 Hz, 1H), 6.92 (d, J=8.2 Hz, 1H), 5.27 (d, J=9.4 Hz, 1H), 4.11 (t, J=6.3 Hz, 2H), 3.58 (t, J=5.9 Hz, 2H), 2.82 (dd, J=13.3, 9.0 Hz, 1H), 1.95-1.83 (m, 2H); MS (ESI): m/z=238 (M+1, positive); HPLC purity: 98.74% (MaxPlot 200-400 nm), 98.38% (220 nm); Chiral HPLC=95.14% ee.

(R)-3-Aminomethyl-7-(3-hydroxy-propoxy)-3H-benzo[c][1,2]oxaborol-1-ol (A50)

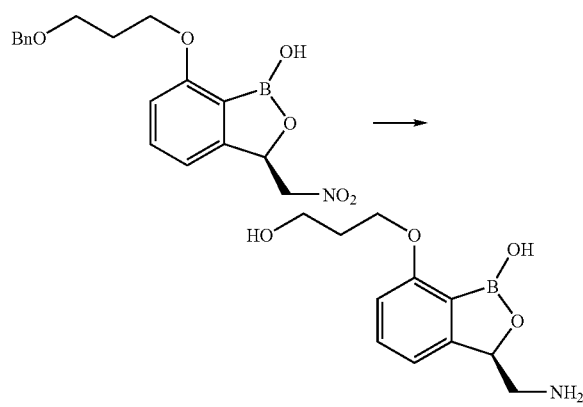

(R)-7-(3-benzyloxy-propoxy)-3-nitromethyl-3H-benzo[c][1,2]oxaborol-1-ol (0.70 g, 2.0 mmol) was dissolved in 20 mL of glacial acetic acid. 350 mg of 20 wt % palladium hydroxide on carbon (Pearlman's catalyst) was added and the reaction mixture was flushed with hydrogen 3× and hydrogenated at 55 psi for 3.5 hours. The mixture was filtered through Celite to remove catalyst and rinsed with methanol. Acetic acid was evaporated to obtain the crude product. HPLC purification gave 65 mg of pure compound. After purification, this acetate salt was combined with material from another reaction. This product was treated with 2N HCl (10 mL) and stirred for 3 h at rt. The material was lyophilized overnight to obtain 74 mg of the hydrochloride salt of (A50) (Yield 14%).

$^1$H NMR (400 MHz, DMSO-d$_6$) δ (ppm): 7.48 (t, J=7.8 Hz, 1H), 7.05 (d, J=7.4 Hz, 1H), 6.92 (d, J=8.2 Hz, 1H), 5.27 (d, J=9.4 Hz, 1H), 4.11 (t, J=6.3 Hz, 2H), 3.58 (t, J=5.9 Hz, 2H), 2.83 (dd, J=13.3, 8.6 Hz, 1H), 1.94-1.82 (m, 2H); MS (ESI): m/z=238 (M+1, positive); HPLC purity: 99.12% (MaxPlot 200-400 nm), 98.74% (220 nm); Chiral HPLC=98.82% ee.

7-Ethoxy-3-nitromethyl-3H-benzo[c][1,2]oxaborol-1-ol (A51)

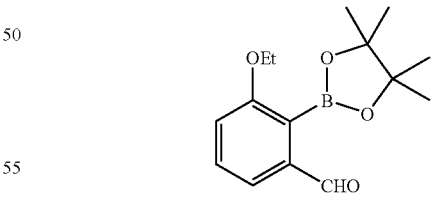

3-Ethoxy-2-(4,4,5,5-tetramethyl-[/, 3, 2]dioxaborolan-2-yl)-benzaldehyde

General procedure 5: trifluoro-methanesulfonic acid 2-ethoxy-6-formyl-phenyl ester (2.0 g, 6.7 mmol), B$_2$pin$_2$ (5.11 g, 20.1 mmol), PdCl$_2$(dppf).CH$_2$Cl$_2$ (0.98 g, 1.3 mmol), KOAc (1.97 g, 20.1 mmol), and dioxane (100 mL). Purification: flash chromatography (10% EtOAc/hexane): yield 1.05 g (57%).

$^1$H NMR (400 MHz, CDCl$_3$) δ (ppm): 9.93 (s, 1H), 7.46 (t, J=7.8 Hz, 1H), 7.40-7.36 (m, 1H), 7.07 (d, J=7.8 Hz, 1H), 4.05 (q, J=7.0 Hz, 2H), 1.46 (s, 12H), 1.42 (t, 3H)

231

7-Ethoxy-3-nitromethyl-3H-benzo[c][1,2]oxaborol-1-ol (A51)

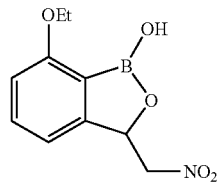 [SMILES: CCOc1cccc2c1B(O)OC2C[N+](=O)[O-]]

General procedure 9: 3-ethoxy-2-(4,4,5,5-tetramethyl-[1,3,2]dioxaborolan-2-yl)-benzaldehyde (1.05 g, 3.8 mmol), MeNO$_2$ (0.26 g, 4.2 mmol), 0.5% NaOH (2 mmol), and CTAC1 (8 mg). The reaction was stirred at rt O/N. Brine (20 mL) was added and the solution was extracted with EtOAc (3×20 mL). The combined organic fractions were washed with 1 M HCl (3×10 mL). The organic layer was dried, filtered, and concentrated in vacuo to give A51: yield 0.6 g (67%).

$^1$H NMR (400 MHz, DMSO-d$_6$) δ (ppm): 9.08 (s, 1H), 7.45 (t, J=7.6 Hz, 1H), 7.07 (d, J=7.4 Hz, 1H), 6.89 (d, J=8.2 Hz, 1H), 5.71 (dd, J=9.4, 2.7 Hz, 1H), 5.31 (dd, J=13.3, 2.7 Hz, 1H), 4.55 (dd, J=13.7, 9.4 Hz, 1H), 4.16-4.05 (m, 2H), 1.33 (t, J=7.0 Hz, 3H); MS (ESI) m/z=236 (M+1, positive); HPLC: 99.14% (MaxPlot), 98.05% (220 nm).

3-Aminomethyl-7-ethoxy-3H-benzo[c][1,2]oxaborol-1-ol hydrochloride (A52)

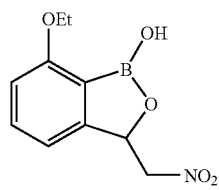

General procedure 13

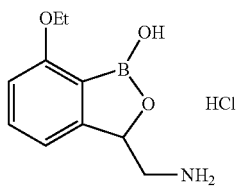

General procedure 13: A51 (1.0 g, 4.2 mmol) Pd(OH)$_2$ (0.3 g), and AcOH (20 mL). Purification: preparative HPLC: yield 103 mg (10%).

$^1$H NMR (400 MHz, DMSO-d$_6$) δ (ppm): 8.86 (bs, 1H), 7.59 (bs, 1H), 7.46 (t, J=7.8 Hz, 1H), 7.03 (d, J=7.4 Hz, 1H), 6.89 (d, J=8.2 Hz, 1H), 5.23 (dd, J=8.2, 2.7 Hz, 1H), 4.14-4.07 (m, 2H), 2.80 (dd, J=13.3, 8.6 Hz, 1H), 1.34 (t, J=6.8 Hz, 3H); MS (ESI) m/z=208 (M+1, positive); HPLC: 97.28% (MaxPlot), 97.88% (220 nm).

232

3-Aminomethyl-7-methoxy-3H-benzo[c][1,2]oxaborol-1-ol hydrochloride (A53)

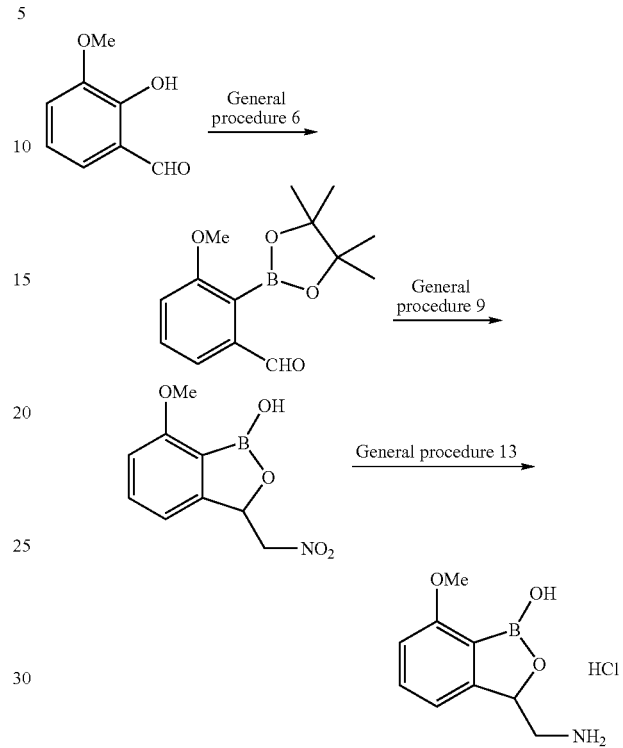

3-Methoxy-2-(4,4,5,5-tetramethyl-[/, 3,2]dioxaborolan-2-yl)-benzaldehyde

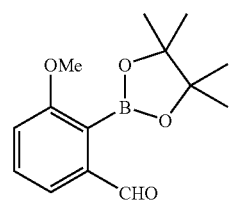 [SMILES: COc1cccc(C=O)c1B1OC(C)(C)C(C)(C)O1]

General procedure 6: 2-hydroxy-3-methoxy-benzaldehyde (20 g, 0.13 mol), Tf$_2$O (33.2 mL, 0.20 mol), pyridine (21 mL, 0.26 mol), and CH$_2$Cl$_2$ (300 mL). Purification: flash chromatography (2.5% EtOAc/hexane): yield 10.3 g (28%).

$^1$HNMR (400 MHz, CDCl$_3$) δ (ppm): 10.26 (s, 1H), 7.56-7.51 (m, 1H), 7.47 (t, J=7.6 Hz, 1H), 7.31 (dd, J=8.2, 1.6 Hz, 1H), 3.97 (s, 3H)

General procedure 5: trifluoro-methanesulfonic acid 2-formyl-6-methoxy-phenyl ester (5.75 g, 20.2 mmol), B$_2$pin$_2$ (15.4 g, 60.7 mmol), PdCl$_2$(dppf).CH$_2$Cl$_2$ (2.96 g, 4.05 mmol), KOAc (5.96 g, 60.7 mmol), and 1,4-dioxane (200 mL). Purification: flash chromatography (10% EtOAc/hexane): yield 4.5 g (85%).

$^1$H NMR (400 MHz, CDCl$_3$) δ (ppm): 9.97 (s, 1H), 7.48 (t, J=7.6 Hz, 1H), 7.40 (d, J=7.6 Hz, 1H), 7.08 (d, J=7.9 Hz, 1H), 3.92 (s, 3H), 1.42 (s, 12H).

233
7-Methoxy-3-nitromethyl-3H-benzo[c][1,2]oxaborol-1-ol

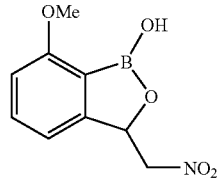 [SMILES: COc1cccc2c1B(O)OC2C[N+](=O)[O-]]

General procedure 9: 3-methoxy-2-(4,4,5,5-tetramethyl-[1,3,2]dioxaborolan-2-yl)-benzaldehyde (4.5 g, 17 mmol), MeNO$_2$ (1.36 g, 22.3 mmol), 0.5% NaOH (0.2 mmol), and CTACl (8 mg). The reaction was stirred at rt O/N and then brine (20 mL) was added. The solution was extracted with EtOAc (3×20 mL). The combined organic layer was washed with 1 M HCl (3×10 mL). The organic layer was dried, filtered, and concentrated in vacuo to give the title compound: yield 2.5 g (61%).

$^1$H NMR (400 MHz, CDCl$_3$) δ (ppm): 7.51 (t, J=8.0 Hz, 1H), 6.91 (d, J=7.8 Hz, 1H), 6.85 (d, J=8.2 Hz, 1H), 5.86 (dd, J=9.8, 3.1 Hz, 1H), 5.10 (s, 1H), 4.75 (dd, J=13.5, 3.3 Hz, 1H), 4.46 (dd, J=12.9, 8.9 Hz, 1H), 3.9 (s, 3H).

3-Aminomethyl-7-methoxy-3H-benzo[c][1,2]oxaborol-1-ol hydrochloride (A53)

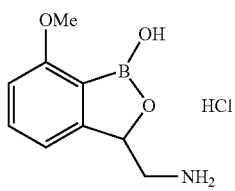 [SMILES: COc1cccc2c1B(O)OC2CN ; Cl]

General procedure 13: 7-methoxy-3-nitromethyl-3H-benzo[c][1,2]oxaborol-1-ol (1.0 g, 4.5 mmol), Pd(OH)$_2$ (0.3 g), and AcOH (20 mL). Purification: preparative HPLC. A53 isolated as a white solid: yield 86 mg (10%).

$^1$H NMR (400 MHz, DMSO-d$_6$) δ (ppm): 8.99 (bs, 1H), 8.12 (bs, 1H), 7.49 (t, 1H), 7.08 (d, 1H), 6.92 (d, 1H), 5.23 (dd, 1H), 3.80 (s, 3H), 3.50-3.39 (m, 1H), 2.85-2.75 (m, 1H); MS (ESI) m/z=194 (M+1, positive); HPLC: 95.13% (220 nm), 98.79% (MaxPlot).

3-(1-Amino-ethyl)-3H-benzo[c][1,2]oxaborol-1-ol (A54)

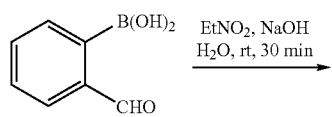

234

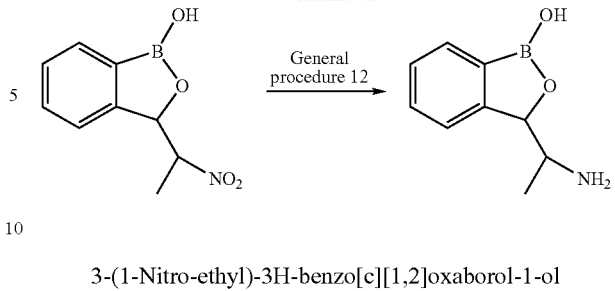

3-(1-Nitro-ethyl)-3H-benzo[c][1,2]oxaborol-1-ol

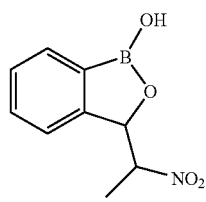

A solution of NaOH (1.6 g, 41 mmol) in H$_2$O (20 mL) was added to 2-formyl phenylboronic acid (5.1 g, 34 mmol) at rt. The mixture was stirred for 15 min then nitroethane (2.9 mL, 41 mmol) was added dropwise. The mixture was stirred for 30 min and then the clear reaction solution was acidified with 2 N HCl and EtOAc was added. The organic layer was separated, washed with H$_2$O then brine, dried (Na$_2$SO$_4$), and concentrated in vacuo. Purification by flash chromatography (2:1 hexane/EtOAc) gave the title compound as a colorless oil: yield 6.72 g (quantitative).

$^1$H NMR (400 MHz, CDCl$_3$) δ (ppm): 7.78 (dd, J=7.2, 2.9 Hz, 1H), 7.58-7.49 (m, 1H), 7.45 (t, J=7.2 Hz, 1H), 7.33 (dd, J=18.2, 7.6 Hz, 1H), 5.89 and 5.60 (d, J=6.6 Hz and J=3.5 Hz, 1H), 5.14 and 5.11 (s, 1H), 4.83 and 4.70 (t, J=6.8 Hz, 1H), 1.74-1.59 (m, 3H); MS (ESI) m/z=207 (M−1, negative).

3-(1-Amino-ethyl)-3H-benzo[c][1,2]oxaborol-1-ol (A54)

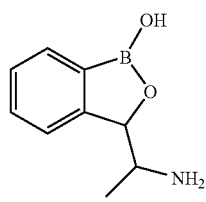

General procedure 12: 3-(1-nitro-ethyl)-3H-benzo[c][1,2]oxaborol-1-ol (3.2 g, 15 mmol), Raney Ni (30% w/w, 1.0 g), 2 M NH$_3$ in EtOH (40 mL). Purification: flash chromatography (10: 10:1 CHCl$_3$/MeOH/NH$_4$OH,). A54 was isolated as a white solid: yield 0.25 g (27%).

mp 118-119° C.; $^1$H NMR (400 MHz, DMSO-d$_6$) δ (ppm): 2 isomers are assigned; 9.13 (bs, 2H), 7.70 (d, J=7.0 Hz, 1H), 7.54-7.39 (m, 2H), 7.39-7.24 (m, 1H), 5.05-4.88 (m, 1H), 3.16 and 3.09-2.93 (m, 1H), 0.99 and 0.75 (d, J=10.2, 6.6 Hz, 3H); MS (ESI) m/z=178 (M+1, positive); HPLC purity: 97.77% (2 isomers, 30.61% and 67.16%) (MaxPlot 200-400 nm), 98.07% (2 isomers, 28.39% and 69.68%) (220 nm), Anal. Calcd for C$_9$H$_{12}$BNO$_2$.0.1H$_2$O: C, 60.30%; H, 6.89%; N, 7.81%. Found: C, 60.27%; H, 6.88%; N, 8.25%.

[1-(1-Hydroxy-1,3-dihydro-benzo[c][1,2]oxaborol-3-yl)-ethyl]-carbamic acid tert-butyl ester (BocA54)

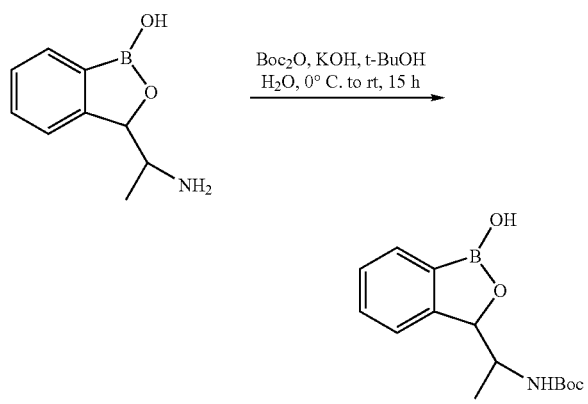

KOH (0.5 g, 8.8 mmol) in H₂O was added to a suspension of A54 (1.3 g, 6.8 mmol) in t-BuOH (20 mL). The mixture was stirred for at rt 10 min and then cooled to 0° C. (bath temp). Boc₂O (1.5 g, 7.1 mmol) was added portionwise and the resulting solution was allowed to warm to rt and was stirred O/N. The mixture was then partially concentrated in vacuo and then extracted with CH₂Cl₂ (4×80 mL). The organic fractions were combined, washed with H₂O, dried (Na₂SO₄), and concentrated in vacuo. The residue was purified by flash chromatography (100:1 CH₂Cl₂/MeOH) to give the title compound as a red sticky gel: yield 1.7 g (93%).

$^1$H NMR (400 MHz, DMSO-$d_6$) δ ppm 9.22 and 9.13 (s, 1H), 7.71-7.61 (m, 1H), 7.47-7.27 (m, 2H), 7.01 and 6.66 (d, J=7.8, J=8.6 Hz 1H), 5.12 and 5.05 (d, J=3.1 Hz, J=5.1 Hz, 1H), 4.12-4.00 (m, 1H), 3.70-3.62 (m, 1H), 1.38 and 1.23 (s, 9H), 0.95 and 0.78 (d, J=6.6 Hz, J=6.6 Hz 3H); MS (ESI) m/z=277 (M−1, negative); HPLC purity: 98.35% (2 isomers 31.05% and 67.30%) (MaxPlot 200-400 nm), 97.43% (2 isomers, 32.72% and 64.71%) (220 nm); Anal. Calcd for C₁₄H₂₀BNO₄: C, 60.68%; H, 7.27%; N, 5.05%. Found: C, 60.86%; H, 7.75%; N, 5.08%.

Separation of [1-(1-Hydroxy-1,3-dihydro-benzo[c][1,2]oxaborol-3-yl)-ethyl]-carbamic acid tert-butyl ester Diastereomers A55 and A56

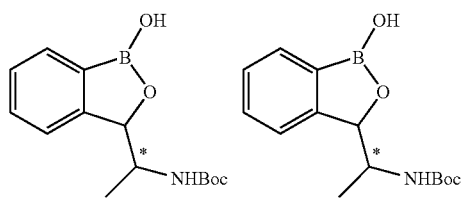 [SMILES: CC(NC(=O)OC(C)(C)C)C1OB(O)c2ccccc21 ; CC(NC(=O)OC(C)(C)C)C1OB(O)c2ccccc21]

A 2:1 mixture of diastereomers of [1-(1-hydroxy-1,3-dihydro-benzo[c][1,2]oxaborol-3-yl)-ethyl]-carbamic acid tert-butyl ester (1.0 g) was separated by reverse phase HPLC (MeCN:H₂O with the H₂O containing 0.1% ACOH) to give the faster eluting A55 (0.275 g) and A56 (0.468 g), both as white lyophilizates.

[1-(1-Hydroxy-1,3-dihydro-benzo[c][1,2]oxaborol-3-yl)-ethyl]-carbamic acid tert-butyl ester (A55)

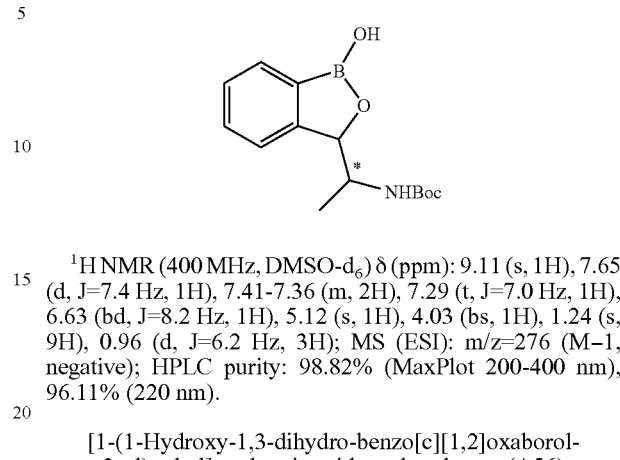

$^1$H NMR (400 MHz, DMSO-$d_6$) δ (ppm): 9.11 (s, 1H), 7.65 (d, J=7.4 Hz, 1H), 7.41-7.36 (m, 2H), 7.29 (t, J=7.0 Hz, 1H), 6.63 (bd, J=8.2 Hz, 1H), 5.12 (s, 1H), 4.03 (bs, 1H), 1.24 (s, 9H), 0.96 (d, J=6.2 Hz, 3H); MS (ESI): m/z=276 (M−1, negative); HPLC purity: 98.82% (MaxPlot 200-400 nm), 96.11% (220 nm).

[1-(1-Hydroxy-1,3-dihydro-benzo[c][1,2]oxaborol-3-yl)-ethyl]-carbamic acid tert-butyl ester (A56)

$^1$H NMR (400 MHz, DMSO-$d_6$) δ (ppm): 9.24 (s, 1H), 7.70 (d, J=7.0 Hz, 1H), 7.43 (t, J=7.2 Hz, 1H), 7.37-7.30 (m, 2H), 7.01 (d, J=8.2 Hz, 1H), 5.05 (d, J=4.7 Hz, 1H), 3.68-3.63 (m, 1H), 1.38 (s, 9H), 0.78 (d, J=6.6 Hz, 3H); MS (ESI): m/z=276 (M−1, negative); HPLC purity: 99.37% (MaxPlot 200-400 nm), 98.65% (220 nm); Anal. Calcd for C₁₄H₂₀BNO₄·0.1H₂O: C, 60.24%; H, 7.30%; N, 5.02%. Found: C, 59.92%; H, 7.34%; N, 5.23%.

3-(1-Amino-ethyl)-3H-benzo[c][1,2]oxaborol-1-ol hydrochloride (A57)

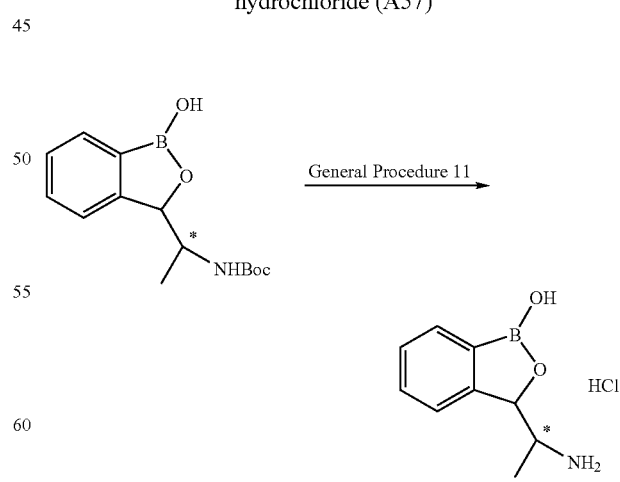

General procedure 11: A55 (0.238 g, 0.860 mmol), 4 N HCl in dioxane (8 mL), and dioxane (8 mL). Purification: preparative HPLC (AcOH). A57 was isolated as a white lyophilizate: yield 56 mg (30%).

$^1$H NMR (400 MHz, DMSO-d$_6$) δ (ppm): 9.57 (bs, 1H), 7.81 (d, J=7.4 Hz, 1H), 7.78 (bs, 3H), 7.51 (d, J=3.5 Hz, 2H), 7.43-7.38 (m, 1H), 5.15 (d, J=5.1 Hz, 1H), 3.47-3.42 (m, 1H), 1.38 (d, J=6.6 Hz, 3H); MS (ESI) m/z=178 (M+1, positive); HPLC purity: 96.55% (MaxPlot 200-400 nm), 98.30% (220 nm).

3-(1-Amino-ethyl)-3H-benzo[c][1,2]oxaborol-1-ol (A58)

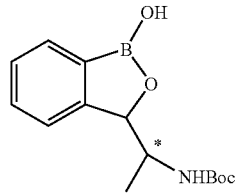

General Procedure 11

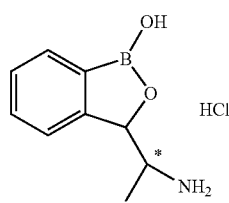

General procedure 11: A56 (0.406 g, 1.47 mmol), 4 N HCl in dioxane (14 mL), and dioxane (10 mL). Purification: reverse phase preparative HPLC (0.1% AcOH). A58 was isolated as a white lyophilizate: yield 124 mg (40%).

$^1$H NMR (400 MHz, DMSO-d$_6$) δ (ppm): 9.66 (bs, 1H), 8.45 (bs, 3H), 7.84 (d, J=7.4 Hz, 1H), 7.52-7.47 (m, 2H), 7.38 (td, J=7.0, 1.2 Hz, 1H), 5.48 (d, J=2.3 Hz, 1H), 3.86-3.79 (m, 1H), 0.65 (d, J=7.0 Hz, 3H); MS (ESI) m/z=178 (M+1, positive); HPLC purity: 98.23% (MaxPlot 200-400 nm), 98.60% (220 nm).

3-(1-Amino-propyl)-3H-benzo[c][1,2]oxaborol-1-ol (A59)

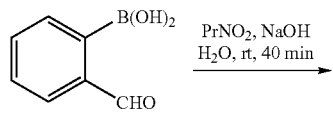

PrNO$_2$, NaOH
H$_2$O, rt, 40 min

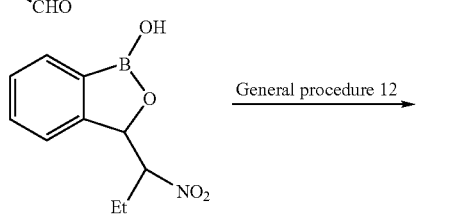

General procedure 12

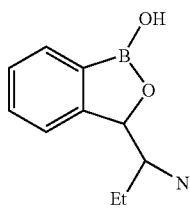

3-(1-Nitro-propyl)-3H-benzo[c][1,2]oxaborol-1-ol

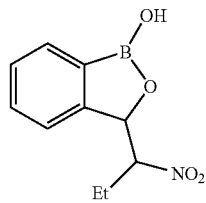 [SMILES: CCC(C1OB(O)c2ccccc21)[N+](=O)[O-]]

A solution of NaOH (2.2 g, 56 mmol) in H$_2$O (30 mL) was added to the aldehyde (7.0 g, 47 mmol) at rt and the reaction mixture was stirred for 10 min. Nitropropane (5.0 mL, 56 mmol) was added dropwise and the mixture was stirred for 40 min. The clear reaction solution was acidified with 2 N HCl and EtOAc was added. The organic layer was separated, washed with H$_2$O then brine, dried (Na$_2$SO$_4$), and concentrated in vacuo. The residue was purified by flash chromatography (2:1 hexane/EtOAc) to give the title compound as a colorless oil: yield 8.8 g (85%).

$^1$H NMR (400 MHz, CDCl$_3$) δ (ppm): 2 isomers are assigned. 7.77 (d, J=7.4 Hz, 1H), 7.59-7.34 (m, 3H), 5.64 and 5.53 (d, J=7.02 Hz and J=5.1 Hz, 1H) 5.03-5.17 (bs, 1H), 4.51 (ddd, J=10.6, 6.9, 3.9 Hz, 1H), 2.34-2.06 (m, 2H), 1.05-0.94 (t, J=7.4 Hz, 3H).

3-(1-Amino-propyl)-3H-benzo[c][1,2]oxaborol-1-ol (A59)

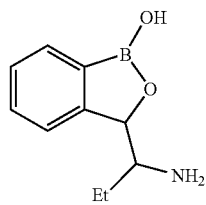 [SMILES: CCC(N)C1OB(O)c2ccccc21]

General procedure 12: 3-(1-nitro-propyl)-3H-benzo[c][1,2]oxaborol-1-ol (4.7 g, 21 mmol), Raney Ni (30% w/w, 1.0 g) and 2 M NH$_3$ in EtOH (50 mL). Purification: flash chromatography (10:10:1 CHCl$_3$/MeOH/NH$_4$OH). A59 was isolated as a light pink solid: yield 0.25 g (20%).

mp 96-97° C.; $^1$H NMR (400 MHz, DMSO-d$_6$) δ (ppm): 2 isomers are assigned; 8.43 (bs, 3H), 7.89-7.69 (m, 2H), 7.60-7.47 and 7.47-7.35 (m, 2H), 5.54 and 5.34 (s, 1H), 3.65 and 3.47 (bs, 1H), 1.71 and 1.25 (dd, J=15.0, 7.6 Hz, 2H), 1.08 and 0.72 (t, J=7.6 Hz, 3H); MS (ESI) m/z=192 (M+1, positive); HPLC purity: 91.65% (2 isomers 41.87% and 49.78%) (MaxPlot 200-400 nm), 98.07% (2 isomers, 43.34% and 49.16%) (220 nm), Anal. Calcd for C$_{10}$H$_{14}$BNO$_2$.0.2H$_2$O: C, 61.71%; H, 7.46%; N, 7.20%. Found: C, 61.75%; H, 7.34%; N, 7.33%.

(S)-3-(aminomethyl)-3-methylbenzo[c][1,2]oxaborol-1(3H)-ol hydrochloride (A61)

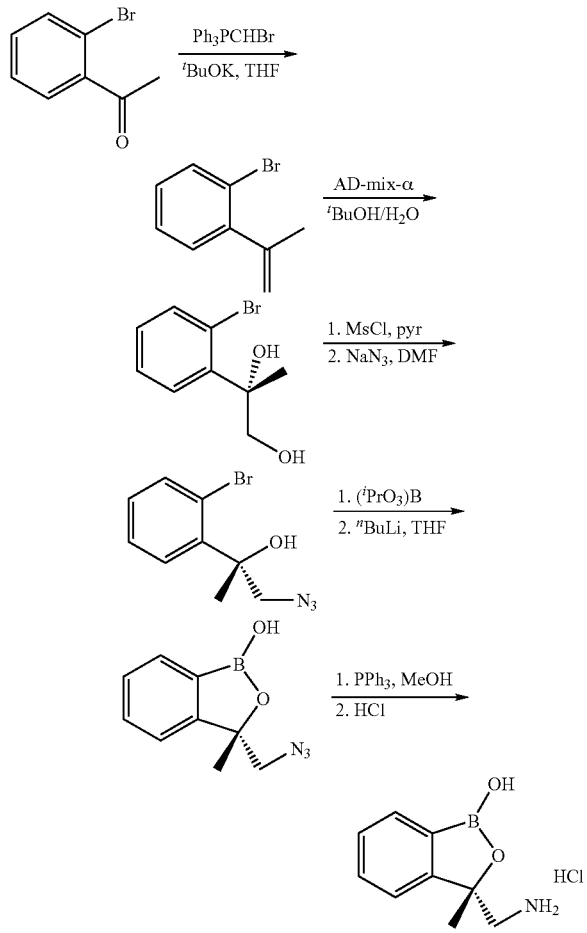

To a suspension of methyltriphenyl phosphonium bromide (108 g, 303 mmol) in THF (750 mL) at room temperature was added KO'Bu (112.24 g, 303 mmol) in portions. After being stirred for 5 min, the reaction mixture was treated with 2'bromoacetophenone (50.3 g, 253 mmol). The reaction mixture was stirred for 3 hrs at room temperature then quenched with saturated ammonium chloride. Extracted 3× with Et₂O and the combined organic layers were washed with brine, dried over MgSO₄ and evaporated under vacuum. Purified by silica gel chromatography (100% petroleum ether) to give 43.8 g (88%) of 1-bromo-2-(prop-1-en-2-yl)benzene as a colorless oil.

AD mix-α (153.4 g) was dissolved in a biphasic mixture of water (550 mL) and 'BuOH (550 mL) and cooled to 0° C. 1-bromo-2-(prop-1-en-2-yl)benzene (21.6 g, 109 mmol) was added and the heterogeneous mixture was stirred at 0° C. for 18 hrs, quenched with sodium sulfate (164 g), warmed to room temperature and stirred for an additional hour. Extracted 5× with DCM and the combined organic layers were dried over MgSO₄ and evaporated under vacuum. Purified by silica gel chromatography (50% petroleum ether/ Et₂O) to give 19.2 g (76%) of (S)-2-(2-bromophenyl)propane-1,2-diol as a pale yellow oil.

(S)-2-(2-bromophenyl)propane-1,2-diol (12.1 g, 52.4 mmol) was dissolved in pyridine (250 mL) and cooled to 0° C. before the addition of methanesulphonyl chloride (4.0 mL, 52.4 mmol). The reaction mixture was allowed to warm to room temperature and stirred for 2 hrs. The pyridine was removed under vacuum and the residue portioned between DCM and aqueous NaHCO₃. The organic layer was dried over MgSO₄ and evaporated under vacuum to give the crude mesylate. This material was combined with NaN₃ (15.3 g, 235.6 mmol), dissolved in DMF (140 mL) and heated to 80° C. for 18 hrs. Water (450 mL) was added and extracted 3× with 500 mL of Et₂O. The combined organic layers were washed with brine, dried over MgSO₄ and evaporated under vacuum. Purified by silica gel chromatography (10-20% Et₂O/petroleum ether) to give 8.7 g (65%) of (S)-1-azido-2-(2-bromophenyl)propan-2-ol as an orange oil.

(S)-1-azido-2-(2-bromophenyl)propan-2-ol (8.7 g, 34.0 mmol) and triisopropyl borate (9.4 mL, 40.8 mmol) were dissolved in 170 mL of toluene. The reaction mixture was refluxed with a Dean/Stark apparatus to remove the toluene and the residue was dissolved in 150 mL of dry THF. This solution was cooled to −78° C. and BuLi (2.5M in Hexanes, 15.6 mL, 39.1 mmol) was added dropwise and stirred for 30 min. The reaction mixture was warmed to room temperature and allowed to stir for 3 hrs before being quenched with 50 mL of 6M HCl and concentrated under vacuum. This was extracted 3× with 100 mL of DCM. The combined organic layers were dried over MgSO₄ and evaporated under vacuum. Purified by silica gel chromatography (20-30% Et₂O/petroleum ether) to give 2.1 g (30%) of (S)-3-(azidomethyl)-3-methylbenzo[c][1,2]oxaborol-1(3H)-ol as a dark yellow oil.

(S)-3-(azidomethyl)-3-methylbenzo[c][1,2]oxaborol-1 (3H)-ol (700 mg, 3.45 mmol) and triphenyl phosphine (1.8 g, 6.9 mmol) were dissolved in 35 mL of acetonitrile. After 5 min concentrated hydrochloric acid (6.9 mL) was added and the reaction mixture was stirred for 24 hrs at room temperature before being concentrated under vacuum. The residue was taken up in DCM and washed 3× with 20 mL of 2M HCl. The combined aqueous layers were evaporated to dryness under vacuum. The resulting solid was washed with EtOH and filtered to remove byproducts, concentrated and crystallized from acetonitrile to give 160 mg (20%) of (S)-3-(aminomethyl)-3-methylbenzo[c][1,2]oxaborol-1(3H)-ol hydrochloride as a white solid.

¹H NMR (300 MHz, DMSO-d₆) δ (ppm): 9.35 (s, 1H), 8.08 (bs, 3H), 7.85-7.83 (d, J=6.9 Hz, 1H), 7.56-7.23 (m, 3H), 3.40-3.33 (m, 1H), 3.07-3.03 (m, 1H), 1.52 (s, 3H).

(S)-3-(aminomethyl)-7-(3-hydroxypropoxy)-3-methylbenzo[c][1,2]oxaborol-1(3H)-ol hydrochloride (A62)

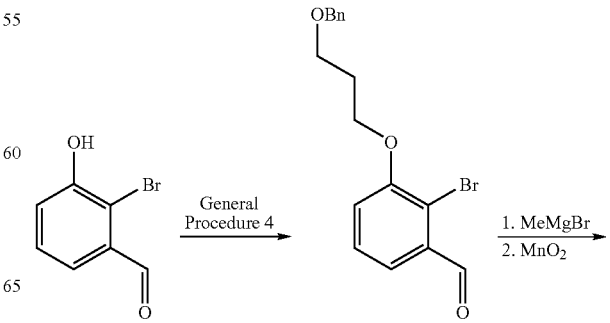

-continued
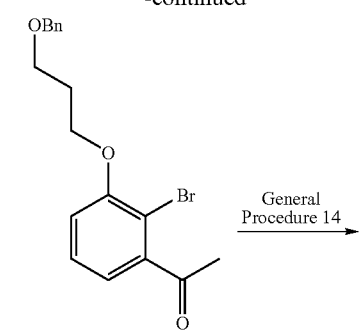
General Procedure 14 →
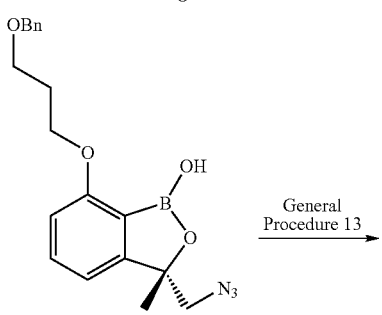
General Procedure 13 →
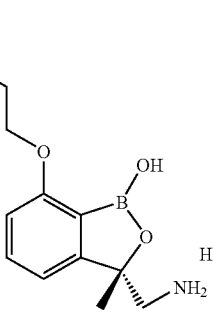
7-(3-aminopropylthio)benzo[c][1,2]oxaborol-1(3H)-ol acetate (A63)
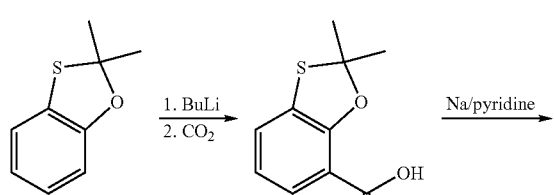
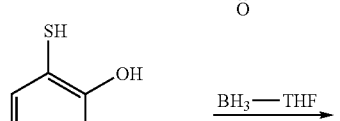
BH₃—THF →
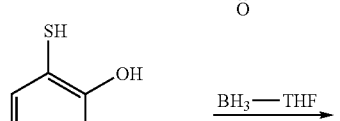
MnO₂ →
-continued
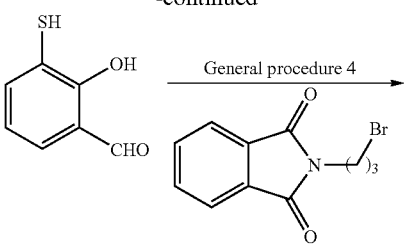
General procedure 4 →
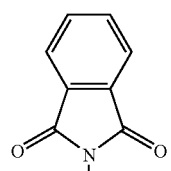
General procedure 6 →
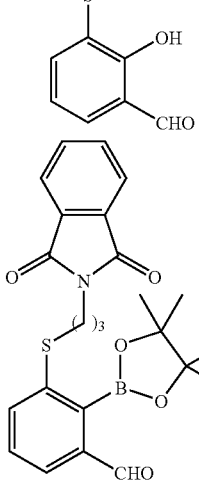
1. General procedure 7
2. AcOH, 80° C., 5 h
→
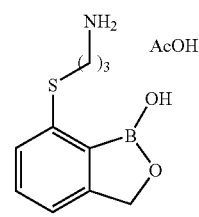
2-(1-hydroxy-1,3-dihydrobenzo[c][1,2]oxaborol-7-ylthio)acetic acid (A64)
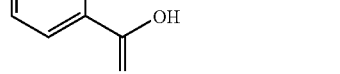
Na/pyridine →

243
-continued
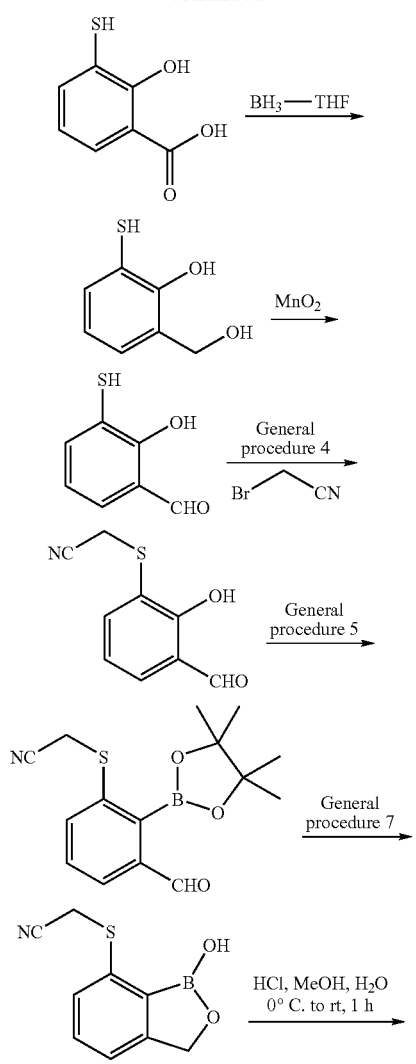
7-(3-hydroxypropylthio)benzo[c][1,2]oxaborol-1(3H)-ol (A65)
244
-continued
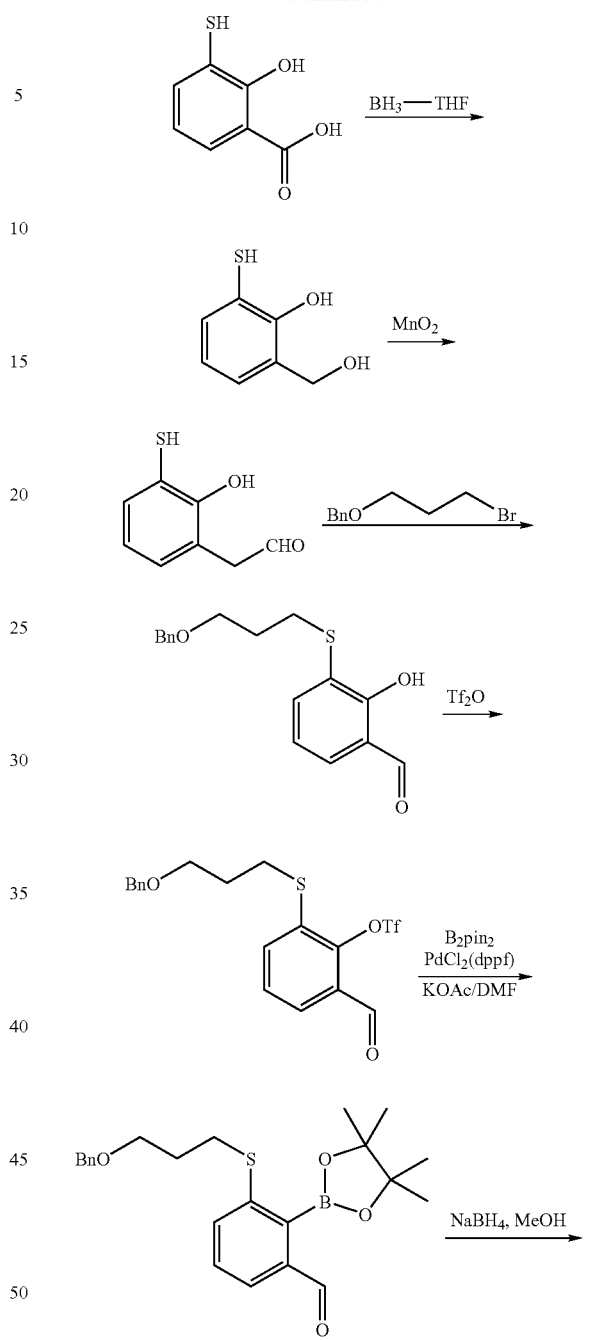
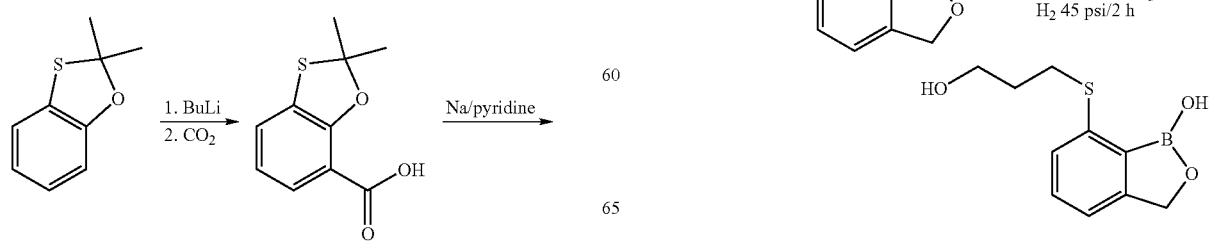

245
3-Aminomethyl-7-(3-hydroxy-propylthio)-3H-benzo[c][1,2]oxaborol-1-ol hydrochloride (A66)
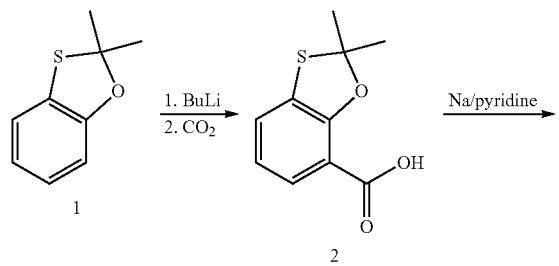
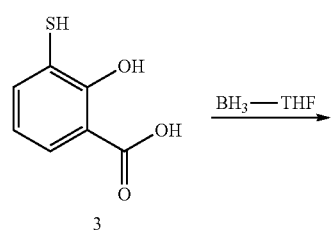
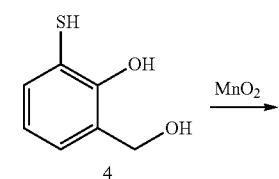
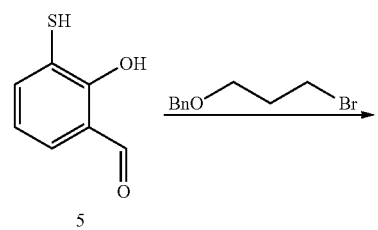
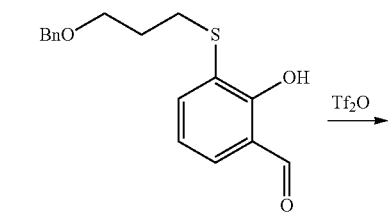
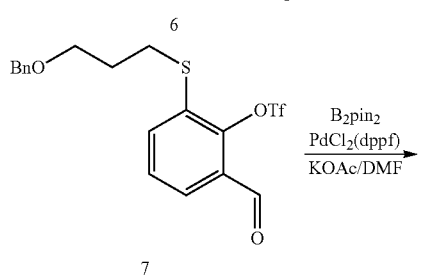
246
-continued
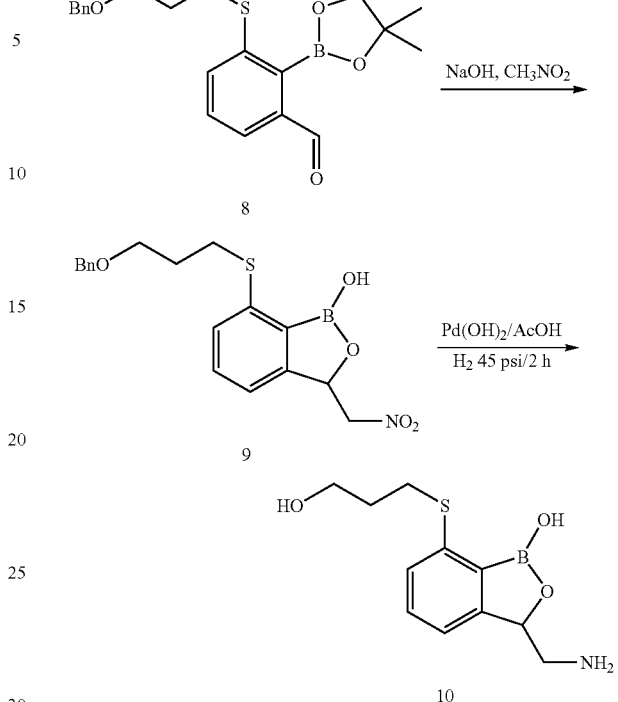
* Compound 3 is a literature prep - *J. Heterocyclic Chem.* 18(3), 639-640, 1981.
3-Aminomethyl-6-(2-hydroxy-ethylsulfanyl)-3H-benzo[c][1,2]oxaborol-1-ol hydrochloride salt (A67)

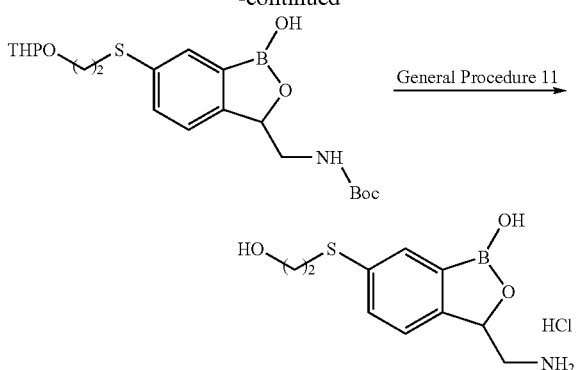

2-(Tetrahydro-pyran-2-yloxy)-ethanethiol can be generated according to J. Med. Chem. 1999, 42, 706-721.

3-Aminomethyl-6-(3-hydroxy-propylsulfanyl)-3H-benzo[c][1,2]oxaborol-1-ol hydrochloride salt (A68)

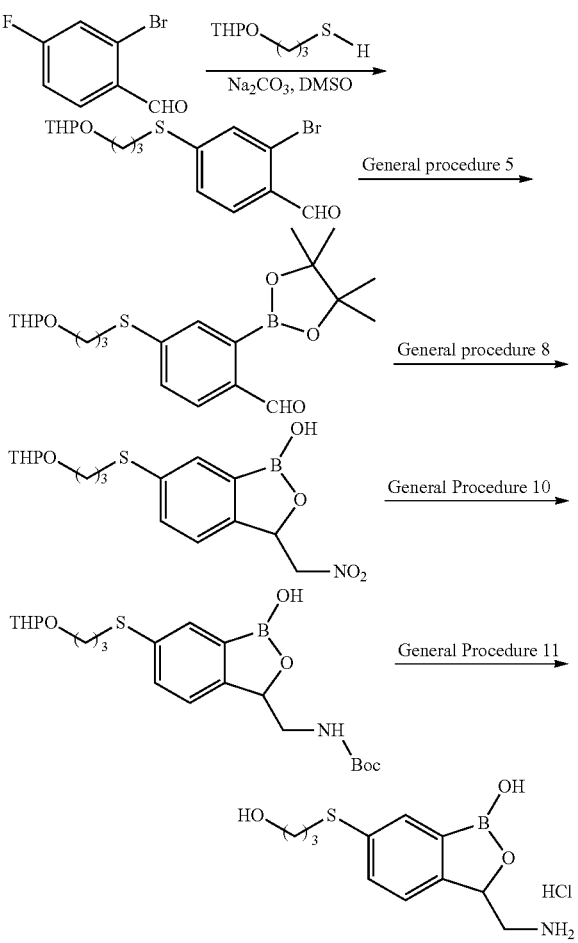

3-(Tetrahydro-pyran-2-yloxy)-propane-1-thiol can be generated according to J. Med. Chem. 1999, 42, 706-721.

Example 2

Antifungal and Antibacterial MIC Testing

All MIC testing of bacteria followed the Clinical and Laboratory Standards Institute (CLSI) guidelines for antimicrobial testing of aerobic bacteria (Methods for Dilution Antimicrobial Susceptibility Tests for Bacteria That Grow Aerobically; Approved Standard—Seventh Edition) (M07-A7) and anaerobic bacteria (Methods for Antimicrobial Susceptibility Testing of Anaerobic Bacteria; Approved Standard—Seventh Edition) (M11-A7).

MIC testing of yeasts and filamentous fungi can follow the National Committee for Clinical Laboratory Standards (NCCLS) guidelines for antimicrobial testing of yeasts (M27-A2 NCCLS) and filamentous fungi (Pfaller et al., NCCLS publication M38-A—Reference Method for Broth Dilution Antifungal Susceptibility Testing of Filamentous Fungi; Approved Standard. Wayne, Pa.: NCCLS; 2002 (Vol. 22, No. 16).

Example 3

Keratin Assay

The affinities of the compounds for keratin powder can be determined by a method described in Tatsumi, *Antimicrobial Agents and Chemotherapy*, 46(12):3797-3801 (2002).

Example 4

Assay for Determining that a Compound Inhibits the Editing Domain of tRNA Synthetase in a Bacteria This example sets forth a representative assay for determining whether a particular compound inhibits the editing domain of an ARS in a bacterium.

The [$^3$H]-isoleucine mischarged tRNAleu was synthesized by incubating 1 μM of *Saccharomyces cerevisiae* editing defective Cdc60p (C326F) in 500 μL of 50 mM Tris-HCl (pH 8.0), 60 mM MgCl$_2$, 4 mM ATP, 1 mM DTT, 0.02% (w/v) BSA, 4 mg/mL crude *E. coli* tRNA tRNA (Roche), 0.1 mM isoleucine and 5 mCi L-[4, 5-3H]isoleucine (100 Ci/mmole, GE Healthcare) and 20% (v/v) DMSO for 1 hour at 30° C. The reaction was stopped by adding 10 μL of 10% (v/v) acetic acid followed by two acidic phenol (Sigma) extractions. The mischarged tRNA in the top aqueous phase was removed and precipitated by adding two volumes of 96% (v/v) ethanol and incubating at −20° C. for 30 minutes. The precipitate was pelleted by centrifugation at 13,200×g for 30 minutes and the mischarged tRNA pellet was washed twice with 70% (v/v) ethanol and then resuspended in 50 mM potassium phosphate buffer pH 5.2.

The reaction was terminated after 2 hours incubation at 30° C. by the addition of acetic acid to 0.17% (v/v). The isoleucylated crude tRNA$^{Leu}$ was purified by extracting twice with acidic phenol-chloroform extractions (pH 4.3), followed by ethanol precipitation. The tRNA pellet was washed twice with 70% ethanol, dried and then resuspended in 50 mM potassium phosphate (pH 5.0) and stored at −20° C. An aliquot was precipitated with 10% (w/v) TCA to quantify ile-tRNA$^{Leu}$.

Post-transfer editing hydrolysis assays were carried out at 30° C. in 50 mM Hepes (pH 8), 10 mM MgCl$_2$, 30 mM KCl, with $^3$H-isoleucine-tRNA crude (~0.3 μCi/mL). Each reaction was initiated by addition of the 150 nM enzyme. At each time point three 20 μL aliquots of the reaction mixture was added to 200 μL of 10% (w/v) TCA in a Millipore filter plate and precipitated for 20 minutes at 4° C. The precipitate was filtered and washed three times with 200 μL of 5% (w/v) TCA, then dried and 20 μL Supermix scintillation cocktail was added. The Millipore filter plates were counted in the MicroBeta Trilux. The IC$_{50}$ was determined by the amount of inhibitor that inhibited 50% activity, 100% post-transfer editing was calculated by taking the activity of the no enzyme control from the wild-type enzyme activity.

Compare the minimal inhibitory concentration (MIC) of a tolC *Escherichia coli* strain bearing a pUC derived plasmid with and without an leuS gene insert.

If the MIC of the strain bearing the extra copies of leuS is greater than 2-fold more than the control strain then pour LB agar plates with four times the concentration of the MIC of the compound.

Plate $1 \times 10^{10}$ *E. coli* on ten plates containing 4×MIC of the compound. Incubate for 1-2 days at 37° C. and pick ten colonies and restreak on 4×MIC LB agar plates to confirm resistance.

Take one large colony from each of the ten *E. coli* resistant mutants and resuspend in 50 μL of PCR buffer.

Amplify the editing domain of CDC60 using a proof-reading PCR enzyme and the following primers, ggcaccgtggacgtacgacaacatcgc and gggaaacaccccagtcgcgcaggcgg.

Purify the 980 bp PCR product using either Qiagen or Promega PCR cleanup kits.

Sequence amplify the mutant DNA and compared it to wild-type. If the mutant DNA bears mutations in the editing domain the inhibitor affects leucyl-tRNA synthetase via the editing domain.

Example 5

Assay for Determining that a Compound Inhibits the Editing Domain of tRNA Synthetase in a Fungi This example details an exemplary assay for determining whether a selected compound inhibits the editing domain of an ARS in a fungus.

The [$^3$H]-isoleucine mischarged tRNAleu can be synthesized by incubating 1 μM of *Saccharomyces cerevisiae* editing defective Cdc60p (C326F) in 500 μL of 50 mM Tris-HCl (pH 8.0), 60 mM MgCl$_2$, 4 mM ATP, 1 mM DTT, 0.02% (w/v) BSA, 16 μM brewer's yeast tRNA (Roche), 0.1 mM isoleucine and 5 mCi L-[4, 5-3H]isoleucine (100Ci/mmole, GE Healthcare) and 20% (v/v) DMSO for 1 hour at 30° C. The reaction can be stopped by adding 10 μL of 10% (v/v) acetic acid followed by two acidic phenol (Sigma) extractions. The mischarged tRNA in the top aqueous phase can be removed and precipitated by adding two volumes of 96% (v/v) ethanol and incubating at −20° C. for 30 minutes. The precipitate can be pelleted by centrifugation at 13,200×g for 30 minutes and the mischarged tRNA pellet was washed twice with 70% (v/v) ethanol and then resuspended in 50 mM potassium phosphate buffer pH 5.2.

The reaction can be terminated after 2 hours incubation at 30° C. by the addition of acetic acid to 0.17% (v/v). The isoleucylated crude tRNA$^{Leu}$ can be purified by extracting twice with acidic phenol-chloroform extractions (pH 4.3), followed by ethanol precipitation. The tRNA pellet can be washed twice with 70% ethanol, dried and then resuspended in 50 mM potassium phosphate (pH 5.0) and stored at −20° C. An aliquot can be precipitated with 10% (w/v) TCA to quantify ile-tRNA$^{Leu}$.

Post-transfer editing hydrolysis assays can be carried out at 25° C. in 50 mM Hepes (pH 7.5), 10 mM MgCl$_2$, 30 mM KCl, with $^3$H-isoleucine-tRNA crude (~0.3 μCi/mL). Each reaction can be initiated by addition of the 150 nM enzyme. At each time point three 20 μL aliquots of the reaction mixture can be added to 200 μL of 10% (w/v) TCA in a Millipore filter plate and precipitated for 20 min. at 4° C. The precipitate can be filtered and washed three times with 200 μL of 5% (w/v) TCA, then dried and 20 μL Supermix scintillation cocktail can be added. The Millipore filter plates can be counted in the MicroBeta Trilux. The IC$_{50}$ can be determined by the amount of inhibitor that inhibited 50% activity, 100% activity was calculated by taking the activity of the no enzyme control from the wild-type enzyme post-transfer editing activity.

Example 6

Equilibrium Dialysis

Equilibrium dialysis experiments can be performed in 1×AARS buffer containing 50 mM Hepes-KOH (pH 8.0), 30 mM MgCl$_2$ and 30 mM KCl. Experiments can be performed using 5 k MWCO DispoEquilibrium Dialyzer apparatus (Harvard Apparatus, Holliston, Mass.). On one side of the dialysis membrane (side A), [methylene-$^{14}$C] compound of the invention, 2.04 GBq/mmol (Amersham) was added at concentrations ranging from 1 to 200 μM in 20 μL. On the opposite side of the membrane (side B), 30 μM recombinant Cdc60p (*Saccharomyces cerevisiae* cytoplasmic LeuRS) and 10 mM AMP (adenosine 5'-monophosphate, Sigma) was added in 20 μL. Samples were incubated at room temperature (21° C.) while shaking for 4.5 hrs to establish compound of the invention equilibrium across the membrane. At equilibrium, a compound of the invention on each side of the dialysis membrane was quantified by scintillation counting using a Wallac MicroBeta Trilux model 1450 liquid scintillation counter. The amount of compound of the invention bound to Cdc60p was determined by subtracting [compound of the invention]A from [compound of the invention]B.

PPi Exchange Assay

The PPi exchange assay can be performed in 1×AARS buffer containing 50 mM Hepes-KOH (pH 8.0), 30 mM MgCl$_2$ and 30 mM KCl supplemented with 2 mM ATP and [$^{32}$P] PPi (10$^5$ cpm/μmol), 2 mM leucine and 7 nM recombinant Cdc60p. Experiments can also be performed in the presence or absence of compound of the invention (15 μM) and tRNA (16 μM). After a 20 minute incubation at 30° C., reactions can be initiated by the addition of ATP. At various time intervals, 45 μL of reaction mixture can be added to 100 μL of 2% perchloric acid and 0.1 M Na$_4$P$_2$O$_7$ to quench the reaction. Radioactive ATP can then be absorbed to activated charcoal by the addition of 30 μL of a 5% suspension of acid-washed Norit A. This mixture can be filtered though GF/C glass filters and washed 2× with 200 μL of distilled water then 1× with 200 μL of 95% ethanol. Filters can be dried and scintillation counted using a Wallac MicroBeta Trilux model 1450 liquid scintillation counter.

Synthesis of Tritiated Mischarged tRNA$_{leu}$

The [$^3$H]-isoleucine mischarged tRNAleu can be synthesized by incubating 1 μM of *Saccharomyces cerevisiae* editing defective Cdc60p (C326F) in 500 μL of 50 mM Tris-HCl (pH 8.0), 60 mM MgCl$_2$, 4 mM ATP, 1 mM DTT, 0.02% (w/v) BSA, 16 μM brewer's yeast tRNA (Roche), 0.11 mM isoleucine and 5 mCi L-[4, 5-3H]isoleucine (100 Ci/mmole, GE Healthcare) and 20% (v/v) DMSO for 1 hour at 30° C. The reaction can be stopped by adding 10 μL of 10% (v/v) acetic acid followed by two acidic phenol (Sigma) extractions. The mischarged tRNA in the top aqueous phase can be removed and precipitated by adding two volumes of 96% (v/v) ethanol and incubating at −20° C. for 30 minutes. The precipitate can be pelleted by centrifugation at 13,200×g for 30 minutes and the mischarged tRNA pellet can be washed twice with 70% (v/v) ethanol and then resuspended in 50 mM potassium phosphate buffer pH 5.2.

Post-transfer Editing Assay

The [$^3$H]-isoleucine mischarged tRNAleu substrate, 40 nM, can be added to 50 mM Hepes-KOH pH 8.0, 30 mM KCl, 30 mM MgCl$_2$, 0.02% (w/v) BSA, 1 mM DTT, 2.4 nM *S. cerevisiae* Cdc60p at 30° C. to start the reaction and 20 µL aliquots, taken at set time points, were added to ice cold 200 µL 10% (w/v) trichloroacetic acid (TCA). The TCA precipitates can be washed twice with 200 µl ice cold 5% (w/v) TCA and filtered through a Multiscreen HTS HA filter (Millipore). Optiphase (Perkin Elmer) scintillation cocktail can be added to the filters and the TCA precipitate was counted in a Wallac MicroBeta Trilux model 1450 liquid scintillation counter.

Example 7

Assay for Determining that Compounds Inhibit AARS Synthesis Activity

Aminoacylation assays can be performed to determine the rate of net leucine/tRNA$^{Leu}$ synthesis by leucyl tRNA synthetase. Experiments can be performed in 500 ul reaction mixtures containing 1×AARS buffer (50 mM Hepes-KOH (pH 8.0), 30 mM MgCl$_2$ and 30 mM KCl) supplemented with 20 uM [14C]-leucine (Perkin-Elmer, 11.32 GBq/mmol.), 16 uM crude yeast tRNA, 0.02% BSA, 1 mM dithiothreitol, 2 nM recombinant yeast LeuRS (CDC60) and 2 mM ATP. Reactions can be performed at 30 deg Celsius. At time zero reactions can be started by the addition of ATP. At various time intervals, 20 ul aliquots can be added to 150 ul of 10% trichloroacetic acid (TCA) within a single well of a 96-well nitrocelluse membrane filterplate (Millipore Multiscreen HTS, MSHAN4B50). Each well can be washed 3× with 100 ul of 5% TCA. Filterplates can then be dried under a heat lamp and the precipitated [14C]-leucine/tRNA$^{Leu}$ complexes were quantified by liquid scintillation counting using a Wallac MicroBeta Trilux model 1450 liquid scintillation counter. The inhibitory effects of compounds of the invention can be determined by addition of up to a 100 uM of the compound in the reaction mixture for 20 minutes prior to the addition of ATP.

It is to be understood that the present invention covers all combinations of aspects with all other suitable aspects and/or exemplary embodiments described herein. It is to be understood that the present invention also covers all combinations of exemplary embodiments with all other suitable aspects and/or exemplary embodiments described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having a structure according to the formula:

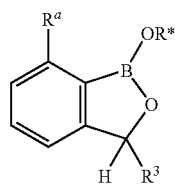

wherein
  R* is H;
  $R^3$ is —$CH_2NH_2$;
  $R^a$ is H or —$YR^5$
  wherein
    Y is O;
    $R^5$ is:

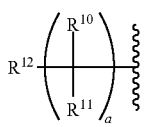

wherein
    a is an integer selected from 1, 2, 3, or 4;
    each $R^{10}$ and each $R^{11}$ is H;
    $R^{12}$ is H;
or a salt thereof.

2. A combination comprising a first therapeutically active agent which is the compound of claim 1, wherein the salt is a pharmaceutically acceptable salt thereof, together with at least one other therapeutically active agent.

3. A pharmaceutical formulation comprising:
  a) the compound of claim 1 or a salt thereof, wherein said salt is a pharmaceutically acceptable salt thereof; and
  b) a pharmaceutically acceptable excipient.

4. The pharmaceutical formulation of claim 3 wherein the pharmaceutical formulation is a unit dosage form.

5. A compound having a structure which is:

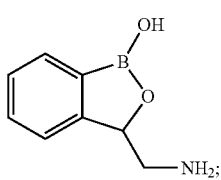 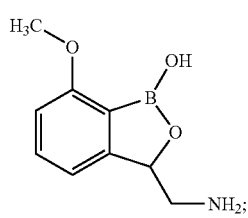

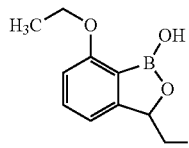 or or a salt thereof.

6. A compound which is

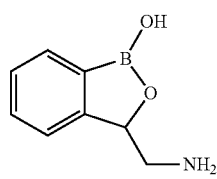 [SMILES: NC[C@H]1OB(O)c2ccccc21]

or a salt thereof.

7. A combination comprising a first therapeutically active agent which is the compound of claim 6 or a salt thereof, wherein the salt is a pharmaceutically acceptable salt thereof, together with at least one other therapeutically active agent.

8. A pharmaceutical formulation comprising:
  a) the compound of claim 6 or a salt thereof, wherein said salt is a pharmaceutically acceptable salt thereof; and
  b) a pharmaceutically acceptable excipient.

9. The compound of claim 6, which is

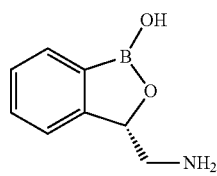

or a salt thereof.

10. A combination comprising a first therapeutically active agent which is the compound of claim 9 or a salt thereof, wherein the salt is a pharmaceutically acceptable salt thereof, together with at least one other therapeutically active agent.

11. A pharmaceutical formulation comprising:
  a) the compound of claim 9 or a salt thereof, wherein said salt is a pharmaceutically acceptable salt thereof; and
  b) a pharmaceutically acceptable excipient.

12. A compound which is

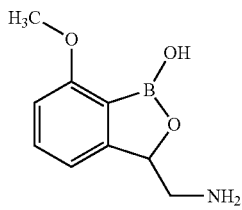

or a salt thereof.

13. A combination comprising a first therapeutically active agent which is the compound of claim 12, wherein the salt is a pharmaceutically acceptable salt thereof, together with at least one other therapeutically active agent.

14. A pharmaceutical formulation comprising:
   a) the compound of claim 12, wherein said salt is a pharmaceutically acceptable salt thereof; and
   b) a pharmaceutically acceptable excipient.

15. The compound of claim 12, which is

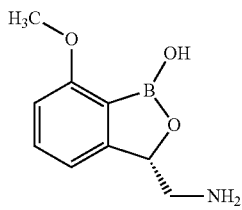

or a salt thereof.

16. A combination comprising a first therapeutically active agent which is the compound of claim 15 or a salt thereof, wherein the salt is a pharmaceutically acceptable salt thereof, together with at least one other therapeutically active agent.

17. A pharmaceutical formulation comprising:
   a) the compound of claim 15 or a salt thereof, wherein said salt is a pharmaceutically acceptable salt thereof; and
   b) a pharmaceutically acceptable excipient.

18. A compound which is

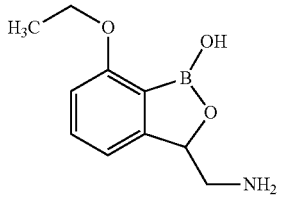

or a salt thereof.

19. A combination comprising a first therapeutically active agent which is the compound of claim 18 or a salt thereof, wherein the salt is a pharmaceutically acceptable salt thereof, together with at least one other therapeutically active agent.

20. A pharmaceutical formulation comprising:
   a) the compound of claim 18 or a salt thereof, wherein said salt is a pharmaceutically acceptable salt thereof; and
   b) a pharmaceutically acceptable excipient.

21. The compound of claim 18, which is

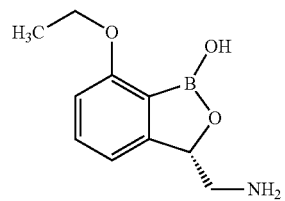

or a salt thereof.

22. A combination comprising a first therapeutically active agent which is the compound of claim 21 or a salt thereof, wherein the salt is a pharmaceutically acceptable salt thereof, together with at least one other therapeutically active agent.

23. A pharmaceutical formulation comprising:
   a) the compound of claim 21 or a salt thereof, wherein said salt is a pharmaceutically acceptable salt thereof; and
   b) a pharmaceutically acceptable excipient.

24. A compound which is

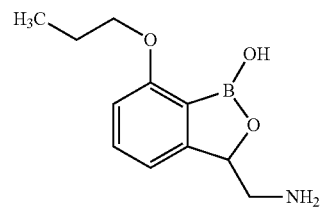 [SMILES: CCCOc1cccc2c1B(O)OC2CN]

or a salt thereof.

25. A combination comprising a first therapeutically active agent which is the compound of claim 24 or a salt thereof, wherein the salt is a pharmaceutically acceptable salt thereof, together with at least one other therapeutically active agent.

26. A pharmaceutical formulation comprising:
   a) the compound of claim 24 or a salt thereof, wherein said salt is a pharmaceutically acceptable salt thereof; and
   b) a pharmaceutically acceptable excipient.

27. The compound of claim 24, which is

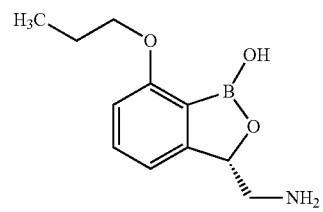 [SMILES: CCCOc1cccc2c1B(O)O[C@@H]2CN]

or a salt thereof.

28. A combination comprising a first therapeutically active agent which is the compound of claim 27 or a salt thereof, wherein the salt is a pharmaceutically acceptable salt thereof, together with at least one other therapeutically active agent.

29. A pharmaceutical formulation comprising:
   a) the compound of claim 27 or a salt thereof, wherein said salt is a pharmaceutically acceptable salt thereof; and
   b) a pharmaceutically acceptable excipient.

* * * * *